(12) United States Patent
Newman et al.

(10) Patent No.: US 12,249,401 B2
(45) Date of Patent: *Mar. 11, 2025

(54) SYSTEMS AND METHODS FOR ANALYZING MIXED CELL POPULATIONS

(71) Applicant: The Board of Trustees of the Leland Stanford Junior University, Stanford, CA (US)

(72) Inventors: Aaron M. Newman, San Mateo, CA (US); Arash Ash Alizadeh, San Mateo, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 434 days.

This patent is subject to a terminal disclaimer.

(21) Appl. No.: 16/631,778

(22) PCT Filed: Jul. 19, 2018

(86) PCT No.: PCT/US2018/042949
§ 371 (c)(1),
(2) Date: Jan. 16, 2020

(87) PCT Pub. No.: WO2019/018684
PCT Pub. Date: Jan. 24, 2019

(65) Prior Publication Data
US 2020/0176080 A1 Jun. 4, 2020

Related U.S. Application Data

(60) Provisional application No. 62/535,645, filed on Jul. 21, 2017.

(51) Int. Cl.
G16B 30/00 (2019.01)
C12Q 1/6881 (2018.01)
G16B 20/00 (2019.01)
G16B 40/20 (2019.01)
G16B 50/10 (2019.01)

(52) U.S. Cl.
CPC .......... *G16B 30/00* (2019.02); *C12Q 1/6881* (2013.01); *G16B 20/00* (2019.02); *G16B 40/20* (2019.02); *G16B 50/10* (2019.02)

(58) Field of Classification Search
CPC ........ C12Q 2600/158; C12Q 2537/165; G16B 25/00; G16B 20/00; G16B 25/10; G16B 40/00; G16B 30/00; G16B 20/20; G16B 50/00; G16B 40/10; G16B 45/00; G16B 50/20; G16B 35/00; G16B 20/40; G16B 10/00; G16B 15/00; G16B 50/30; G01N 2570/00; G06T 7/0012; G06T 2207/30024; G06T 2207/20076; G06T 2207/30004
USPC ......................................................... 702/19
See application file for complete search history.

(56) References Cited

U.S. PATENT DOCUMENTS

| | | | |
|---|---|---|---|
| 6,661,004 B2 | 12/2003 | Aumond et al. | |
| 10,167,514 B2* | 1/2019 | Newman | C12Q 1/6809 |
| 11,802,314 B2* | 10/2023 | Newman | C12Q 1/6886 |
| 12,031,183 B2* | 7/2024 | Newman | G16B 25/10 |
| 2005/0108753 A1 | 5/2005 | Saidi et al. | |
| 2013/0110756 A1 | 5/2013 | Zhang et al. | |
| 2016/0217253 A1* | 7/2016 | Newman | C12Q 1/6886 |
| 2016/0341731 A1 | 11/2016 | Sood et al. | |
| 2021/0040442 A1* | 2/2021 | Rajagopal | G01N 33/5005 |

FOREIGN PATENT DOCUMENTS

| CN | 103217411 | 7/2013 |
|---|---|---|
| JP | T 2014-517954 | 7/2014 |
| WO | WO 2007/035613 | 3/2007 |

OTHER PUBLICATIONS

Chen, Ziyi, et al. "Inference of immune cell composition on the expression profiles of mouse tissue." Scientific reports 7.1 (2017): 1-11.*
Ju, Wenjun, et al. "Defining cell-type specificity at the transcriptional level in human disease." Genome research 23.11 (2013): 1862-1873.*
Sun, Bing-Yu, et al. "Combined feature selection and cancer prognosis using support vector machine regression." IEEE/ACM transactions on computational biology and bioinformatics 8.6 (2010): 1671-1677.*
Johnson, W. Evan, Cheng Li, and Ariel Rabinovic. "Adjusting batch effects in microarray expression data using empirical Bayes methods." Biostatistics 8.1 (2007): 118-127. (Year: 2007).*
Wilhelm-Benartzi, Charlotte S., et al. "Review of processing and analysis methods for DNA methylation array data." British journal of cancer 109.6 (2013): 1394-1402. (Year: 2013).*
Wagner, A. et al. (2016) Revealing the vectors of cellular identity with single cell genomics. Nature Biotechnology vol. 14, No. 11, p. 1145-1168. (Year: 2016).*
Tung P-Y, et al. (Jan. 2017) Batch effects and the effective design of single cell gene expression studies. Scientific reports, volum3 7, e39921, 15 pages. (Year: 2017).*
Goh, W. W-B, et al (Jun. 2017) Why batch effects matter in Omics data and how to avoid them. Trends in Biotechnology, vol. 25, No. 6, p. 498-507. (Year: 2017).*
Chen, C. et al. (2011) Removing batch effects in analysis of expression microarray data: an evaluation of six batch adjustment methods. PLOS One vol. 6, issue 2, e17238, 10 pages. (Year: 2011).*
Caicedo, J. C. et al. (Aug. 11, 2017) Data-analysis strategies for image-based cell profiling. Nature Methods, vol. 14, No. 9, p. 849-863. (Year: 2017).*

(Continued)

*Primary Examiner* — Mary K Zeman
(74) *Attorney, Agent, or Firm* — Edward J. Baba; Bozicevic, Field & Francis LLP

(57) ABSTRACT

The present disclosure provides systems and methods for analyzing a mixed population of cells. In particular, the present disclosure provides systems and methods for digital cytometry of a biological sample, digital analysis of a biological sample, digital purification of a biological sample, evaluation of a disease in an individual, and prediction of a clinical outcome of a disease therapy.

19 Claims, 104 Drawing Sheets

(56) References Cited

OTHER PUBLICATIONS

Definition of normal distribution, wikipedia.com downloaded Jan. 2024 (Year: 2024).*
Definition of sampling, and random sampling, wikipedia.com, downloaded Jan. 2024 (Year: 2024).*
Definition of simple random sampling, wikipedia.com downloade Jan. 2024 (Year: 2024).*
Meng, et al (2013) scalable simple random sampling and stratified sampling, Proceedings of the 30th int conf on machine learning, atlanta georgia, vol. 28. (Year: 2013).*
Le et al. (2020) "A Review of Digital Cytometry Methods: Estimating the Relative Abundance of Cell Types in a Bulk of Cells", Briefings in Bioinformatics: 1-12.
Li et al. (2016) "Comprehensive Analyses of Tumor Immunity: Implications for Cancer Immunotherapy", Genome Biology, 2016, vol. 17, No. 1: 1-16.
Newman et al. (2017) "Data Normalization Considerations for Digital Tumor Dissection", Genome Biology, 2017, vol. 18, No. 1: 1-6.
Newman et al. (2019) "Determining Cell Type Abundance and Expression From Bulk Tissues with Digital Cytometry", Nature Biotechnology, vol. 37, No. 7: 773-782.
Steen et al. (2020) "Profiling Cell Type Abundance and Expression in Bulk Tissues with CIBERSORTx", Methods Mol Bio, vol. 2117: 135-157.
Cobos et al., (2018) "Computational deconvolution of transcriptomics data from mixed cell populations", Bioinformatics, vol. 34(11), pp. 1969-1779.
Krishnan et al., (2011) "Quantitative Analysis of Sub-Epithelial Connective Tissue Cell Population of Oral Submucous Fibrosis Using Support Vector Machine", Journal of Medical Imaging and Health Informatics, vol. 1, No. 1, pp. 4-12.
Newman et al., (2015) "Robust enumeration of cell subsets from tissue expression profiles", Nature Methods, vol. 12, No. 5, pp. 453-457.
Abbas et al., "Immune response in silico (IRIS): immune-specific genes identified from a compendium of microarray expression data" Genes and Immunity, 2005, pp. 319-331, vol. 6, No. 4.
Abbas et al., "Deconvolution of Blood Microarray Data Identifies Cellular Activation Patterns in Systematic Kupus Erythematosus", PLOS One, Jul. 2009, p. e6098, vol. 4, No. 7.
Ahn et al., "DeMix: deconvolution for mixed cancer transcriptomes using raw measured data" Bioinformatics, 2013, pp. 1865-1871, vol. 29, No. 15.
Benita et al., "Gene enrichment profiles reveal T-cell development, differentiation, and lineage-specific transcription factors including ZBTB25 as a novel NF-AT repressor", Blood, 2010, pp. 5376-5384, vol. 115.
Burdick and Murray, "Deconvolution of gene expression from cell populations across the C. elegans lineage", BMC Bioinformatics, Jun. 22, 2012, p. 204, vol. 14.
Cherlassky et al., "Practical selection of SVM parameters and noise estimation for SVM regression", Neural Netk, 2004, pp. 113-126, vol. 17.
Coussens et al., "Neutralizing tumor-promoting chronic inflammation: a magic bullet?", Science, 2013, pp. 286-291, vol. 339.
Drucker et al., "Support Vector Regression Machines", MIT Press, 1997, pp. 155-161, vol. 9.
Farrar et al., "Multicollinearity in Regression Analysis: The Problem Revisited", R. R. Rev. Econ. Stat., 1967, pp. 92-107, vol. 49.
Gaujoux and Seoighe, "CellMix: a comprehensive toolbox for gene expression deconvolution", Bioinformatics, 2013, pp. 2211-2212, vol. 29, No. 17.
Gong and Szutakowski, "DeconRNASeq: a statistical framework for deconvolution of heterogeneous tissue samples based on mRNA-Seq data", Bioinformatics, 2013, pp. 1083-1085, vol. 29, No. 8.
Gong et al., "Optimal Deconvolution of Transcriptional Profiling Data Using Quadratic Programming with Application to Complex Clinical Blood Samples", PLOS One, Nov. 2011, p. e27156.
Hanahan et al., "Hallmarks of Cancer: The Next Generation", Cell, 2011, pp. 646-674, vol. 144.
Kuhn et al., "Population-specific expression analysis (PSEA) reveals molecular changes in diseased brain", Nat Methods, 2011, pp. 945-947, vol. 8.
Levy et al., "Active Idiotypic Vaccination Versus Control Immunotherapy for Folicular Lymphoma", J Clin. Oncol., 2014, pp. 1797-1803, vol. 32.
Liebner et al., "MMAD: microarray microdissection with analysis of difference is a computational tool for deconvoluting cell type= speficic contributions from tissue samples", Bioinformatics, 2014, pp. 682-689, vol. 30, No. 5.
Lu et al., "Expression deconvolution: A reinterpretation of DNA microarray data reveals dynamic changes in cell populations", PNAS, 2003, pp. 10370-10375, vol. 100, No. 18.
Lukk et al., "A global map of human gene expression", NAt. Biotechnol, 2010, pp. 322-324, vol. 28.
Mackey et al. (2011) "Divide-and-Conquer Matrix Factorization" Advances in Neural Information Processing Systems 24, edited by J. Shawe-Taylor et al. Proceedings from the conference, "Neural information Processing Systems" 2011 [online]. [Retrieved on Oct. 19, 2018] Retrieved from the internet <URL: https:/lwww.cs.cmu.edu/-atalwalk!dfc.pdf > pp. 1-21.
Newman et al. (2014) "An ultrasensitive method for quantitating circulating tumor DNA with broad patient coverage" Nature Medicine 20: 548-554.
Qiao et al., "PERT: A Method for Expression Deconvolution of Human Blood Samples from Varied Microenvironmental and Developmental Conditions", PLOS Comput. Biol., 2012, p. e1002838, vol. 8.
Scholkopf et al., "New Support Vector Algorithms", Neural Comput., 2000, pp. 1207-1245, vol. 12.
Shen-Orr and Gajoux, "Computational deconvolution: extracting cell type-specific information from heterogeneous samples", Curr. Opin. Immunol., 2013, pp. 571-578, vol. 25.
Shen-Orr et al., "Cell type-specific gene expression differences in complex tissues", Nat. Methods., 2010, pp. 287-289, vol. 7.
Storey et al., "Statistical significance for genomewide studies", Proc. Natl. Acad. Sci. U. S. A., 2003, pp. 9440-9445, vol. 100.
Wang et al., "The doubly regularized support vector machine", Statistica Sinica, 2006, pp. 589-615, vol. 16, No. 2.
Wang et al. (2013) "Non-negative matrix factorization by maximizing correntropy for cancer clustering" BMC Bioinformatics 14(107): 107 (pp. 1-11).
Yoshihara et al., "Inferring tumour purity and stromal and immune cell a dmixture from expression data", Nat. Commun., 2013, p. 2612, vol. 4.
Zhong and Liu, "Gene expression deconvolution in linear space", Nat. Methods., 2012, pp. 8-9, vol. 9.
Zhong et al., "Digital sorting of complex tissues for cell type-specific gene expression profiles", BMC Bioinformatics, 2013, p. 89, vol. 14.
Zuckerman (2013) PLOS Computational Biology 9:e1003189.
Gaiteri et al., (2013) "Beyond modules and hubs: the potential of gene co-expression networks for investigating molecular mechanisms of complex brain disorders.", Genes, Brain and Behavior, 13: 13-24.
Newmen et al., (2014) "Identifying stem cell gene expression patterns and phenotypic networks with AutoSOME.", Methods in Molecular Biology, 1150: 115-130.
Rivenbark et al., (2013) "Molecular and cellular heterogeneity in breast cancer: challenges for personalized medicine", American Journal of Pathology, 183 (4): 1113-1124.
Smola, (2004) "A tutorial on support vector regression.", Statistics and computing, 14: 199-222.
Sotiriou et al., (2009) "Gene-expression patterns in Breast Cancer.", The New England Journal of Medicine, 360 (8): 790-800.
Thiebaut, (2002) "Optimization issues in blind deconvolution algorithms", Proc. SPIE 4847, Astronomical Data Analysis II, 1-9.
Yin, (2013) "Identification of differential gene pathways with sparse principal component analysis", Georgia State University, 1-26.

(56) References Cited

OTHER PUBLICATIONS

Zheng et al., (2014) "Deconvolution of High Dimensional Mixtures via Boosting, with Application to Diffusion-Weighted MRI of Human Brain", Advances in Neural Information Processing Systems, 27: 2699-2707.

\* cited by examiner

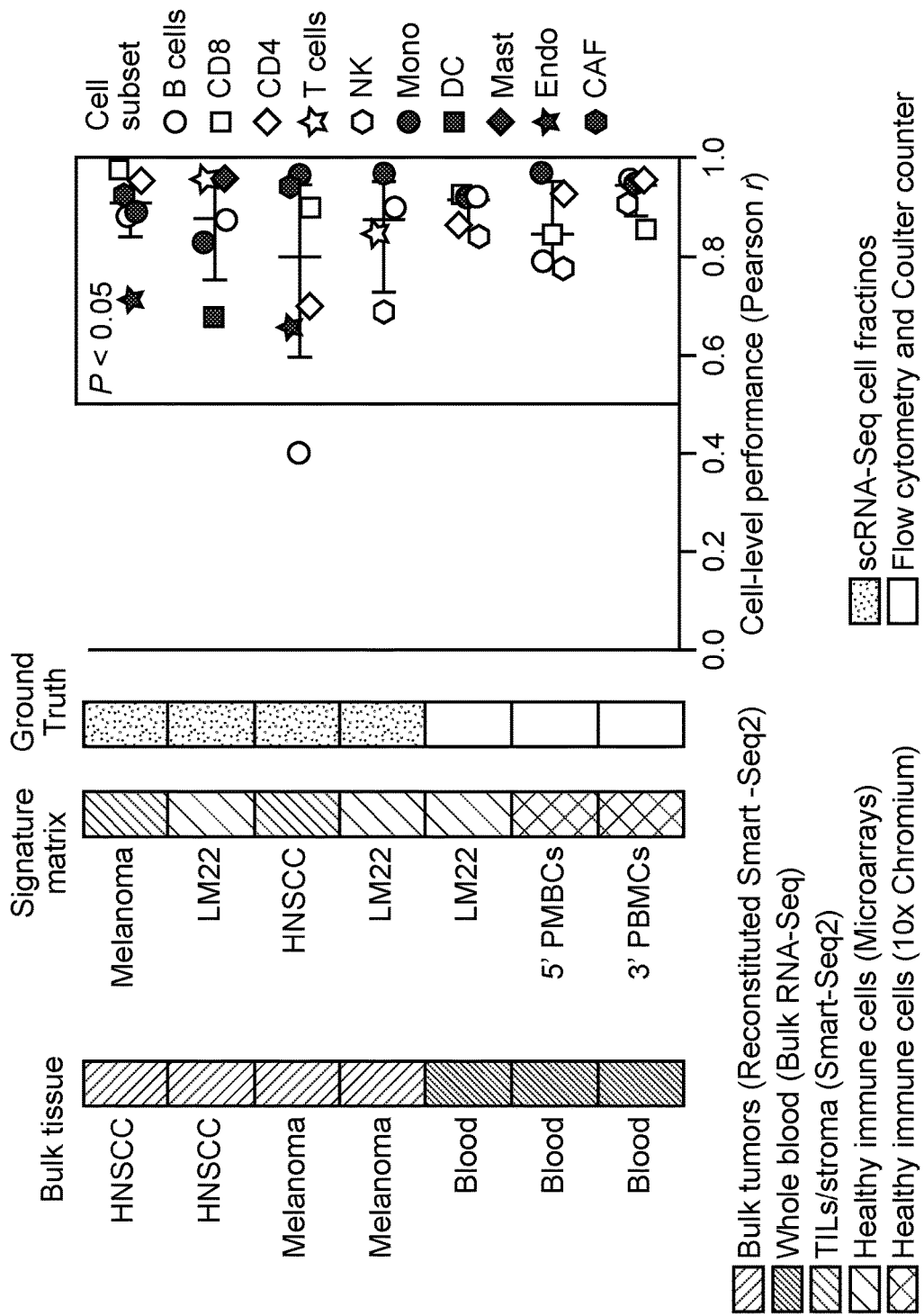

F

F (Cont.)

C

Unsupervised analysis and class discovery

E

E (Cont.)

Validation: FACS-purified subsets

F

F (Cont.)

B

D

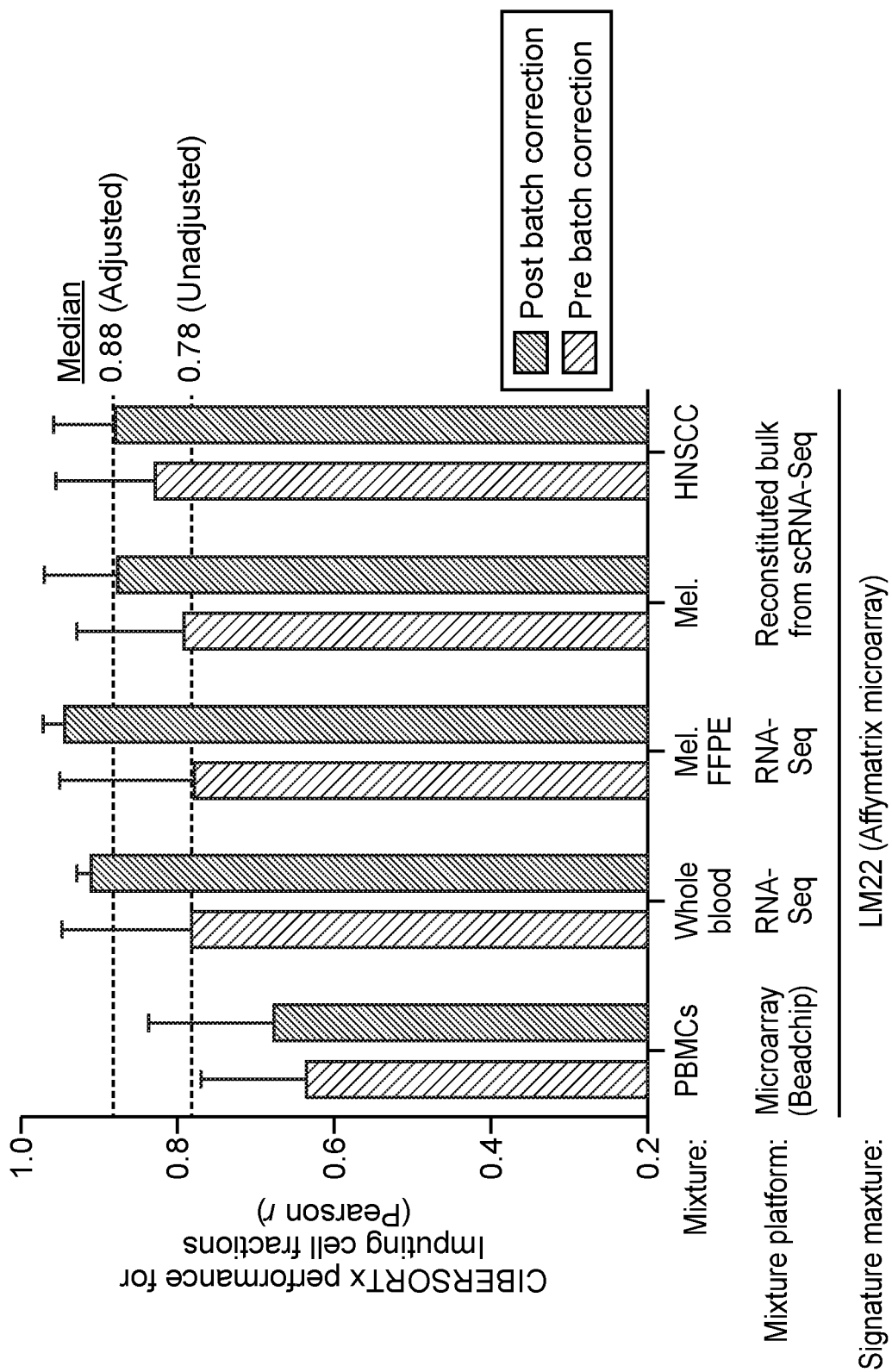

| Solve for: | Objective function: | Range: | Figures: |

Cell subset fractions $$\begin{bmatrix} \vdots \end{bmatrix} = F$$
samples × cell subsets $B \times f \approx M_{,j}$ Signature matrix | Unknown fractions | Input mixtures For all samples $j$ 2-6

Representative cell type GEPs $$\begin{bmatrix} \vdots \end{bmatrix} = H$$
samples × cell subsets $h \times F \approx M_i$ Unknown cell type GEPs | CIBERSORTx fractions | Input mixtures For all genes $i$ 3,6

"Single sample" cell type GEPs $$\begin{bmatrix} \vdots \end{bmatrix} = G$$
samples × cell subsets (gene $i$)

$\text{diag}(F \times G_i) \approx M_i$

CIBERSORTx fractions | Unknown cell type GEPs | Input mixtures

For all genes $i$ 4-6

FIG. 12 (Cont.)

B $$\text{diag}(F \times G_i) \approx M_i \quad \text{s.t.}$$
$$\min \| M_i - \text{diag}(F \times G_i) \|_2$$
$$i \in n, G \geq 0$$

$M \in \mathbb{R}^{n \times c}$ = input mixtures     $c$ = No. of mixture samples $G_i \in \mathbb{R}^{c \times k}$ = cell type-specific expression, gene $i$     $n$ = No. of genes in M

$F \in \mathbb{R}^{k \times c}$ = cell subset fractions in M     $k$ = No. of cell phenotypes

C (Cont.)

input:
=

Bulk mixture $M_j$ (observed)

(i) Sort $M_j$ by expression (ii) For each $t$, solve $g_1$, $g_2$ $g_1^t$  $g_2^t$ C (Cont.)

(iv)

(v)

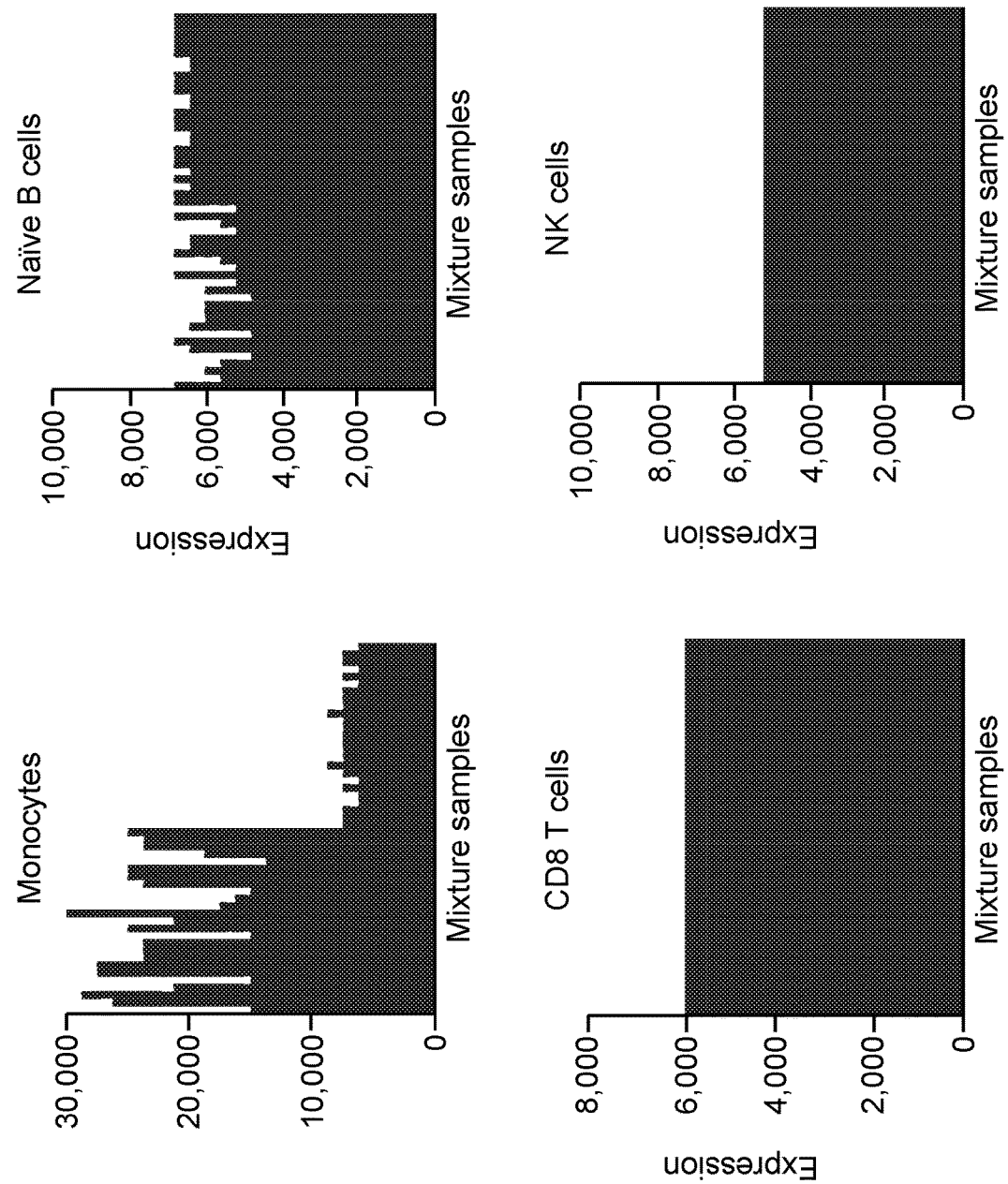

C

D

A

*In silico* purified malignant cell GEPs from bulk melanoma tumors (*n* = 342)

scRNA-Seq of malignant cells from melanoma tumors (*n* = 1,159 cells)

Malignant cells (mean scRNA-Seq)

*BRAF* MT    *BRAF* WT $Log_2$ expression
-0.25 ▬▬▬ 0.25

B

*In silico* purified malignant cell GEPs from bulk melanoma tumors (*n* = 342)

DEGs (*n* = 600)
- MT Up
- WT Up scRNA-Seq of malignant cells from melanoma tumors (*n* = 1,159 cells)

- MT Up
- WT Up

Malignant cells (mean scRNA-Seq)

*NRAS* MT    *NRAS* WT

Log$_2$ expression
-0.25 ▬▬▬ 0.25

B (Cont.)

*In silico* purified CAF GEPs from bulk melanoma tumors (*n* = 342)

scRNA-Seq of CAFs from melanoma tumors (*n* = 61 cells)

CAFs (mean scRNA-Seq)

NRAS MT   NRAS WT

Log$_2$ expression
-0.25 ▬▬▬ 0.25

| Version | Figure | No. Phenotypes | Phenotypic Labels | | | | | | | | |
|---|---|---|---|---|---|---|---|---|---|---|---|
| | | | B cells naive | B cells memory | Plasma cells | T cells CD8 | T cells CD4 naive | T cells CD4 memory resting | T cells CD4 memory activated | T cells follicular helper | T cells regulatory (Tregs) |
| LM22 (original) | FIGS. 3b-f and 11a-c | 22 | | | | | | | | | |
| LM22-merge4 | FIG. 11d | 4 | B cells | B cells | | CD8 T | CD4 T cells | CD4 T cells | CD4 T cells | CD4 T cells | CD4 T cells |
| LM22-merge5 | FIGs. 5a-c, 16a-c, 17a-e, and 18a-b | 5 | B cells | B cells | | CD8 T | CD4 remaining | CD4 remaining | CD4 remaining | Tfh cells | CD4 remaining |
| LM22-merge10 | | 10 | B cells | B cells | PCs | CD8 T | CD4 T cells | CD4 T cells | CD4 T cells | CD4 T cells | CD4 T cells |
| LM22-merge11 | FIGs. 6c and 20 | 11 | B cells | B cells | PCs | CD8 T | CD4 T cells | CD4 T cells | CD4 T cells | CD4 T cells | CD4 T cells |

FIG. 25 (Cont.)

| Phenotypic Labels | | | | | |
|---|---|---|---|---|---|
| T cells gamma delta | CD8 T | CD8 T | CD8 T | gdT cells |
| NK cells resting | Remaining | Remaining | NK cells | NK cells |
| NK cells activated | | | | |
| Monocytes | Remaining | Remaining | Monocytes and Macrophages | Monocytes and Macrophages |
| Macrophages M0 | | | | |
| Macrophages M1 | | | | |
| Macrophages M2 | | | | |
| Dendritic cells resting | Remaining | Remaining | Dendritic cells | Dendritic cells |
| Dendritic cells activated | | | | |
| Mast cells resting | Remaining | Remaining | Mast cells | Mast cells |
| Mast cells activated | | | | |
| Eosinophils | Remaining | Remaining | Eos | Eos |
| Neutrophils | Remaining | Remaining | PMNs | PMNs |

SYSTEMS AND METHODS FOR ANALYZING MIXED CELL POPULATIONS

CROSS-REFERENCE

This application is a 371 of International Application Serial No. PCT/US2018/042949, filed Jul. 19, 2018, which claims priority to U.S. Provisional Patent Application No. 62/535,645, filed Jul. 21, 2017, which is entirely incorporated herein by reference.

BACKGROUND

Tissues can be complex ecosystems comprised of diverse cell types that can be distinguished by their distinct developmental origins and functional states. While strategies for studying tissue composition can provide significant insights into basic biology and medicine, comprehensive assessment of cellular heterogeneity can be challenging.

SUMMARY

The present disclosure provides a computational framework for performing in silico tissue dissection to accurately infer cell type abundance and cell type (e.g., cell type-specific) gene expression from RNA profiles of intact tissues. By leveraging cell type expression signatures from single-cell experiments or sorted cell subsets, systems and methods of the present disclosure can provide comprehensive portraits of tissue composition without physical dissociation, antibodies, or living material. Such approaches may include, for example, a method for enumerating cell composition from tissue gene expression profiles (GEPs) with techniques for cross-platform data normalization and in silico cell purification. The latter can allow the transcriptomes of individual cell types of interest to be digitally "purified" from bulk RNA admixtures without physical isolation. As a result, changes in cell type gene expression can be inferred without cell separation or prior knowledge.

To illustrate the technical performance and clinical utility of this framework, termed CIBERSORTx, systems and methods of the present disclosure may be used to (1) profile bulk tissue composition with single-cell expression data, (2) purify GEPs of malignant and tumor-associated cell types without dissociation, and (3) explore cell type (e.g., cell type-specific) signatures with relevance to anti-cancer therapies. These results illustrate that CIBERSORTx may be a useful tool for deciphering complex tissues, with implications for high-resolution cell phenotyping in research and clinical settings.

Features of the CIBERSORTx platform can include an integrated framework for cell type enumeration and gene expression purification, dedicated normalization schemes to suppress cross-platform variation, and improved approaches for separating RNA admixtures into cell type (e.g., cell-type specific) expression profiles. These results illustrate that CIBERSORTx can deliver accurate portraits of tissue heterogeneity using expression profiles derived from disparate sources.

In an aspect, the present disclosure provides a method for digital cytometry of a biological sample from a subject, the method comprising: (a) obtaining a biological sample comprising biological macromolecules from a plurality of distinct cell types; (b) processing said biological sample to generate a feature profile of said biological macromolecules, wherein said feature profile comprises features associated with said plurality of distinct cell types; and (c) processing said feature profile, using a deconvolution module, to quantify the abundance of at least one of said plurality of distinct cell types in said biological sample, wherein quantifying said abundance comprises applying a batch correction procedure to remove technical variation in said quantification.

In some embodiments, obtaining said biological sample does not comprise physical isolation of cells (e.g., single cells) from said biological sample. In some embodiments, said feature profile comprises a plurality of gene expression profiles (GEPs), each of said plurality of GEPs corresponding to a distinct cell type among said plurality of distinct cell types. In some embodiments, said plurality of GEPs is generated from single-cell gene expression measurements of a plurality of cells of each of said plurality of distinct cell types. In some embodiments, said single-cell gene expression measurements are generated by single-cell RNA sequencing (scRNA-Seq). In some embodiments, said abundance is the fractional abundance of said at least one of said plurality of distinct cell types in said biological sample. In some embodiments, quantifying said abundance comprises optimizing a regression between said feature profile and a reference matrix of feature signatures for a second plurality of distinct cell types, wherein said feature profile is modeled as a linear combination of said reference matrix. In some embodiments, optimizing said regression comprises solving for a set of regression coefficients of said regression, wherein said solution minimizes a linear loss function and an $L_2$-norm penalty function. In some embodiments, said linear loss function is a linear ε-insensitive loss function. In some embodiments, said optimizing comprises using a support vector regression (SVR) or a non-negative matrix factorization (NMF). In some embodiments, said SVR is ε-SVR or v(nu)-SVR. In some embodiments, said biological sample comprises bulk tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, metabolites, carbohydrates, sugars, lipids, or a combination thereof. In some embodiments, said biological macromolecules comprise nucleic acids. In some embodiments, said nucleic acids are RNA molecules. In some embodiments, said nucleic acids are DNA molecules. In some embodiments, said batch correction procedure is applied in a single cell reference mode (S-mode). In some embodiments, said batch correction procedure is applied in a bulk reference mode (B-mode).

In another aspect, the present disclosure provides a method for digital cytometry of a biological sample from a subject, the method comprising: (a) obtaining a biological sample comprising biological macromolecules from a plurality of distinct cell types; (b) processing said biological sample to generate a feature profile of said biological macromolecules; and (c) processing said feature profile, using a deconvolution module, to (i) identify at least one of said plurality of distinct cell types in said biological sample and (ii) generate a cell-type state for said identified at least one of said plurality of distinct cell types.

In some embodiments, the method further comprises processing said feature profile, using said deconvolution module, to quantify the abundance of said identified at least one of said plurality of distinct cell types in said biological sample. In some embodiments, obtaining said biological sample does not comprise physical isolation of (e.g., single cells) cells from said biological sample. In some embodiments, said feature profile comprises a plurality of gene expression profiles (GEPs), each of said plurality of GEPs corresponding to a distinct cell type among said plurality of distinct cell types; and said cell-type state comprises a cell-type GEP. In some embodiments, said plurality of GEPs is generated from single-cell gene expression measurements of a plurality of cells of each of said plurality of distinct cell types. In some embodiments, said single-cell gene expression measurements are generated by single-cell RNA sequencing (scRNA-Seq). In some embodiments, said abundance is the fractional abundance of said at least one of said plurality of distinct cell types in said biological sample. In some embodiments, quantifying said abundance comprises optimizing a regression between said feature profile and a reference matrix of feature signatures for a second plurality of distinct cell types, wherein said feature profile is modeled as a linear combination of said reference matrix. In some embodiments, optimizing said regression comprises solving for a set of regression coefficients of said regression, wherein said solution minimizes a linear loss function and an $L_2$-norm penalty function. In some embodiments, said linear loss function is a linear ε-insensitive loss function. In some embodiments, said optimizing comprises using a support vector regression (SVR) or a non-negative matrix factorization (NMF). In some embodiments, said SVR is ε-SVR or v(nu)-SVR. In some embodiments, said biological sample comprises bulk tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, metabolites, carbohydrates, sugars, lipids, or a combination thereof. In some embodiments, said biological macromolecules comprise nucleic acids. In some embodiments, said nucleic acids are RNA molecules. In some embodiments, said nucleic acids are DNA molecules. In some embodiments, quantifying said abundance comprises applying a batch correction procedure to remove technical variation in said quantification. In some embodiments, said batch correction procedure is applied in a single cell reference mode (S-mode). In some embodiments, said batch correction procedure is applied in a bulk reference mode (B-mode). In some embodiments, said cell-type state is a high resolution cell-type state. In some embodiments, said cell-type state is a group-level cell-type state.

In another aspect, the present disclosure provides a method for digital cytometry of a biological sample from a subject, the method comprising: (a) obtaining a plurality of biological samples comprising biological macromolecules from a first plurality of distinct cell types; (b) for each of said plurality of biological samples, processing said biological sample to generate a feature profile of said biological macromolecules, wherein each of said feature profiles comprises features associated with said first plurality of distinct cell types, thereby producing a first plurality of feature profiles; and (c) processing said first plurality of feature profiles, using a deconvolution module, to determine, for each of said plurality of biological samples, a second plurality of feature profiles of a second plurality of distinct cell types selected from among said first plurality of distinct cell types, thereby deconvolving said plurality of biological samples into said second plurality of feature profiles of said second plurality of distinct cell types.

In some embodiments, the method further comprises processing said feature profile, using said deconvolution module, to quantify the abundance of each of said second plurality of distinct cell types in said biological sample. In some embodiments, said abundance is the fractional abundance of said at least one of said plurality of distinct cell types in said biological sample. In some embodiments, obtaining said biological sample does not comprise physical isolation of cells (e.g., single cells) from said biological sample. In some embodiments, said first plurality of feature profiles and said second plurality of feature profiles comprise gene expression profiles (GEPs), each of said GEPs corresponding to a distinct cell type among said plurality of distinct cell types. In some embodiments, said plurality of GEPs is generated from single-cell gene expression measurements of a plurality of cells of each of said plurality of distinct cell types. In some embodiments, said single-cell gene expression measurements are generated by single-cell RNA sequencing (scRNA-Seq). In some embodiments, quantifying said abundance comprises optimizing a regression between said feature profile and a reference matrix of feature signatures for a second plurality of distinct cell types, wherein said feature profile is modeled as a linear combination of said reference matrix. In some embodiments, optimizing said regression comprises solving for a set of regression coefficients of said regression, wherein said solution minimizes a linear loss function and an $L_2$-norm penalty function. In some embodiments, said linear loss function is a linear ε-insensitive loss function. In some embodiments, said optimizing comprises using a support vector regression (SVR) or a non-negative matrix factorization (NMF). In some embodiments, said SVR is ε-SVR or v(nu)-SVR. In some embodiments, said biological sample comprises bulk tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, metabolites, carbohydrates, sugars, lipids, or a combination thereof. In some embodiments, said biological macromolecules comprise nucleic acids. In some embodiments, said nucleic acids are RNA molecules. In some embodiments, said nucleic acids are DNA molecules. In some embodiments, the method further comprises using said determined second plurality of feature profiles to identify distinct cell type features, wherein said identifying does not comprise prior knowledge of biological or functional groupings. In some embodiments, quantifying said abundance comprises applying a batch correction procedure to remove technical variation in said quantification. In some embodiments, said batch correction procedure is applied in a single cell reference mode (S-mode). In some embodiments, said batch correction procedure is applied in a bulk reference mode (B-mode).

In another aspect, the present disclosure provides a method for digital cytometry of a biological sample from a subject, the method comprising: (a) obtaining a biological sample comprising biological macromolecules from a first plurality of distinct cell types, wherein obtaining said biological sample does not comprise physical isolation of cells (e.g., single cells) from said biological sample; (b) processing said biological sample to generate a feature profile m of said biological macromolecules, wherein said feature profile comprises features associated with said first plurality of distinct cell types; (c) optimizing a regression between said feature profile m and a reference matrix B of feature signatures for a second plurality of distinct cell types, wherein said feature profile m is modeled as a linear combination of B, and wherein said optimizing comprises solving for f comprising a set of regression coefficients of said regression; and (d) quantifying in said biological sample the abundance of a distinct cell type selected from among said second plurality of distinct cell types based at least on said set of regression coefficients.

In another aspect, the present disclosure provides a method for digital cytometry of a biological sample from a subject, the method comprising: (a) obtaining a biological sample comprising biological macromolecules from a first plurality of distinct cell types, said biological sample comprising an archived tissue; (b) processing said biological sample to generate a feature profile m of said biological macromolecules, wherein said feature profile comprises features associated with said first plurality of distinct cell types; (c) optimizing a regression between said feature profile m and a reference matrix B of feature signatures for a second plurality of distinct cell types, wherein said feature profile m is modeled as a linear combination of B, and wherein said optimizing comprises solving for f comprising a set of regression coefficients of said regression; and (d) quantifying in said biological sample the abundance of a distinct cell type selected from among said second plurality of distinct cell types based at least on said set of regression coefficients.

In another aspect, the present disclosure provides a method for digital cytometry of a biological sample from a subject, the method comprising: (a) obtaining a biological sample comprising biological macromolecules from a first plurality of distinct cell types; (b) processing said biological sample to generate a feature profile m of said biological macromolecules, wherein said feature profile comprises features associated with said first plurality of distinct cell types; (c) optimizing a regression between said feature profile m and a reference matrix B of feature signatures for a second plurality of distinct cell types, wherein said feature profile m is modeled as a linear combination of B, and wherein said optimizing comprises solving for f comprising a set of regression coefficients of said regression; and (d) quantifying in said biological sample the abundance of a distinct cell type selected from among said second plurality of distinct cell types based at least on said set of regression coefficients, wherein said feature profile comprises a plurality of gene expression profiles (GEPs), each of said plurality of GEPs corresponding to a distinct cell type among said first plurality of distinct cell types.

In another aspect, the present disclosure provides a method for digital cytometry of a biological sample from a subject, the method comprising: (a) obtaining a biological sample comprising biological macromolecules from a first plurality of distinct cell types; (b) processing said biological sample to generate a feature profile m of said biological macromolecules, wherein said feature profile comprises features associated with said first plurality of distinct cell types; (c) optimizing a regression between said feature profile m and a reference matrix B of feature signatures for a second plurality of distinct cell types, wherein said feature profile m is modeled as a linear combination of B, and wherein said optimizing comprises solving for f comprising a set of regression coefficients of said regression; and (d) using a batch correction procedure, quantifying in said biological sample the abundance of a distinct cell type selected from among said second plurality of distinct cell types based at least on said set of regression coefficients, wherein said batch correction procedure removes technical variation between said reference matrix B and said biological sample.

In some embodiments, said biological sample comprises bulk tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, metabolites, carbohydrates, sugars, lipids, or a combination thereof. In some embodiments, said biological macromolecules comprise nucleic acids. In some embodiments, said nucleic acids are RNA molecules. In some embodiments, said nucleic acids are DNA molecules. In some embodiments, said feature profile comprises a plurality of gene expression profiles (GEPs), each of said plurality of GEPs corresponding to a distinct cell type among said first plurality of distinct cell types. In some embodiments, said plurality of GEPs is generated from single-cell gene expression measurements of a plurality of cells of each of said first plurality of distinct cell types. In some embodiments, said single-cell gene expression measurements are generated by single-cell RNA sequencing (scRNA-Seq). In some embodiments, said batch correction procedure is applied in a single cell reference mode (S-mode). In some embodiments, said batch correction procedure is applied in a bulk reference mode (B-mode).

In another aspect, the present disclosure provides a method for digital analysis of a biological sample from a subject, the method comprising: (a) obtaining, for each of a plurality of biological samples M comprising biological macromolecules from a first plurality of distinct cell types, a feature profile m of said biological macromolecules, wherein each of said feature profiles m comprises features associated with said first plurality of distinct cell types; (b) obtaining a matrix comprising a plurality of sets of coefficients F; and (c) using a noise thresholding procedure, determining from said plurality of biological samples M a plurality of representative features G of a second plurality of distinct cell types selected from among said first plurality of distinct cell types based at least on said plurality of sets of coefficients F, wherein said noise thresholding procedure reduces noise in said feature determination of said plurality of representative features G.

In some embodiments, (b) comprises optimizing a regression between each of said feature profiles m and a reference matrix B of feature signatures for said second plurality of distinct cell types, wherein said feature profile m is modeled as a linear combination of B, and wherein said optimizing comprises solving for f comprising a set of regression coefficients of said regression, thereby providing said plurality of sets of coefficients F. In some embodiments, said feature determination comprises unreliable cell-type specific gene expression determination. In some embodiments, each of said biological samples comprises bulk tissue. In some embodiments, (a) does not comprise physical isolation of cells (e.g., single cells) from said biological samples. In some embodiments, each of said biological samples comprises an archived tissue. In some embodiments, each of said biological samples comprises a formalin-fixed, paraffin-embedded (FFPE) tissue or a frozen tissue. In some embodiments, each of said biological samples comprises a blood sample or is derived from a solid tissue sample. In some embodiments, said solid tissue sample comprises a tumor sample. In some embodiments, said biological macromolecules comprise nucleic acids, proteins, metabolites, carbohydrates, sugars, lipids, or a combination thereof. In some embodiments, said biological macromolecules comprise nucleic acids. In some embodiments, said nucleic acids are RNA molecules. In some embodiments, said nucleic acids are DNA molecules. In some embodiments, said feature profile comprises a plurality of gene expression profiles (GEPs), each of said plurality of GEPs corresponding to a distinct cell type among said first plurality of distinct cell types. In some embodiments, said plurality of gene expression profiles is generated from single-cell gene expression measurements of a plurality of cells of each of said first plurality of distinct cell types. In some embodiments, said single-cell gene expression measurements are generated by single-cell RNA sequencing (scRNA-Seq).

In another aspect, the present disclosure provides a method for digital analysis of a biological sample from a subject, the method comprising: (a) obtaining, for each of a plurality of biological samples M comprising biological macromolecules from a first plurality of distinct cell types, a feature profile m of said biological macromolecules, wherein each of said feature profiles m comprises features associated with said first plurality of distinct cell types; (b) obtaining a matrix comprising a plurality of sets of coefficients F; and (c) for each of said plurality of biological samples M, performing a non-negative matrix factorization (NMF) to determine a plurality of feature profiles G of a second plurality of distinct cell types selected from among said first plurality of distinct cell types based at least on said plurality of sets of coefficients F, thereby deconvolving said plurality of biological samples M into said G given said F and said M.

In some embodiments, (b) comprises optimizing a regression between each of said feature profiles m and a reference matrix B of feature signatures for said second plurality of distinct cell types, wherein each of said feature profiles m is modeled as a linear combination of B, and wherein said optimizing comprises solving for f comprising a set of regression coefficients of said regression, thereby providing said plurality of sets of coefficients F.

In another aspect, the present disclosure provides a method for digital analysis of a biological sample from a subject, the method comprising: (a) obtaining, for each of a plurality of biological samples M comprising biological macromolecules from a first plurality of distinct cell types, a feature profile m of said biological macromolecules, wherein each of said feature profiles m comprises features associated with said first plurality of distinct cell types; (b) obtaining a matrix comprising a plurality of sets of coefficients F; and (c) determining, for each of said plurality of biological samples M, a plurality of cellular abundances G of a second plurality of distinct cell types selected from among said first plurality of distinct cell types based at least on said plurality of sets of coefficients F, wherein said determining comprises performing a non-negative matrix factorization (NMF) to separate said plurality of biological samples M into said G given said F and said M.

In some embodiments, (b) comprises optimizing a regression between each of said feature profiles m and a reference matrix B of feature signatures for said second plurality of distinct cell types, wherein each of said feature profiles m is modeled as a linear combination of B, and wherein said optimizing comprises solving for f comprising a set of regression coefficients of said regression, thereby providing said plurality of sets of coefficients F. In some embodiments, said NMF model comprises partial observations. In some embodiments, said biological sample comprises bulk tissue. In some embodiments, (a) does not comprise physical isolation of cells (e.g., single cells) from said biological sample. In some embodiments, said biological sample comprises an archived tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, or a combination thereof. In some embodiments, said biological macromolecules comprise nucleic acids. In some embodiments, said nucleic acids are RNA molecules. In some embodiments, said nucleic acids are DNA molecules. In some embodiments, said feature profile comprises a plurality of gene expression profiles (GEPs), each of said plurality of GEPs corresponding to a distinct cell type among said plurality of distinct cell types. In some embodiments, said NMF model comprises a divide-and-conquer approach. In some embodiments, a matrix Z comprises a product of said G and said F, and wherein said G and off-diagonal elements of said Z are unknown. In some embodiments, the method further comprises using said determined plurality of feature profiles G to identify distinct cell type-specific features, wherein said identifying does not comprise prior knowledge of biological or functional groupings. In some embodiments, determining said plurality of feature profiles G comprises applying a batch correction procedure to remove technical variation in said determination. In some embodiments, said batch correction procedure is applied in a single cell reference mode (S-mode). In some embodiments, said batch correction procedure is applied in a bulk reference mode (B-mode).

In another aspect, the present disclosure provides a method for digital purification of a biological sample from a subject, the method comprising: (a) obtaining a biological sample comprising biological macromolecules from a plurality of distinct cell types; (b) processing said biological sample to generate a feature profile of said biological macromolecules, wherein said feature profile comprises a combination of features associated with said plurality of distinct cell types; and (c) identifying in said biological sample a fractional portion of said feature profile corresponding to a distinct cell type selected from among said plurality of distinct cell types.

In some embodiments, said biological sample comprises bulk tissue. In some embodiments, (a) does not comprise physical isolation of cells (e.g., single cells) from said biological sample. In some embodiments, said biological sample comprises an archived tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, or a combination thereof. In some embodiments, said biological macromolecules comprise nucleic acids. In some embodiments, said nucleic acids are RNA molecules. In some embodiments, said nucleic acids are DNA molecules. In some embodiments, said feature profile comprises a plurality of gene expression profiles (GEPs), each of said plurality of GEPs corresponding to a distinct cell type among said plurality of distinct cell types.

In another aspect, the present disclosure provides a non-transitory computer readable storage medium storing one or more programs, said one or more programs comprising instructions that, when executed by one or more processors of a computer system, cause said one or more processors to perform a method disclosed herein.

In another aspect, the present disclosure provides a system comprising one or more processors; and a memory storing one or more programs, said one or more programs comprising instructions that, when executed by one or more processors of a computer system, cause said one or more processors to perform a method disclosed herein.

In another aspect, the present disclosure provides a method for evaluating a disease in an individual, comprising: (a) obtaining a biological sample from an individual having or suspected of having a disease; (b) quantifying the abundance of a distinct cell type in said biological sample by performing a method disclosed herein; and (c) comparing said estimated abundance of said distinct cell type in said biological sample to a reference abundance of said distinct cell type in a reference biological sample, wherein said reference biological sample is derived from a cohort of individuals having said disease, and wherein said estimated abundance of said distinct cell type is indicative of a diagnosis or prognosis of said disease.

In some embodiments, said reference abundance is quantified by performing a method disclosed herein.

In another aspect, the present disclosure provides a method for evaluating a disease in an individual, comprising: (a) obtaining a biological sample from an individual having or suspected of having a disease; (b) determining a feature of a distinct cell type in said biological sample by performing a method disclosed herein; and (c) comparing said determined feature of said distinct cell type in said biological sample to a reference feature of said distinct cell type in a reference biological sample, wherein said reference biological sample is derived from a cohort of individuals having said disease, and wherein said feature of said distinct cell type is indicative of a diagnosis or prognosis of said disease. In some embodiments, said reference feature is determined by performing a method disclosed herein.

In another aspect, the present disclosure provides a method for monitoring the progression of a disease in a subject, comprising performing a method disclosed herein at a first time point and at a second time point, said second time point occurring at a later time than said first time point. In some embodiments, said first time point is before treating said subject for said disease and said second time point is after treating said subject for said disease.

In another aspect, the present disclosure provides a method for predicting a clinical outcome of a disease therapy, comprising: (a) quantifying the abundance of a distinct cell type among a plurality of distinct cell types present in a sample obtained from a subject, wherein said subject has received a therapy for a disease, by performing a method disclosed herein; (b) comparing said quantified abundance of said distinct cell type in said sample and a predetermined association of said distinct cell type with clinical outcomes for said therapy; and (c) predicting said clinical outcome of said therapy based at least on said comparison.

In another aspect, the present disclosure provides a method for digital cytometry of a biological sample from a subject, the method comprising: (a) obtaining a biological sample comprising biological macromolecules from a plurality of distinct cell types; (b) processing said biological sample to generate a feature profile of said biological macromolecules; (c) processing said feature profile to identify at least one of said plurality of distinct cell types in said biological sample; and (d) processing said feature profile, using a deconvolution module, to generate a cell-type state for said identified at least one of said plurality of distinct cell types.

In some embodiments, the method further comprises quantifying the abundance of said identified at least one of said plurality of distinct cell types in said biological sample. In some embodiments, obtaining said biological sample does not comprise physical isolation of cells (e.g., single cells) from said biological sample. In some embodiments, said feature profile comprises a plurality of gene expression profiles (GEPs), each of said plurality of GEPs corresponding to a distinct cell type among said plurality of distinct cell types; and said cell-type state comprises a cell-type GEP. In some embodiments, said plurality of GEPs is generated from single-cell gene expression measurements of a plurality of cells of each of said plurality of distinct cell types. In some embodiments, said single-cell gene expression measurements are generated by single-cell RNA sequencing (scRNA-Seq). In some embodiments, said abundance is the fractional abundance of said at least one of said plurality of distinct cell types in said biological sample. In some embodiments, quantifying said abundance comprises optimizing a regression between said feature profile and a reference matrix of feature signatures for a second plurality of distinct cell types, wherein said feature profile is modeled as a linear combination of said reference matrix. In some embodiments, optimizing said regression comprises solving for a set of regression coefficients of said regression, wherein said solution minimizes a linear loss function and an $L_2$-norm penalty function. In some embodiments, said linear loss function is a linear ε-insensitive loss function. In some embodiments, said optimizing comprises using a support vector regression (SVR) or a non-negative matrix factorization (NMF). In some embodiments, said SVR is ε-SVR or v(nu)-SVR. In some embodiments, said biological sample comprises bulk tissue. In some embodiments, said biological sample comprises a formalin-fixed, paraffin-embedded (FFPE) tissue or a frozen tissue. In some embodiments, said biological sample comprises a blood sample or is derived from a solid tissue sample. In some embodiments, said solid tissue sample comprises a tumor sample. In some embodiments, said biological macromolecules comprise nucleic acids, proteins, metabolites, carbohydrates, sugars, lipids, or a combination thereof. In some embodiments, said biological macromolecules comprise nucleic acids. In some embodiments, said nucleic acids are RNA molecules. In some embodiments, said nucleic acids are DNA molecules. In some embodiments, quantifying said abundance comprises applying a batch correction procedure to remove technical variation in said quantification. In some embodiments, said batch correction procedure is applied in a single cell reference mode (S-mode). In some embodiments, said batch correction procedure is applied in a bulk reference mode (B-mode). In some embodiments, said cell-type state is a high resolution cell-type state. In some embodiments, said cell-type state is a group-level cell-type state.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 25 illustrates LM22 phenotypic groupings used for expression imputation.

DETAILED DESCRIPTION OF THE INVENTION

Figure 1:
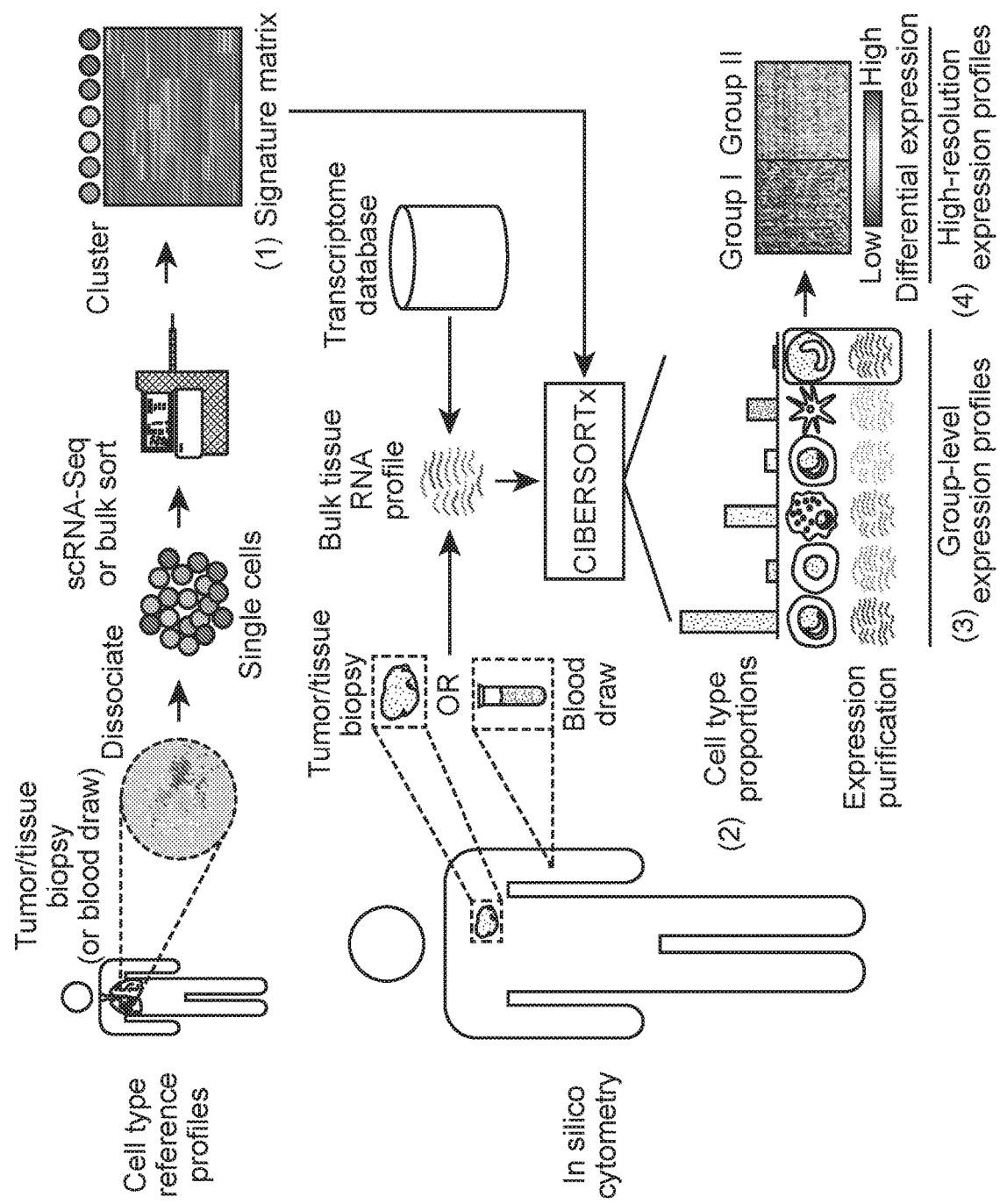
FIG. 1 illustrates a framework for in silico cytometry. A CIBERSORTx workflow can involve: (1) profiling RNA from single cells or sorted cell subpopulations to define a "signature matrix" consisting of barcode genes that can discriminate each cell subset of interest in a given tissue type; (2) applying the signature matrix to bulk tissue RNA profiles in order to infer cell type proportions and (3) representative cell type expression signatures; (4) purifying multiple transcriptomes for each cell type from a cohort of related tissue samples (e.g., melanoma tumor biopsies from responders and non-responders to checkpoint blockade); and (5) analyzing digital profiles of cell type abundance and expression variation to address biological or clinical questions.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Still, certain terms are defined below for the sake of clarity and ease of reference.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

The term "physical system," as used herein, may refer to any collection of elements (molecules, cells, tissues, organisms, electrical circuits, devices, appliances, computers, vehicles, buildings, etc.), where the elements are functionally related, directly or indirectly, to each other (e.g., the presence, position or activity of one element of the system directly or indirectly affects the presence, position or activity of another element in the system). In some cases, the physical system is a physical sample.

The term "physical sample," as used herein, may refer to any collection of matter (e.g., in liquid, solid of gaseous form) that can be physically isolated as a coherent unit from an environment from which the collection is obtained. The term "biological sample," as used herein refers to any physical sample (e.g., in solid or liquid form) that is either obtained from an organism, or contains an organism, or a portion thereof (e.g., tissue sample, biopsies, cell samples of an organism). The biological sample may be obtained from cell culture or from an organism. The biological sample may be purified through the removal of one or more components of the biological sample.

The term "distinct component," as used herein, may refer to any form of matter (e.g., molecule, compound, protein, nucleic acid, cell, etc.), or a collection thereof, that is categorized into a group based on one or more empirically determined properties and/or functional relationships. Each distinct component may have one or more members that share one or more empirically determined properties and/or functional relationships among.

The term "cell subset," as used herein, may refer to any group of cells in a biological sample whose presence is characterized by one or more features, such as gene expression on the RNA level, protein expression, genomic mutations, biomarkers, and so forth. A cell subset may be, for example, a cell type or cell sub-type.

The term "estimated relative proportions of cell subsets" or "vector of relative proportions of cell subsets," as used herein, may refer to the relative proportion of each of the cell subsets (e.g., as estimated by embodiments of the subject methods). As such, the relative proportions of each cell subset may be understood as a vector (with each cell subset being a different dimension of said vector). As used herein, "relative proportion of a cell subset" refers to the proportion (e.g., abundance) of the cell subset to another cell subset, to other cell subset, or to all cell subsets whose relative proportions are being estimated.

The term "feature," as used herein, may refer to any empirically determined property of a physical sample or a physical system (e.g., a physical sample, a biological sample, etc.). In some cases, the abundance (e.g., value) of a feature may be indicative of the abundance of a distinct component in the sample or the physical system (e.g., indicative of the abundance of one or more cell subsets in a biological sample). In some cases, features include gene expression on the mRNA, protein expression, specific genotypes, biomarkers, or a combination thereof.

The term "feature profile," as used herein, may refer to a set of measured values for a collection of features in a physical sample (e.g., a biological sample) or in a physical system. Where the physical sample or physical system contains a plurality of distinct components, the measured value for any given feature may be a combination (e.g., sum, such as a linear sum) of the contribution of each distinct component to the feature, according to the amount of each distinct component present. The feature profile may be represented by a vector m whose elements correspond to the measured values of each of the features.

The term "feature profile" of a biological sample as used herein, may refer to the measured values of a collection of features of the biological sample. Examples of sample feature profiles include a "gene expression profile" or "GEP" (e.g., as obtained by microarray analysis), a protein expression profile, a genotype profile (e.g., of a sample having heterogeneous tumor cells), a biomarker profile (e.g., of free biomarkers in the sample or biomarkers on/in cells of the sample), a DNA methylation profile (e.g., of a sample having cells containing DNA with varying levels or alterations of methylation), and so forth. Feature profiles may be representative of one or more cell-type, tissue-type, or cell-stage states. States may be cell-type specific, tissue-type specific, or cell-stage specific. States may correspond to, for example, gene expression profiles, protein expression profiles, genotype profiles, biomarker profiles, or DNA methylation profiles of a specific cell type, tissue type, or cell stage. States may be group-level states or high resolution states, as described elsewhere herein. For example, DNA methylation profiles may be cell-specific, tissue-specific, and/or cell stage-specific; therefore, feature profiles may include DNA methylation profiles across cell types, tissue types, etc.

The term "feature signature," as used herein, may refer to a feature profile that is characteristic of (or representative of) a substantially pure or highly enriched collection of members of a distinct component. A group of feature signatures for a plurality of distinct elements may be represented by a matrix B. One distinct element in the matrix may or may not have the same set of features in the feature signature than another distinct element.

The term "cell subset reference profile" or "cell subset feature profile," as used herein, may refer to the feature profile (e.g., values of features) associated with a specific cell subset. Reference profiles may be obtained by measuring features of purified or enriched cell subsets. In some cases, the term "reference matrix of cell subset feature signatures," as used herein refers to a matrix of expected feature values for multiple cell subsets. Some reference profiles exhibit "multicollinearity," a phenomenon in which reference profiles of different cell subsets are highly correlated, which can prevent reliable deconvolution.

The term "deconvolution," as used herein, may refer to the process of identifying (e.g., estimating) the relative proportions or the abundance (e.g., an absolute or fractional abundance) of cell subsets or cell populations in a mixture of cell subsets or cell populations.

The terms "fractional representation," "relative proportion," and "contribution" may be used interchangeably to refer to the portion of the measured value of a feature that is attributable to a distinct component relative to the total value of the feature attributable to all the distinct components included in a reference matrix of feature signatures.

The term "subset," as used herein, may refer to a matrix or vector (e.g., a feature profile) obtained by reducing one or more dimensions (e.g., number of features) of an initial matrix of vector (e.g., an initial feature profile). "Superset," as used herein, may refer to a matrix or vector obtained by increasing one or more dimensions of an initial matrix or vector. A "parent matrix" or "parent vector" may refer to a superset of the matrix or vector (e.g., "child" matrix or vector). In some cases, a parent feature profile differs from a feature profile of which the parent is a superset by having more features.

The term "reconstituted feature profile" or "deconvolution result," as used herein, may refer to a feature profile calculated based on estimated relative proportions (or fractional representation) of distinct components (e.g., cell subsets) and a known reference matrix. Specifically, a reconstituted feature profile may be calculated from the product of the estimated relative proportions of distinct components, e.g., cell subsets (or "vector of relative proportions of cell subsets") and a reference matrix.

The term "support vector regression" or "SVR," as used herein, may refer to an instance of support vector machine (SVM), a class of optimization methods for binary classification problems, in which a hyperplane is discovered that maximally separates both classes. The support vectors are a subset of the input data that determine hyperplane boundaries. Unlike standard SVM, SVR fits a hyperplane to the input data points, thus performing a regression, and does so within a margin of error e, and a unique linear error penalty (e.g., an ε-insensitive loss function), rendering it relatively robust to outliers and overfitting. Two major types of SVR are "nu-support vector regression" (or "v-SVR") and "epsilon-support vector regression" (or ε-SVR). In v-SVR, the v parameter conveniently controls both the upper bound of training errors e and the sparsity of support vectors.

The term "Monte Carlo sampling," as used herein, may refer to repeated random sampling to obtain a distribution over an unknown probabilistic entity.

The term "significance value," as used herein, may refer to the probability of obtaining a result assuming that the null hypothesis is true. In certain embodiments, the null hypothesis is that no cell subsets in the signature matrix are represented in a given feature profile of the biological sample. In certain aspects, the significance value may be a "p-value," which as used herein is the probability of obtaining a test statistic result at least as extreme or as close to the one that was actually observed, assuming that the null hypothesis is true.

The term "difference measurement," as used herein, may refer to any measurement of the relationship (e.g., difference, correlation, deviation, etc.) between two values or vectors.

The term "error," as used herein, may refer to the deviation of a calculated value or values from an expected value or values. The term "root-mean square error" or "RMSE" refers to the amount by which the values predicted by an estimator differ from the quantities being estimated. The RMSE of an estimator with respect to an estimated parameter is defined as the square root of the mean square error.

The term "correlation coefficient," as used herein, may refer to a measure of linear fit. A "Pearson product-moment correlation coefficient" or "Pearson's R" is a measure of the strength and direction of the linear relationship between two variables and is defined as the covariance of the variables divided by the product of their standard deviations.

The term "RNA transcriptome," as used herein, may refer to the aggregate RNA expression levels of cells in a biological sample.

The term "leukocytes" or "white blood cell," as used herein, may refer to any immune cell, including monocytes, neutrophils, eosinophils, basophils, and lymphocytes. The term "lymphocytes," as used herein refer to cells commonly found in lymph, and include natural killer cells (NK cells), T-cells, and B-cells. It will be appreciated by one of skill in the art that the above listed immune cell types can be divided into further subsets.

The term "tumor infiltrating leukocytes" (TILs) as used herein, may refer to leukocytes that are present in a solid tumor.

The term "subject," as used herein, may refer to a human or an animal (e.g., a non-human mammal, ape, monkey, chimpanzee, reptile, amphibian, or bird). The subject may be a person with a disease or disorder, or a person that is suspected of having the disease or disorder, or a person that does not have or is not suspected of having the disease or disorder. The disease or disorder may be an infectious disease, an immune disorder or disease, a cancer, a genetic disease, a degenerative disease, a lifestyle disease, an injury, a rare disease or an age related disease. The infectious disease may be caused by bacteria, viruses, fungi, and/or parasites.

The term "biological macromolecules," as used herein, may refer to large biological molecules comprising smaller biological molecules covalently linked together. Biological macromolecules may comprise nucleic acids, proteins, metabolites, carbohydrates, sugars, lipids, or a combination thereof. Nucleic acids may comprise ribonucleic acid (RNA) molecules or deoxyribonucleic acid (DNA) molecules.

Physical Samples and Physical Systems

A physical system of interest may include any physical system, where multiple components are present within a physical system and contribute (e.g., contribute in a manner that can be approximated by a linear model) to a feature profile of the physical system. The physical system may or may not include a component of interest. The physical system may include any number of components. In some cases, the physical system includes 5 or more, e.g., 10 or more, 20 or more, including 100 or more, e.g., $10^3$ or more, $10^4$ or more (such as 15,000; 20,000 or 25,000 or more), distinct (e.g., different) components, that differ from each other in terms an empirically determined property.

In some cases, the physical system is a physical sample containing a plurality of distinct components, as described further below. In some embodiments, the physical system is a collection of cells in vivo or ex vivo (e.g., a collection of cells in a tissue sample), a collection of tissues in an organism, a collection of organisms in an ecosystem or a society, etc. In some embodiments, the physical system is a collection of electrical circuits in a device, a collection of devices in a room, a collection of computers on a network, a collection of appliances in a building, a collection of buildings in a city or portion thereof, a collection vehicles on a road or highway system, etc.

A physical sample may be any suitable sample that contains a mix of distinct components, where multiple distinct components contribute (e.g., contribute in a manner that can be approximated by a linear model) to a feature profile of the physical sample. In some embodiments, the physical sample is a biological sample, as described further below.

In some cases, the physical sample is an environmental sample, such as an air sample, water sample, or a soil sample. The environmental sample may be obtained from any suitable source, such as, without limitation, a river, ocean, lake, rain, snow, reservoir, sewage, sewage processing runoff, agricultural runoff, industrial runoff, tap water, drinking water, exhaust system (e.g., industrial exhaust, vehicular exhaust, etc.), compost, land fill, urban development site or farm land. In some cases, the physical sample is a food stuff sample, e.g., material that is suitable for, or being prepared for consumption by an animal, e.g., human, dog, cat, bird, fish, etc. In some cases, the physical sample is a synthetic chemical mix, e.g., commercially sold chemical mixes, such as fertilizer, coatings (e.g., paint, lacquer, etc.), drugs, detergent, etc.

Biological Samples

The term "biological sample," ("sample") as used herein, may refer to any sample obtained from a subject or derived from a sample obtained from a subject.

Biological samples may comprise bulk tissue or archived tissue (e.g., formalin-fixed, paraffin-embedded (FFPE) tissue, or a frozen tissue). Biological samples may comprise a blood sample or be derived from a solid tissue sample (e.g., a tumor sample).

The term "blood sample," as used herein, may refer to any sample prepared from blood, such as plasma, blood cells isolated from blood, and so forth. Biological samples may comprise a blood sample or derived from a blood sample. For example, samples may be collected from peripheral blood of subjects (e.g., cancer patients). For example, whole blood samples may be collected from subjects (e.g., healthy donors) and processed to enumerate leukocyte composition by FACS (BD BTNK 6-color IVD) and Coulter counter in a CLIA hematology lab setting, and aliquots from samples may be stored in PAXgene blood RNA tubes (Qiagen) for subsequent RNA extraction and library preparation. For example, peripheral blood mononuclear cells (PBMCs) may be collected from peripheral blood of subjects, such as by using Ficoll-Paque (GE Healthcare) density gradient centrifugation. Biological samples may be processed into single-cell suspensions by dissociation. Single-cell suspensions may be processed by staining, such as with FITC anti-human CD3 clone UCHT1 (BD Biosciences), Pacific Blue anti-human CD4 clone RPA-T4 (BD Biosciences), APC anti-human CD14 clone M5E2 (BD Biosciences), AlexaFluor700 anti-human CD8 clone RPA-T8 (BD Biosciences), APC-H7 anti-human CD19 clone SJ25C1 (BD Biosciences), PE anti-human CD45RO clone UCHL1 (BD Biosciences), PE-Cy7 anti-human CD56 clone HCD56 (BioLegend), or a combination thereof. Single-cell suspensions may be processed by fixation, such as with 4% paraformaldehyde (PFA). Cell samples may be processed by immunophenotyping, such as with a FACSAria IIu flow cytometer instrument (BD Biosciences) with analysis performed using FlowJo (FlowJo, LLC). When performing immunophenotyping, doublets may be excluded based on forward and side scatter profiles.

The term "solid tissue sample" or "bulk tissue sample," as used herein, may refer to a sample obtained from solid tissue, such as a lymph node, harvested organ, biopsy (e.g., tumor biopsy), and so forth. The sample itself may be reconstituted and suspended. Biological samples may comprise bulk tissue. Bulk tissue may be collected from freshly resected surgical tumor samples of subjects (e.g., cancer patients). Biological samples may be processed into single-cell suspensions by dissociation. Single-cell suspensions may be processed by FACS sorting with one or more cell markers, such as an A700 anti-human CD45 clone HI30 (pan-immune cell marker), PE anti-human CD31 clone XWM59 (endothelial cell marker), APC anti-human EpCAM clone X9C4 (epithelial cell marker), PE-Cy7 anti-human CD10 clone XHI10a (fibroblast marker), or a combination thereof.

The term "archived tissue sample," as used herein refers to a tissue sample that has undergone long-term storage. Biological samples may comprise archived tissue. Archived tissue may be obtained by processing bulk tissue using one or more preservation methods, such as formalin fixation and paraffin embedding (to obtain FFPE tissue) or freezing (e.g., cryopreservation) to obtain frozen tissue. For example, cryopreserved tumor cell suspensions may be thawed, processed, and sorted to isolate a single-cell suspension (e.g., CD5-CD19+ B cells from FL tumor cell suspension).

The term "purified sample," as used herein, may refer to any sample in which one or more cell subsets are enriched. A sample may be purified by the removal or isolation of cells based on characteristics such as size, protein expression, and so forth.

The term "gene expression profiling," as used herein, generally refers to a performing a measurement method on a biological sample or single-cell suspension to measure gene expression. Gene expression profiling may comprise single-cell RNA-Seq (scRNA-Seq), bulk RNA-Seq, microarrays, or a combination thereof.

In some embodiments, the biological sample may be obtained in vitro from a cell culture or from an organism. In certain aspects, the organism may be an animal, such as a primate (e.g., human), rodent (e.g., mouse, rat, hamster, guinea pig), rabbit, or any other suitable animal. A biological sample collected from an organism may be a tissue samples such blood, solid tissue from brain, lymph node, thymus, bone marrow, spleen, skeletal muscle, heart, colon, stomach, small intestine, kidney, liver, lung, and so forth. A tissue sample may be obtained by harvesting an organ or by performing a biopsy as known in the art. In certain aspects, the biological sample is a blood sample, such as whole blood, plasma or cells obtained from blood.

In certain aspects, the biological sample may be a tumor biopsy. A biopsy refers to any tissue sample containing cancer cells that is obtained (e.g., by excision, needle aspiration, etc.) from a subject. The biopsy may be in the form of a cell suspension, thin section (e.g., a tissue section mounted on a slide), or any other suitable form.

In certain aspects, the biological sample may be a cell dispersion or suspension in a solution. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. The separated cells may be collected in any appropriate medium that maintains the viability of the cells. Various media are commercially available and may be used according to the nature of the cells, including dMEM, HBSS, dPBS, RPMI, Iscove's medium, etc., frequently supplemented with fetal calf serum or human platelet lysate. In other aspects, the biopsy may be a tissue section. For example, the biopsy may be a thin tissue section mounted on a microscopy slide. The biological sample of any of the above embodiments may be fixed and/or permeabilized as known to one of skill in the art.

The sample may be a whole sample, e.g., in crude form. Alternatively, the sample may be fractionated prior to analysis, e.g., by density gradient centrifugation, panning, magnetic bead sorting, fluorescence activated cell sorting (FACS), etc., to enrich for one or more cell types of interest.

In some cases, the biological sample is a cell-free sample, e.g., a cell or tissue homogenate. In some cases, the biological sample comprises a single cell.

In certain aspects, the subject methods include obtaining a sample, e.g., biological sample (e.g., as discussed above) prior to estimating the relative proportions of cell subsets in the biological sample.

Distinct Cell Subsets

The distinct cell subsets (e.g., cell types) of the biological sample according to the present disclosure may be any distinct cell types that contribute to the feature profile of the biological sample.

In some embodiments, the distinct subsets of cells comprise subsets of cells at different cell cycle stages. A subset of cells may include cells in any suitable cell cycle stage, including, but not limited to, interphase, mitotic phase or cytokinesis. In some embodiments, cells in a subset of cells are at prophase, metaphase, anaphase, or telophase. In some cases, the cells in a subset of cells is quiescent ($G_0$ phase), at the $G_1$ checkpoint ($G_1$ phase), replicated DNA but before mitosis ($G_2$ phase), or undergoing DNA replication (S phase).

In some embodiments, the distinct cell subsets include different functional pathways within one or more cells. Functional pathways of interest include, without limitation, cellular signaling pathways, gene regulatory pathways, or metabolic pathways. Thus, in some embodiments, the method of the present disclosure may be a method estimating the relative activity of different signaling or metabolic pathways in a cell, a collection of cells, a tissue, etc., by measuring multiple features of the signaling or metabolic pathways (e.g., measuring activation state of proteins in a signaling pathway; measuring expression level of genes in a gene regulatory network; measuring the level of a metabolite in a metabolic pathway, etc.). The cellular signaling pathways of interest include any suitable signaling pathway, such as, without limitation, cytokine signaling, death factor signaling, growth factor signaling, survival factor signaling, hormone signaling, Wnt signaling, Hedgehog signaling, Notch signaling, extracellular matrix signaling, insulin signaling, calcium signaling, G-protein coupled receptor signaling, neurotransmitter signaling, and combinations thereof. The metabolic pathway may include any suitable metabolic pathway, such as, without limitation, glycolysis, gluconeogenesis, citric acid cycle, fermentation, urea cycle, fatty acid metabolism, pyrimidine biosynthesis, glutamate amino acid group synthesis, porphyrin metabolism, aspartate amino acid group synthesis, aromatic amino acid synthesis, histidine metabolism, branched amino acid synthesis, pentose phosphate pathway, purine biosynthesis, glucoronate metabolism, inositol metabolism, cellulose metabolism, sucrose metabolism, starch and glycogen metabolism, and combinations thereof.

In some embodiments, a cell subset may be any group of cells in a biological sample whose presence is characterized by one or more features (such as gene expression on the RNA level, protein expression, genomic mutations, biomarkers, and so forth). A cell subset may be, for example, a cell type or cell sub-type.

In certain aspects, one or more cell subsets may be leukocytes (e.g., white blood cells or WBCs). Potential leukocyte cell subsets include monocytes, dendritic cells, neutrophils, eosinophils, basophils, and lymphocytes. These leukocyte subsets can be further subdivided, for example, lymphocyte cell subsets include natural killer cells (NK cells), T-cells (e.g., CD8 T cells, CD4 naïve T cells, CD4 memory RO unactivated T cells, CD4 memory RO activated T cells, follicular helper T cells, regulatory T cells, and so forth) and B-cells (naïve B cells, memory B cells, Plasma cells) Immune cells subsets may be further separated based on activation (or stimulation) state.

In certain aspects, leukocytes may be from an individual with a leukocyte disorder, such as a blood cancer, an autoimmune disease, mycleodysplastic syndrome, and so forth. Examples of a blood disease include Acute lymphoblastic leukemia (ALL), Acute myelogenous leukemia (AML), Chronic lymphocytic leukemia (CLL), Chronic myelogenous leukemia (CML), Acute monocytic leukemia (AMoL), Hodgkin's lymphoma, Non-Hodgkin's lymphoma, and myeloma. Examples of autoimmune disease include alopecia areata, autoimmune hemolytic anemia, autoimmune hepatitis, dermatomyositis, diabetes (type 1), glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, and systemic lupus erythematosus.

In certain aspects, one or more cell subsets may include tumor infiltrating leukocytes (TILs). Tumor infiltrating leukocytes may be in mixture with cancer cells in the biological sample, or may be enriched by any methods described above or known in the art.

In certain aspects, one or more cell subsets may include cancer cells, such as blood cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

Cell subsets of interest may include brain cells, including neuronal cells, astrocytes, oligodendrocytes, and microglia, and progenitor cells thereof. Other cell subsets of interest include stem cells, pluripotent stem cells, and progenitor cells of any biological tissue, including blood, solid tissue from brain, lymph node, thymus, bone marrow, spleen, skeletal muscle, heart, colon, stomach, small intestine, kidney, liver, lung, and so forth.

Features

Features of interest include any characteristic of a physical sample, e.g., a biological sample, or a physical system that may be indicative of the presence of one or more distinct components, e.g., cell subsets. In certain aspects, the abundance (e.g., value) of a feature may be indicative of the abundance of one or more distinct components, e.g., cell subsets. Features may be aggregate features of the sample, e.g., biological sample, such as total amounts of mRNA, protein, specific genotypes, biomarkers, and so forth.

Features such as gene expression and/or cell genotype may be of interest. For example, cell types and/or states may be differentiated by gene expression. In another example, cancer cells may be differentiated based on genetic heterogeneity resulting from mutation. Such features may be measured by any means known in the art, including polymerase chain reaction (PCR) methods (e.g., quantitative PCR of complementary DNA (cDNA) synthesized from RNA), RNA-Seq, DNA-seq, DNA microarray, tiling array, NanoString® nCounter®, northern blot, serial analysis of gene expression (SAGE) and so forth. Features such as protein expression may be measured by any means known in the art, including western blot, protein microarray, ELISA, other immunoassays, mass spectrometry, and so forth.

In some embodiments, the feature profile includes suitable, measured properties of distinct chemical compounds, obtained by any suitable method. In some cases, the features include nuclear magnetic resonance (NMR) (such as $^{1}$H, $^{13}$C, $^{2}$H, $^{6}$Li, $^{10}$B, $^{11}$B, $^{14}$N, $^{15}$N, $^{17}$O, $^{19}$F, $^{23}$Na, $^{29}$Si, $^{31}$P, $^{35}$Cl, $^{113}$Cd, $^{129}$Xe, or $^{195}$Pt NMR) spectra, electromagnetic radiation (e.g., ultraviolet, visible, infrared radiation) absorbance and/or emission spectra, circular dichroism spectra, Raman spectra, mass spectra, and chromatograms (e.g., from affinity chromatography, liquid chromatography, size-exclusion chromatography, etc.).

Features (such as cell-free biomarkers) may be measured by any means known in the art, including western blot, enzyme-linked immunosorbent assay (ELISA), mass spectrometry, chromatography (e.g., thin layer chromatography, gas chromatography, liquid chromatography, and so forth). For example, a feature may be the intensity of a peak observed on a chromatograph or a mass spectrum.

In certain aspects, the method may include obtaining feature measurements from a physical sample, e.g., a biological sample, or a physical system. In other aspects, the method may include obtaining feature measurements from a database, such as, without limitation, a publically available DNA microarray database, RNA-seq database, and/or a DNA-seq database, or any other suitable database of feature measurements.

Reference profiles of feature signatures may be obtained by measuring features of purified or enriched distinct components, e.g., distinct cell subsets. For example, a cell subset may be purified by density gradient centrifugation, panning, magnetic bead sorting, fluorescence activated cell sorting (FACS), etc., as described above. Alternatively, a cell subset may be cultured in vitro, e.g., through stimulation and/or differentiation of precursor cells. After isolation of a cell subset, features of the cell subset may be measured (e.g., as described above or as known to one of skill in the art). In certain aspects, gene expression of a cell subset may be measured (e.g., by DNA microarray analysis) to obtain a gene expression profile (GEP) of the cell subset.

In some cases, feature signatures for a distinct component that is a signaling pathway is obtained by measuring the features in a functional cell-free system that includes components of the signaling pathway, by selectively activating the signaling pathway pharmacologically or inducibly in a cellular environment, etc. In some cases, feature signatures for a distinct component that is a chemical compound is obtained by measuring the features in substantially pure or enriched sample of the chemical compound.

In certain aspects, a signature matrix includes levels of specific mRNA, protein, genotypes, and/or biomarkers for any of the cell subsets described above. Signature matrices are often termed 'base or basis matrices' in prior studies, and can be obtained, for example by differential expression analysis of purified or enriched cell populations. Gene signature matrices can be made more robust by minimizing an inherent matrix property called the condition number, which measures the stability of the linear system to input variation or noise. In certain aspects, signature matrix stability may be measured via the 2-norm condition number, calculated with the kappa function, e.g., in R.

Some reference profiles in the same signature matrix may exhibit "multicollinearity," a phenomenon in which reference profiles of multiple distinct components, e.g., cell types, are highly correlated. Multicollinearity may prevent deconvolution, or reduce confidence in deconvolution of the relative amounts of distinct components, e.g., cell subsets, in a physical sample, e.g., biological sample, as could be reported by a significance value in the subject methods. The severity of multicollinearity between two reference profiles in a signature matrix of the subject invention as measured by the variance inflation factor (VIF), may be 1 or greater, e.g., 2 or more, 5 or more, 10 or more, 15 or more, including 20 or more, and in some cases may be 50 or less, e.g., 40 or less, 30 or less, 20 or less, 15 or less, including 10 or less.

In some cases, the reference matrix has a 2-norm condition number of 1 or more, e.g., 2 or more, 5 or more, 8 or more, 10 or more, 15 or more, 20 or more, 50 or more, 100 or more, 500 or more, including 1,000 or more, and in some embodiments has a 2-norm condition number of $10^4$ or less, e.g., $10^3$ or less, 500 or less, 250 or less, 200 or less, 150 or less, 100 or less, 50 or less, 30 or less, 20 or less, 15 or less, 8 or less, including 5 or less. In some embodiments, the reference matrix has a 2-norm condition number in the range of 1 to 5, e.g., 5 to 8, 8 to 10, 8 to 15, 10 to 15, 15 to 20, 20 to 30, 20 to 50, 50 to 100, 100 to 150, 100 to 200, 100 to 250, 100 to 500, 500 to 1,000, including 1,000 to 10,000.

The condition number of a reference matrix may be adjusted using any suitable method. In some cases, the condition number of an initial reference matrix is reduced by adding or removing one or more features from the matrix, thereby generating a superset or subset of the initial reference matrix that has a lower condition number. This process may be iterated until a sufficiently low condition number for the final reference matrix is obtained.

In certain aspects, the reference matrix may include at least one feature (e.g., gene), e.g., at least 2, at least 3, at least 5, at least 10, at least 20, at least 50, including at least 100 features that are associated with (e.g., expressed by) two or more, e.g., 5 or more, 10 or more, including 15 or more of the distinct components (e.g., cell subsets), and in some cases, by 20 or fewer, e.g., 15 or fewer, 12 or fewer, 10 or fewer, including 8 or fewer of the distinct components. In some cases, the reference matrix may include at least one feature (e.g., gene), e.g., at least 2, at least 3, at least 5, at least 10, at least 20, at least 50, including at least 100 features that are associated with (e.g., expressed by) 2 to 20, e.g., 2 to 15, 2 to 12, including 5 to 10 distinct components (e.g., cell subsets). In some cases, the reference matrix may include 10,000 or fewer, e.g., 5,000 or fewer, 1,000 or fewer, 500 or fewer, 200 or fewer, including 100 or fewer features (e.g., genes) that are associated with (e.g., expressed by) a plurality of distinct components (e.g., cell subsets).

In certain aspects, candidate features for inclusion in the signature matrix may be filtered. In certain embodiments, features with low values and/or variance may be filtered from the signature matrix. For example, features with values and/or variance that is in the lower 90%, lower 80%, lower 75%, lower 50%, or lower 25% as compared to other candidate features may be filtered out. In another example, features with values and/or variance that is higher than 90%, 80%, 75%, 50%, or 25% as compared other candidate features may be included in the signature matrix. In some embodiments, features enriched in distinct components that are not represented in the signature matrix are not included in the signature matrix. In some embodiments, features having a value higher than a threshold value in distinct components that are not represented in the signature matrix are not included in the signature matrix.

Features that are more predictive for distinct components, e.g., cell subsets, of interest may be included in the signature matrix. For example, the method may comprise calculating an enrichment score (ES) for a given feature in a given distinct component, e.g., cell subset, or physical sample/physical system based on the sum of linear model coefficients from all pairwise comparisons of that feature with other distinct components, e.g., cell subsets, or physical samples/physical systems. In certain aspects, features may be selected for inclusion in the signature matrix based on fold change in the value of the feature for a distinct component, e.g., cell subset, as compared to other distinct components, e.g., cell subsets. For example, features that are 2-fold or higher, 5-fold or higher, 10-fold or higher, or 20-fold or higher in one distinct component, e.g., cell subset, than any other distinct component, e.g., cell subset, may be selected to be included in the signature matrix. Conversely, features may be excluded from the signature matrix to reduce multicollinearity.

Figure 17:
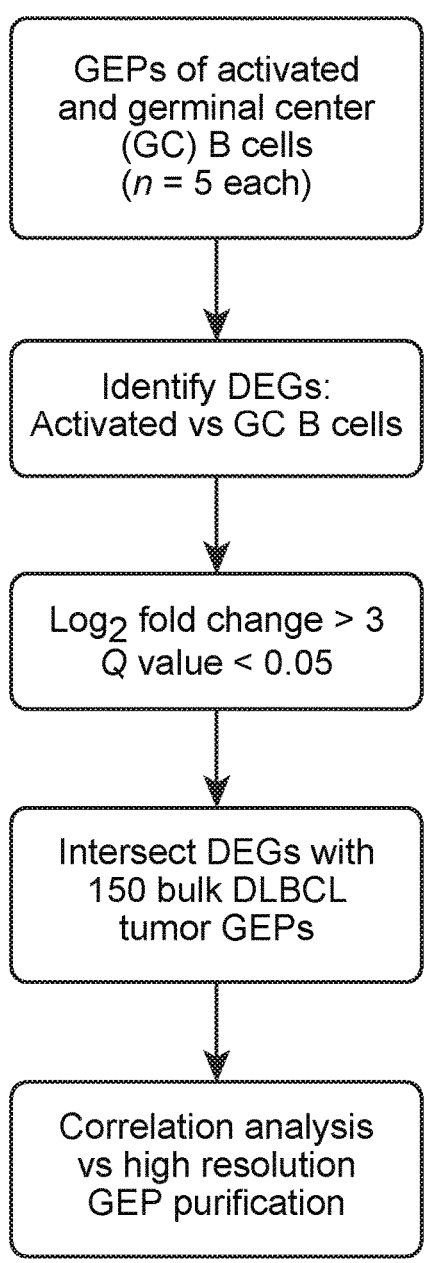
FIGS. 17a-e illustrate relative utility of high-resolution purification versus a correlation-based approach. (17a) Schema for the identification and assessment of DEGs that distinguish activated and germinal center B cells profiled by microarray. (17b) Heat map showing DEGs identified as described in panel (17a). (17c) Heat map showing the most correlated cell type (of 10 evaluated immune subsets; columns) with each gene from (17b) (rows) in 150 bulk DLBCL tumors (GCB/ABC DLBCL, CHOP cohort, as described, for example, by Lenz et al.). Correlations were calculated as the Pearson correlation between the non-log expression vector of each gene and the imputed fractional abundance of each cell type across all bulk tumors, using LM22 fractions collapsed into the indicated lineages. Genes are ordered identically in panels (17b) and (17c). (17d) and (17e) PCA plots showing transcriptional variation ($log_2$-adjusted) among the 5 most abundant cell types in DLBCL tumors, color-coded by previously annotated molecular subtypes (ABC DLBCL, blue; GCB DLBCL, orange). Each PCA plot in panel (17d) was generated by uniquely assigning each gene in panel (17c) to its most correlated cell type (e.g., only genes highlighted yellow in the leftmost column of (17c) were used for B cells). Each plot in panel (17e) was generated by applying PCA to the output of high resolution expression purification, which was run on the same 150 bulk DLBCL tumor GEPs as the correlation-based strategy, and filtered to restrict the analysis to the same 1,100 DEGs (identified as described in panel (17a)).
Figure 17:
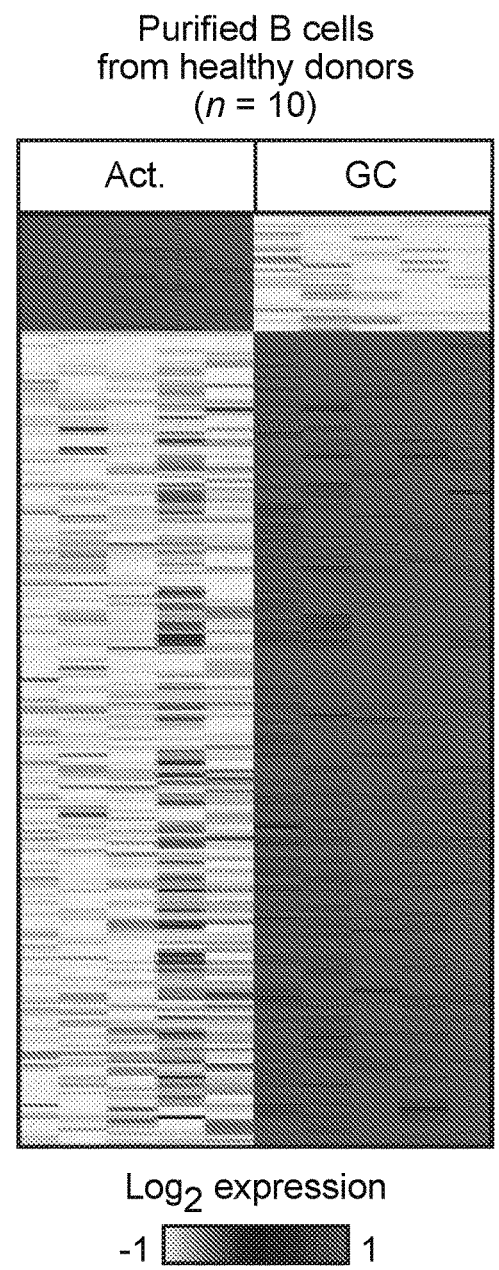
Figure 17:
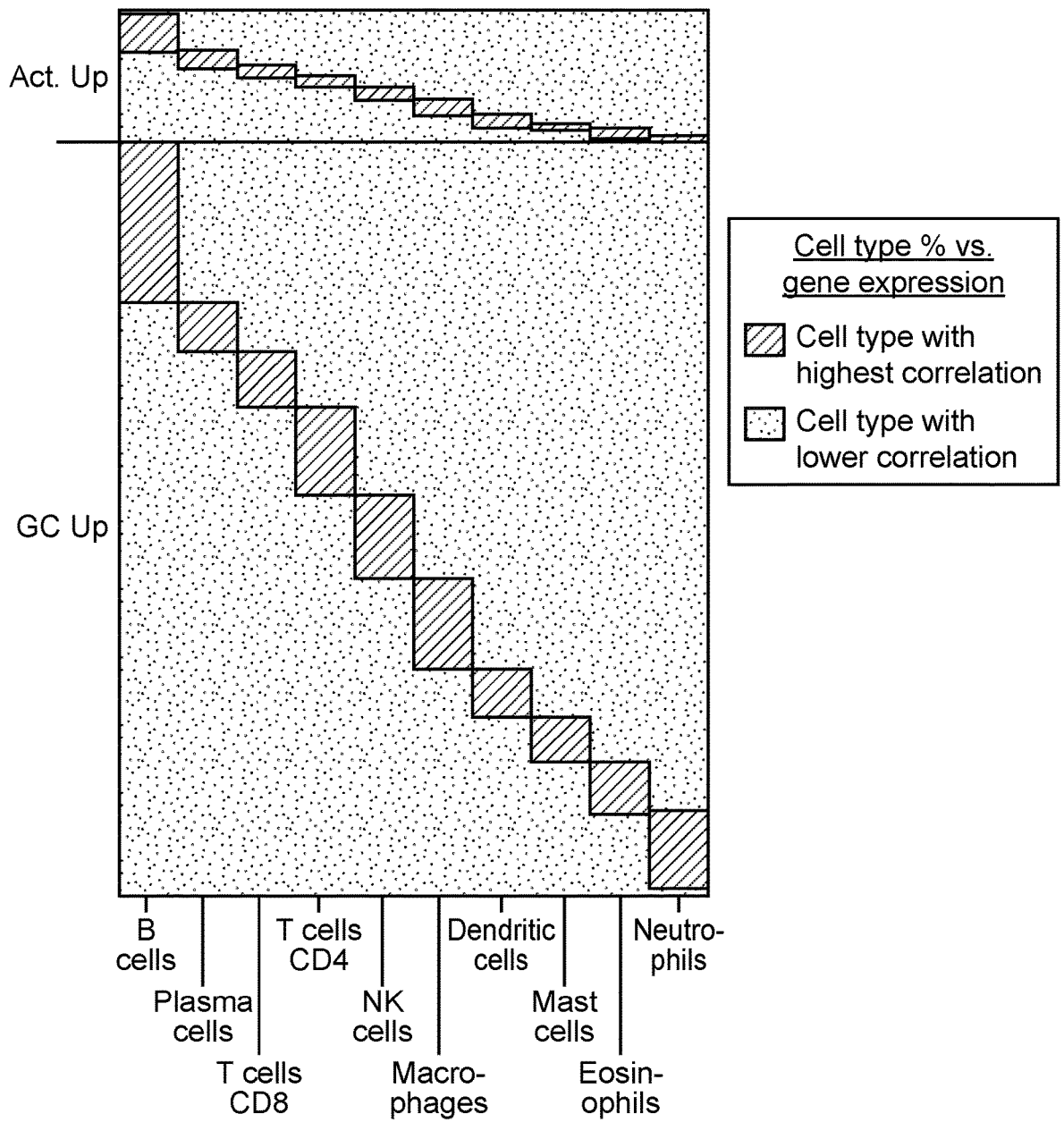
Figure 17:
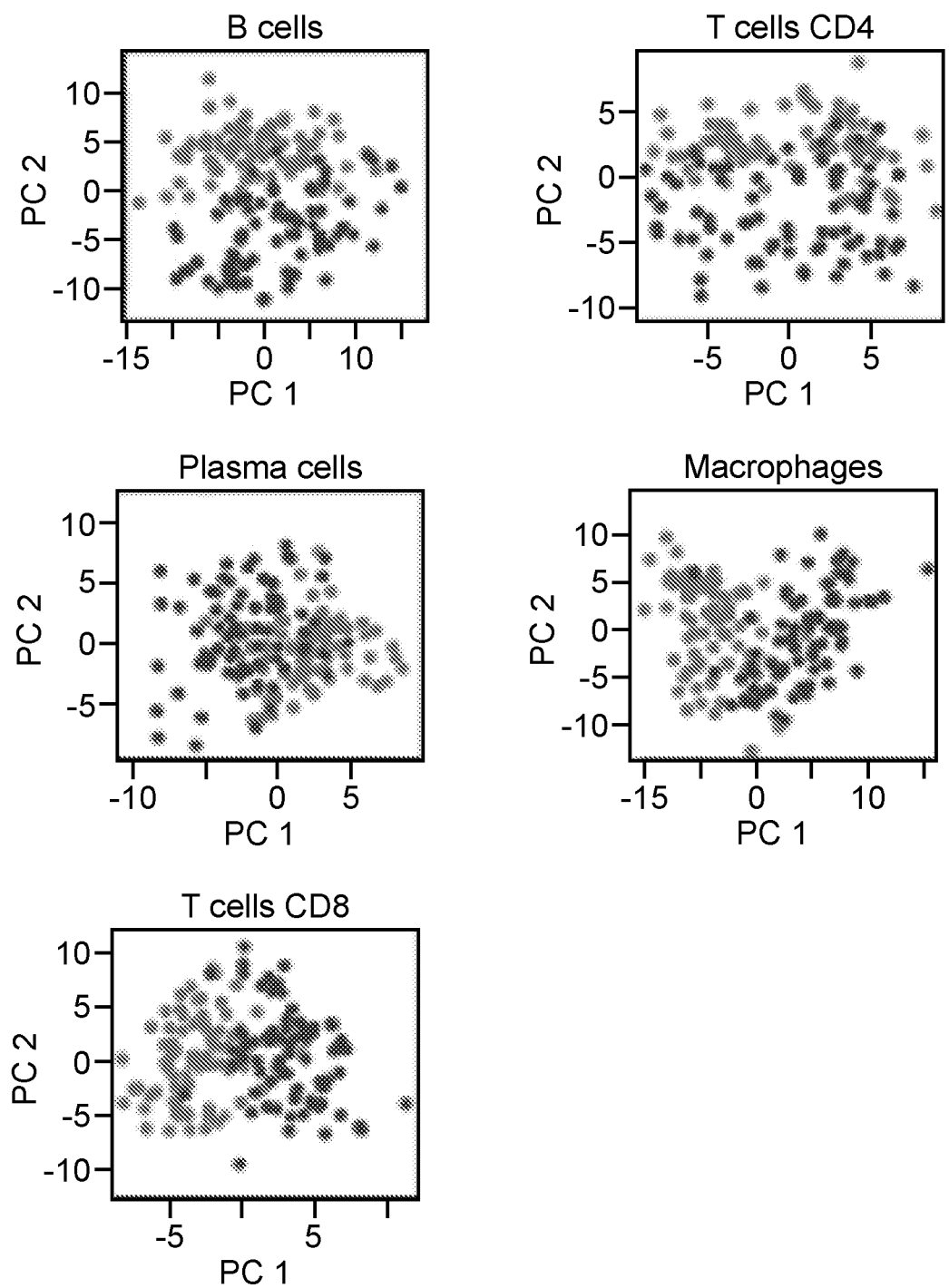
Figure 17:
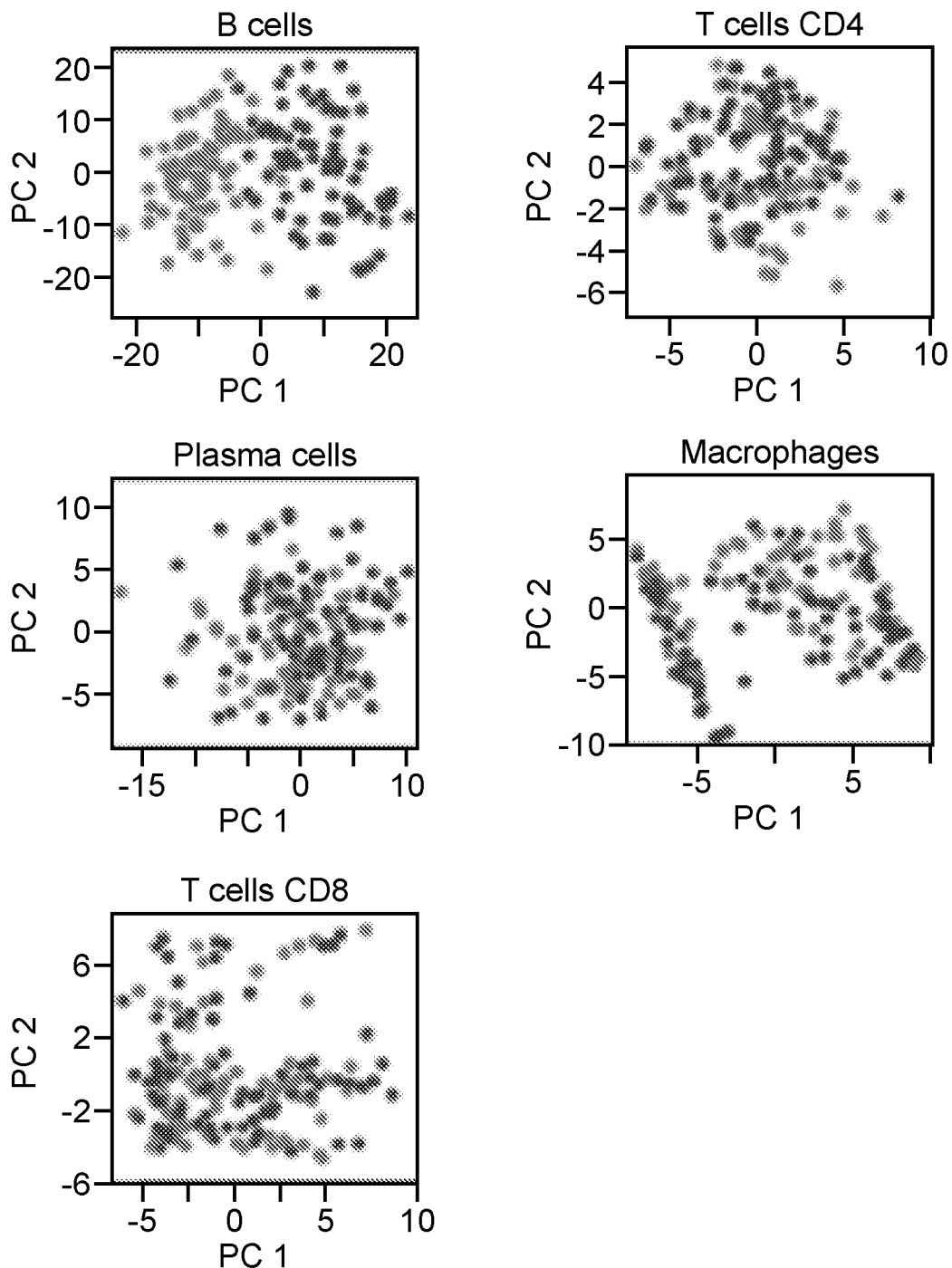

In certain aspects, the subject methods include isolating one or more distinct components e.g., cell subsets, and measuring features of the one or more distinct components e.g., cell subsets to obtain a signature matrix. For example, cells in a first biological sample may be separated into separate cell subsets by FACS. Separate cell subsets may be analyzed by DNA microarray to obtain a gene expression profile (GEP) for each of the separate cell subsets. The GEP for each cell subset may then be compiled to generate a signature matrix with values for expression of a number of genes for each of the cell subsets (e.g., as seen in FIG. 17).

Examples of sample feature profiles include a "gene expression profile" or "GEP" (e.g., as obtained by microarray analysis), a protein expression profile, a genotype profile (e.g., of a sample having heterogeneous tumor cells), a biomarker profile (e.g., of free biomarkers in the sample or biomarkers on/in cells of the sample), a DNA methylation profile (e.g., of a sample having cells containing DNA with varying levels or alterations of methylation), or a combination thereof. For example, DNA methylation profiles may be cell-specific, tissue-specific, and/or cell stage-specific; therefore, feature profiles may include DNA methylation profiles across cell types, tissue types, etc. DNA methylation profiles may be measured by, for example, bisulfite sequencing of a sample.

A feature profile of a sample may be obtained as described above (e.g., features may be measured directly from a biological sample or the feature profile may be obtained from a database, such as a publically available DNA microarray database). As discussed above, a biological sample may include any cell type. In certain embodiments, the feature profile of a sample may be a benchmarking data set.

The present method may provide for a sensitive method of estimating the fractional representation of a distinct component in a physical sample or physical system, where the distinct component is present at a low fraction. In some embodiments, the physical sample or physical system includes at least one distinct component represented in the feature signature at a concentration of 10% or less, e.g., 8.0% or less, 6.0% or less, 4.0% or less, 2.0% or less, including 1.0% or less, and in some cases at a concentration of 0.01% or more, e.g., 0.05% or more, 0.1% or more, 0.5% or more, including 1.0% or more, of the total amount of the second plurality of distinct components present in the sample. In some embodiments, the physical sample or physical system includes at least one distinct component represented in the feature signature at a concentration in the range of 0.01% to 10%, e.g., 0.05% to 8.0%, 0.1% to 6.0%, 0.1% to 4.0%, including 0.1% to 2.0%, of the total amount of the second plurality of distinct components present in the sample.

The present method may provide for robustly estimating the fractional representation of a distinct component in a physical sample or physical system in the presence of distinct components that are not represented in the signature matrix. In some embodiments, distinct components represented in the feature signature are present in the sample at 50% or less, e.g., 45% or less, 40% or less, 35% or less, 30% or less, 25% or less, 20% or less, 10% or less, including 5% or less, and in some cases, 1% or more, e.g., 5% or more, 10% or more, 20% or more, 30% or more, 35% or more, including 40% or more of the total amount of distinct components in the sample. In some embodiments, distinct components represented in the feature signature are present in the sample in the range of 1 to 50%, e.g., 5 to 50%, 10 to 50%, including 20 to 45%.

In certain aspects, a biological sample may include cells that are not represented by the signature matrix. For example, 5% or more, 10% or more, 25% or more, 50% or more, 75% or more, 5% to 50%, 5% or less, 10% or less, 25% or less, or 50% or less of the cells in the biological sample may not be represented by cell subsets in the signature matrix.

Alternatively or in addition, a biological sample may include cell subsets represented by the signature matrix that are present in low amounts, such as 10% or less, 5% or less, 2% or less, 1% or less, 0.5% or less, 0.25% or less, 0.1% or less, between 0.1% and 10%, between 0.25% and 2%, and so forth.

Introduction

Tissue composition can be a major determinant of phenotypic variation and a key factor influencing disease outcomes. Although scRNA-Seq can be a powerful technique for characterizing cellular heterogeneity, it can be impractical for large sample cohorts and may not be applied to fixed specimens collected as part of routine clinical care. To overcome these challenges, the present disclosure provides a platform for in silico cytometry that can enable the simultaneous inference of cell type-specific gene expression profiles (GEPs) and cell type abundance from bulk tissue transcriptomes. Using the methods disclosed herein for in silico purification, bulk tissue composition can be accurately estimated using scRNA-Seq-derived reference signatures. The disclosed methods and systems may link unbiased cell type discovery with large-scale tissue dissection. The utility of this integrated framework, called CIBERSORTx, can be demonstrated in multiple tumor types, including melanoma, where single-cell reference profiles are used to dissect fresh, frozen, and fixed clinical specimens, revealing associations between tumor infiltrating leukocytes (TILs) and immunotherapy response. Digital cytometry can augment single-cell profiling efforts, enabling cost-effective, high-throughput tissue characterization without antibodies, disaggregation, or viable cells.

Immunophenotyping approaches, such as flow cytometry and immunohistochemistry (IHC), can rely on small combinations of preselected marker genes, which can limit the number of cell types that can be simultaneously interrogated. By contrast, single-cell mRNA sequencing (scRNA-Seq) can be used for unbiased transcriptional profiling of hundreds to thousands of individual cells from a single-cell suspension (scRNA-Seq). Despite the power of this technology, analyses of large sample cohorts may not be practical, and many fixed clinical specimens (e.g., formalin-fixed, paraffin embedded (FFPE) samples) may not be dissociated into single-cell suspensions. Furthermore, the impact of tissue disaggregation on cell type representation may be poorly understood.

Computational techniques for dissecting cellular content directly from genomic profiles of mixture samples may rely on a specialized knowledgebase of cell type-specific "barcode" genes (e.g., a "signature matrix"), which is derived from FACS-purified or in vitro differentiated/stimulated cell subsets. Although useful when cell types of interest are well defined, such gene signatures may be suboptimal for the discovery of novel cell types and cell type GEPs, and for capturing the full spectrum of major cell phenotypes in complex tissues.

The present disclosure provides a computational framework to accurately infer cell type abundance and cell type-specific gene expression from RNA profiles of intact tissues (FIG. 1). By leveraging cell type expression signatures from single-cell experiments or sorted cell subsets, systems and methods of the present disclosure can provide comprehensive portraits of tissue composition without physical dissociation, antibodies, or living material. Such approaches may include, for example, a method for enumerating cell composition from tissue GEPs with techniques for cross-platform data normalization and in silico cell purification. The latter can allow the transcriptomes of individual cell types of interest to be digitally "purified" from bulk RNA admixtures without physical isolation. As a result, changes in cell type-specific gene expression can be inferred without cell separation or prior knowledge. To illustrate the technical performance and clinical utility of this framework, termed CIBERSORTx, systems and methods of the present disclosure may be used to (1) profile bulk tissue composition with single-cell expression data, (2) purify GEPs of malignant and tumor-associated cell types without dissociation, and (3) explore cell type-specific signatures with relevance to anticancer therapies. These results illustrate that CIBERSORTx may be a useful tool for deciphering complex tissues, with implications for high-resolution cell phenotyping in research and clinical settings.

The CIBERSORTx platform may be used for in silico tissue dissection. Features of the platform can include an integrated framework for cell type enumeration and gene expression purification, dedicated normalization schemes to suppress cross-platform variation, and improved approaches for separating RNA admixtures into cell-type specific expression profiles. CIBERSORTx may be used for analysis of peripheral blood, pancreatic islet specimens, and malignant tumors (for example, 350 of which are profiled). The results illustrate that CIBERSORTx can deliver accurate portraits of tissue heterogeneity using expression profiles derived from disparate sources.

The systems and methods described herein can be used to define a comprehensive human cell atlas. Given a rapid pace of data generation coupled with emerging techniques to combine scRNA-Seq datasets, methods to broadly apply single-cell reference maps can be important, especially in settings where tissue is limited, fixed, or challenging to disaggregate. In studies of neoplastic and healthy tissues, single-cell reference profiles can be used to perform detailed interrogation of tissue composition, and inter-subject heterogeneity is not a major factor influencing deconvolution results. CIBERSORTx may outperform current approaches to enable robust molecular profiling of cell subset GEPs from complex tissues, independent of platform or preservation state. By flexibly incorporating a plurality of techniques for expression analysis, CIBERSORTx can facilitate rapid assessment of cell type GEPs when phenotypic categories are known (FIG. 1, step 3; FIGS. 3a-g), and high-resolution profiling of expression variation when additional detail is desired (FIG. 1, step 4; FIGS. 4a-e). With these features, CIBERSORTx analysis may provide an improved understanding of heterotypic interactions within tumor microenvironments, with implications for informing diagnostic and therapeutic approaches that rely on targeting specific cell types.

Additionally, CIBERSORTx can be used to decode cellular heterogeneity in complex tissues. This strategy can be used to "digitally gate" cell subsets of interest from single-cell transcriptomes, profile the identities and expression patterns of these cells in cohorts of bulk tissue GEPs (e.g., fixed specimens from clinical trials), and systemically determine their associations with diverse metadata, including genomic features and clinical outcomes. CIBERSORTx can therefore have utility for increasing the statistical power for biological discovery, thereby promoting reproducible research. Given the generality of the CIBERSORTx approaches and its ability to seamlessly integrate with other techniques, in silico cytometry can enhance the analysis of multicellular systems in humans, mice, and other metazoans.

The term "scRNA-Seq," as used herein, generally refers to a single-cell RNA sequencing method to obtain expression profiles of individual cells. For example, single-cell libraries can be prepared from PBMC single-cell suspensions (e.g., from cancer patients) using Chromium with v2 chemistry (10× Genomics). Such single-cell libraries can be sequenced (e.g., a NextSeq 500 (Illumina)). Sequencing reads may be processed, for example, by alignment, filtration, de-duplication, and/or conversion into a digital count matrix using Cell Ranger 1.2 (10× Genomics). Outlier cells may be identified and filtered based on (1) anomalously high/low mitochondrial gene expression (e.g., cells with >10% or <1% mitochondrial content may be removed) and/or (2) potential doublets/multiplets, as identified by comparing the number of expressed genes detected by per cell versus the number of unique molecular identifiers (UMIs) detected per cell (e.g., cells with greater than 3,500 and less than 500 expressed genes may be removed). Clusters may be identified (e.g., using Seurat v.1.4.0.16) by (1) regressing out the dependence of gene expression on the number of UMIs and the percentage of mitochondrial content, and (2) by running "FindClusters" on a suitable number (e.g., 1, 2, 3, 4, 5, 6, 7, 8, 9, 10, or more than 10) of principal components of the data. Cell labels may be assigned according to the expression of canonical leukocyte marker genes (e.g., MS4A1 high=B cells; CD8A high and GNLY low=CD8 T cells; CD3E high, CD8A low, and GNLY low=CD4 T cells; GNLY high and CD3E low=NK cells; GNLY high and CD3E high=NKT cells; CD14 high=monocytes). Publicly available PBMC datasets from healthy donors profiled by Chromium v2 (5' and 3' kits) may be downloaded (Table 1) and preprocessed as above, with the following minor modifications. During quality control, cells with >5000 expressed genes for 5' PBMCs, >4000 expressed genes for 3' PBMCs, and <200 expressed genes may be excluded. Seurat "FindClusters" may be applied on the first 20 principal components, with the resolution parameter set to 0.6. Cell labels may be assigned as described above. In addition, myeloid cells may be defined by high CD68 expression, megakaryocytes may be defined by high PPBP expression, and dendritic cells may be defined by high FCER1A expression.

The term "bulk RNA-Seq," as used herein, generally refers to a bulk RNA sequencing method to obtain expression profiles of bulk cell populations or tissues. For example, total RNA may be isolated from blood samples stored in, e.g., PAXgene tubes using, e.g., the PAXgene Blood RNA Kit (Qiagen) according to the manufacturer's recommendations. RNA may be quantitated and quality assessed using, e.g., a 2100 Bioanalyzer (Agilent). Library preparation may be performed using, e.g., an RNA exome kit (Illumina®) per the manufacturer's recommendations. RNA-Seq libraries may be multiplexed together and sequenced using, e.g., a single HiSeq® 4000 lane (Illumina®) using 2×150 bp reads. For example, total RNA may be isolated from PBMC samples (e.g., from NSCLC cancer patients) using TRIzol (Invitrogen) per the manufacturer's recommendations. RNA molecules may be quantitated and quality assessed, e.g., using a 2100 Bioanalyzer (Agilent) with a RNA 6000 Pico chip (Agilent). Library preparation of the RNA molecules may be performed, e.g., using the SMARTer Stranded Total RNA-Seq-Pico kit (Takara Biosciences) per the manufacturer's recommendations. Libraries may be quantified, e.g., with the dsDNA HS Assay kit (Thermo Fisher Scientific) using a Qubit 3.0 fluorometer (Thermo Fisher Scientific). Library quality may be assessed, e.g., using a 4200 TapeStation Instrument (Agilent) with D1000 ScreenTape. RNA-Seq libraries may be sequenced on a suitable sequencing instrument (e.g., a NextSeq® 500 (Illumina®) using 2×150 base-pair (bp) reads. As another example, total RNA may be extracted from bulk tumors (e.g., NSCLC) and sorted cell populations (e.g., in a range of about 100, about 200, about 300, about 400, about 500, about 1,000, about 5,000, about 10,000, about 15,000, about 20,000, about 25,000, or more than 25,000 cells), e.g., using an AllPrep DNA/RNA Micro kit (Qiagen). An amount of total RNA (e.g., about 10 nanograms (ng), about 20 ng, about 30 ng, about 40 ng, about 50 ng, or more than 50 ng) may be amplified, e.g., using an Ovation RNA-Seq System V2 (NuGEN). The resulting complementary DNA (cDNA) may be sheared (e.g., by sonication (Covaris S2 System) to an average size of 150-200 bp) and used to construct DNA libraries (e.g., using the NEBNext DNA Library Prep Master Mix (New England Biolabs)). Libraries may be sequenced on a suitable sequencing instrument (e.g., a single HiSeq® 2000 (Illumina®) to generate 100 bp paired end reads with an average of 100 million (M) reads per sample).

To maximize linearity in the context of deconvolution analyses, raw FASTQ reads may be processed (e.g., with Salmon v0.8.265) using GENCODE v23 reference transcripts, the—biasCorrect flag, and otherwise default parameters. RNA-Seq quantification results may be merged into a single gene-level TPM matrix using an R package, tximport66.

Figure 3:
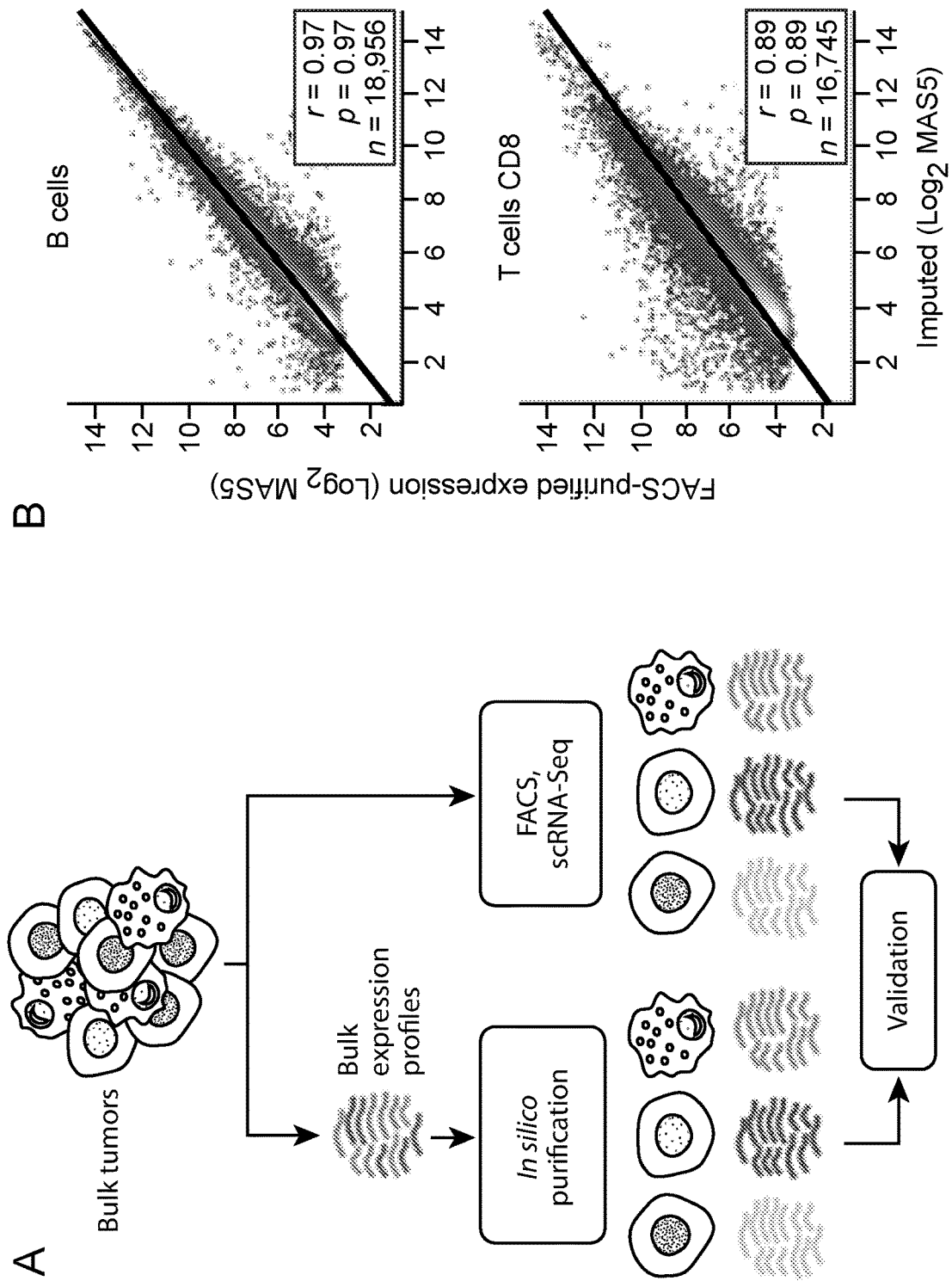
FIGS. 3a-g illustrate purification of representative cell type-specific transcriptome profiles. (a) Approach for in silico purification and validation of group-level cell type-specific GEPs. (b) Scatterplots comparing genome-wide expression profiles of digitally purified (x-axis) and fluorescence-activated cell sorting (FACS)-purified (y-axis) B cells and CD8 T cells from follicular lymphoma (FL) lymph nodes. (c) Scatterplots showing the predicted expression level of each gene in panel (b) (y-axis) as a function of its uncertainty, as captured by the geometric coefficient of variation (c.v.) (x-axis). (d) Same as (b), but after applying a noise filter based on the transcriptome-wide distribution of c.v. values for each cell type. (e) Spearman correlation between purified and ground truth transcriptomes for three FL cell subsets, evaluated as a function of sample size (FL tumors), with and without filtration. For each sample size, tumors were subsampled without replacement from a larger cohort (n=319) 10 times. Data are presented as boxplots (center line indicates median; box limits indicate upper and lower quartiles; whiskers indicate 1.5× interquartile range; and points indicate outliers). (f) Heat map comparing imputed and ground truth expression profiles for three FL immune subsets, with the set of LM22 genes as rows and immune cell types as columns. Genes that were not predicted to be expressed or that were removed by adaptive noise filtration are colored navy blue. (g) Same as (d), but for immune (CD45+), epithelial (epithelial cell adhesion molecule-positive, EpCAM+), and stromal (CD10+ or CD31+) cell types digitally sorted from RNA-Seq profiles of 31 NSCLC tumors. Ground truth GEPs (y-axis) were obtained from FACS-purified populations.
Figure 3:
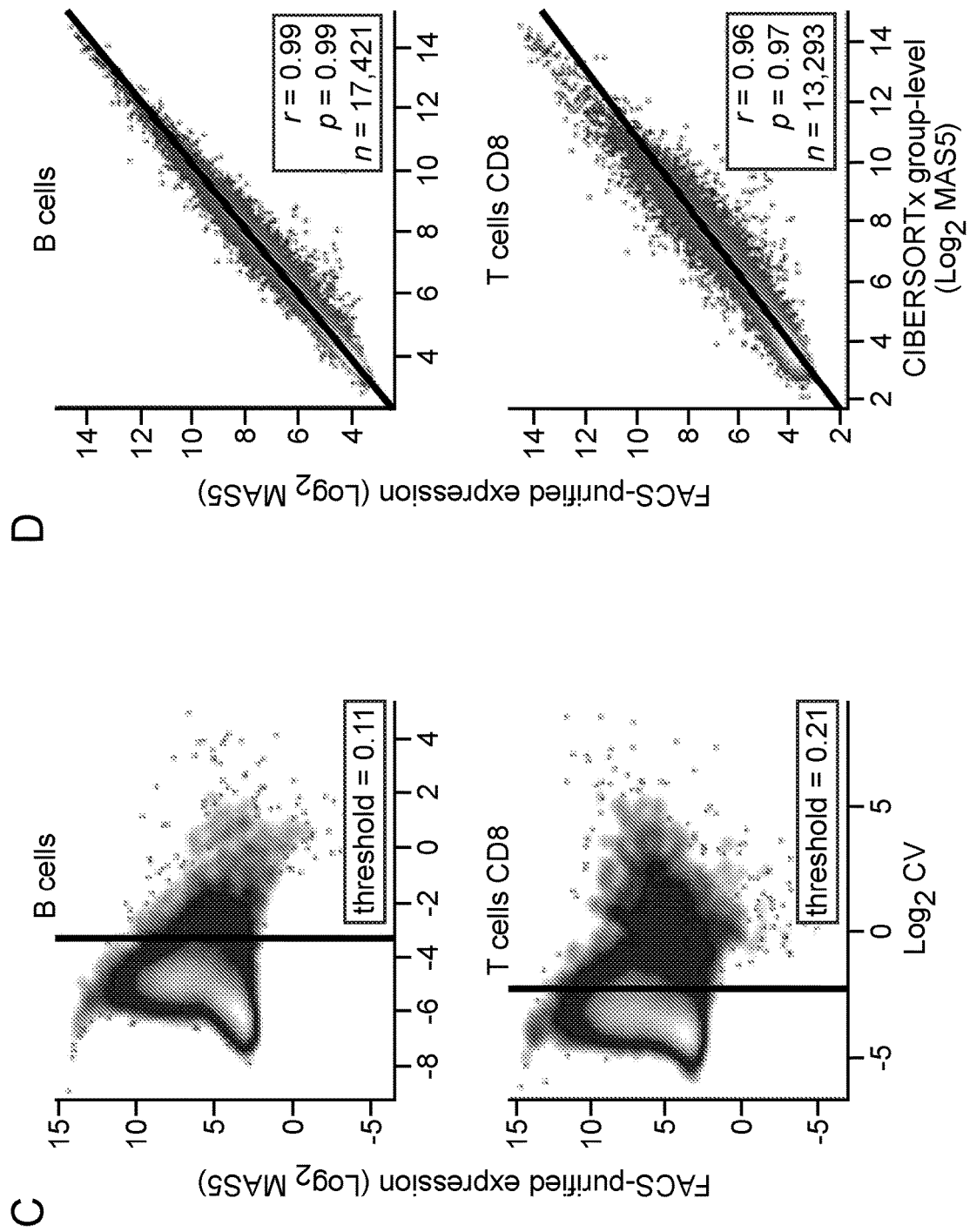
Figure 3:
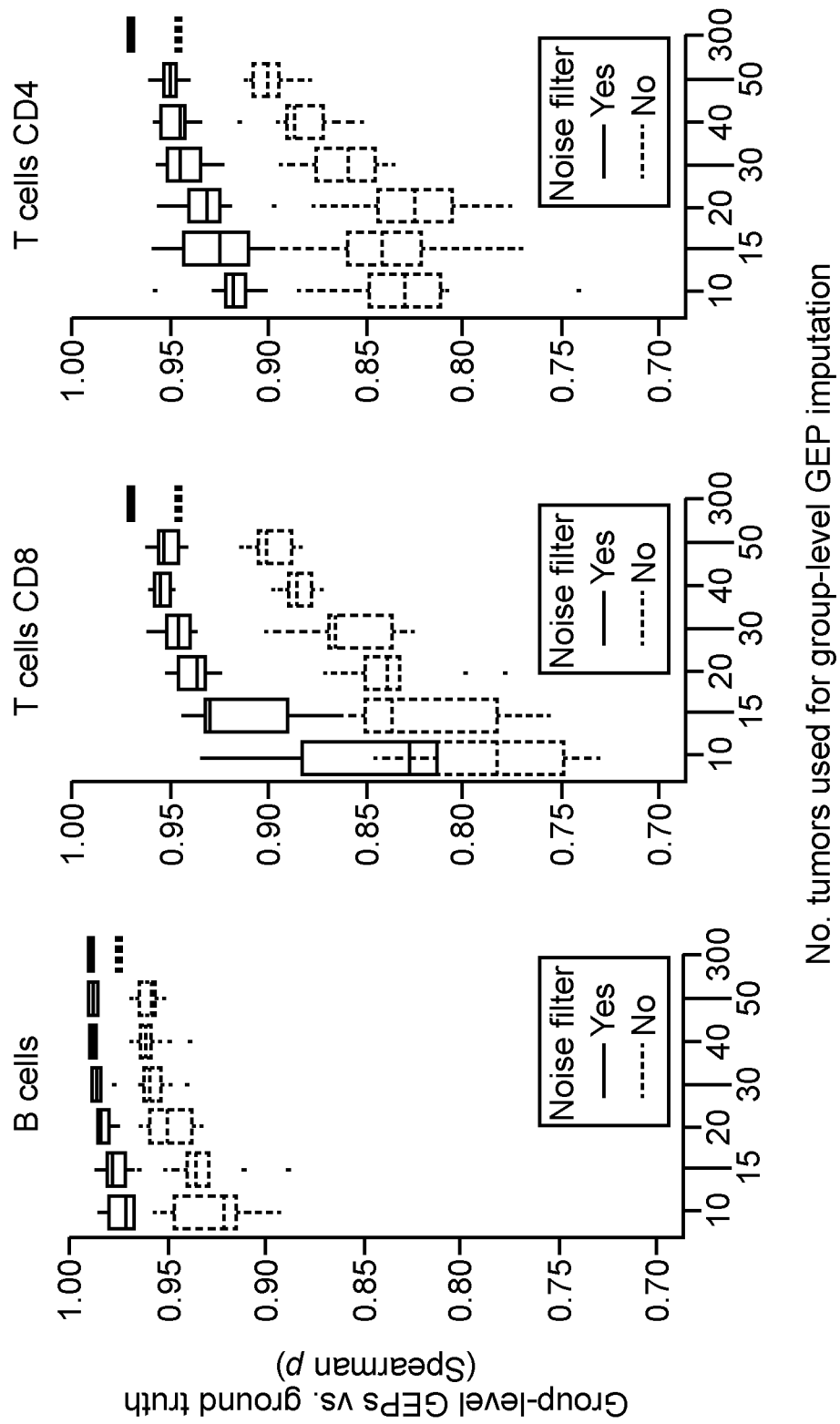
Figure 3:
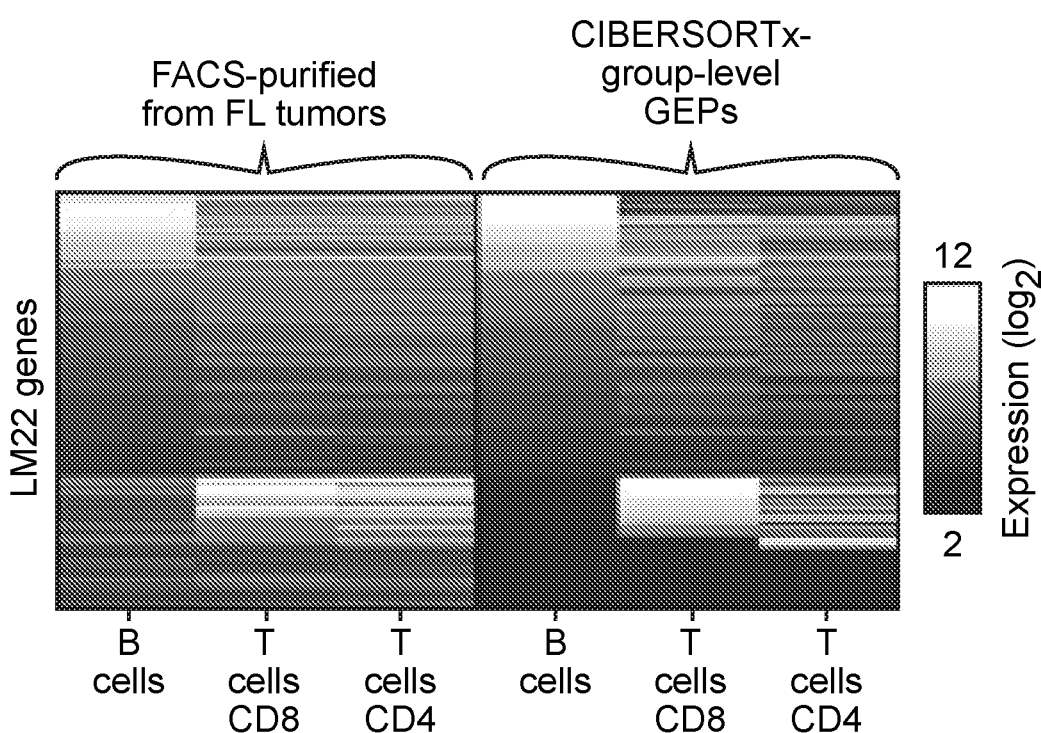
Figure 3:
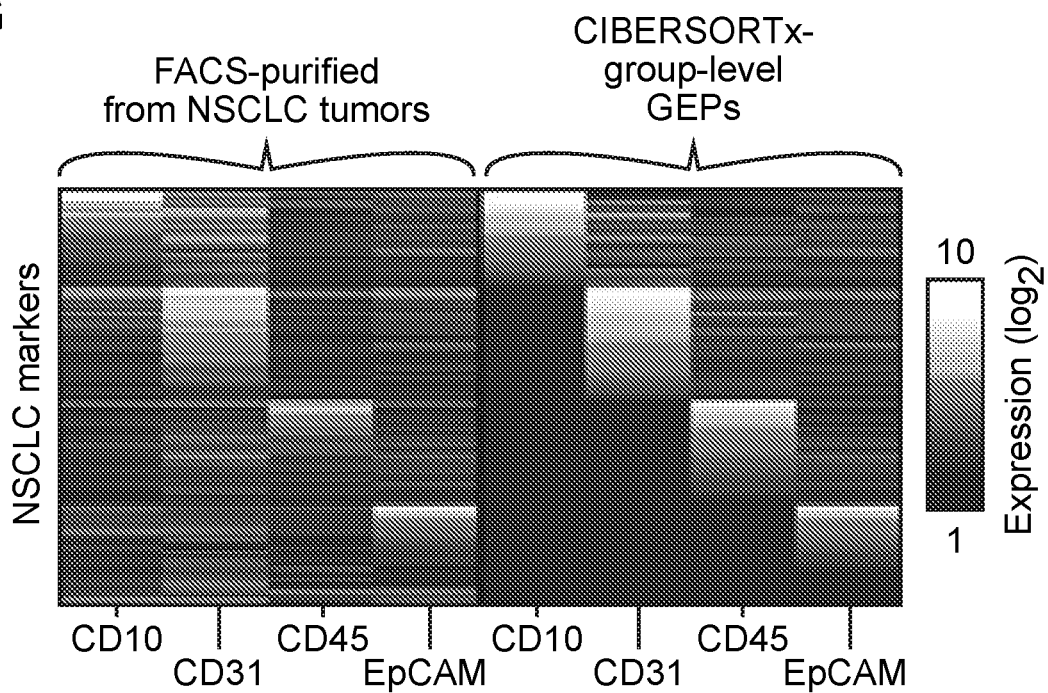

Microarrays may be used to generate ground truth reference profiles using microarrays. Total RNA may be extracted from bulk FL specimens and sorted B cells, and assessed for yield and quality. Complementary RNA (cRNA) may be prepared from 100 ng of total RNA following linear amplification (3' IVT Express, Affymetrix), and then hybridized to HGU133 Plus 2.0 microarrays (Affymetrix) according to the manufacturer's protocol. Obtained CEL data files may be pooled with a publicly available Affymetrix dataset containing CD4 and CD8 tumor-infiltrating lymphocytes (TILs) which are FACS-sorted from FL lymph nodes (GSE2792840). Resulting datasets may be RMA normalized using the "affy" package in Bioconductor, mapped to NCBI Entrez gene identifiers using a custom chip definition file (e.g., Brainarray version 21.0; http://brainarray.mbni.med.umich.edu/Brainarray/), and converted to HUGO gene symbols. Replicates of sorted cell subsets may be combined to create ground truth reference profiles (e.g., as shown in FIG. 3b) using the geometric mean of expression values.

External datasets may comprise next generation sequencing (NGS) datasets which are downloaded and analyzed using normalization settings. Such external datasets may comprise one or more of: transcripts per million (TPM), reads per kilobase of transcript per million (RPKM), or fragments per kilobase of transcript per million (FPKM) space. For analyses in log 2 space, values of 1 may be added to expression values prior to log 2 adjustment. Affymetrix microarray datasets may be summarized and normalized as described with microarrays, using RMA in cases where bulk tissues and ground truth cell subsets were profiled on the same Affymetrix platform, and otherwise using MASS normalization. NanoString nCounter data may be downloaded and analyzed with batch correction in non-log linear space, but without any additional preprocessing.

The term "single-cell signature matrix," as used herein, generally refers to a matrix comprising phenotypes of cell types which may be represented in a biological sample. Expression data from input datasets may be summarized as described above. Given the variability in cell type representation and the inherent noise in scRNA-Seq data, techniques may be developed to address stochastic dropout, impute cell-level scaling factors, and model technical and biological noise components in single-cell differential expression analysis. Although useful for defining single cell phenotypes, significant gains in deconvolution performance may not be observed when applying such techniques after cell labels were assigned. Since the discovery of cell subpopulations in scRNA-Seq data may not be a focus, pre-processing steps may be limited, as described in the following approach.

Single-cell expression values may be first normalized to transcript per million (TPM) and divided by 10 to better approximate the number of transcripts per cell. For each cell phenotype, genes with low average expression in log 2 space may be set to 0 as a quality control filter. Because of sparser gene coverage, filter may not be applied to data generated by 10× Chromium. For each cell type represented by at least 3 single cells, 50% of all available single cell GEPs may be selected using random sampling without replacement (fractional sample sizes may be rounded up such that 2 cells were sampled if only 3 were available). The profiles may be aggregated by summation in non-log linear space and each population-level GEP may be normalized into TPM. This process may be repeated in order to generate aggregated transcriptome replicates (e.g., 2, 3, 4, 5, or more than 5) per cell type. For example, scRNA-Seq and bulk RNA-Seq signature matrices may be generated as described previously with the following typical parameters: minimum number of genes per cell type=300, maximum number of genes per cell type=500, q-value of 0.01, and no quantile normalization.

Figure 2:
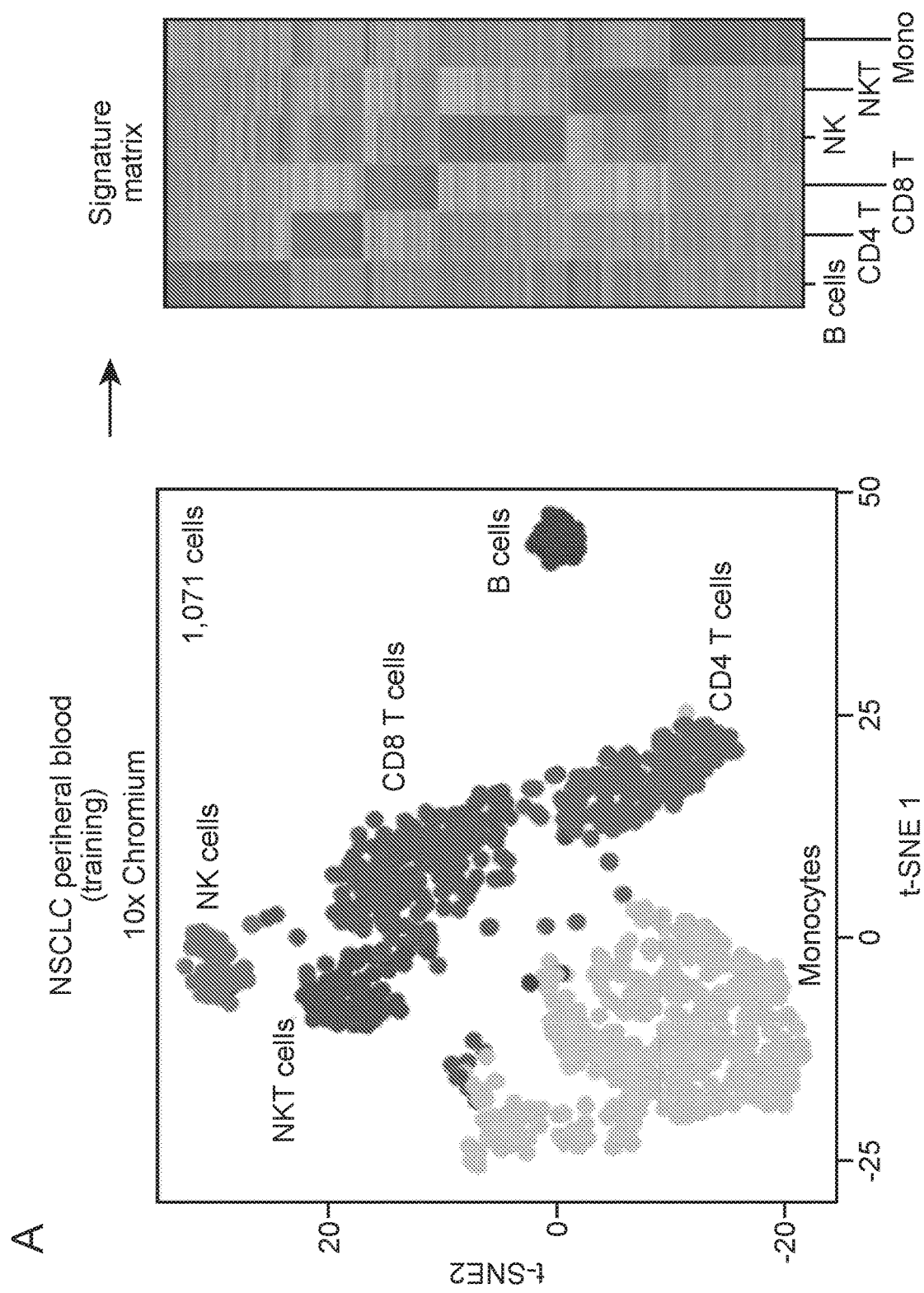
FIGS. 2a-f illustrate bulk tissue deconvolution with single-cell reference profiles. (2a) Left: d t-Distributed Stochastic Neighbor Embedding (t-SNE) embedding of scRNA-Seq data from the peripheral blood of a patient with non-small cell lung cancer (NSCLC), with 6 major leukocyte populations indicated. Right: Heat map of signature matrix genes. (2b) Enumeration of leukocyte frequencies in whole blood (n=12 healthy donors) using the PBMC signature matrix from panel (2a), shown before and after batch correction. Performance is shown as RMSE and assessed across 5 cell types for each blood sample, as compared to ground truth proportions determined by flow cytometry and complete blood counts (CBCs). The following cell types were evaluated: B cells (B), NK cells (NK), CD8 T cells (CD8), CD4 T cells (CD4), and monocytes (Mono). Statistical significance was determined using a Wilcoxon signed-rank test. (2c) t-SNE depiction of scRNA-Seq data from 23 head and neck squamous cell carcinoma tumors (left) and approach for testing single-cell deconvolution performance (right). Macs indicate macrophages; DCs indicate dendritic cells; CAFs indicate cancer-associated fibroblasts; Endo indicates endothelial cells; and Myo indicates myocytes. (2d) Concordance between cell type proportions measured by scRNA-Seq and CIBERSORTx deconvolution for 20 held-out head and neck squamous cell carcinoma (HNSCC) tumors from panel (2c). All tumor GEPs were reconstructed from single-cell data. (2e) Analysis of cell subset enumeration across diverse signature matrices, tissues, and platforms. Deconvolution was run with B-mode (LM22, HNSCC, and melanoma signature matrices) or S-mode (5' PBMC and 3' PBMC signature matrices) batch correction (FIGS. 7a-h). Ground truth cell proportions were determined by scRNA-Seq (HNSCC, melanoma) or by flow cytometry and Coulter counter (blood). Cell subsets within the gray band are significantly concordant with ground truth by Pearson correlation (P<0.05). Signature matrices are provided in FIG. 25, with the exception of LM22, which has been previously reported. HNSCC, head and neck squamous cell carcinoma. Cell subset abbreviations: DC, dendritic cells; Mast, mast cells; Endo, endothelial cells; CAF, cancer-associated fibroblasts. (2f) Left: t-SNE plot of pancreatic islet subsets from ten donors, five of which were profiled by scRNA-Seq, bulk RNA-Seq, and IHC (see also FIGS. 8f-i). Right: Scatterplots depicting concordance between the frequencies of four major islet subsets quantitated by IHC versus scRNA-Seq (top) and CIBERSORTx deconvolution of bulk RNA-Seq (bottom).
Figure 2:
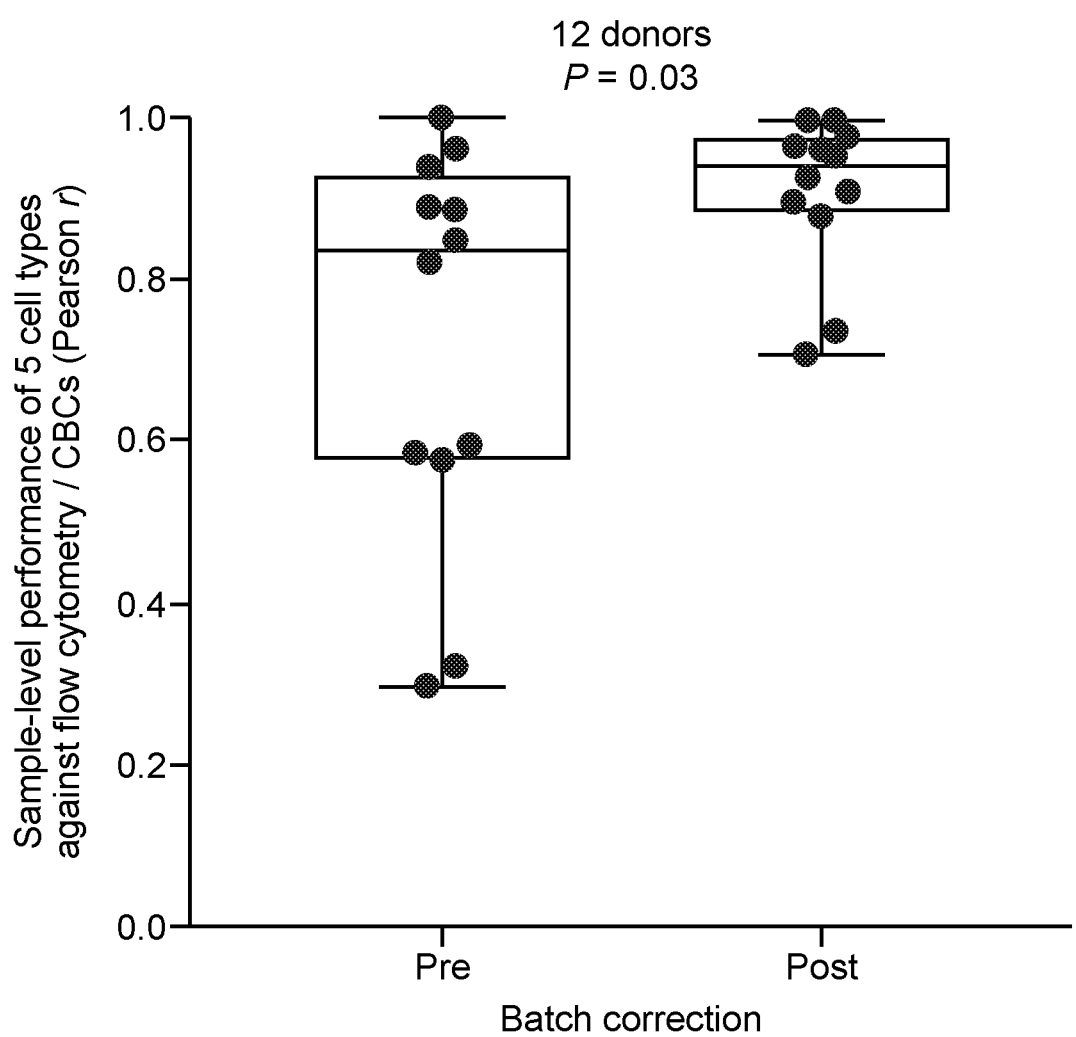
Figure 2:
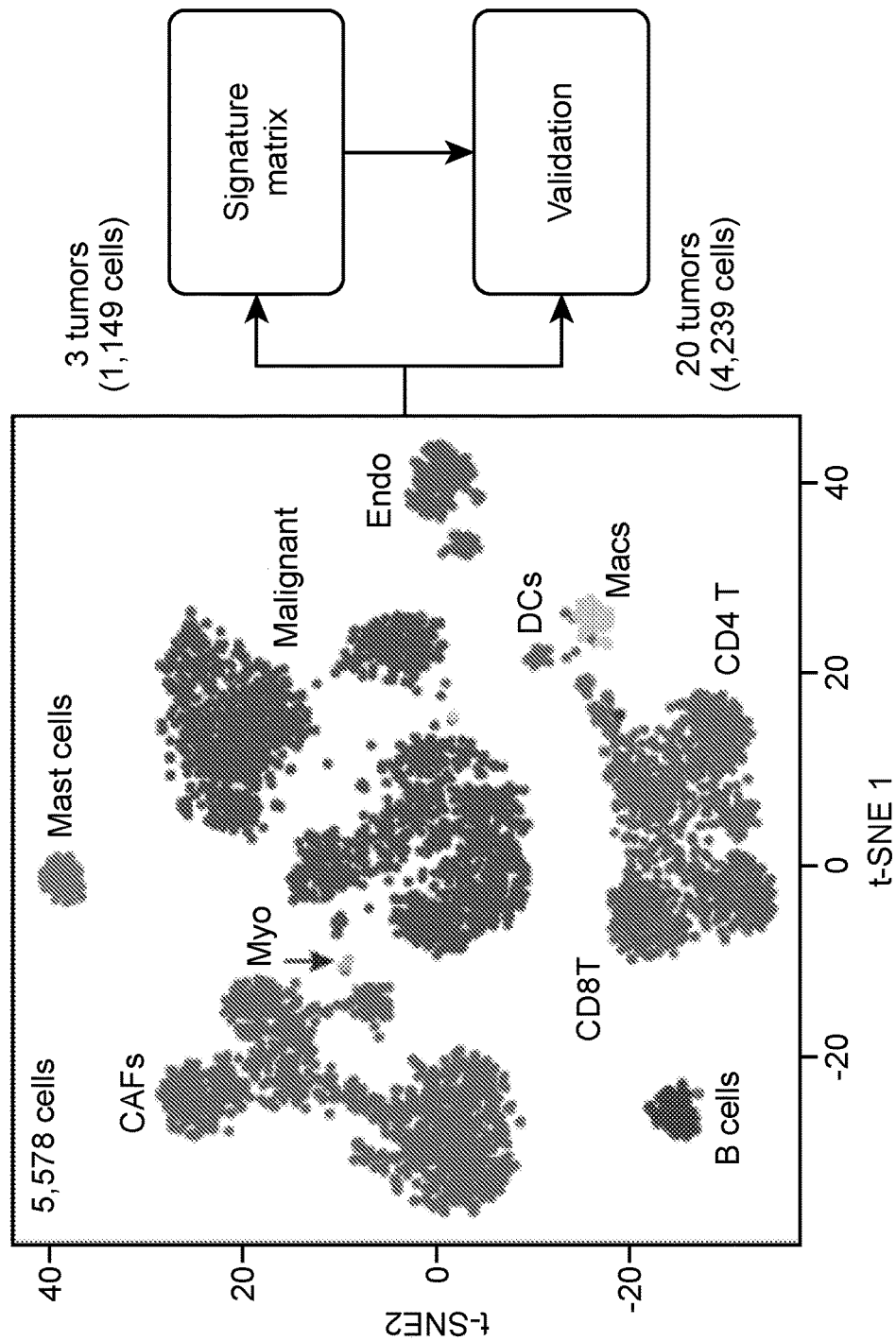
Figure 2:
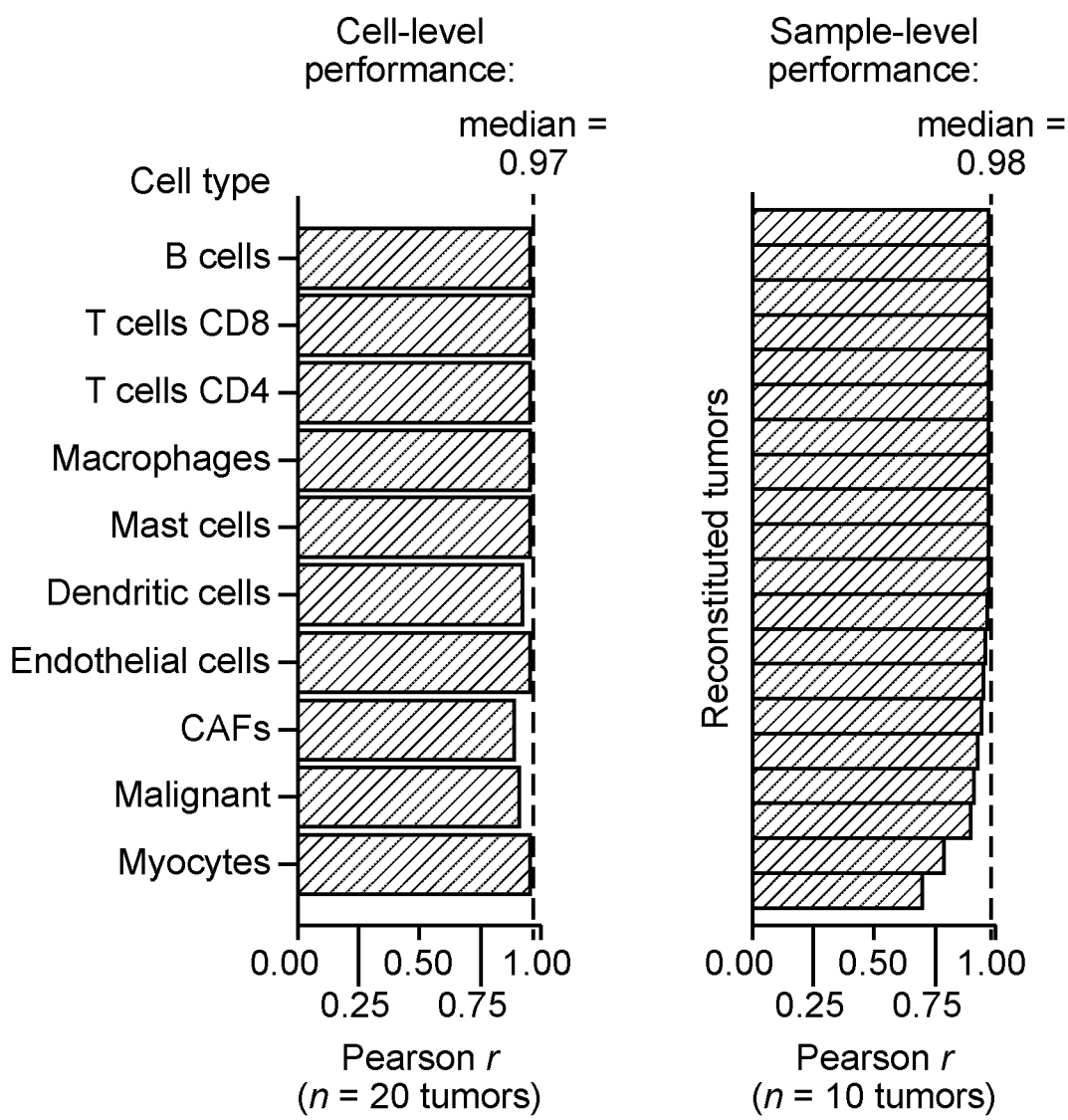
Figure 2:
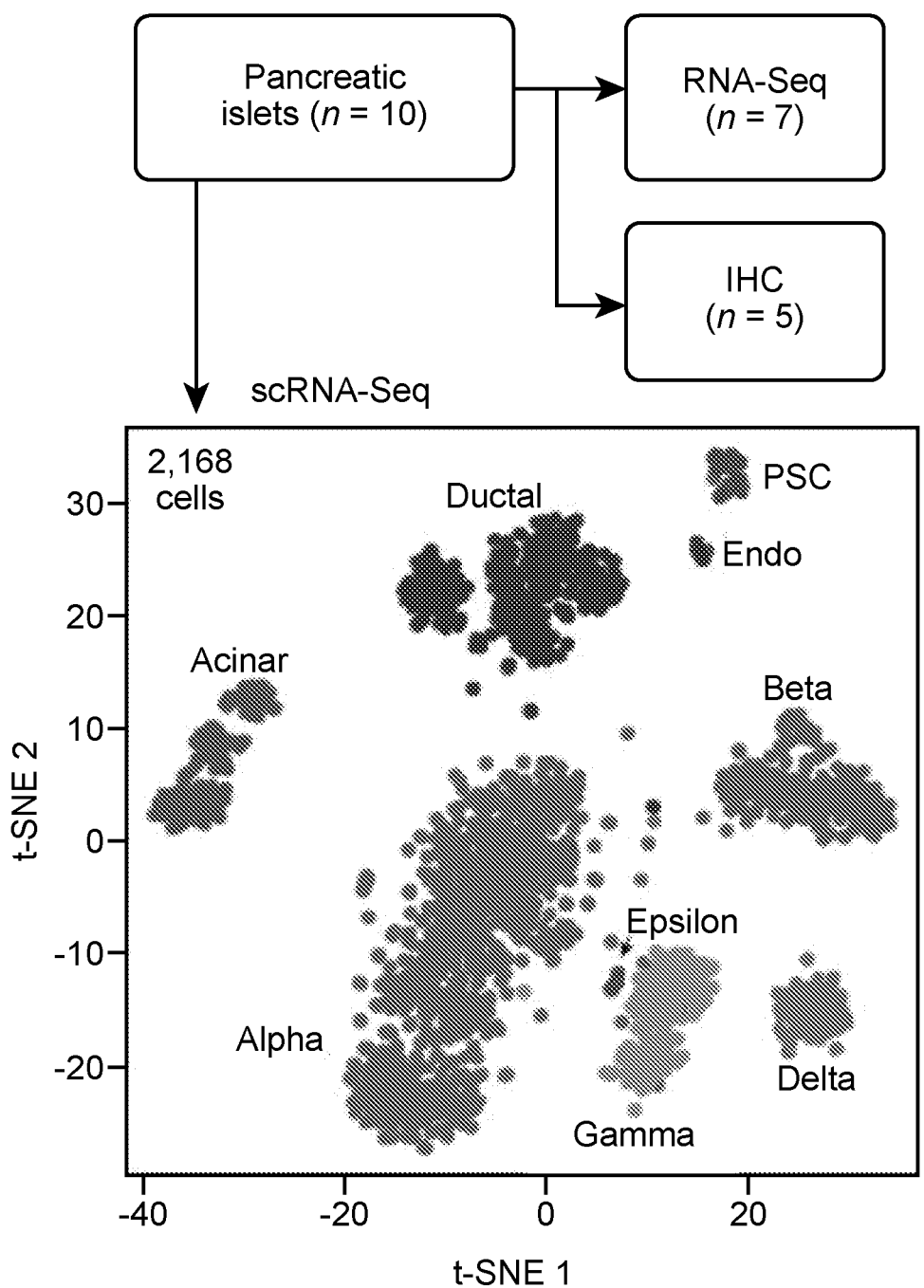
Figure 2:
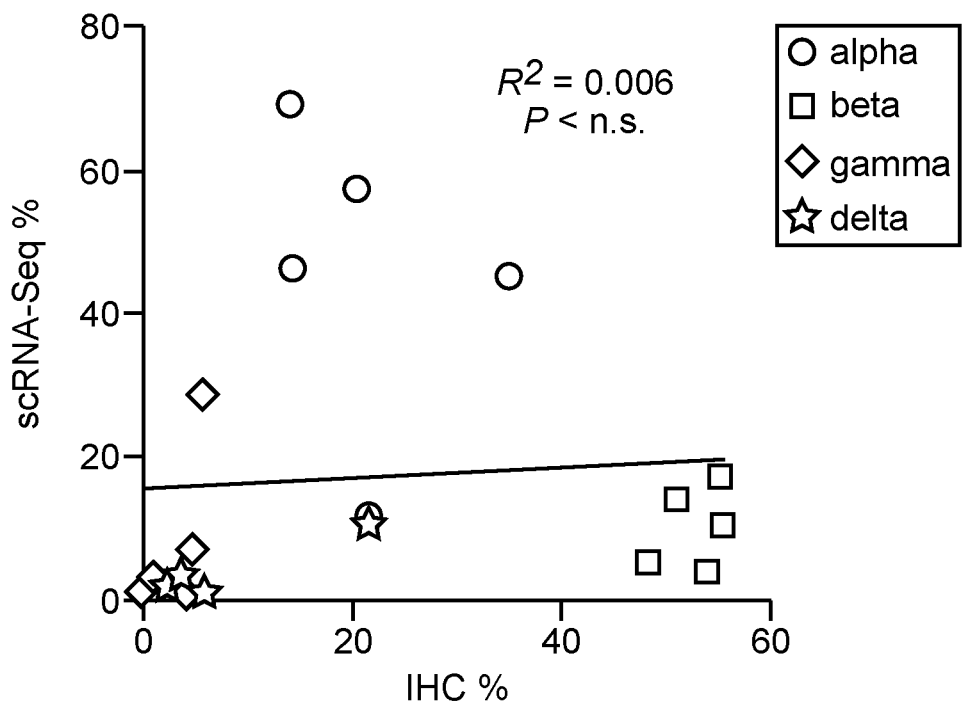
Figure 2:
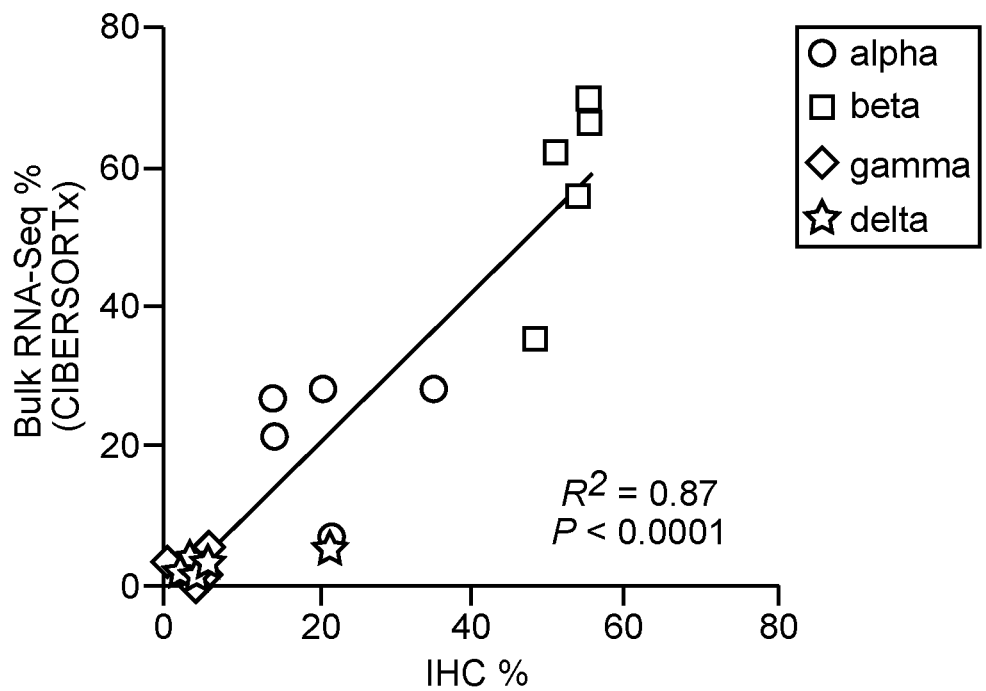

For example, signature matrices derived from HNSCC scRNA-Seq data may be trained on tumor ID MEEI18 (primary tumor) and MEEI25 (primary tumor and paired lymph node metastasis) (FIG. 2c). As another example, signature matrices derived from the scRNA-Seq data may be trained on tumor IDs 80 and 88 (FIGS. 6a, 8b-e, 9, 15, and 19). Previously annotated cell phenotype labels may be employed in both cases, with the exception of CD8 T cells, which may be defined as T lymphocytes expressing CD8A or CD8B (non-log TPM>0). A pancreatic islet signature matrix (FIGS. 2f and 8f-i) may be trained on sample IDs HP1508501T2D and HP1504901 using the previously assigned cell phenotypes. Mast cells and major histocompatibility complex (MHC) II cells may be omitted from the islet signature matrix if they have insufficient single cells in the training cohort (e.g., fewer than 3 cells). Glucagon, a highly expressed marker gene in alpha cells, may be omitted since it may adversely affect deconvolution performance on pancreatic islet training data.

Figure 9:
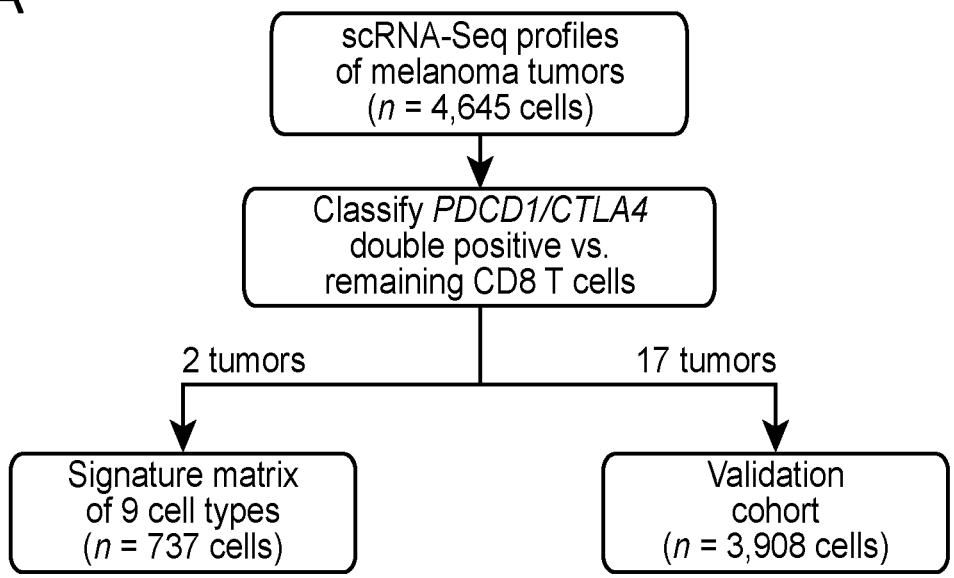
FIGS. 9a-b illustrate evaluation of digital gating for deconvolution of specific cell subsets in bulk tissue expression profiles. (9a) Schema for creating and validating a single cell-derived signature matrix to enumerate PDCD1+/CTLA4+ CD8 T cells along with eight other major melanoma tumor cell types (shown in panel (b), upper left). (9b) The framework in panel (9a) was applied to create three additional signature matrices: one testing the performance of PDCD1+ CD8 T cells, one assessing CTLA4+ CD8 T cells, and one evaluating tissue resident memory (TRM) CD8 T cells. Shown are bar plots depicting the deconvolution performance of each signature matrix applied to 17 reconstituted melanoma tumors held out from signature matrix construction. The Pearson correlation (and corresponding statistical significance) between imputed and known cell proportions is provided for each cell subset.
Figure 9:
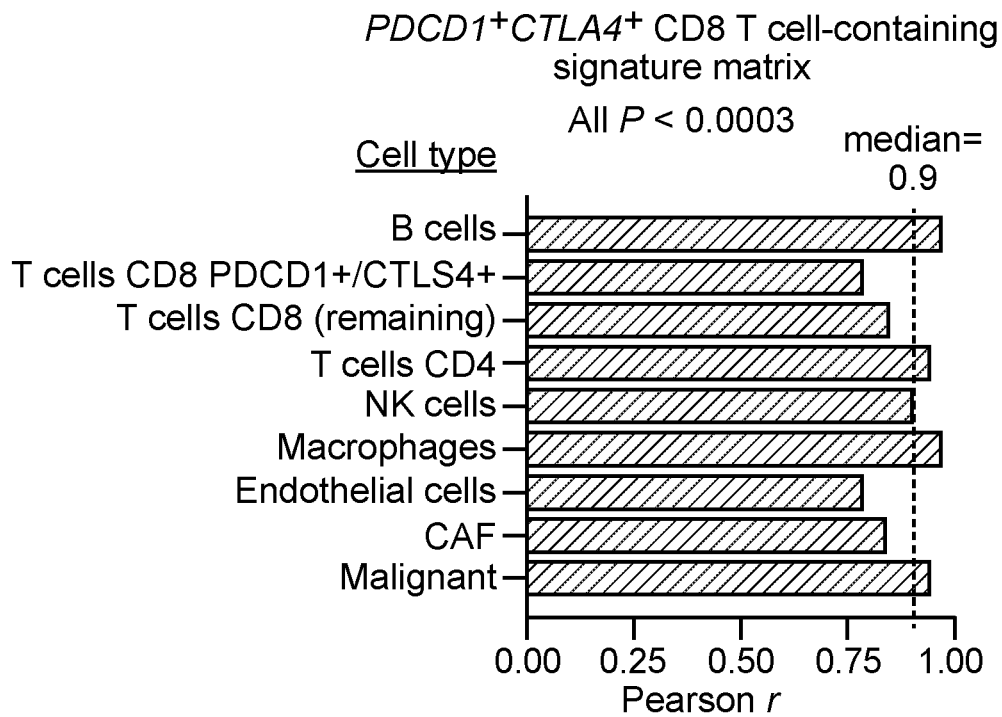
Figure 9:
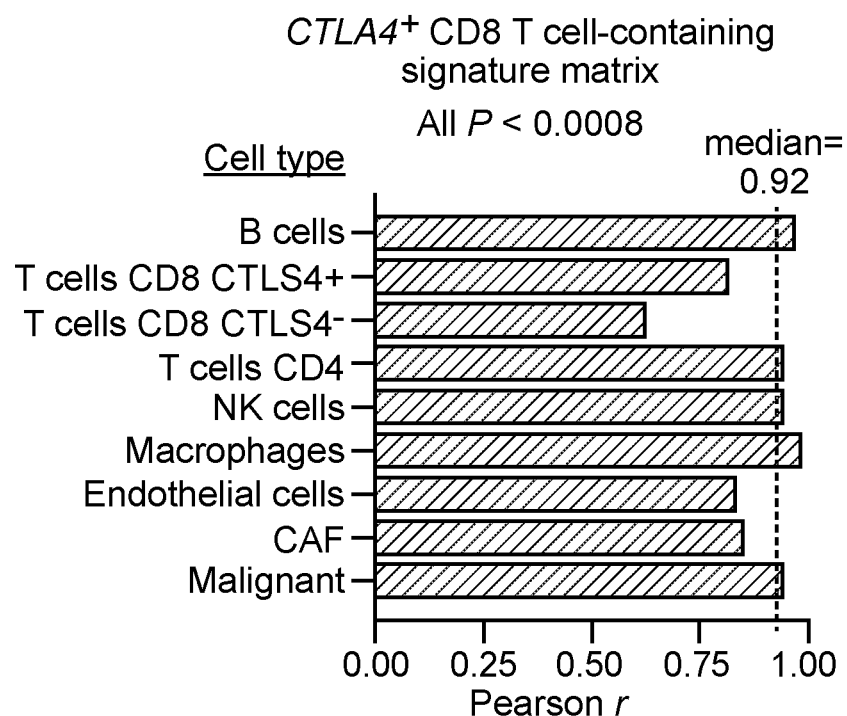
Figure 9:
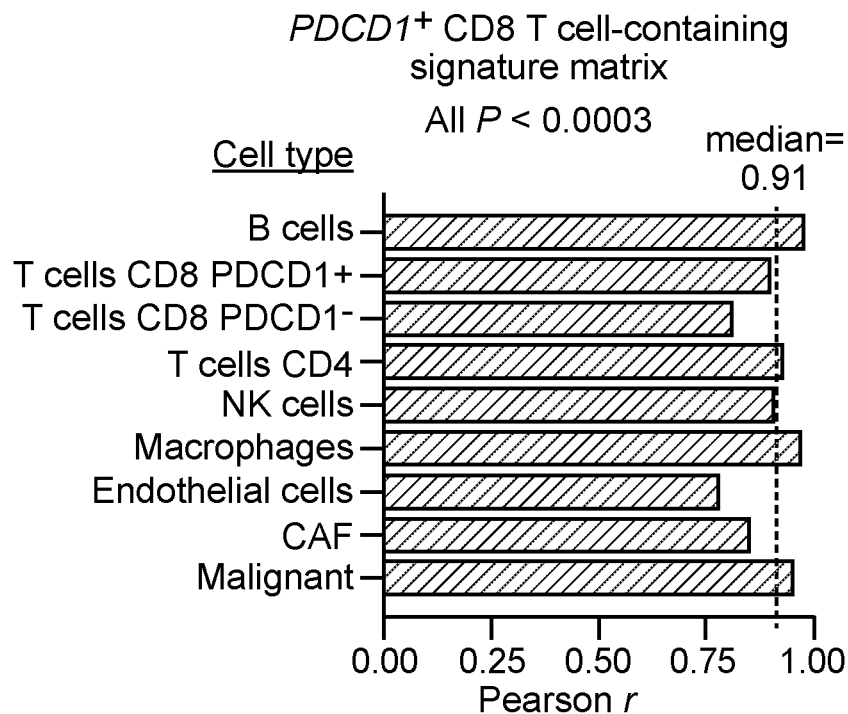
Figure 9:
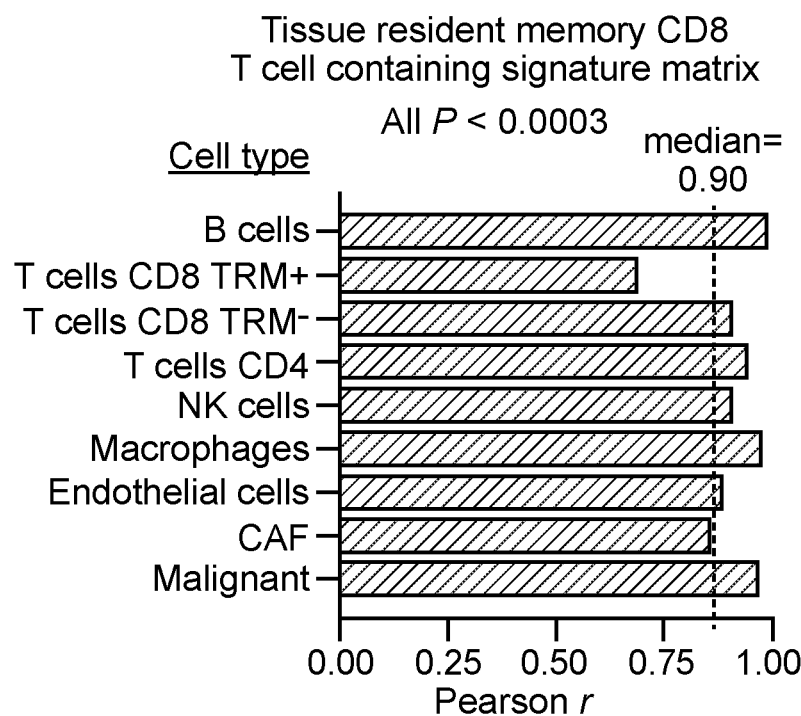

The term "digital gating," as used herein, generally refers to sorting (such as by selection, inclusion, or exclusion) cell populations into two or more distinct sets (e.g., based on high/low or high/medium/low expression of a marker gene). As shown in FIGS. 6d and 9, single cells may be pre-labeled according to a plurality of (e.g., 7) previously annotated phenotypes: B cells, T cells, NK cells, macrophages, endothelial cells, cancer-associated fibroblasts, and malignant melanocytes. T lymphocytes may be further divided into CD4 and CD8 T cells by the expression of CD8A or CD8B (non-log TPM>0). For example, CD8 T cells may be further subdivided into distinct subpopulations as follows. To isolate candidate CD8 T cells positive for PDCD1 and/or CTLA4 expression, CD8 T cells may be split by the expression of PDCD1 (non-log TPM>5th percentile of PDCD1 expression values among CD8 T cells) and/or CTLA4 (non-log TPM>5th percentile of CTLA4 expression values among CD8 T cells). To isolate candidate tissue resident memory (TRM) CD8 T cells, CD8 T cells may be selected that express ITGAE (non-log TPM>0) and CD69 (non-log TPM>0), but not CCR7 (non-log TPM=0).

Visualization of scRNA-Seq data by t-distributed stochastic neighbor embedding (t-SNE) may be performed using an Rtsne package in R with default parameters. As shown in FIGS. 2f and 8f, ComBat may be to eliminate donor-specific variation prior to t-SNE projection.

Overview of CIBERSORTx Analytical Framework

Various computational methods may be developed to infer cell type abundance, cell type-specific GEPs, or both from bulk tissue expression profiles. These methods may assume that biological mixture samples can be modeled as a system of linear equations, where a single mixture transcriptome m with n genes is represented as the product of H, a n×k cell type expression matrix consisting of expression profiles for the same n genes across k distinct cell types, and a vector f of size k, consisting of cell type mixing proportions.

As an example of a method to infer cell type abundance using this model within CIBERSORTx, let M be an n×c matrix with n genes and c mixture GEPs, and let matrix B be a subset of H containing discriminatory marker genes for each of the k cell subsets (e.g., signature or basis matrix). Given M and B, the following equation can then be used to impute F, a k×c fractional abundance matrix with columns $[f_1, f_2, \ldots, f_c]$:

$$B \times F_{\bullet,j} = M_{\bullet,j}, \quad 1 \leq j \leq c \qquad (1)$$

where $F_{i,j} \geq 0$ for all i, j, the system is overdetermined (e.g., n>k), and expression data in m and B are represented in non-log linear space. (Note that $M_{i,\bullet}$ and $M_{\bullet,j}$ may denote row i and column j of matrix M, respectively). Some approaches may either normalize F or impose an additional constraint on F such that for each mixture sample, the inferred mixing coefficients sum to one, allowing F to be directly interpreted as cell type proportions (with respect to the cell subsets in B). For example, a CIBERSORT method may be used to estimate F using an implementation of v-support vector regression, which is a machine learning technique that may be robust to noise, unknown mixture content, and collinearity among cell type reference profiles (as described, for example, in U.S Pat. Pub. No. US2016/0217253, which is hereby incorporated by reference in its entirety). The CIBERSORT method can be used to impute F, e.g., with a suitable batch correction technique for cross-platform analyses.

Group-Level Cell Type-Specific Gene Expression Purification

Figure 11:
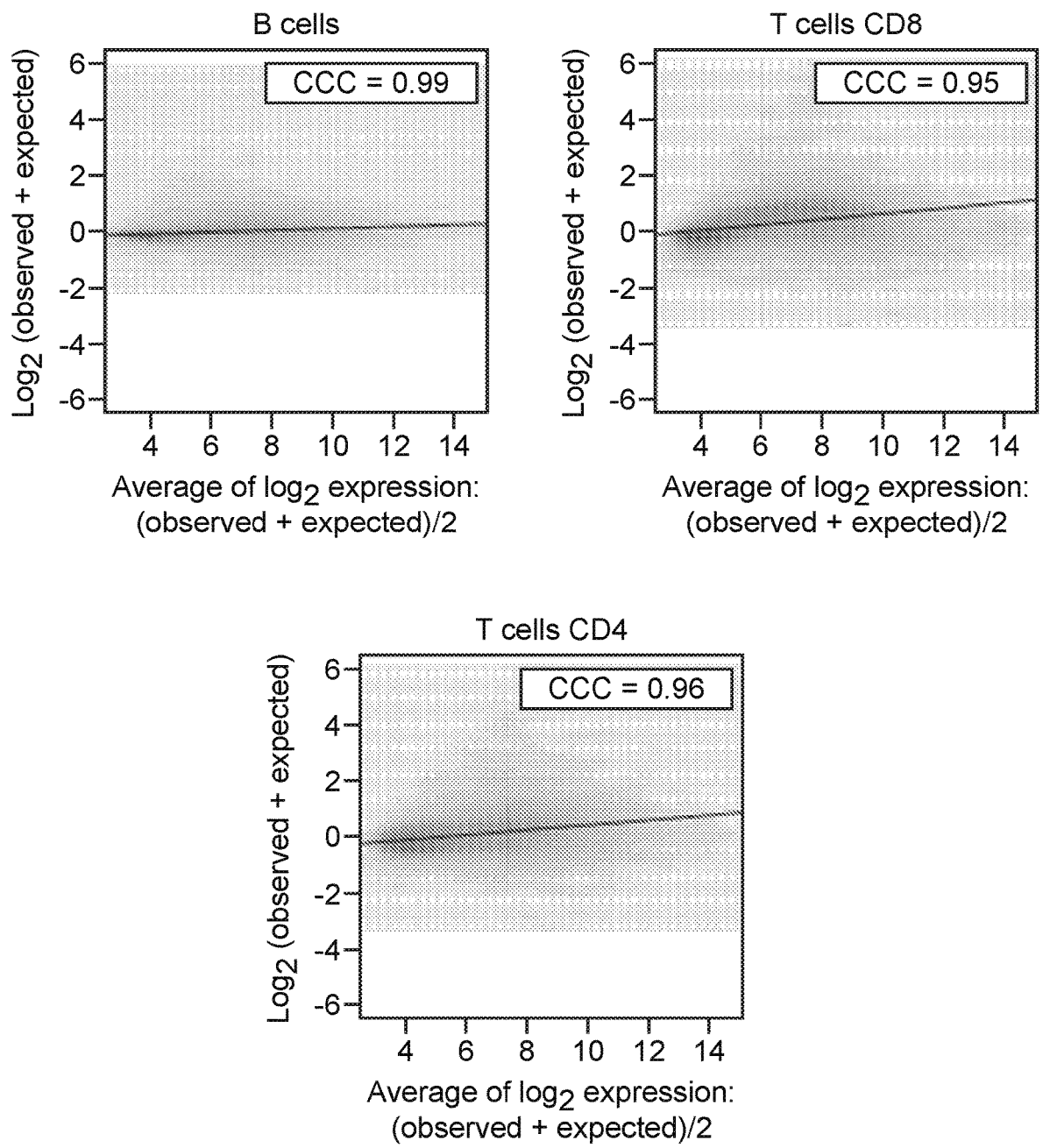
FIGS. 11a-h illustrate impact of key parameters on group-level expression purification. (11a) Bland-Altman plots for imputed group-level GEPs of B cells, CD8 T cells, and CD4 T cells learned from 302 FL tumor samples, related to FIG. 3d. Concordance is quantitatively captured by a linear regression line and a concordance correlation coefficient (CCC). (11b) Same as FIG. 3e, but showing the distribution of CCC values as a function of the number of tumors used for group-level GEP imputation, related to FIG. 3e. (11c) Related to FIG. 3e, but showing the number of detectable genes (e.g., genes with nonzero expression) in relation to the number of FL tumors used for expression imputation. Data are presented as boxplots (center line, median; box limits, upper and lower quartiles; whiskers, 1.5× interquartile range; points, outliers). (11d) Analysis of group-level expression purification for reconstructing the transcriptome of follicular helper T cells from 302 FL GEPs. The profile was generated as described for B cells and CD8 T cells in FIG. 3d. Imputed GEPs in panels a, b, and d were processed by adaptive noise filtration prior to analysis. (11e) Same as FIG. 3e, but showing the relationship between the number of mixture samples analyzed and the performance of leukocyte transcriptome imputation, shown before and after adaptive noise filtration, on a large cohort of PBMC samples. Samples were subsampled without replacement from the entire PBMC cohort (n=83) five times. The LM22 signature matrix was collapsed into 10 major leukocyte subsets after cell type enumeration and prior to transcriptome purification. Leukocyte reference profiles were derived from sorted peripheral blood populations obtained from healthy donors and normalized. (11f) Same as (11e), but showing the effect of the number of PBMC samples on the recovery of genes with nonzero expression. Lines in (11e) and (11f) are expressed as means with error bars indicating s.e.m. (11g) and (11h) Same as (11e) and (11f), but illustrating the impact of inferred leukocyte abundance on both the accuracy of transcriptome purification (11g) and the fraction of protein coding genes with nonzero expression (11h), both before and after adaptive noise filtration ('Unfiltered' and 'Filtered', respectively) on the same PBMC dataset. Linear regression lines in (d) were extrapolated to x=0 in order to model the impact of lower cell fractions on performance.
Figure 11:
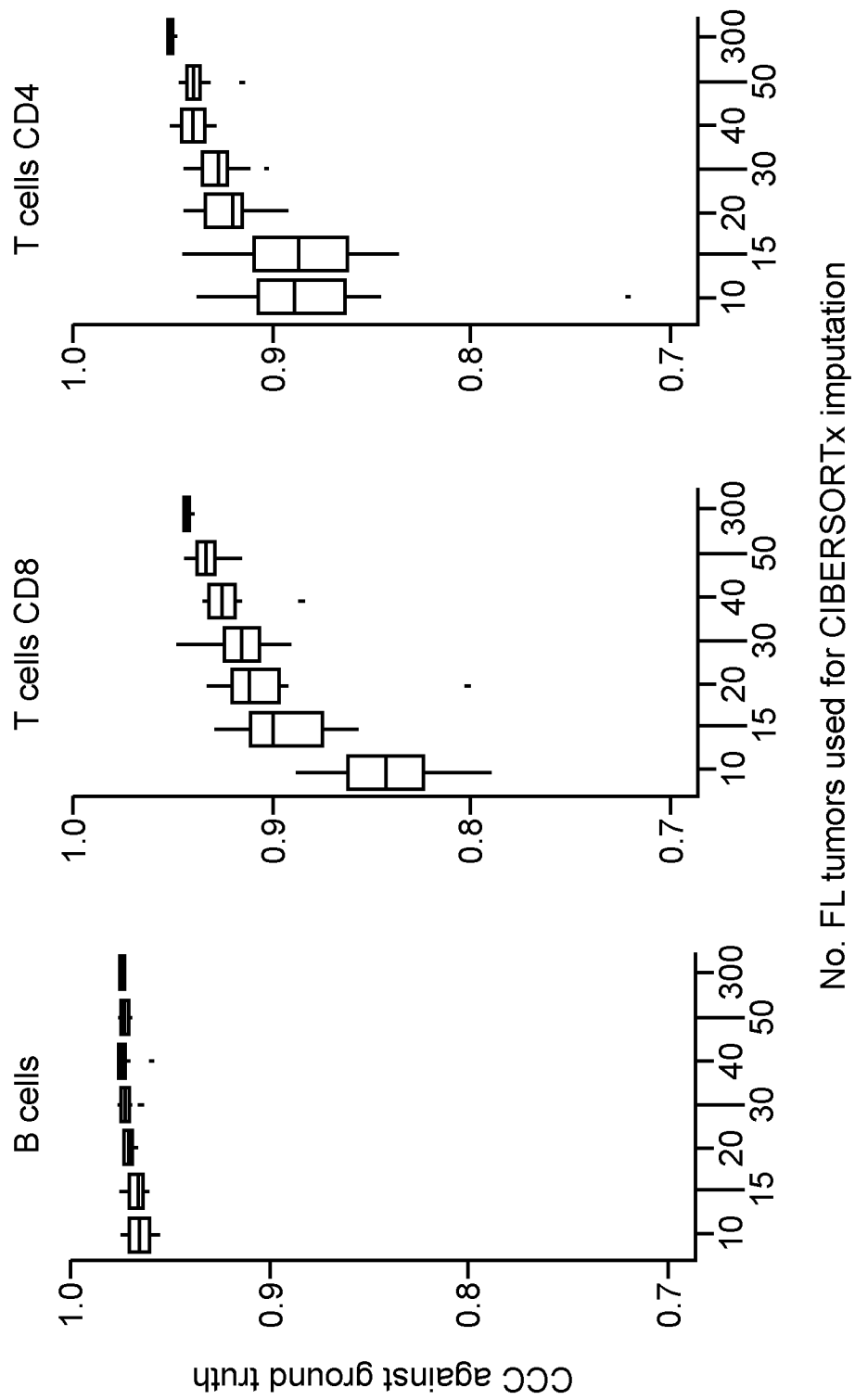
Figure 11:
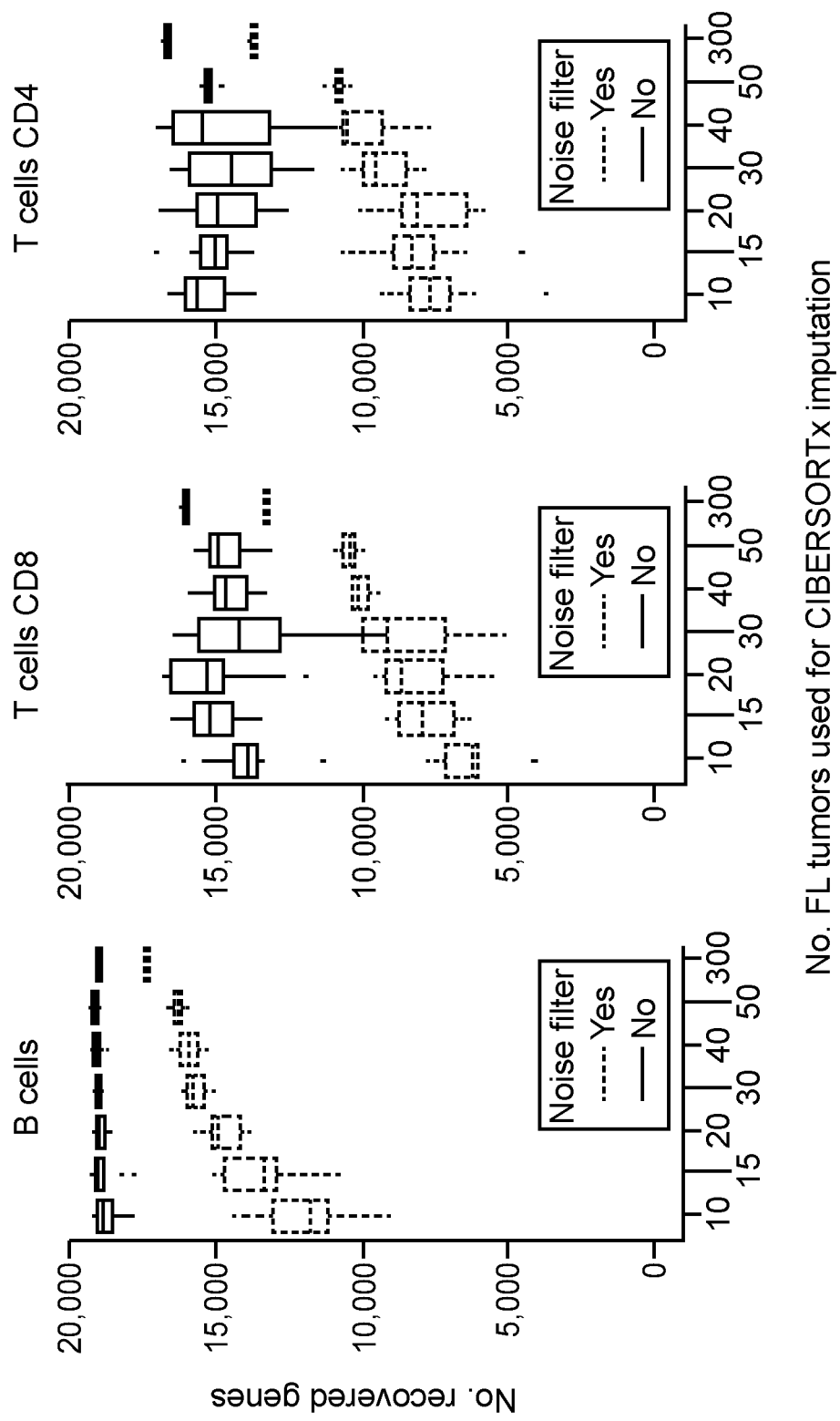
Figure 11:
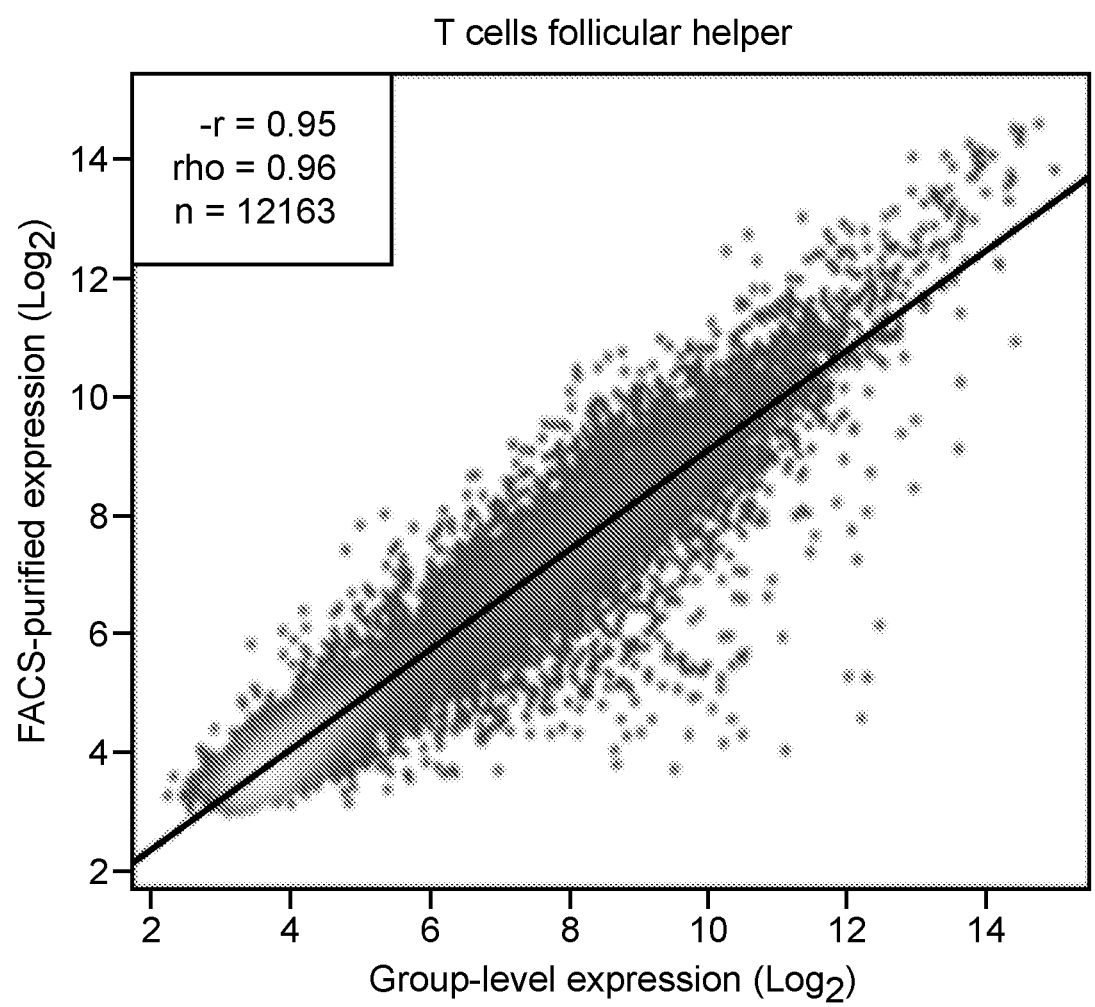
Figure 11:
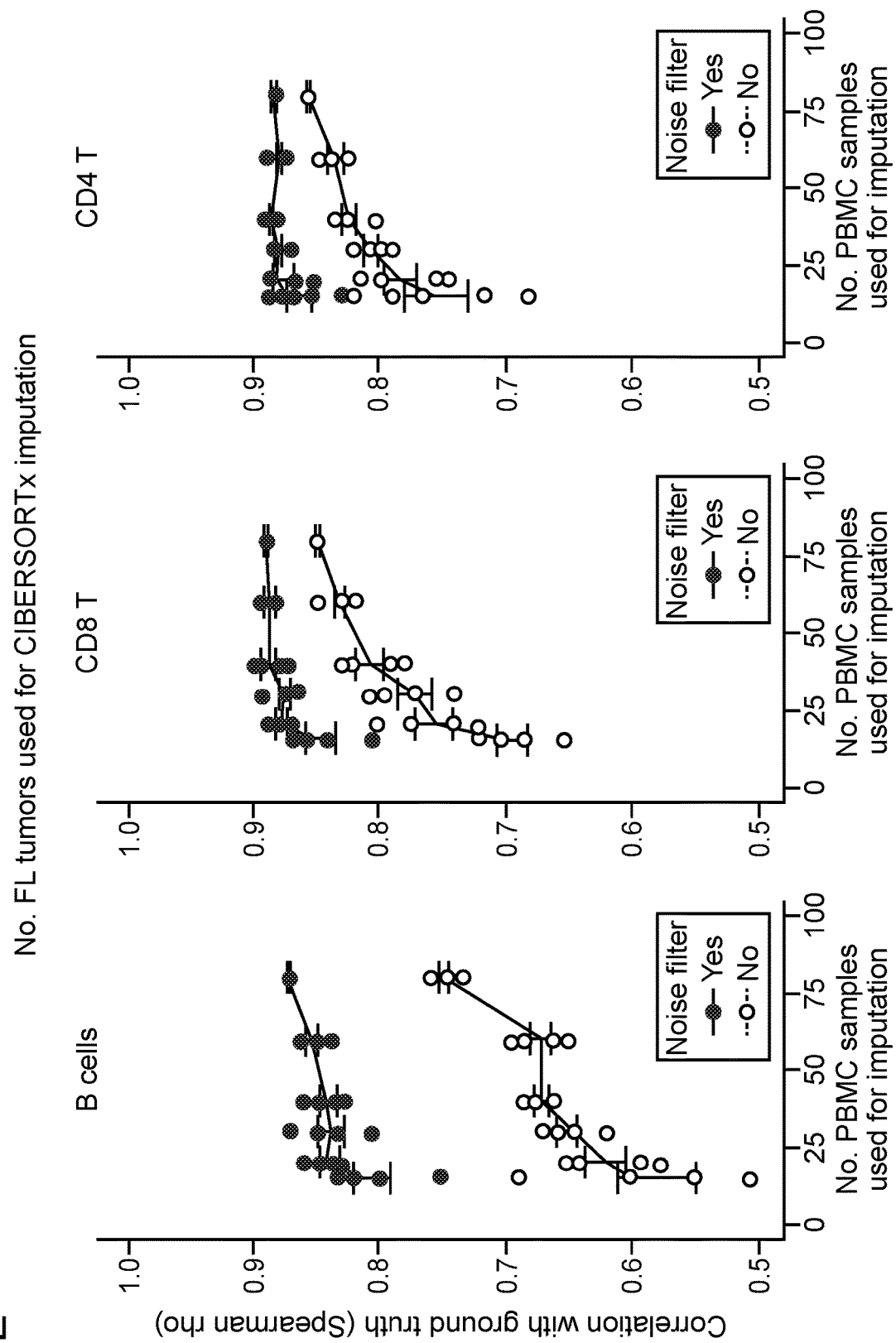
Figure 11:
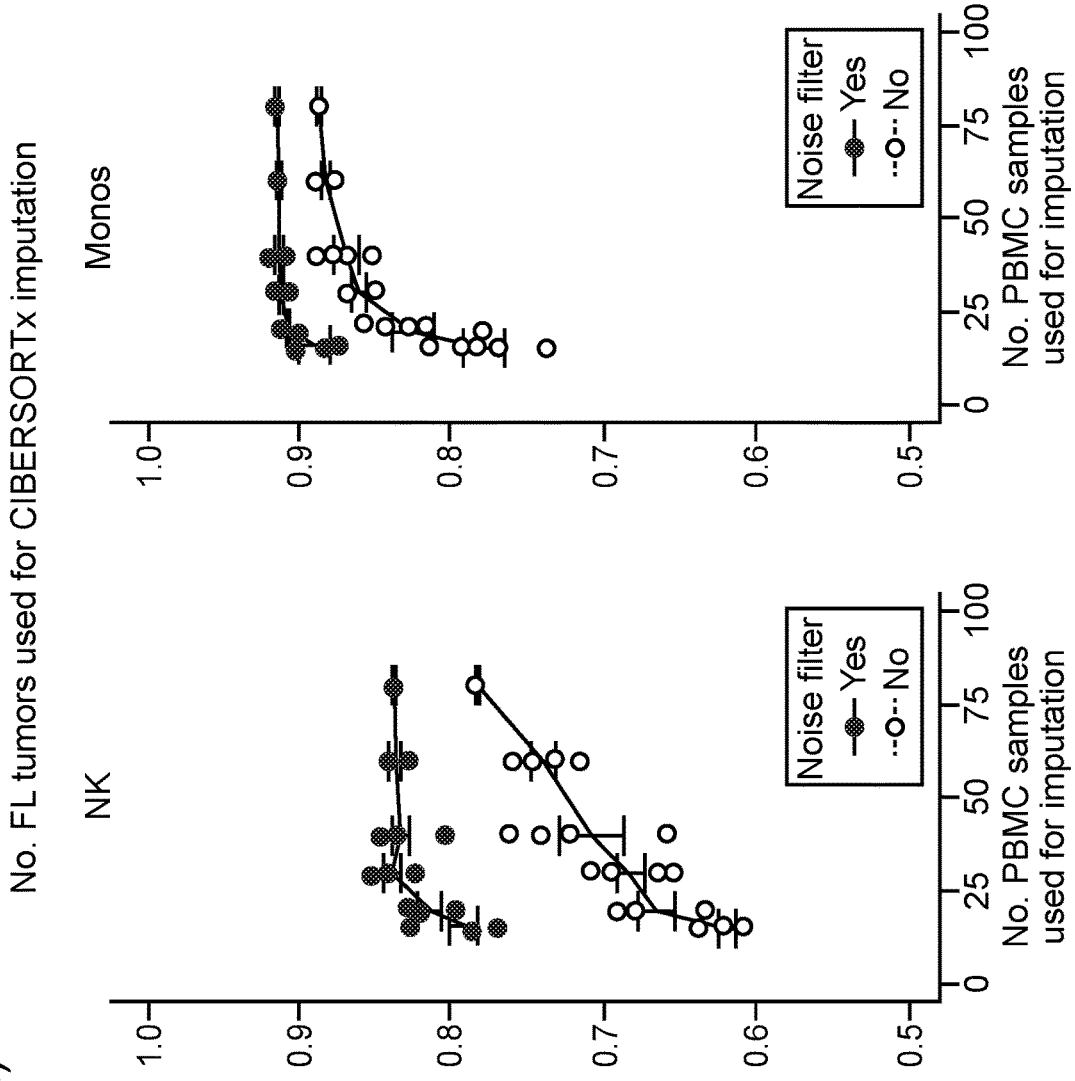
Figure 11:
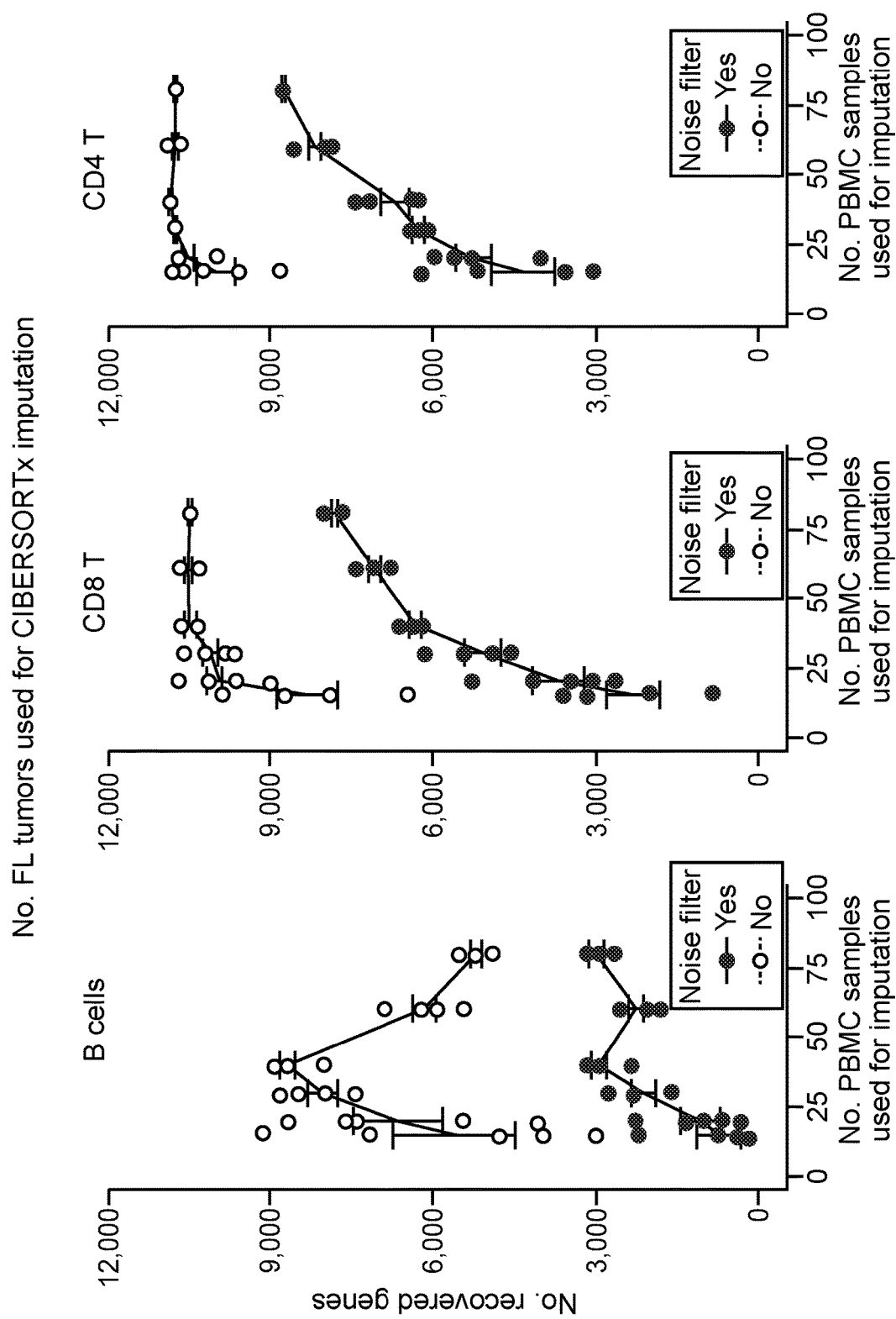
Figure 11:
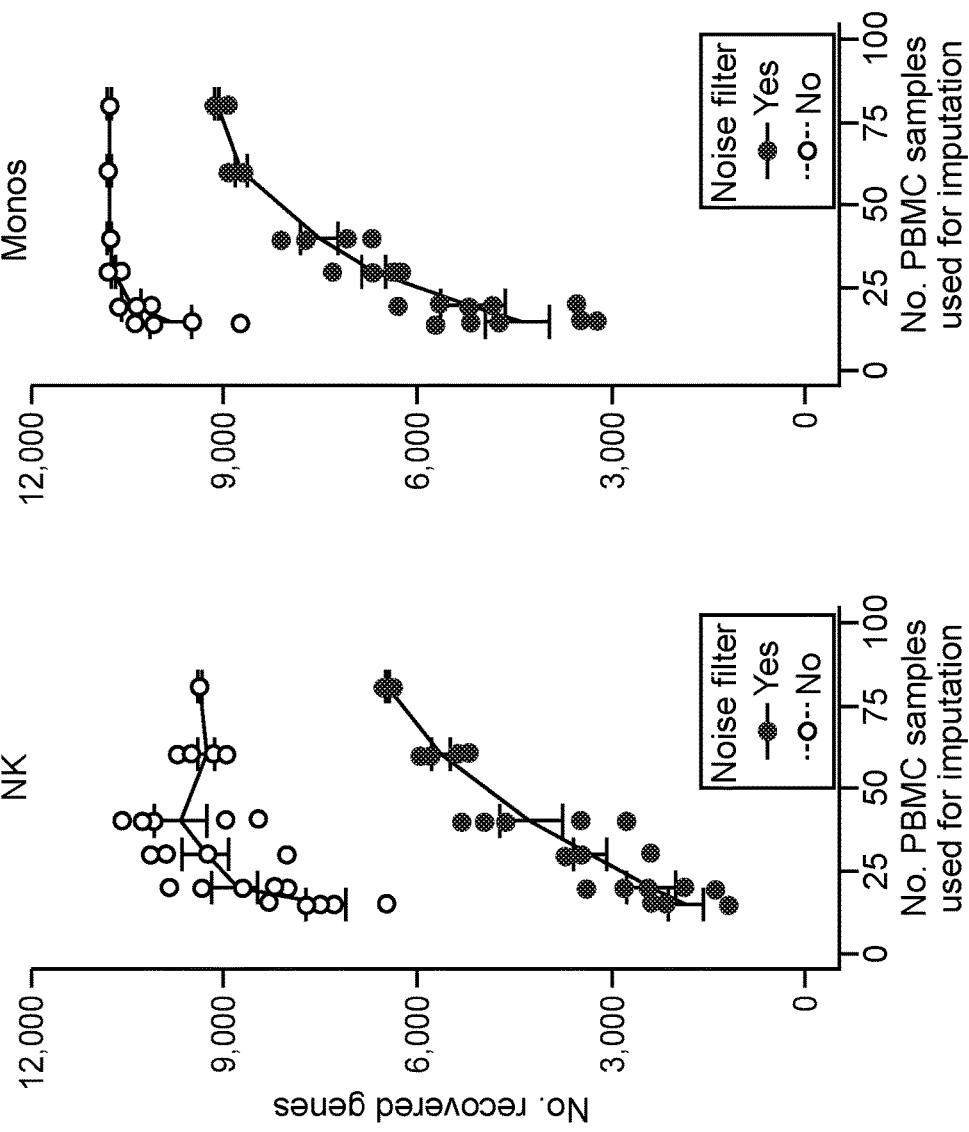
Figure 11:
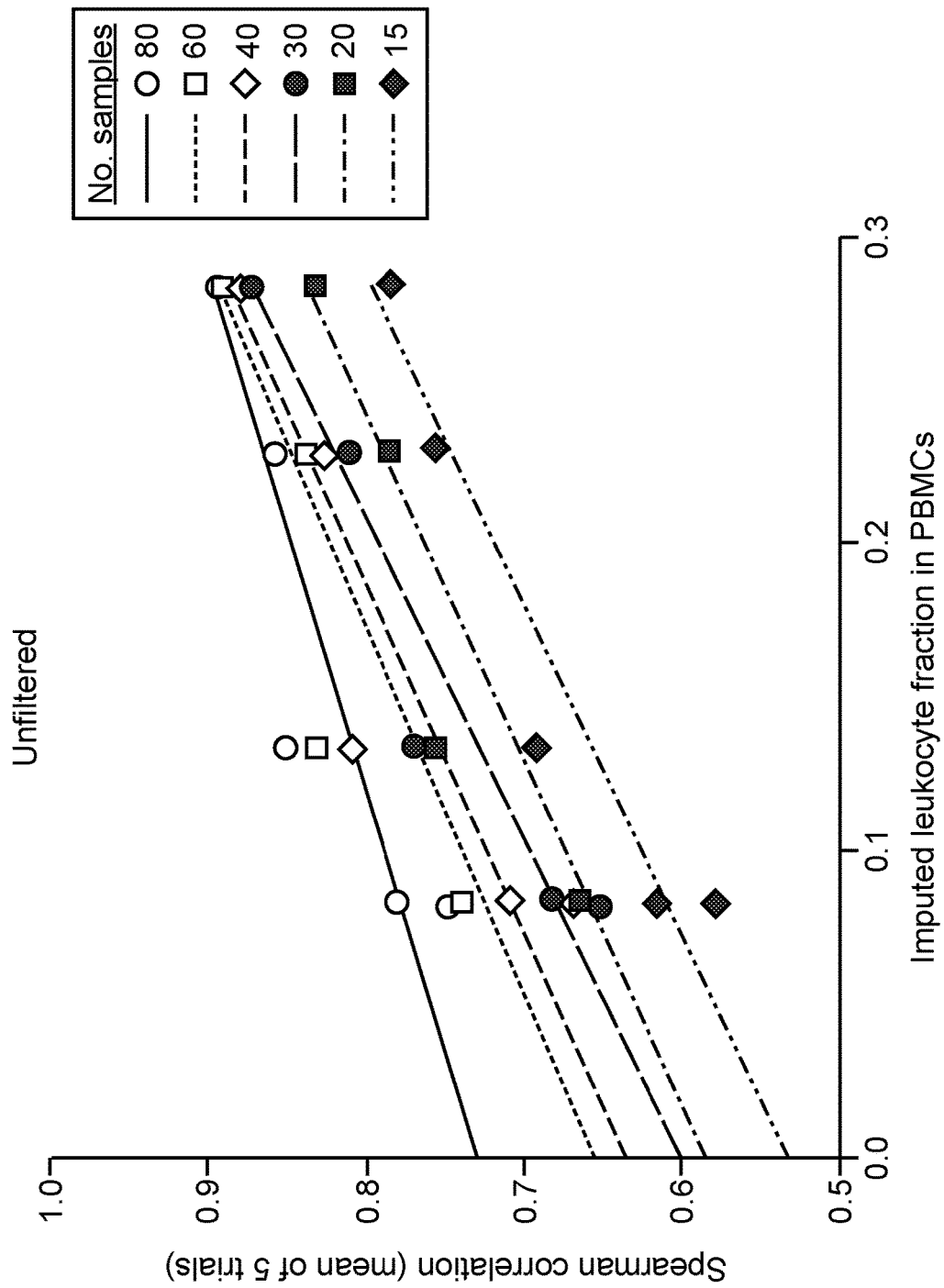
Figure 11:
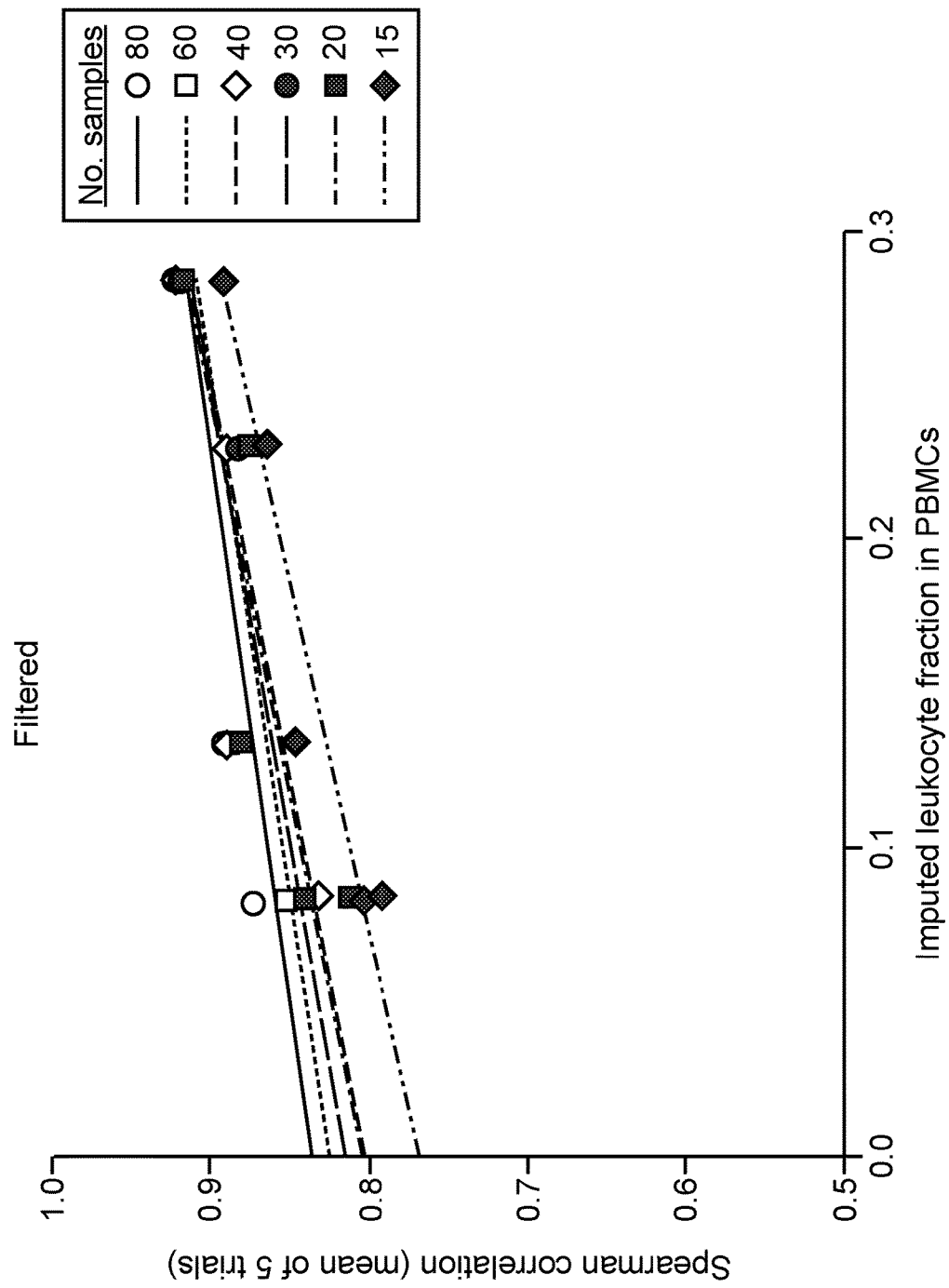
Figure 11:
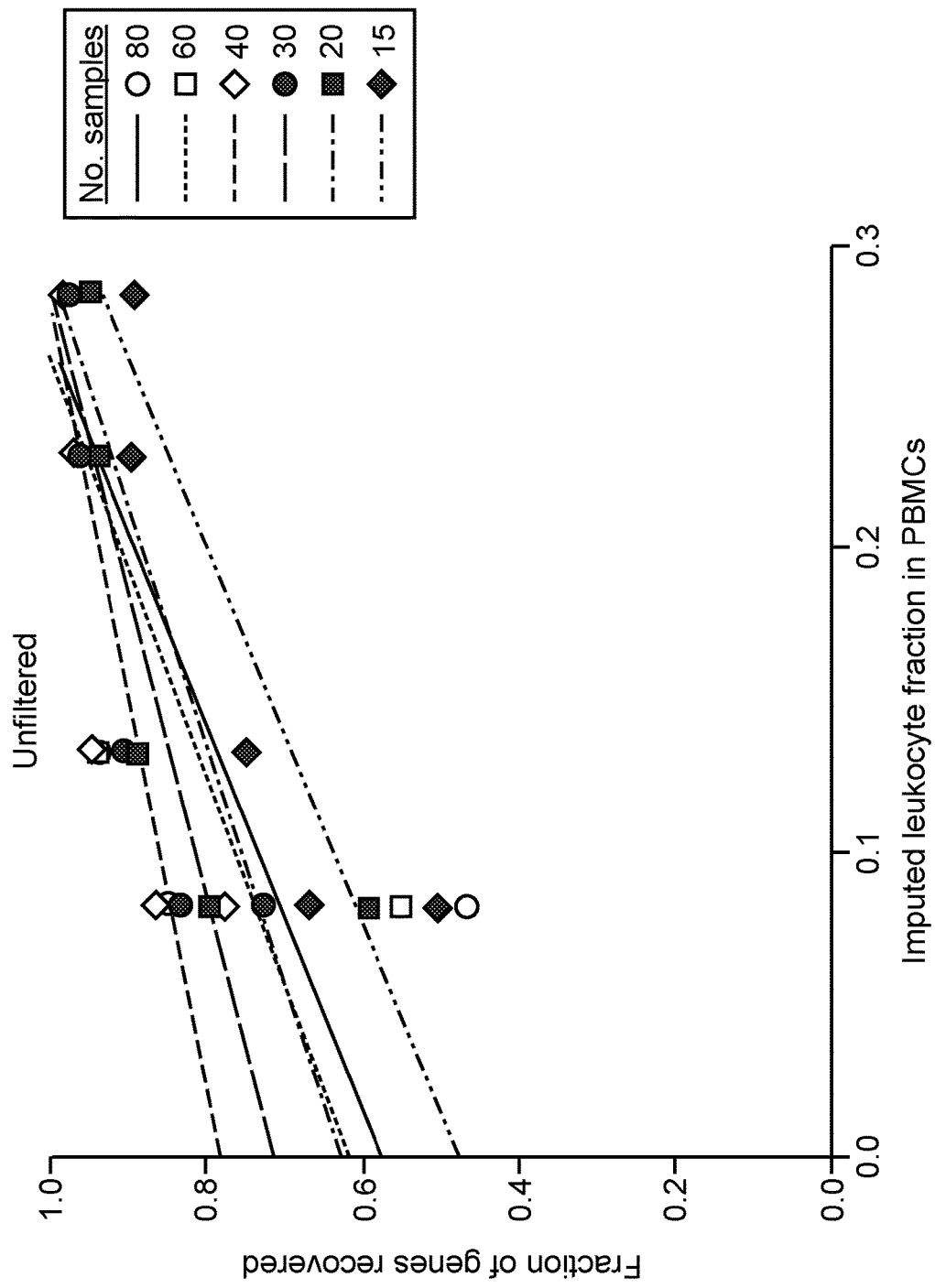
Figure 11:
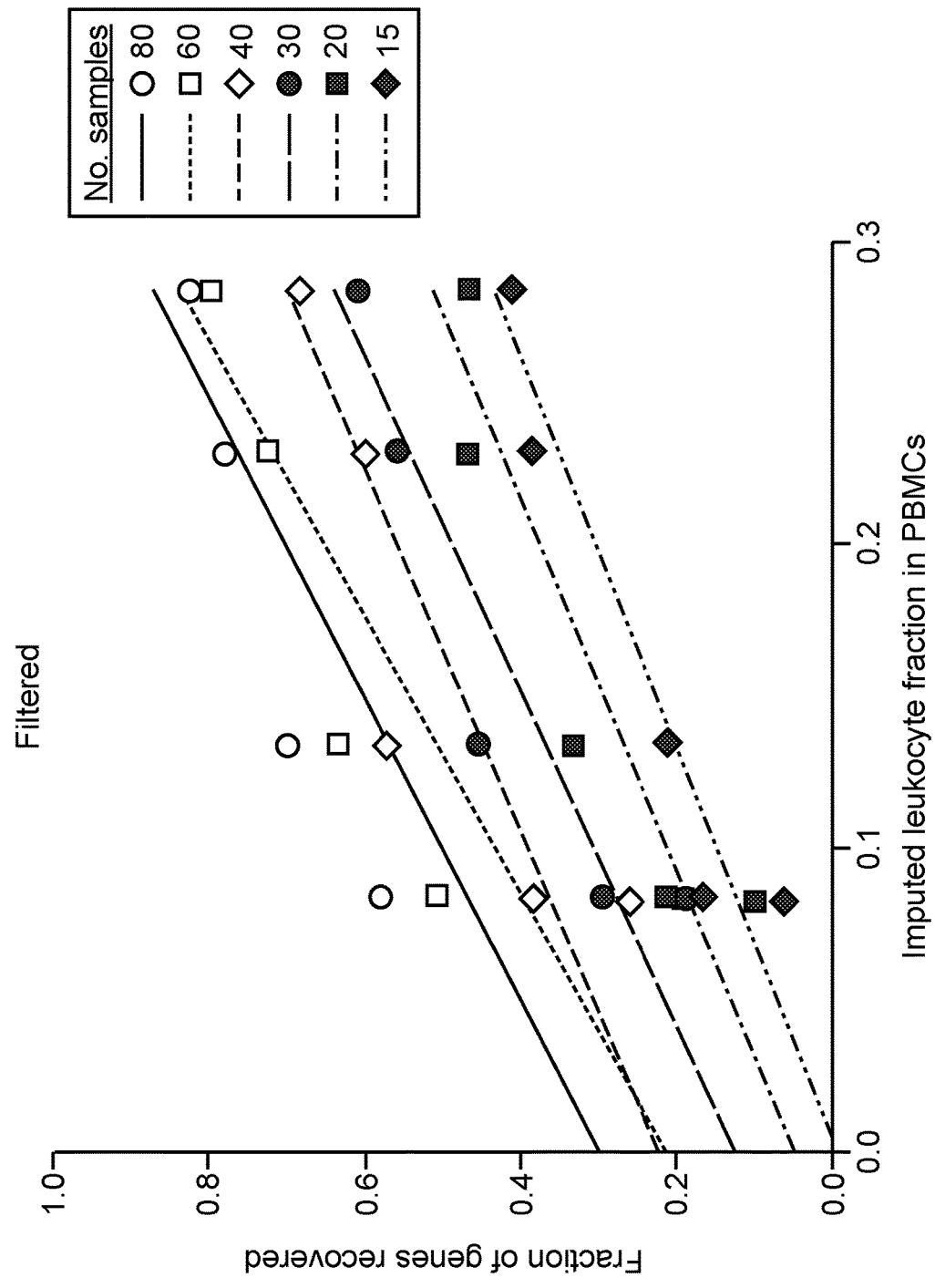

Once F is determined for M, either through expression deconvolution or prior knowledge (e.g., Coulter counter, flow cytometry), a representative imputed GEP for each cell type in F can be estimated by solving the following system of linear equations:

$$H_{i,\bullet} \times F = M_{i,\bullet}, \quad 1 \leq i \leq n \qquad (2)$$

where H is a n×k expression matrix of n genes and k cell types, $H_{i,j} \geq 0$ for all i, j, and F is defined as above with the constraint that relative cell fractions sum to one for each mixture sample. Like Equation 1 above, the system may be overdetermined (c>k), with a greater delta between c and k generally leading to improved GEP estimation (FIGS. 3e and 11). To ensure biologically realistic estimates of gene expression, non-negative least squares regression (NNLS) may be employed, an optimization framework to solve the least squares problem with non-negativity constraints. Although NNLS may be robust on simple mixtures and toy examples, its performance on more complex mixtures inherent within real tissue samples can be affected by noise, imprecision, and missing data in the linear system. A variety of data normalization and filtering techniques may be applied to help mitigate such issues (FIGS. 3b-d).

High-Resolution Expression Purification

Despite the utility of Equation 2 for imputing cell type-specific gene expression from bulk tissues (e.g., in silico purifications in FIGS. 3a-g), it may be limited to estimating a single representative GEP for each cell type. Therefore, to explore cell type-specific differentially expressed genes (DEGs) between a plurality of conditions of interest, cell type transcriptomes may need to be re-generated for each condition (e.g., responders versus non-responders to a given therapy, early versus advanced stage disease, etc.). To more broadly address this issue, the model in Equation 2 may be extended within a method for "high-resolution" in silico cell purification (e.g., CIBERSORTx).

Such an approach may comprise decomposing a matrix of bulk tissue GEPs (e.g., M) into k gene expression matrices of equal size, one for each cell subset in F. This method may be agnostic to phenotypic class structure and can be formulated as a non-negative matrix factorization (NMF) problem with partial observations. For example, let M and F be defined as above (n×c and c×k matrices, respectively), and assume the latter is estimated by CIBERSORT. Then, for each gene i, an expression matrix $G_i$, defined here as a c×k expression matrix of c mixture samples by k cell types, can be determined. Fixing M and F to solve for G may yield the following constrained matrix decomposition problem:

$$F \times G_{i,\bullet,\bullet} = P_{i,\bullet,\bullet}, \quad 1 \leq i \leq n \qquad (3)$$

where $$\mathrm{diag}(P_{i,\bullet,\bullet}) = M_{i,\bullet}, \quad 1 \leq i \leq n \qquad (4)$$

and $G_{i,j,k} \geq 0$ for all i, j, k. Unlike the linear systems in Equations 1 and 2, there may be no closed-form solutions for G, which may be a 3-dimensional (3D) n×c×k matrix, and existing techniques for non-negative matrix factorization (NMF) may be unlikely to yield biologically plausible estimates, especially without additional constraints (e.g., regularization). Therefore, a heuristic algorithm can be used to estimate G, depicted schematically in FIG. 14.

An approach for inferring G may make two distinct assumptions that may improve the tractability of the problem while generating biologically plausible solutions. First, an assumption may be made that each gene can be analyzed independently. Although ignoring gene-gene covariance relationships may impact the resolving power for some genes, this assumption may be found effective in practice (FIGS. 4a-e, 5, 6a-b, and 13). Second, for a given gene, as assumption may be made that at least some evidence of cell type-specific differential expression is detectable in bulk tissue samples, even if statistically insignificant.

This hypothesis may be evaluated using a previously published dataset of cell type-specific DEGs. Specifically, DEGs may be previously defined as those genes exhibiting >1.2-fold-change when considering expression within pancreatic endocrine islet cell types (e.g., 5 cell types) (where each cell type comprises about 5% to about 44% median fractional abundance within whole endocrine pancreatic islets), and comparing differential expression levels between non-diabetic normal subjects (e.g., 6 subjects) and patients with type 2 diabetes mellitus (T2D) (e.g., 4 patients). Importantly, these DEGs were identified by scRNA-seq profiling, allowing the testing for evidence of differential expression in bulk islets reconstructed in silico. When grouped by known phenotypic classes, 98% of DEGs associated with T2D show at least some fold difference in the correct orientation in reconstructed islets (FIG. 13a). This result may suggest that cell type-specific DEGs may be discernible in bulk tissues without prior knowledge of phenotypic class labels. Indeed, when each gene is independently ordered in reconstructed islets by expression levels, and each vector is split evenly into high and low expression groups (e.g., $50^{th}$ percentile split), data from diabetic patients may be skewed to low or high expression for 80% of previously defined cell type-specific DEGs. Among these genes, the enrichment direction matched the orientation of the known fold change in 99% of cases (FIG. 13b). Thus, variation in bulk gene expression data can be leveraged to infer latent phenotypic class structure in the underlying cell subpopulations.

Given these foundational assumptions along with a mixture matrix M and cell type fractional abundance matrix F, a heuristic algorithm can be developed for high-resolution purification. An overview of this heuristic is outlined below, with a corresponding graphical summary in FIG. 12c.

Figure 12:
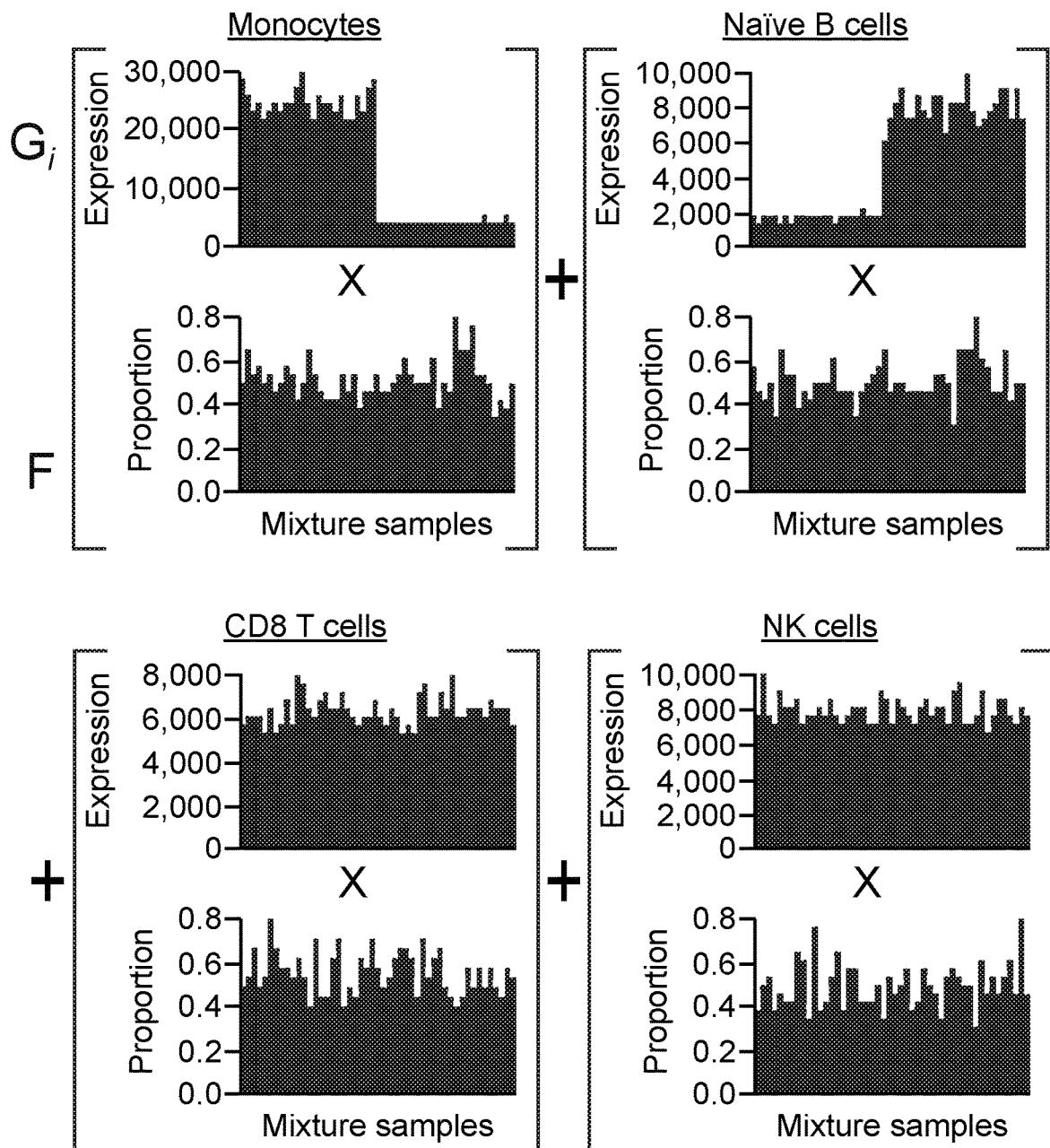
FIGS. 12a-c illustrate CIBERSORTx framework and approach for high-resolution expression purification. (12a) Key objective functions within the CIBERSORTx framework for (1) enumeration of cell proportions (Top), (2) imputation of representative cell type-specific transcriptomes, (Middle), and (3) high-resolution transcriptome purification (Bottom). Corresponding main figures are indicated to the right and unknown quantities are colored orange. (12b) Objective function for high-resolution CIBERSORTx. Here, M is known, F is previously estimated (panel (a), top), and G, the subject of estimation, is a three-dimensional matrix of n genes×c mixture samples×k cell types. (12c) Overview of high-resolution CIBERSORTx, illustrated by a simple anecdotal example. Here, a single gene is expressed by four immune subsets with mutually exclusive expression patterns in monocytes and naïve B cells and no differential expression in CD8 T cells and NK cells. The four profiles are randomly admixed into a bulk admixture GEP $M_i$. The algorithm proceeds in five major steps: (i) Sort the bulk profile in ascending order. (ii) Split the sorted vector by iterator t, and apply bootstrapped NNLS to either side of the ranked vector to impute representative cell type-specific expression coefficients ($g^t_1$ and $g^t_2$). Repeat this process for all possible values of t that satisfy regression constraints and window length w. (iii) For each value of t, estimate $M_i$ using $g^t_1$, $g^t_2$, and F and choose the $g^t_1$, $g^t_2$ pair that that results in the best approximation of $M_i$. (iv) Evaluate whether the expression estimates of gene i are significant for each cell type, and if so, whether expression is significantly different between each cell type of the best $g_1$ and $g_2$ pair from step iii. (v) Impute initial estimate of $G^*_i$ using bootstrapped NNLS and a sliding window, refine $g_1$, $g_2$ based on step iv, fit $\hat{G}_i$ to anchor coefficients (adjusted $g_1$, $g_2$), and restore the original ordering to finalize the estimate of $\hat{G}_i$.
Figure 12:
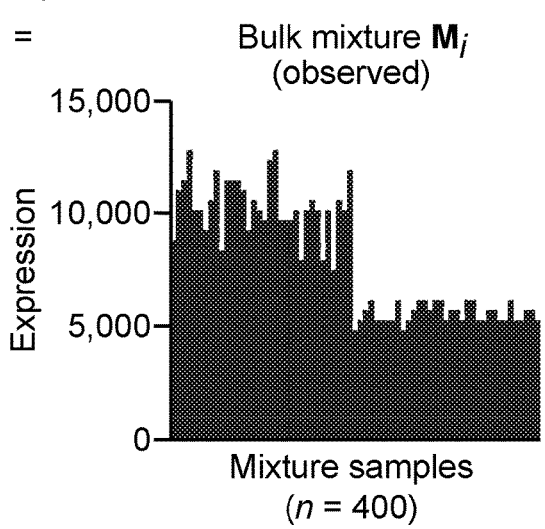
Figure 12:
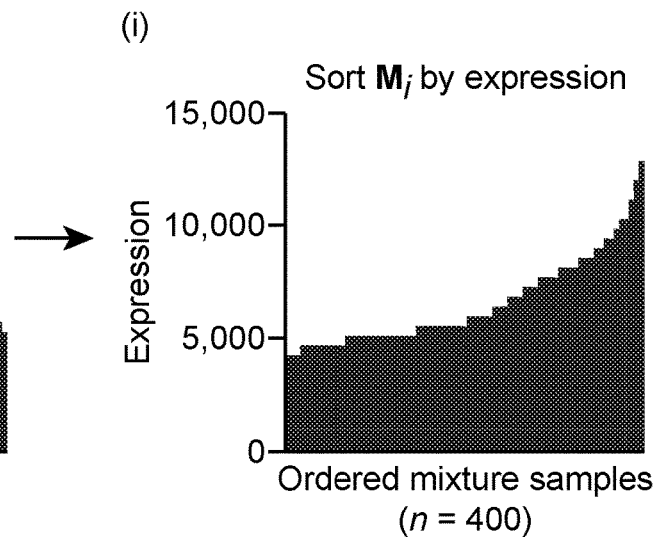
Figure 12:
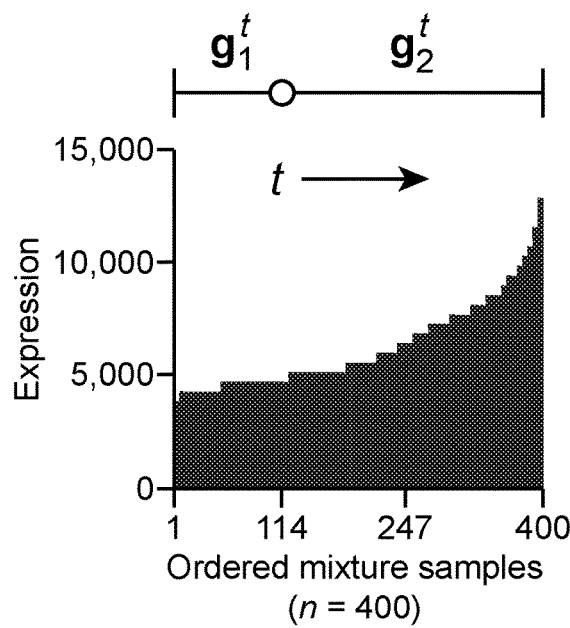
Figure 12:
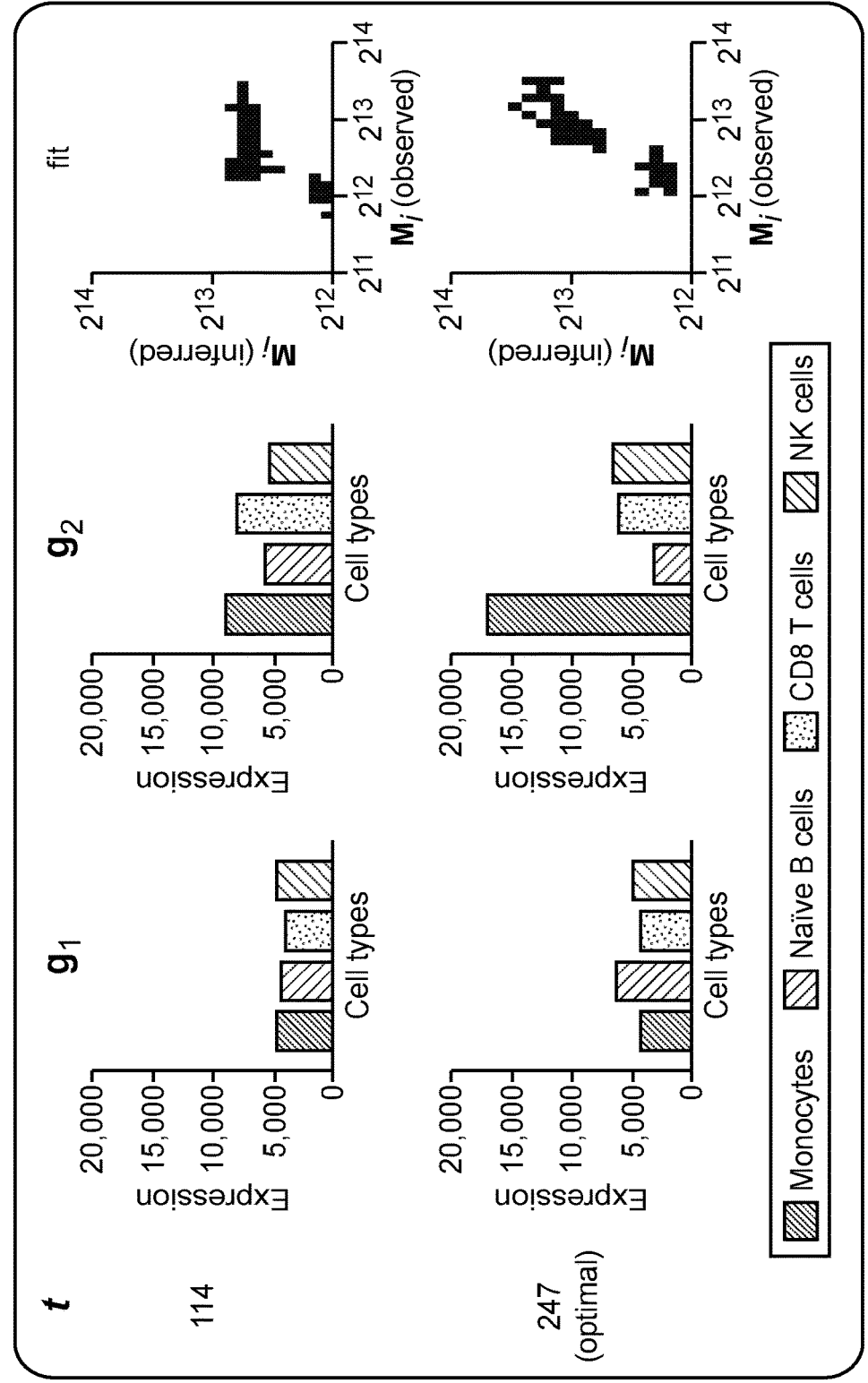
Figure 12:
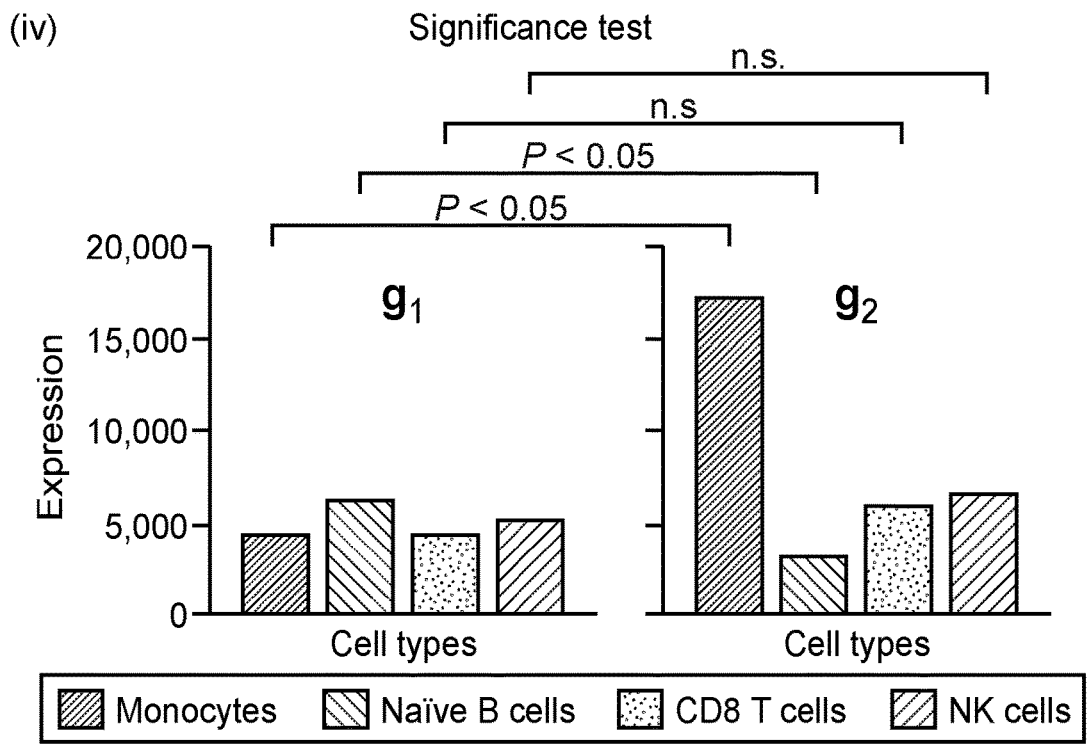
Figure 12:
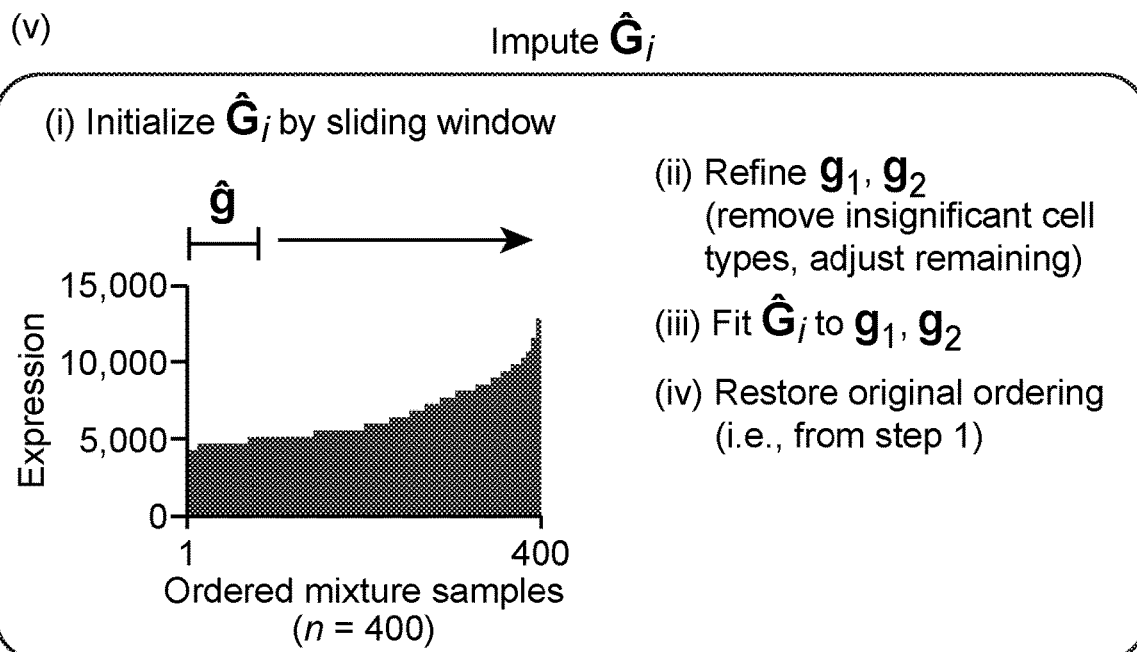
Figure 13:
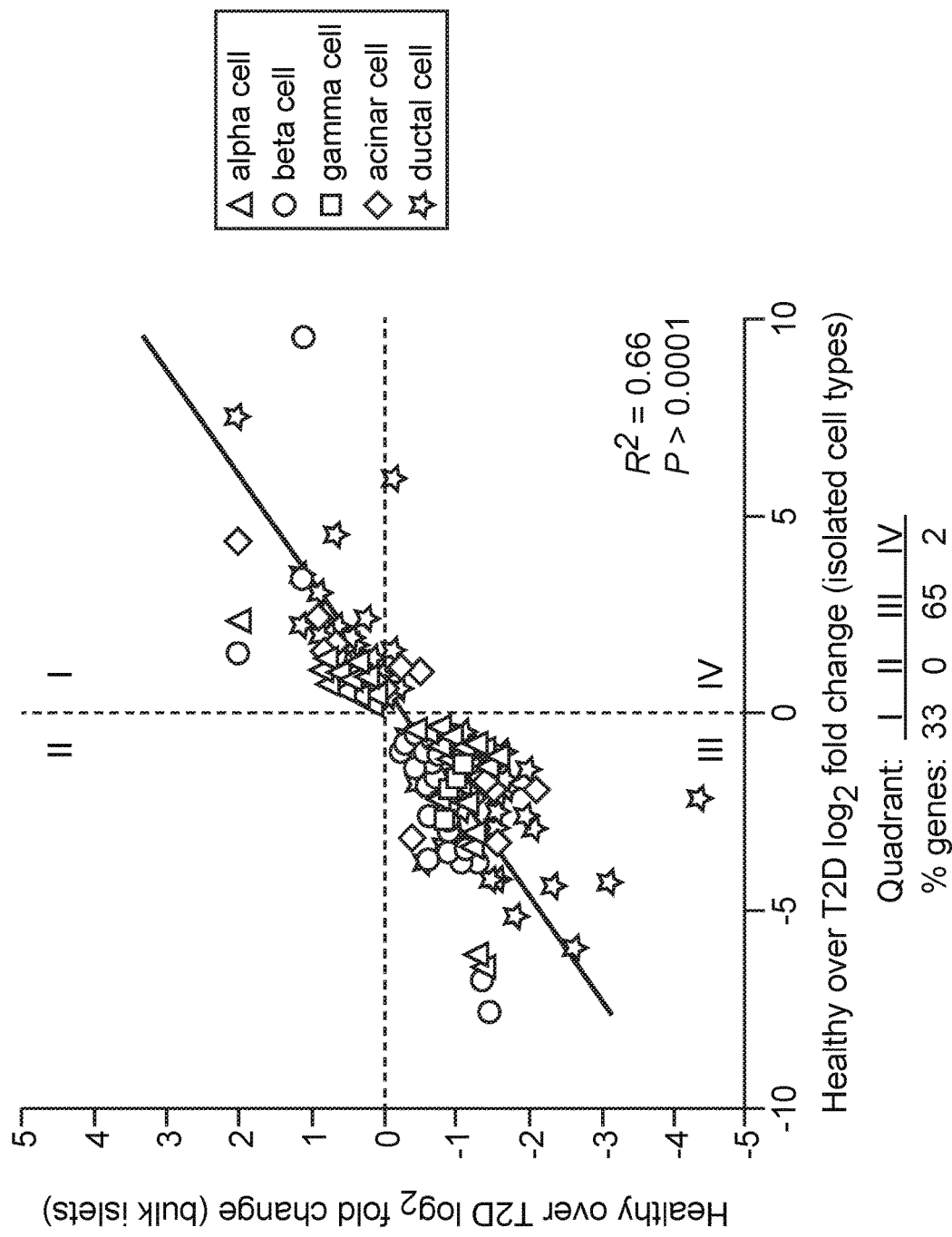
FIGS. 13a-b illustrate analysis of DEGs identified in single cells compared to their expression in bulk tissues. (13a) Scatterplot showing fold changes of differentially expressed genes between healthy donors and patients with type II diabetes (T2D) in several major pancreatic islet cell types (x-axis) versus bulk islets reconstituted from single cells (y-axis). All DEGs and corresponding fold changes in isolated cell types can be obtained, for example, as described in Supplemental Table 6 by Segerstolpe et al. (Single-Cell Transcriptome Profiling of Human Pancreatic Islets in Health and Type 2 Diabetes, *Cell Metab* 24, 593-607 (2016)), which is hereby incorporated by reference in its entirety. Fold changes in bulk islets were obtained by summing all single-cell GEPs in each pancreatic islet specimen (as described, for example, by Segerstolpe et al.), normalizing the resulting transcriptomes to TPM, and calculating the $\log_2$ fold change between healthy and T2D specimens for each DEG. In all, 98% of cell type-specific DEGs showed a fold change in the same orientation, whether analyzed in bulk islets or individual cell types. (13b) Same as (13a), but comparing the fold change of DEGs in isolated cell types (x-axis) to the relative skewing of T2D donors after sorting each gene in order of ascending expression (y-axis). To calculate enrichment, a binary matrix was defined such that patients with T2D were represented as 1 and healthy donors as 0. Then, for each gene, the fraction of T2D patients in the top 50th percentile of expression was subtracted from 0.5. Consequently, genes with no skew received an enrichment of 0, genes skewed toward T2D received a negative value, and genes skewed toward health donors received a positive value. This allowed for an equitable comparison with the fold change orientation in the x-axis (e.g., Healthy/T2D). This analysis shows that sorting each gene by its expression in bulk admixtures can inform cell type-specific transcriptional heterogeneity. This concept is leveraged for the first step of high-resolution transcriptome purification with CIBERSORTx (FIG. 12c).
Figure 13:
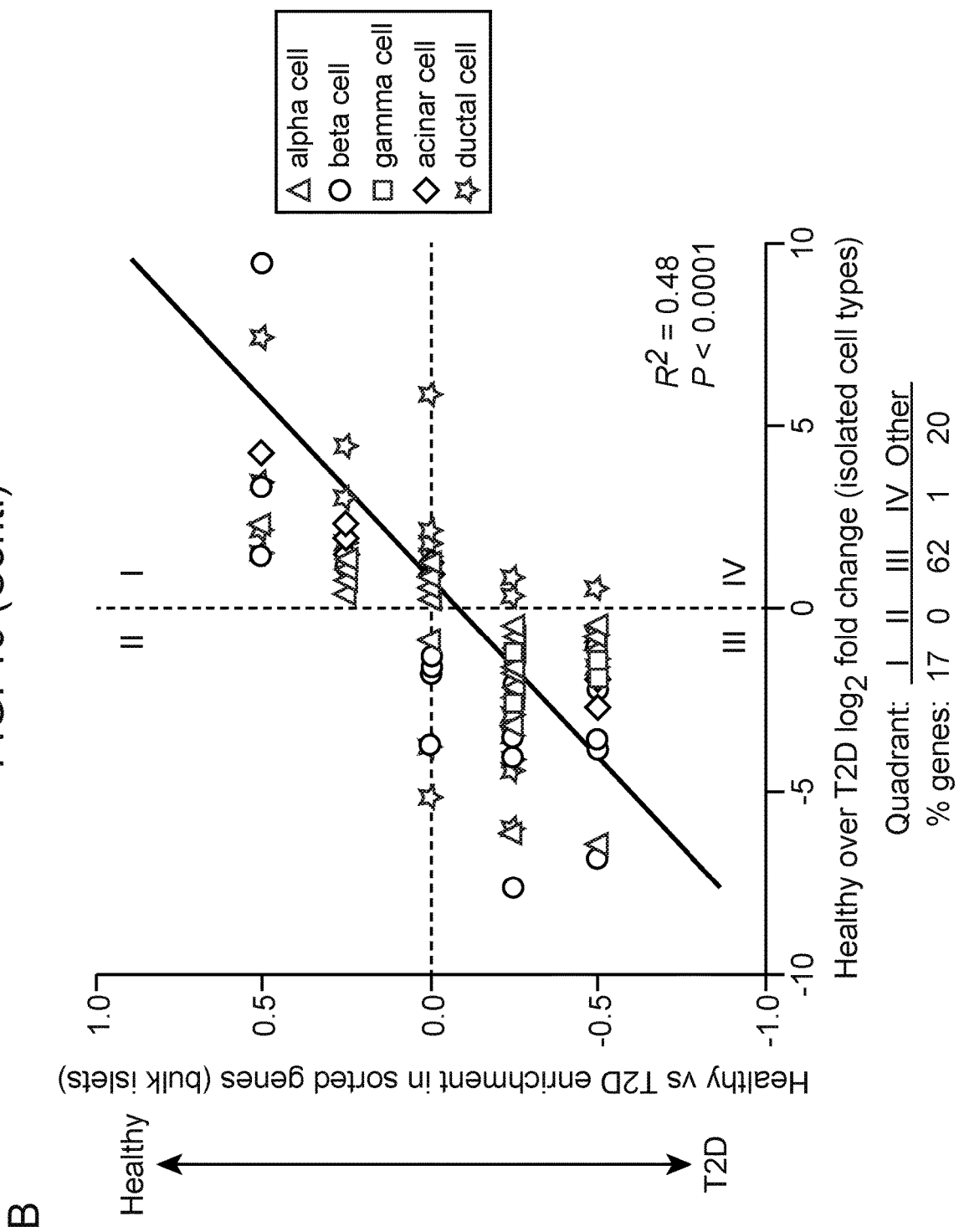

For each gene i, its corresponding mixture vector $M_{i,\bullet}$ may be stratified into two classes based on differences in bulk expression using an unsupervised approach (FIG. 12c, steps i, ii). Cell type-specific gene expression coefficients $g_1$ and $g_2$ may be imputed for each class (FIG. 12c, step ii), and the $g_1$, $g_2$ pair with the best fit to the data may be found (FIG. 12c, step iii).

Next, statistical tests may be performed to determine whether a given gene is expressed by each cell type, and if so, to assess whether it is significantly different between $g_1$ and $g_2$ (FIG. 12c, step iv).

Next, for the gene/cell type combinations that satisfy the previous step, continuous expression values may be imputed by a recursive divide and conquer algorithmic strategy. If a gene is significantly expressed, but not significantly variable across the mixture samples, a constant expression value may be imputed; otherwise it may be set to unexpressed. Matrix $\hat{G}$ may be populated with cell type-specific expression data (FIG. 12c, step v-i).

Next, the $g_1$ and $g_2$ coefficients may be revised according to the results of the significance tests (e.g., if expression is not significantly different between gi and g2 for a given cell type, the coefficients in $g_1$ and $g_2$ may be set to the same value; FIG. 12c, step v-ii).

Next, continuous expression vectors in $\hat{G}$ may be adjusted to maximize their agreement with the adjusted $g_1$ and $g_2$ coefficients previously determined (FIG. 12c, step v-iii).

Finally, final estimated cell type specific expression matrix (e.g., G) may be saved to a database (e.g., written to disk).

Within this framework, cell type-specific gene expression vectors may be imputed with Equation 2 (above) using NNLS. In order to capture variation in expression across $M_{i,\bullet}$, Equation 2 may be iteratively solved on subsets of mixture samples grouped by similar expression values. The size of each subset may be governed by a sliding window of length w. In order to satisfy NNLS constraints and to avoid overlapping phenotypic classes, w may be bounded by the interval $k<w\le(c/2)$, where k denotes the number of cell types and c denotes the number of samples. Favorable performance of this approach may be observed across a broad range of w values. Nevertheless, given the marginal gains observed with increasingly large w values within saturation analysis of group-level expression purification (FIGS. 3e, 11), w may be set to 4-5 fold greater than k, which may balance performance with practical considerations. To address potential instability in the linear system and to infer expression coefficients with robust standard errors and confidence intervals, NNLS may be run using bootstrapping.

CIBERSORTx Batch Correction

Batch correction techniques may be developed to minimize technical variation in expression profiling, and may be applied to gene expression deconvolution. Using previous methods, such batch correction can be very challenging if not impossible in certain circumstances. For example, a previous approach using cubic splines with four degrees of freedom to model gene-level technical variation between paired microarray and RNA-Seq profiles from TCGA tumor samples, although potentially useful when paired samples are available, can be very challenging if not impossible in cases where new and archival expression datasets lack such pairs. As another example, ComBat, an empirical Bayesian method which may be applied to eliminate technical variation between cell reference profiles and bulk tissue GEPs, although potentially useful when the batches represent GEPs from the same tissue type, can be very challenging if not impossible when the batches represent GEPs from different tissue types, due to introduction of significant distortions in cell abundance estimation.

To overcome issues with technical variation in expression profiling, the present disclosure provides batch correction procedures to minimize technical differences (e.g., between the signature matrix and an input set of mixture samples M). For example, such an approach may perform batch correction between M and a matching set of mixture samples M* that are estimated from the cell reference profiles. Technical variation such as cross-platform technical variation or cross-sample technical variation may be reduced, minimized, or removed. Performing batch correction may help to ensure that sample types are comparable between batches, thus avoiding potential estimation artifacts and the need for paired samples profiled on both platforms.

A deconvolution method (e.g., to identify or quantify cell-type states from a mixture of different cell types) may comprise performing a batch correction procedure to reduce technical variation (e.g., between the signature matrix and the bulk mixture profiles). For example, a bulk-reference mode (e.g., B-mode) batch correction may be performed as follows. Generally, while a deconvolution method (e.g., CIBERSORT) may be applied to RNA-Seq, including to reference phenotypes derived from single-cell transcriptome profiling, such a method may not explicitly handle technical variation between the signature matrix and bulk mixture profiles. Technical variation may include cross-platform technical variation or cross-sample technical variation. For example, technical variation may arise from obtaining feature profiles of the signature matrix and feature profiles of the bulk mixture across different platforms (e.g., RNA-Seq, scRNA-Seq, microarrays, 10× Chromium, SMART-Seq2, droplet-based techniques, UMI-based techniques, non-UMI-based techniques, 3'/5'-biased techniques) and/or different sample types (e.g., fresh/frozen samples, FFPE samples, single-cell samples, bulk sorted cell populations or cell types, and samples containing mixtures of cell populations or cell types). For example, cross-platform technical variation may arise in cases where feature profiles with a same type of expression data (e.g., GEPs) are obtained using different platforms. Since technical variation can variably confound deconvolution results, a normalization workflow (FIGS. 7a-h), which may comprise at least two distinct strategies, can be applied to reliably apply gene expression deconvolution across platforms (e.g., RNA-Seq, microarrays) and tissue storage types (e.g., fresh/frozen versus FFPE). For example, a decision tree to guide users in selecting the most appropriate strategy is provided in FIG. 7a. The decision tree may be used to assist in selecting a bulk-mode batch correction (e.g., B-mode) procedure and/or a single cell batch correction (e.g., S-mode) procedure to be performed.

Figure 7:
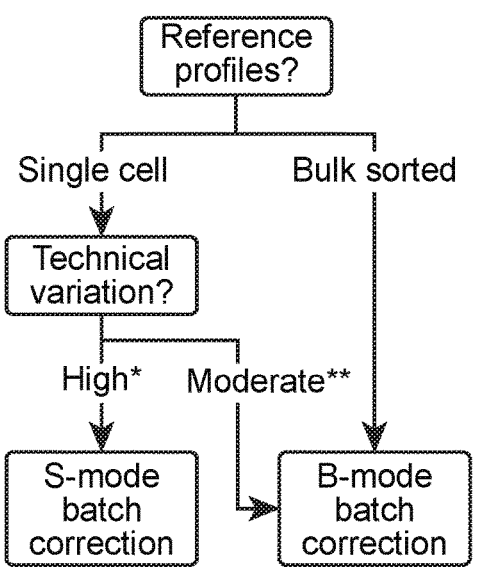
FIGS. 7a-h illustrate cross-platform deconvolution using CIBERSORTx. (7a) Decision tree for selecting the most appropriate CIBERSORTx batch correction strategy for a given input signature matrix: (i) single cell reference mode ('S-mode', panels (7b), (7e) or (ii) bulk reference mode ('B-mode', panels (7c), (7f-(7h). (7b)-(7c) Schematics for S-mode (7b) and B-mode (7c) batch correction. (7d) t-SNE projections of two publicly available single cell transcriptome datasets of PBMCs profiled by 10× Genomics using 3' and 5' kits. Cell labels were determined manually using Seurat (e.g., v1.4.0.16) and canonical marker gene assessment, and used to generate signature matrices. (7e) Evaluation of S-mode, showing leukocyte deconvolution of whole blood from healthy donors (n=12 RNA-Seq profiles) using single cell reference profiles of PBMC subsets generated by 10× Chromium (panel (7d)). Pearson correlation (Left) and RMSE (Right) before and after S-mode batch correction. Ground truth cell proportions were determined by flow cytometry and complete blood counts. Group differences were evaluated by a Wilcoxon signed-rank test. (7f) Results of applying CIBERSORTx to enumerate LM22 immune subsets in fixed melanoma tumor samples profiled by RNA-Seq, both before and after B-mode batch adjustment. To evaluate performance without ground truth proportions, deconvolution results for selected leukocyte subpopulations were compared to the expression of canonical marker genes in unadjusted RNA-Seq data. CIBERSORTx results were scaled by total immune content using a previously described approach to calculate a 'normalized immune index' for each tumor sample. (7g) Impact of B-mode batch correction on cell subset enumeration with LM22 (Affymetrix microarrays) across 5 platforms, 3 tissue types, and fresh/frozen vs. fixed tissue preservation states: Illumina Beadchip microarrays of cryopreserved PBMCs vs. flow cytometry (GSE65133), bulk RNA-Seq of fresh whole blood vs. flow cytometry/CBCs (as disclosed elsewhere herein), bulk RNA-Seq of FFPE melanoma (Mel.) tumors vs. surrogate cell markers (same as panel b), and reconstituted bulk melanoma (Mel) and HNSCC tumors from scRNA-Seq profiles (Smart-Seq2; TIL subset frequencies in reconstituted single cell expression data from melanoma and HNSCC tumors, respectively). Points represent Pearson correlation coefficients between expected and inferred fractions for each cell type, and bar plots show medians with 95% confidence intervals expressed as error bars. (7h) Left: Heat map showing the transcriptome-wide impact of CIBERSORTx batch correction on the same dataset in (c), ranked by the absolute difference in rank after batch correction. Right: Application of pre-ranked gene set enrichment analysis (GSEA) to the ranked list of genes in the left panel and a set of genes (n=139) that are highly specific for non-hematopoietic cells in melanoma tumors. The gene set was derived by analyzing melanoma scRNA-Seq data for genes with a signal-to-noise ratio (SNR) in $\log_2$ space greater than 2 between non-immune and immune cells. Prior to this analysis, the single-cell data were aggregated to yield five transcriptome replicates per cell type. NES indicates normalized enrichment score.
Figure 7:
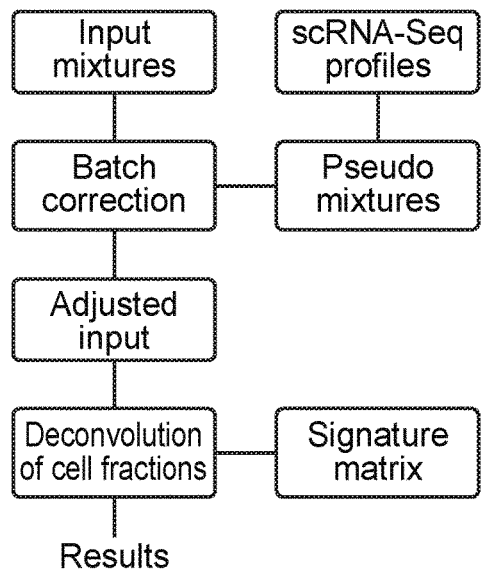
Figure 7:
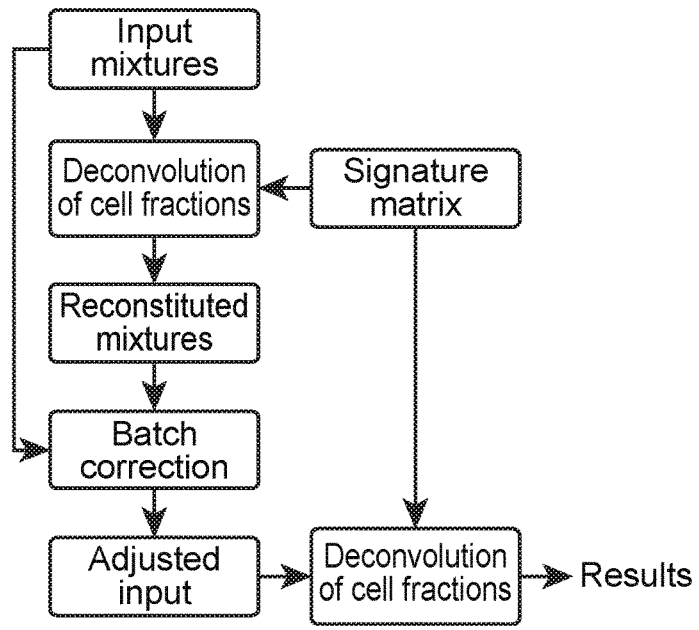
Figure 7:
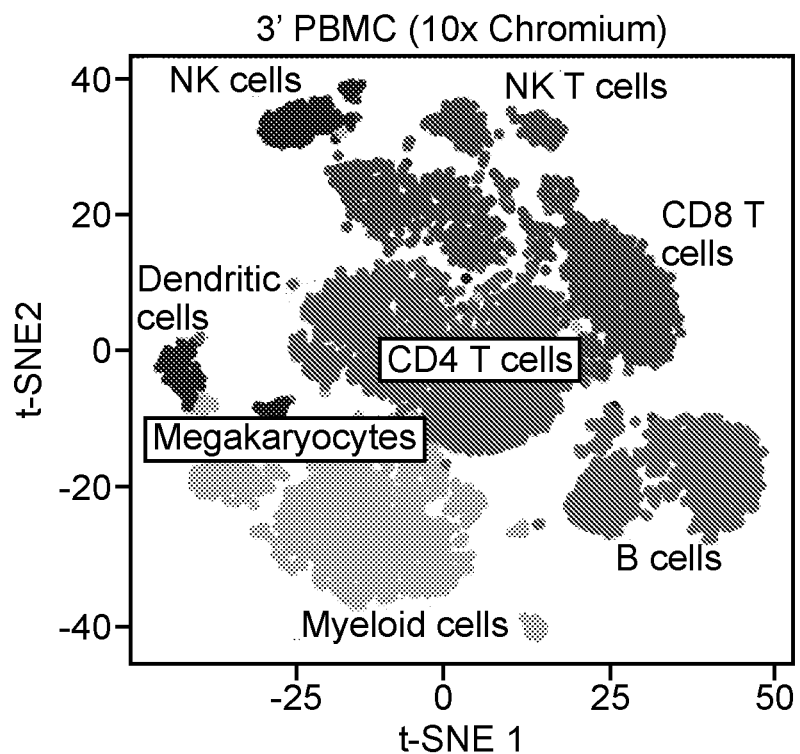
Figure 7:
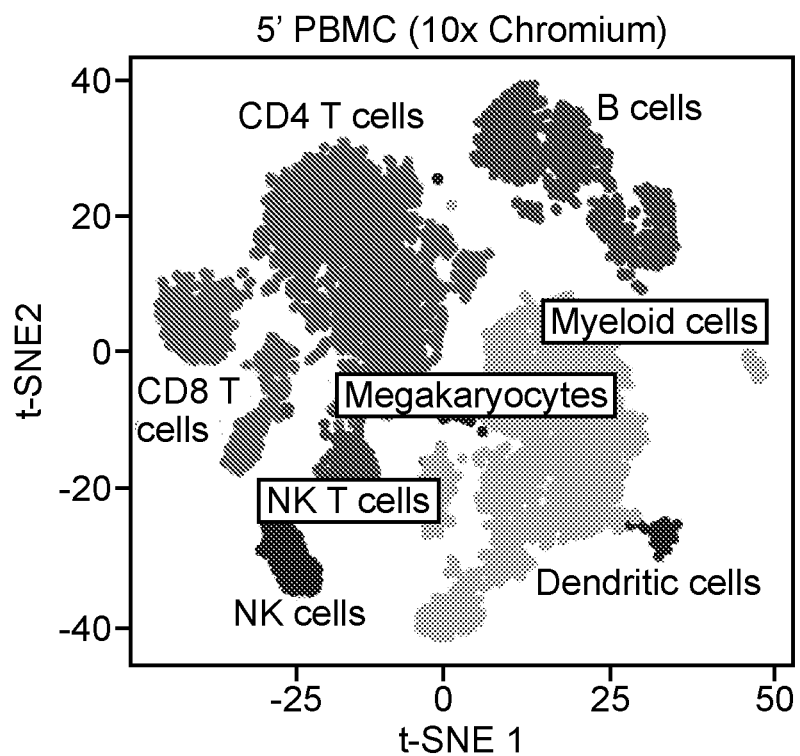
Figure 7:
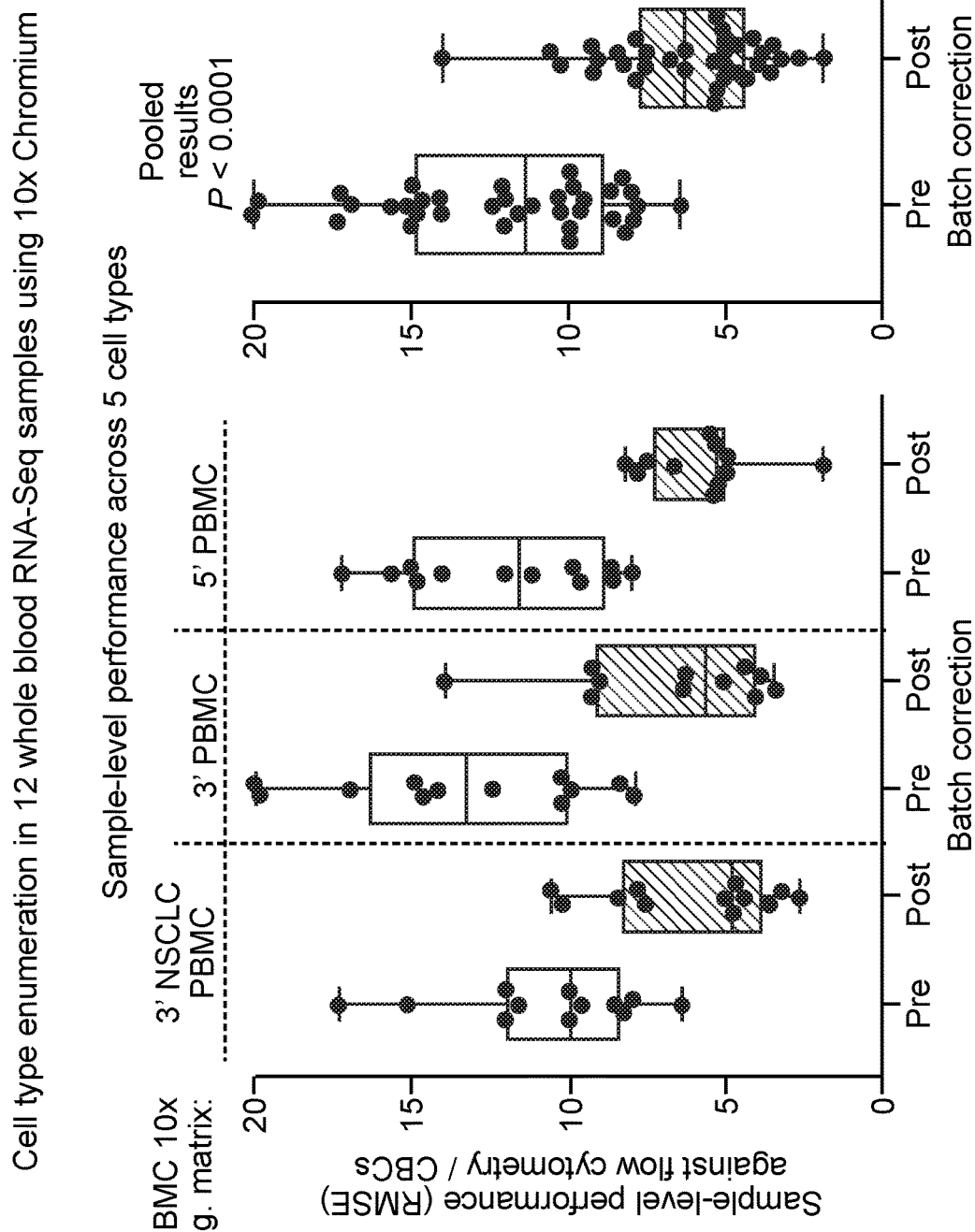
Figure 7:
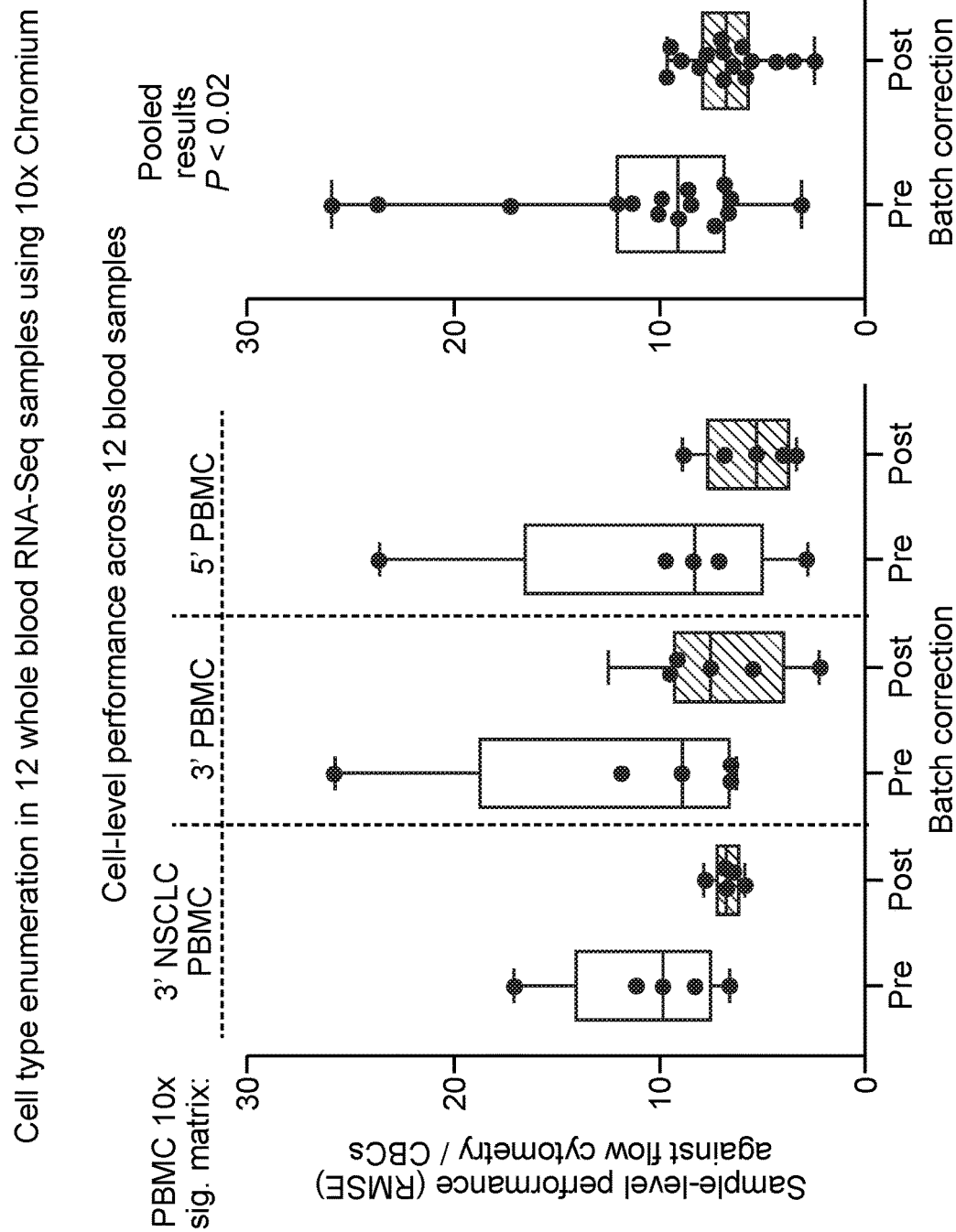
Figure 7:
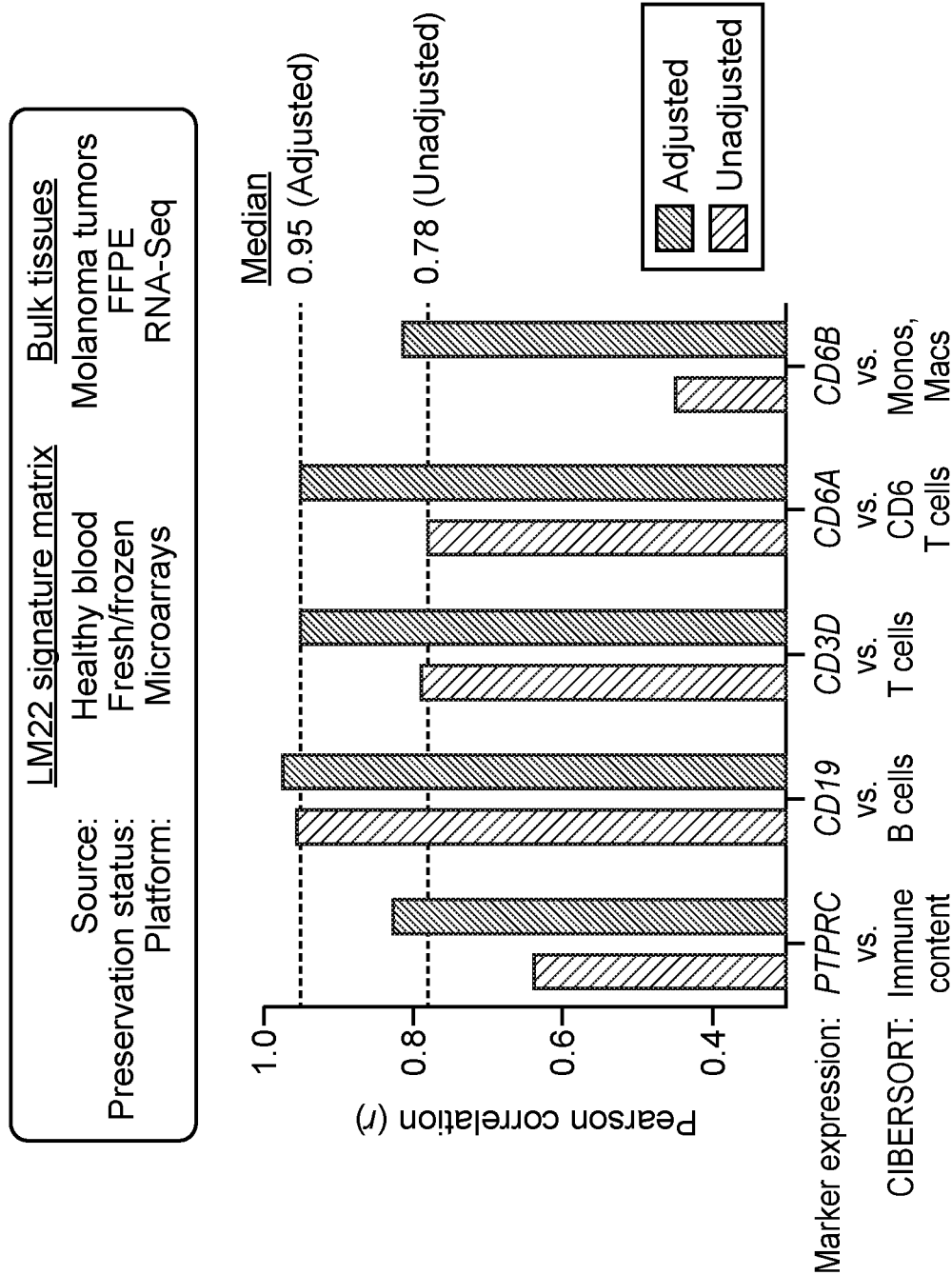
Figure 7:
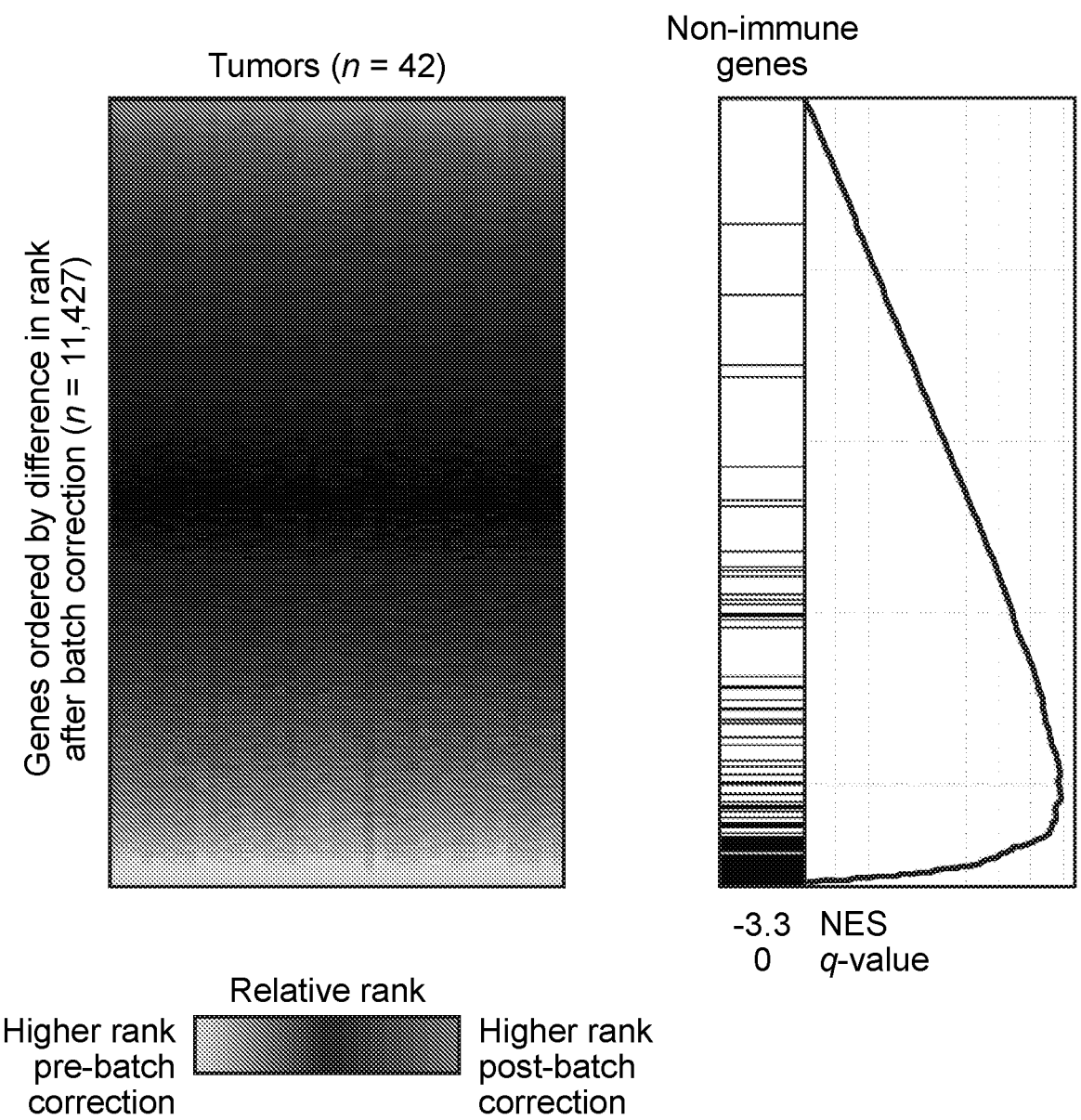
Figure 8:
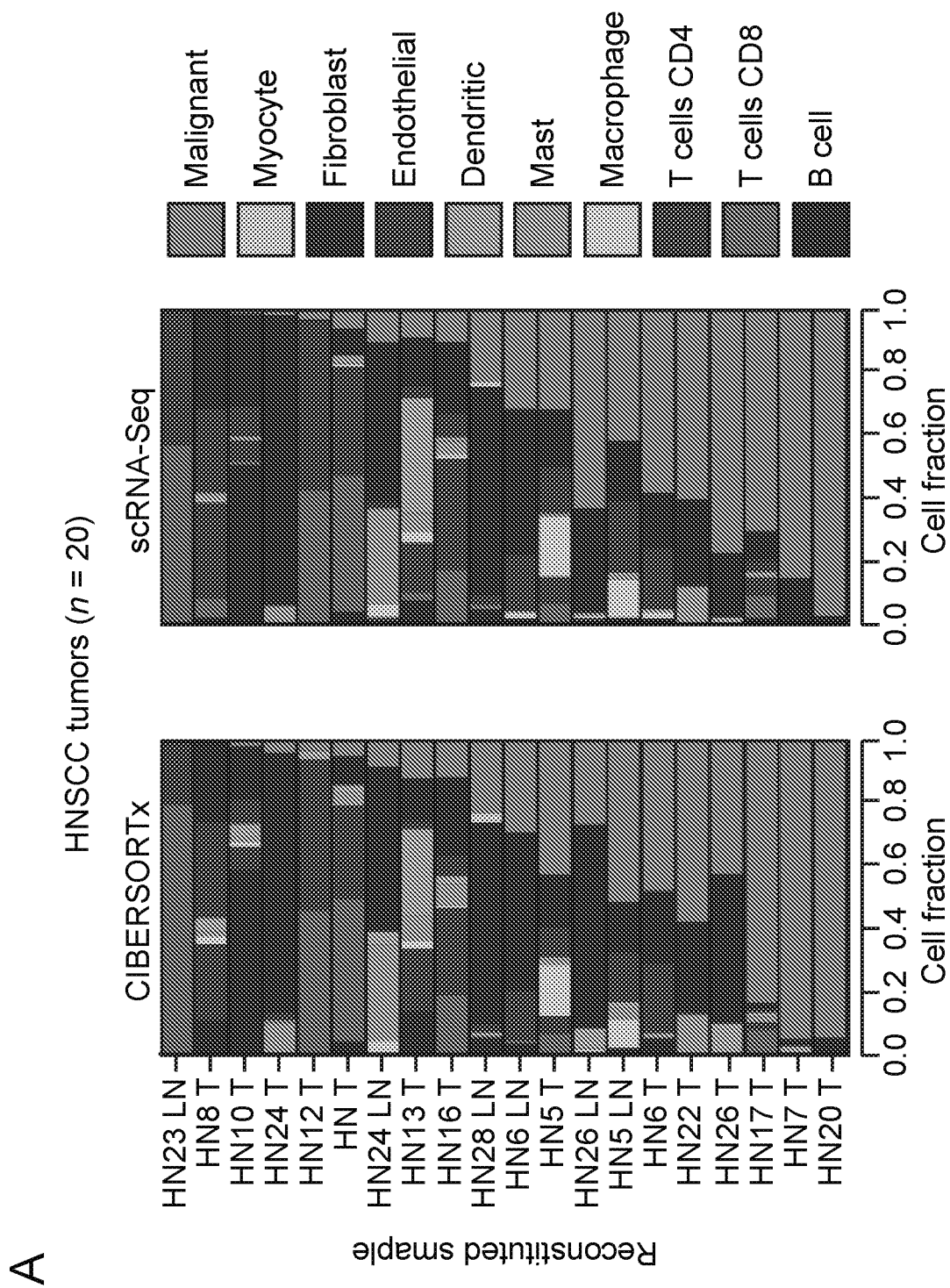
FIGS. 8a-i illustrate dissection of solid tumors and pancreatic islets using single cell reference profiles. (8a) Stacked bar plot depiction of the results in FIG. 2d, showing estimated (Left) and expected (Right) cell subset frequencies in 20 HNSCC tumor samples reconstituted from single cell transcriptomes. (8b)-(8e) Single cell-guided deconvolution of melanoma tumors. (b) t-SNE visualization of scRNA-Seq data from 19 melanoma tumors (Left) and approach for testing single cell deconvolution performance (Right). (8c)-(8d) Concordance between cell type proportions measured by CIBERSORTx deconvolution and scRNA-Seq for 17 held-out melanoma tumors reconstituted from single cell data, related to panel (8b). Shown are stacked bar plots (Left) and Pearson correlations (Right) of observed versus expected cell subset proportions. (8e) Analysis of melanoma TIL proportions as measured by scRNA-Seq, deconvolution of bulk RNA-Seq profiles of skin cutaneous melanoma tumors using the signature matrix from panel (8b), and IHC quantification. (8f)-(8i) Single cell-guided deconvolution of pancreatic islets. (8f) t-SNE visualization of scRNA-Seq data from 10 pancreatic islet specimens (Left) and approach for testing single cell deconvolution performance (Right). (8g) Scatterplot comparing scRNA-Seq and CIBERSORTx proportions for 9 pancreatic cell types in 8 held-out islets (Left), with corresponding Pearson correlation coefficients for individual cell types (Right). Data points in the scatterplot are color-coded by cell type to match the bar plot (Right). (8h) Same as (8g), but for 7 islet samples profiled by bulk RNA-Seq and scRNA-Seq. The same single cell-derived signature matrix used to analyze reconstructed tumors in (g) was applied to the same islet specimens profiled by bulk RNA-Seq (x-axis). Prominent cell types are highlighted with ellipses. (i) Comparison of alpha, beta, gamma, and delta cell proportions in pancreatic islets, as measured by (1) scRNA-Seq (using annotated cell labels), (2) CIBERSORTx deconvolution of bulk islets using a single cell-derived signature matrix (panel (8f), and (3) IHC quantification in non-disaggregated islets. Data in (8e) and (8i) are expressed as means+/−s.e.m.
Figure 8:
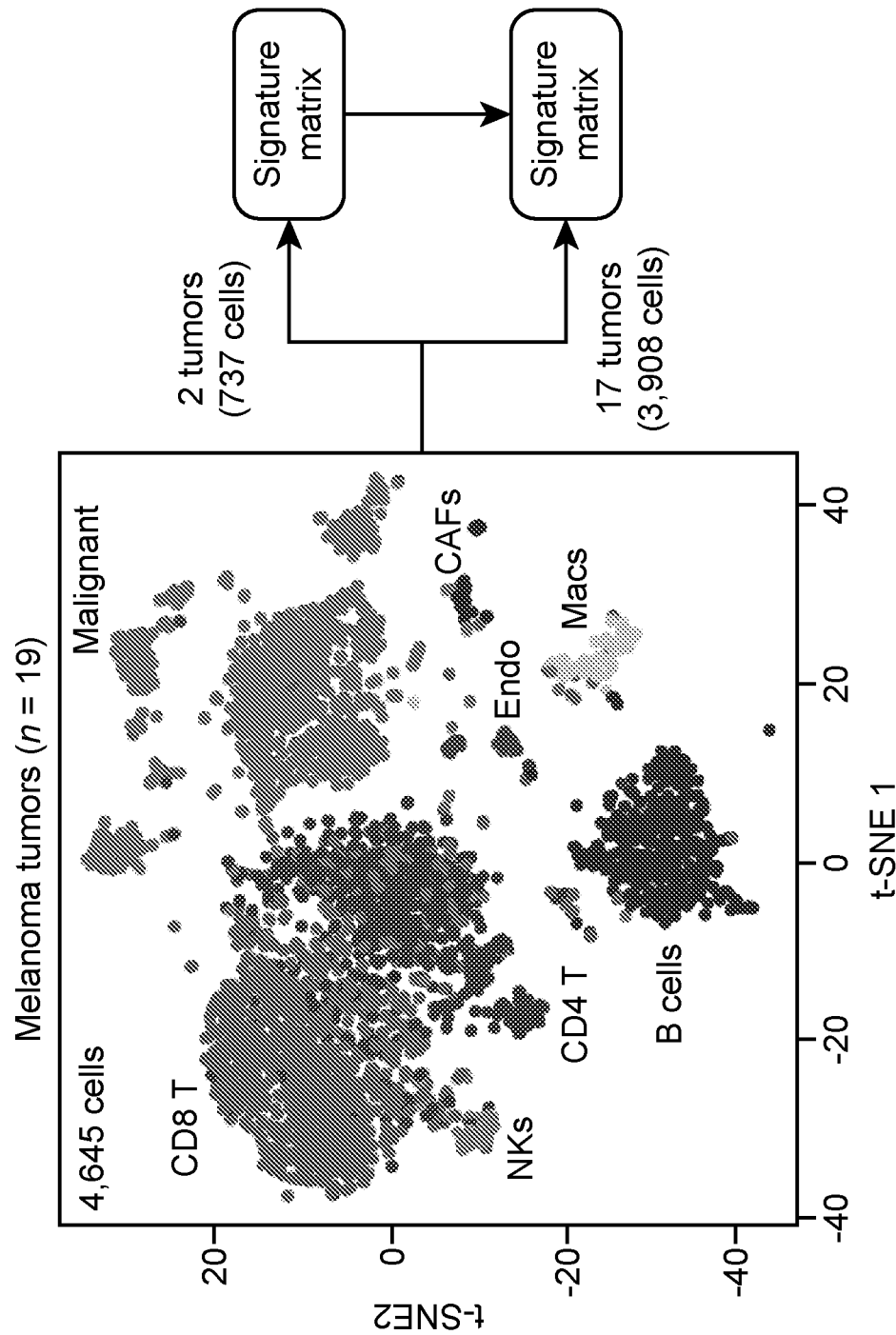
Figure 8:
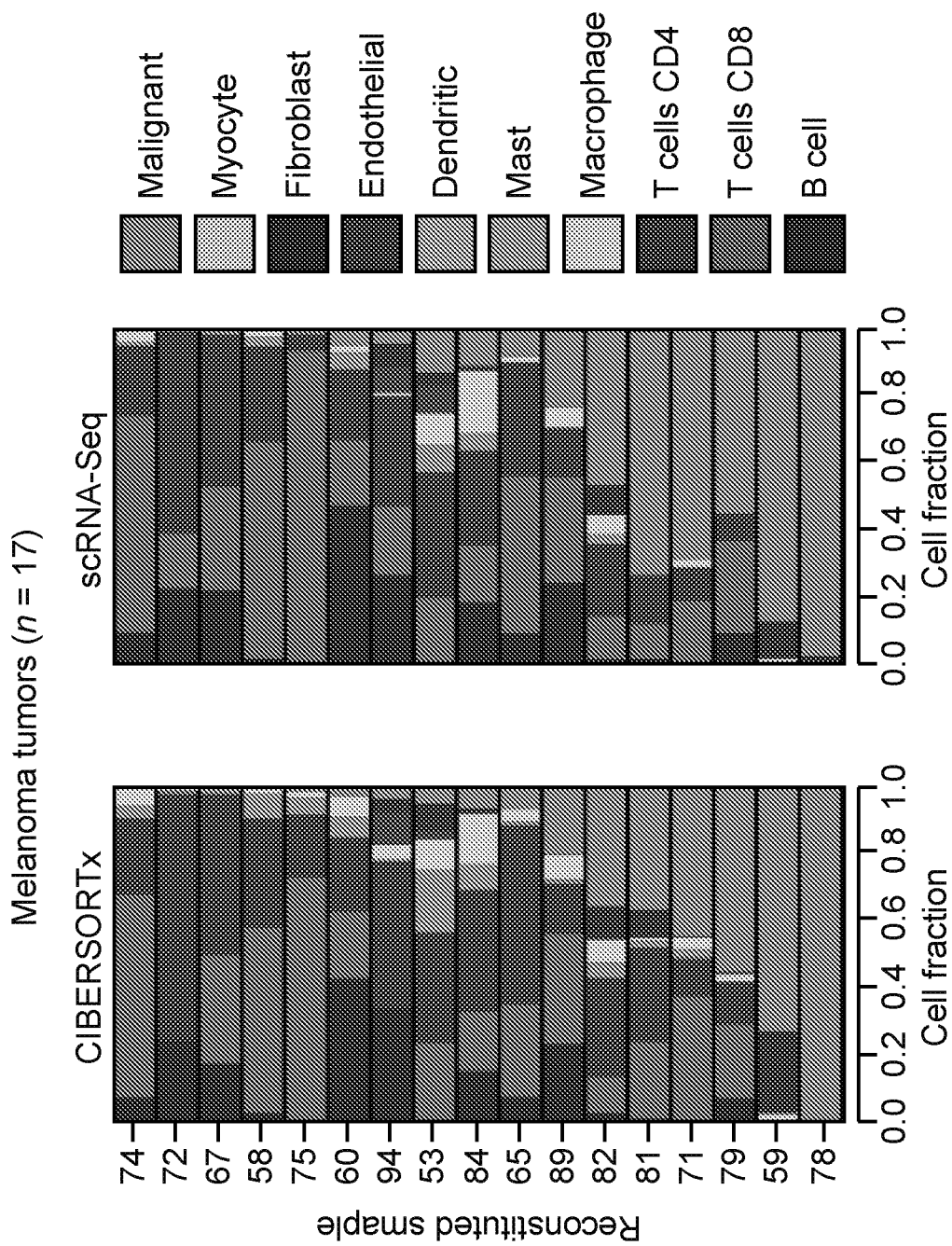
Figure 8:
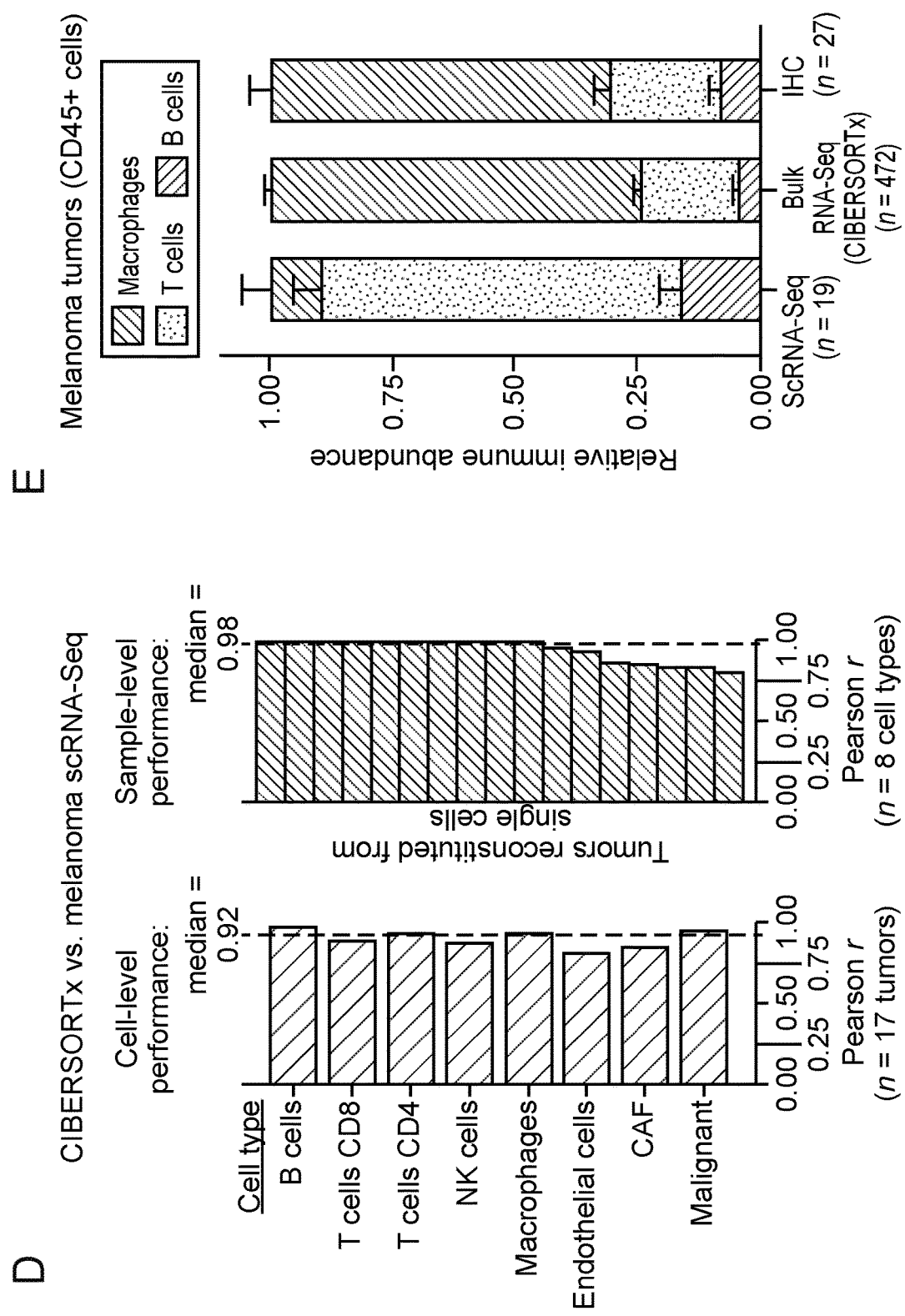
Figure 8:
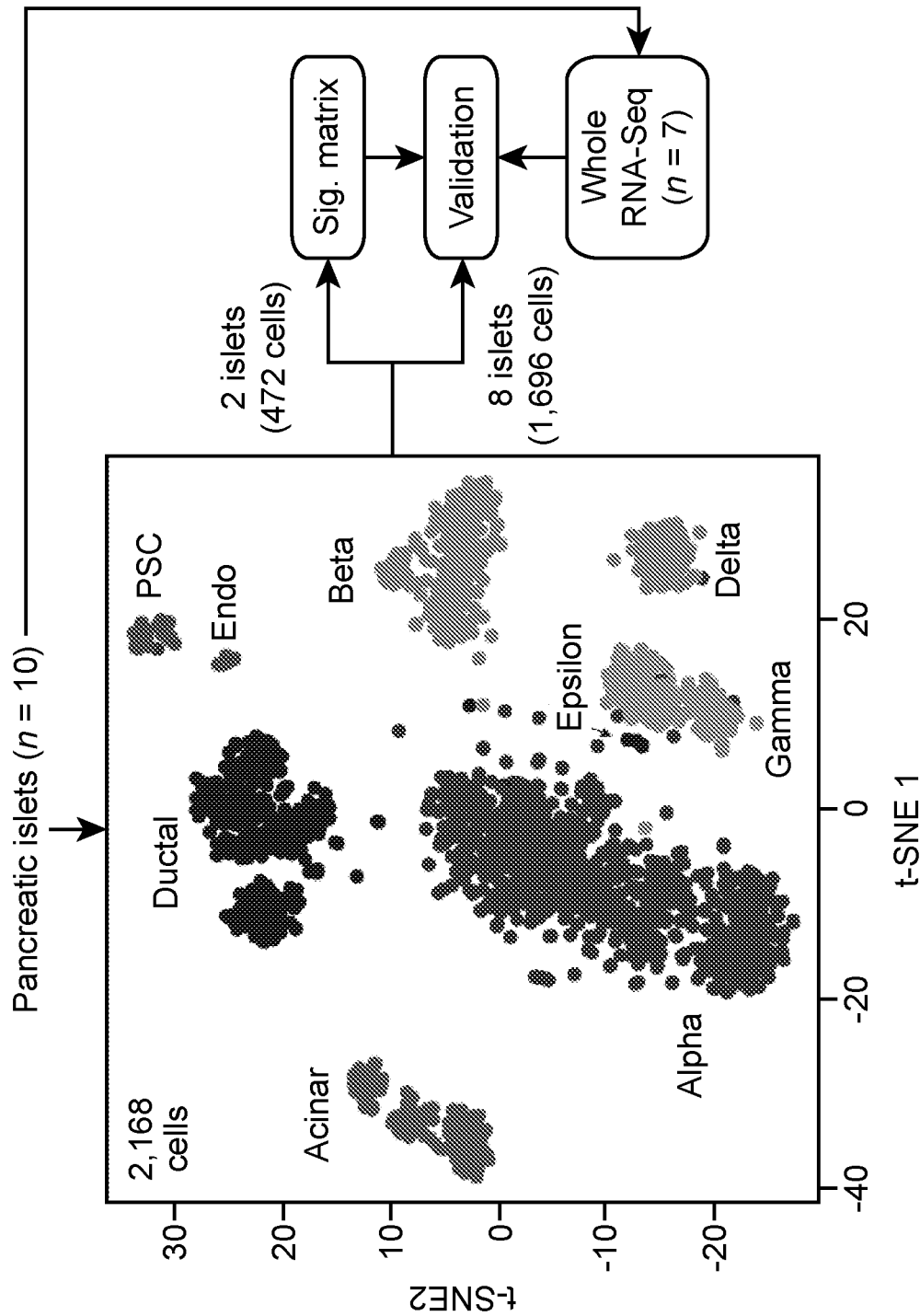
Figure 8:
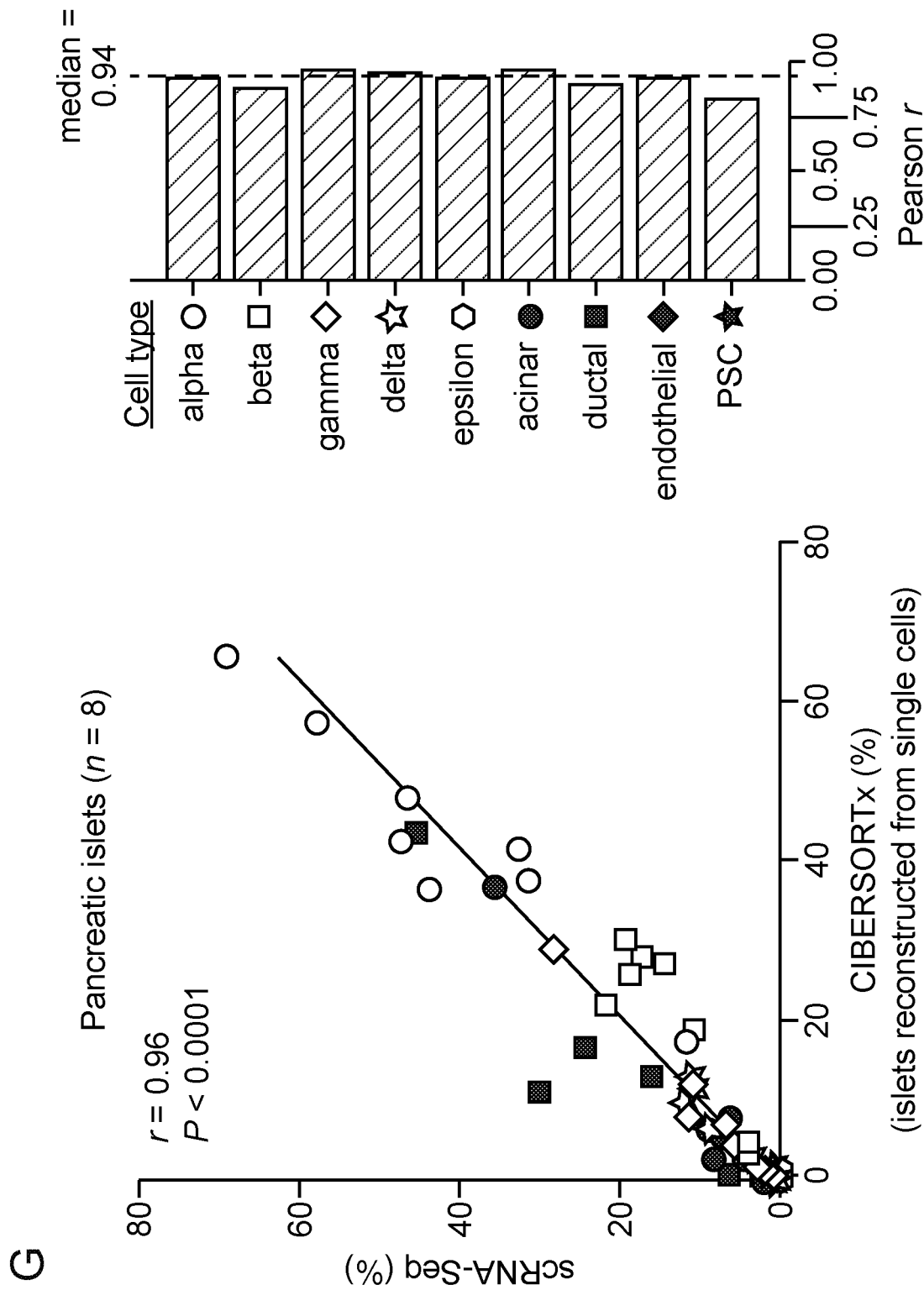
Figure 8:
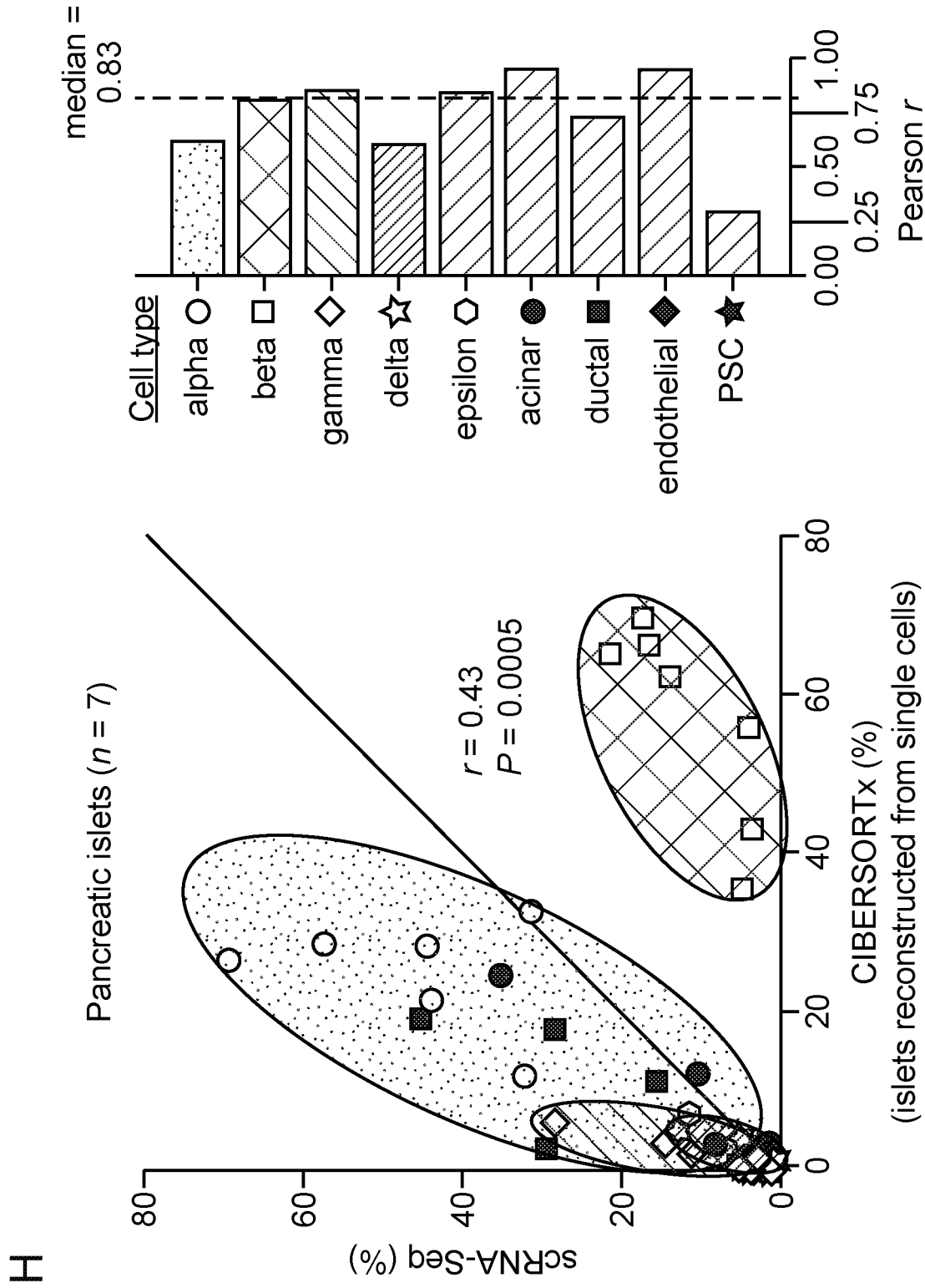
Figure 8:
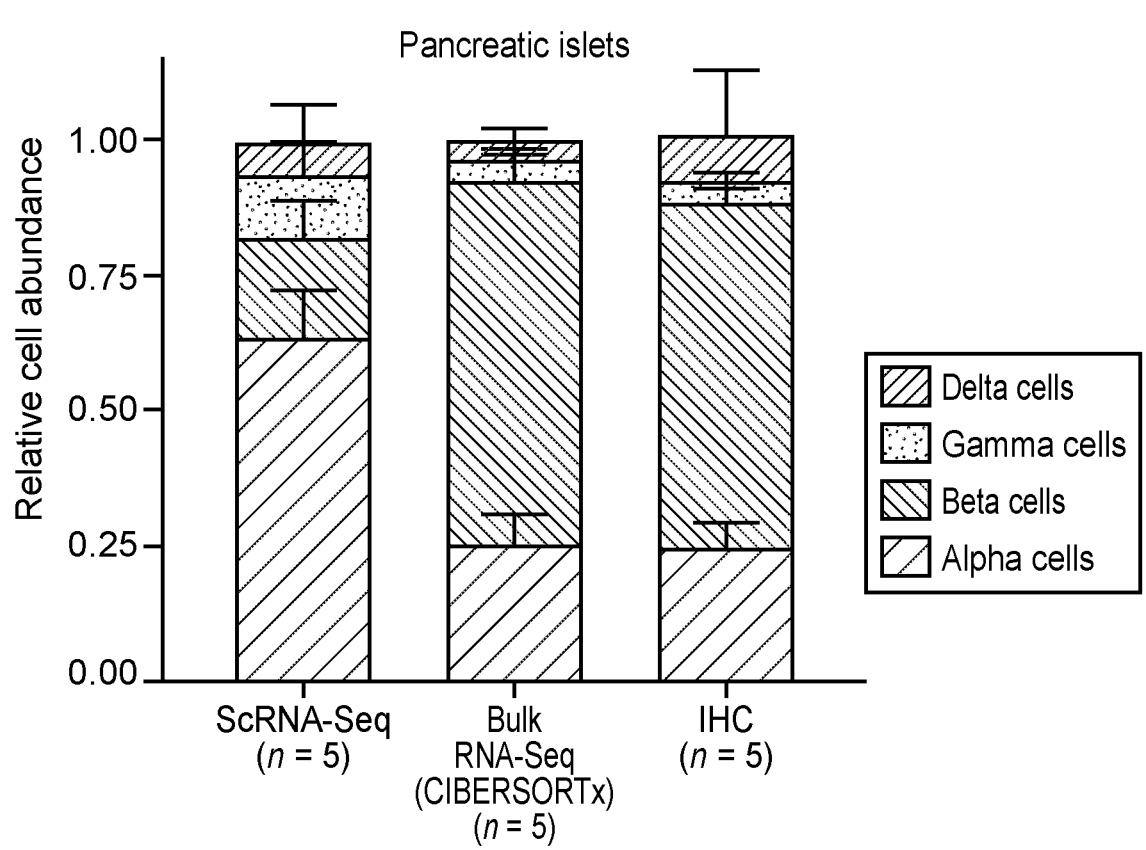

A bulk-reference mode (e.g., B-mode) batch correction may remove technical differences between a signature matrix derived from bulk sorted reference profiles (e.g., bulk RNA-Seq or microarrays) and an input set of mixture samples (FIG. 7c). For example, the batch correction may remove technical differences between feature profile of one cell type against a mixture of different cell types. The technique can also be applied to signature matrices derived from scRNA-Seq platforms, provided that transcripts are measured analogously to bulk mixture GEPs (e.g., full-length transcripts without UMIs profiled by SMART-Seq2). Given a set of mixture samples M, the bulk-reference mode batch correction approach may comprise creating a series of estimated mixture samples M*, where the latter comprises a linear combination of imputed cell type proportions in M and the corresponding signature matrix profiles (in non-log linear space). Although the strategy may be general and can flexibly accommodate different deconvolution and batch correction methods (FIGS. 7f-h), ComBat (an empirical Bayesian method) may be used to eliminate batch effects between M and M* after $\log_2$-adjustment. Once batch effects have been removed, cell proportions may be re-estimated using the adjusted mixture samples in non-log linear space (FIGS. 7f-g). In addition to cell type enumeration, this approach can also be applied to cell type-specific gene expression purification, thereby allowing for down-weighting of genes whose expression levels are low or absent from the collection of cell types in the signature matrix (FIG. 7h). This technique may require a minimum of about 3-5 mixture samples to perform the batch correction procedure.

Figure 24:
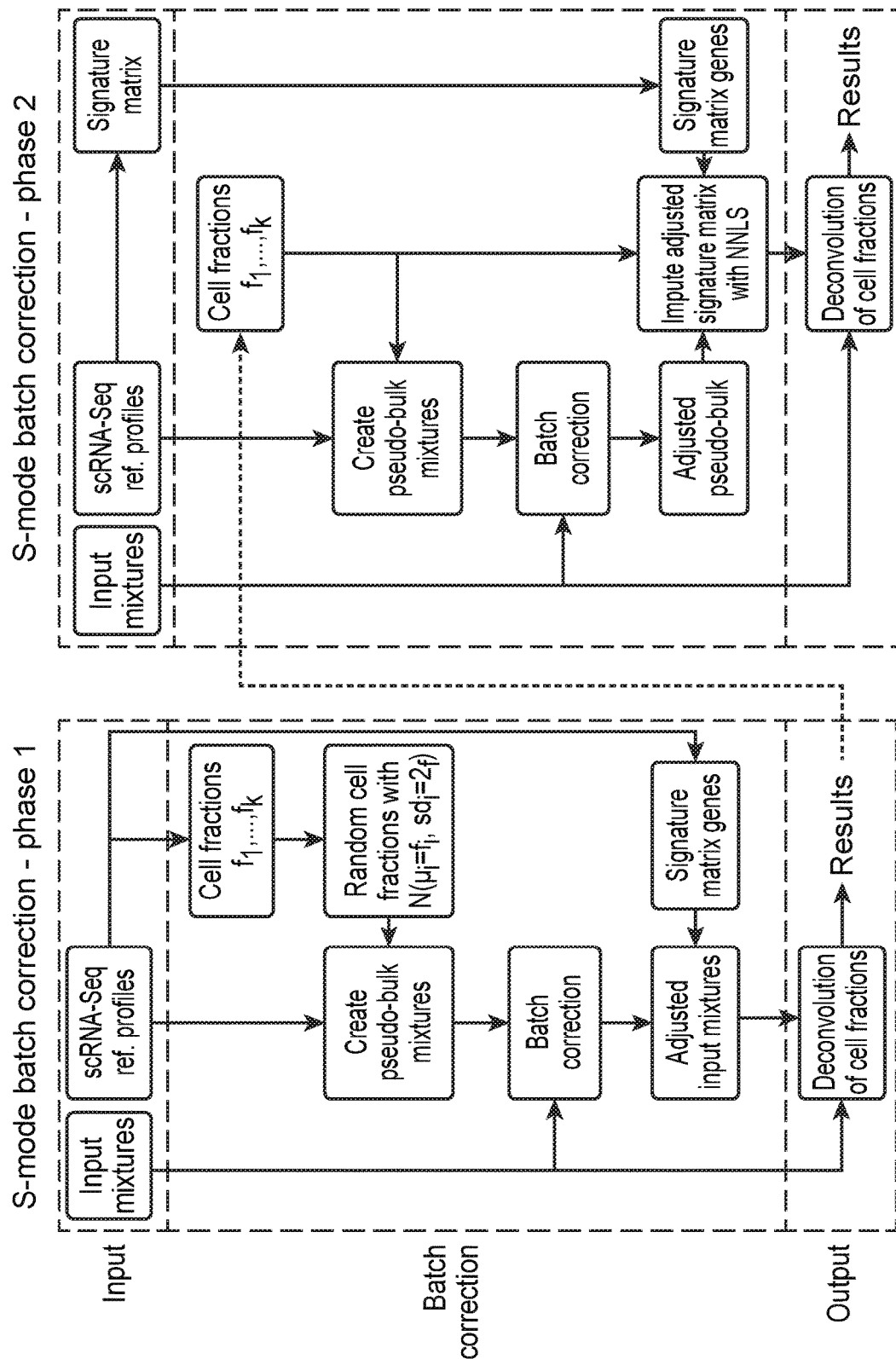
FIG. 24 illustrates a schematic representation of S-mode batch correction.

Regardless of the above B-mode batch correction technique, deconvolution may perform poorly or even fail when excessive cross-platform technical variation is present (e.g., when cell types that are expected to be present are observed to drop out in bulk GEP samples). For example, this phenomenon may be observed using signature matrices derived from 10× Chromium (FIGS. 2b and 7e). Such a discrepancy may be unsurprising given the major differences in transcriptome representation between UMI-based and 3'/5'-biased methods, such as 10×, and those that capture full transcripts without UMIs, such as SMART-Seq2. Since B-mode batch correction may not adequately address cellular dropout and thus may be insufficient to overcome such variation, a single cell reference mode batch correction may be applied to deconvolution methods involving signature matrices derived from 10× Chromium and other droplet-based or UMI-based techniques (FIG. 7b). A single cell reference mode (e.g., S-mode) batch correction may be performed as follows (as illustrated by the schematic representation in FIG. 24).

Like B-mode batch correction, an objective of S-mode may be to obtain cell frequencies F from a set of mixture GEPs M containing c samples, while minimizing technical variation. For high overall performance, this approach may comprise a serial application of at least two procedures: an initial cell frequency estimation phase (phase 1), and a refinement phase in which the signature matrix, rather than the mixture matrix, is adjusted (phase 2). In phase 1, a goal may be to obtain initial estimates of cell frequencies F* within a set of mixture samples M given (1) a signature matrix B and (2) the set of single cell reference profiles R from which B was derived (FIG. 7b). To accomplish this, first a series may be created of c artificial mixture profiles M* reconstituted from single cell GEPs within R. Mixing coefficients may be determined according to a Normal distribution $N(\mu, \sigma)$, where $\mu$ is set to the fractional abundance of each cell type from B in R $\{\mu_1, \mu_2, \ldots, \mu_n\}$ and $\sigma$ is set to $\{2\mu_1, 2\mu_2, \ldots, 2\mu_n\}$ Single cell transcriptomes from each cell subset may be then randomly sampled according to this distribution and aggregated into c bulk expression profiles in TPM space. ComBat may be subsequently applied to M and M* in $\log_2$ space, yielding adjusted mixtures $M^{adj}$ and $M^{adj}$*, respectively, and estimated cell frequencies (F*) may be imputed from $M^{adj}$ (in log-space) using the original signature matrix (B).

In the second phase, the cell proportion estimates may be further refined by (1) performing batch correction on the signature matrix B, and by (2) applying the adjusted signature matrix to the original set of mixtures M. Similar to phase 1, the process may start by sampling single cells to create c artificial mixtures from R. However, in this case, cell types may be sampled according to their estimated frequencies F* obtained from phase 1, resulting in a new matrix of estimated mixtures M. ComBat may be then applied to M and M in $\log_2$ space, yielding adjusted mixtures $M^{adj}$ and $M^{adj}$, respectively. After converting $M^{adj}$ to non-log linear space, both $M^{adj}$** and F* may be used as inputs to NNLS in order to reconstruct cell type expression coefficients for each gene in B (see equation 2), yielding an adjusted signature matrix $B^{adj}$. Notably, unlike group-mode expression purification (FIG. 1), this use of NNLS in S-mode may not require adaptive noise filtration. This is because (1) the cell mixing proportions of each artificial mixture in $M^{adj}$** may be derived from F* and thus known with 100% certainty, and (2) ComBat may only apply a linear transformation to each gene's $\log_2$ expression profile, thereby preserving the relative ordering of bulk expression values. Therefore, the conditions for applying NNLS to propagate the adjustments in $M^{adj}$** to B may be ideal. Once $B^{adj}$ is obtained, cell frequencies may be estimated from the original mixtures M. As with the B-mode batch correction, a minimum of about 3-5 mixture samples may be required for applying ComBat within S-mode. Although more mixture samples than cell types may be required to run NNLS (see equation 2), for datasets that fail to meet this requirement, additional artificial mixtures may be created from R using randomly drawn frequency vectors from F*. Each additional pseudo-mixture may be paired with its corresponding mixture sample in M prior to batch correction.

Software Implementation

CIBERSORTx may be developed within a web framework with its back-end based on R and PHP (as described, for example, by http://cibersortx.stanford.edu). This web framework may minimize inherent dependencies on specific hardware, software packages and libraries, and file-system attributes. Users may be presented with a detailed guide employing several step-by-step tutorials, which may allow the recreation of results described herein, including for each step in FIG. 1. Through this interface, CIBERSORTx may allow users to process gene expression data representing a bulk admixture of different cell types, along with (1) a signature gene file that enumerates the genes defining the expression profile for each cell type of interest. For the latter, users can either use existing/curated signature matrices for reference cell types, or can create custom signature gene files by providing the reference gene expression profiles of pure cell populations. Specifically, to create a custom signature gene matrix, users can provide single-cell RNA sequencing data or data from bulk sorted samples, along with the phenotypic identities of single cell types or cell populations of interest.

Given these input files, CIBERSORTx may allow (2) imputation of the fractional representations of each cell type present in the mixture, similar to its predecessor. CIBERSORTx also supports deconvolution from bulk RNA-Seq data in implementing the critical batch-correction methods described above. CIBERSORTx also allows imputation of GEPs for individual in silico purified cell-types in two distinct modes as described above (e.g., Group-Level and High-Resolution). The resulting imputed fractions and imputed GEPs then may be rendered as heat maps, tables, and stacked bar plots for visualization and downloading.

The interactive CIBERSORTx user interface may be implemented using a jQuery JavaScript library and open source libraries (including phpMailer, idiorm, blueimp jQuery-File-Upload, DataTables, phpExcel and mPDF), with the graphical user interface (GUI) of the website implementing using Twitter Bootstrap 2.3.2. The site may run on an Apache server on a virtual machine and store user and job data in a MySQL database. However, users may have complete control over their data and can delete them as desired. Each user's environment includes example datasets used for benchmarking, tutorials for the use of CIBERSORTx and preparation of input data, and other example files.

Group-Level Purification of NSCLC Cell Subsets

Despite the use of enzymatic ribosomal RNA (rRNA) depletion on the NSCLC samples analyzed in FIG. 3g, a large fraction of TPM-scaled reads (30-90%) may be derived from mitochondrial rRNA, specifically MT-RNR1 (Mitochondrially Encoded 12S RNA) and MT-RNR2 (Mitochondrially Encoded 16S RNA). To eliminate this confounding variable, these transcripts may be removed and the data matrix may be renormalized into TPM space. To generate an NSCLC signature matrix for expression purification (FIG. 3g), GEPs of epithelial (EpCAM$^+$), hematopoietic (CD45$^+$), endothelial (CD31$^+$), and stromal (CD10$^+$) cells were analyzed, each of which was FACS-sorted from primary NSCLC tumor biopsies obtained from donors. Signature matrix parameters may be identical to those described for signature matrix construction elsewhere herein, but without the preprocessing steps employed for scRNA-Seq. The resulting signature matrix, comprised of hundreds of genes (in one case, 933 genes), may be applied to whole transcriptome profiles of bulk NSCLC tumor samples obtained from another set of donors (in one case, n=26), and the results may be analyzed to impute group-level cell type-specific GEPs. Ground truth cell type GEPs may be derived by taking the geometric mean of replicate RNA-Seq profiles of EpCAM$^+$, CD45$^+$, CD31$^+$, and CD10$^+$ cells FACS-sorted from the second set of donors.

Generation and Analysis of Synthetic GEP Admixtures

Figure 4:
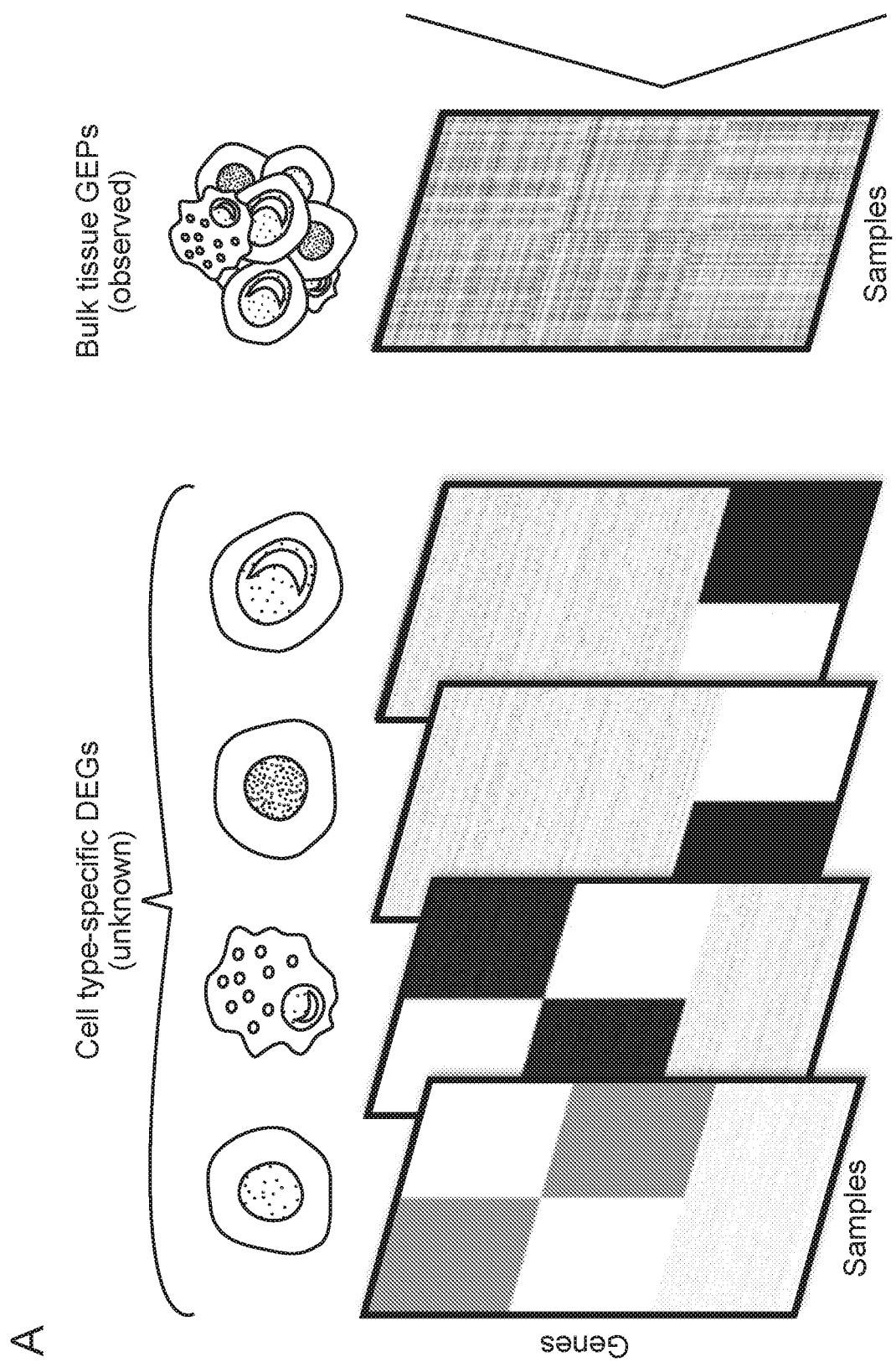
FIGS. 4a-e illustrate high-resolution purification of cell type-specific expression. (4a) Schematic illustrating an anecdotal example of unobserved (left) and observed (right) expression data for a series of four randomly admixed immune subsets, each with one or more sets of ground truth differential expressed genes (DEGs) (indicated by colored block-like patterns). (4b) Results of in silico purification applied to the bulk tissue expression matrix in panel a. (4c) t-SNE representation of purified expression matrices in (b), performed separately for each cell type and color-coded by the class corresponding to each block pattern in b (red=leftmost block, blue=rightmost block). (4d) Left: Synthetic GEP matrix of four randomly admixed immune subsets, one of which contains DEGs in the shape of a bullseye (monocytes). Right: Results of in silico purification. (4e) Analysis of the sensitivity and specificity of DEG recovery in synthetic mixtures when sample classes are known. Left: DEGs with a given fold change were added into the reference profile of CD8 T cells, which were spiked at a predetermined proportion into random mixtures of three other immune subsets. A colon cancer cell line GEP was added into each mixture to simulate ~50% unknown content. After in silico purification, known CD8 T cell DEGs were assessed in each purified cell type by ranking genes by fold change with respect to known DEG classes. The area under the curve (AUC) for DEG recovery was calculated for each combination of fold change and cell type spike-in fraction, and shown as a heat map. Data in panels (4a), (4b), and (4d) were log 2 adjusted and median-centered for each gene prior to rendering the heat maps.
Figure 4:
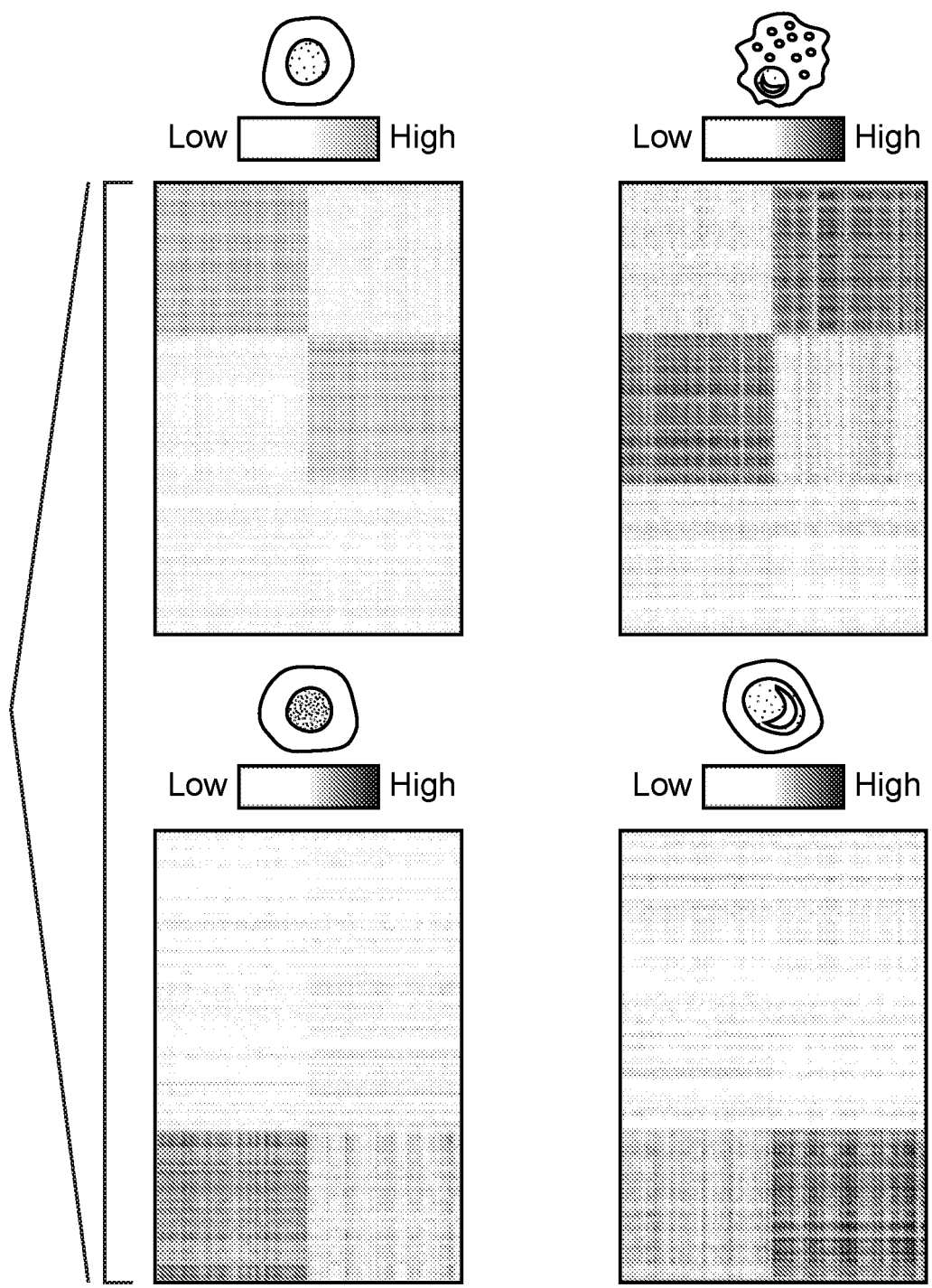
Figure 4:
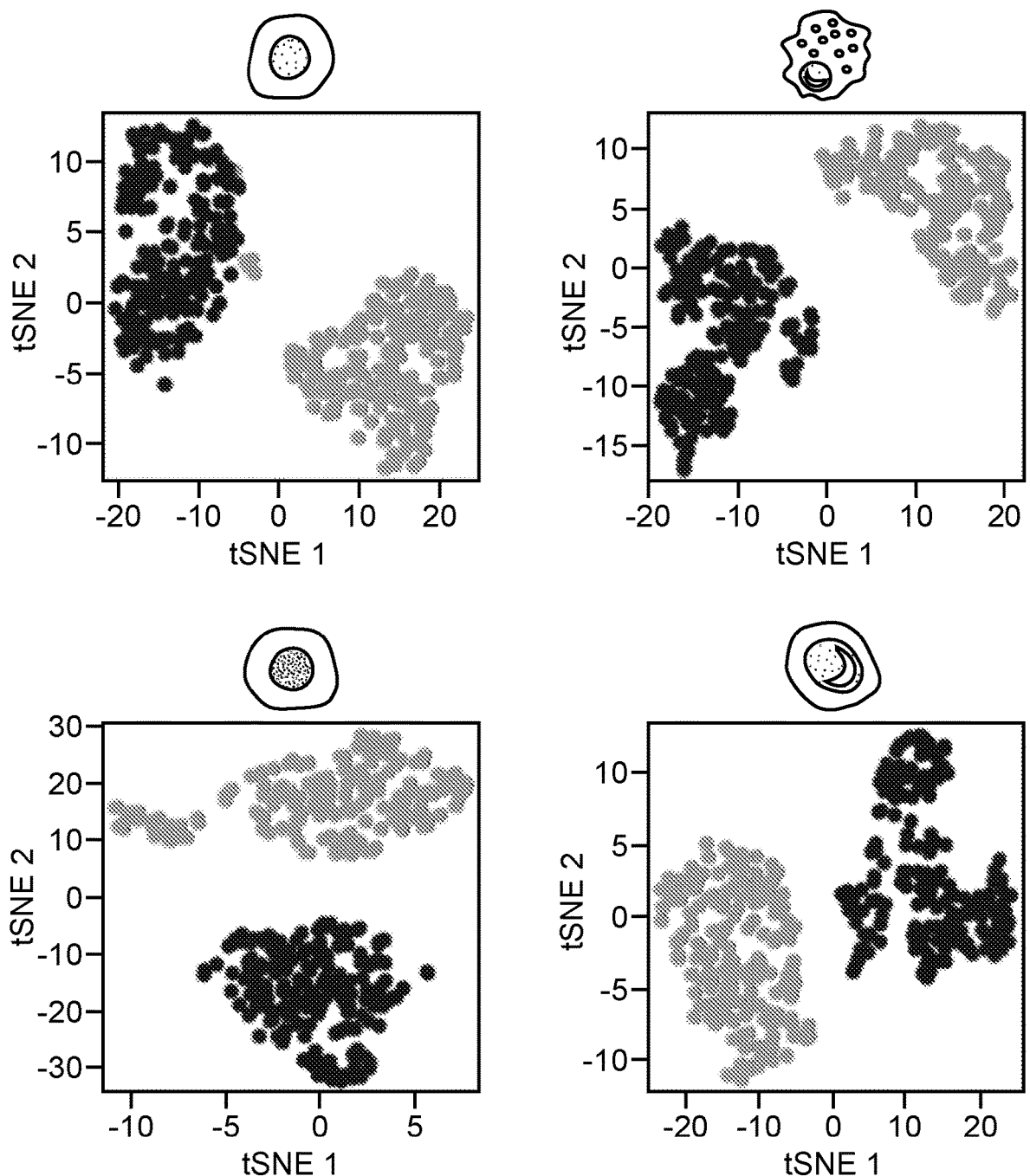
Figure 4:
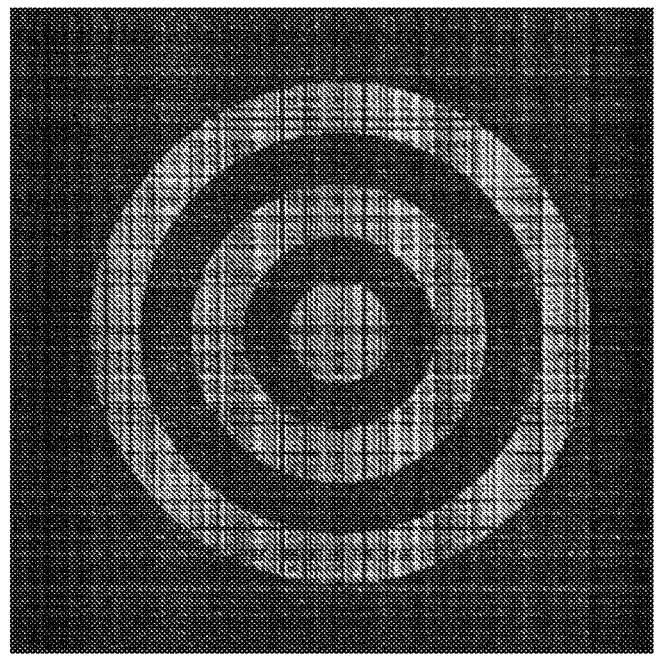
Figure 4:
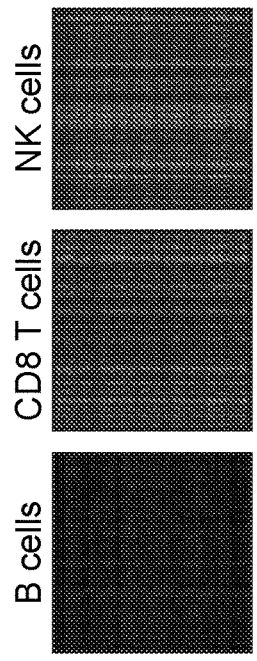
Figure 4:
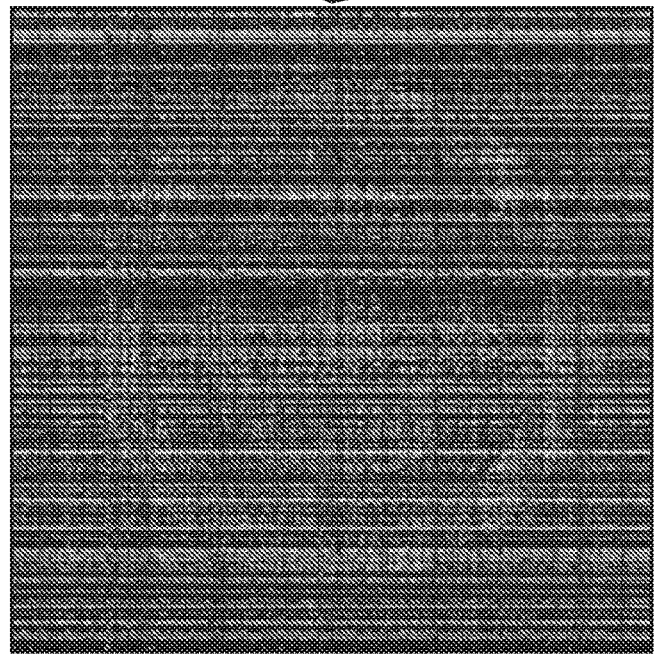
Figure 4:
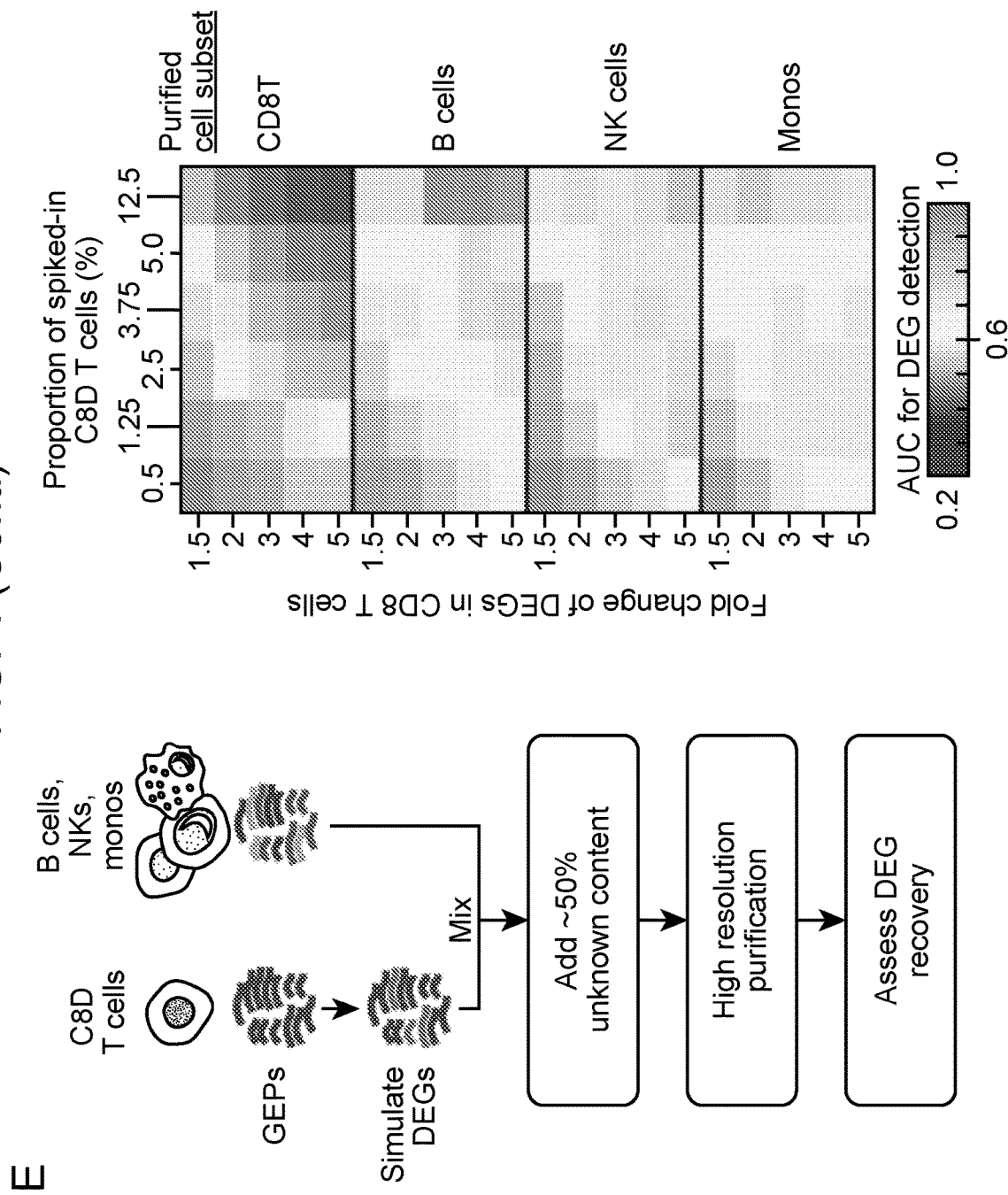
Figure 5:
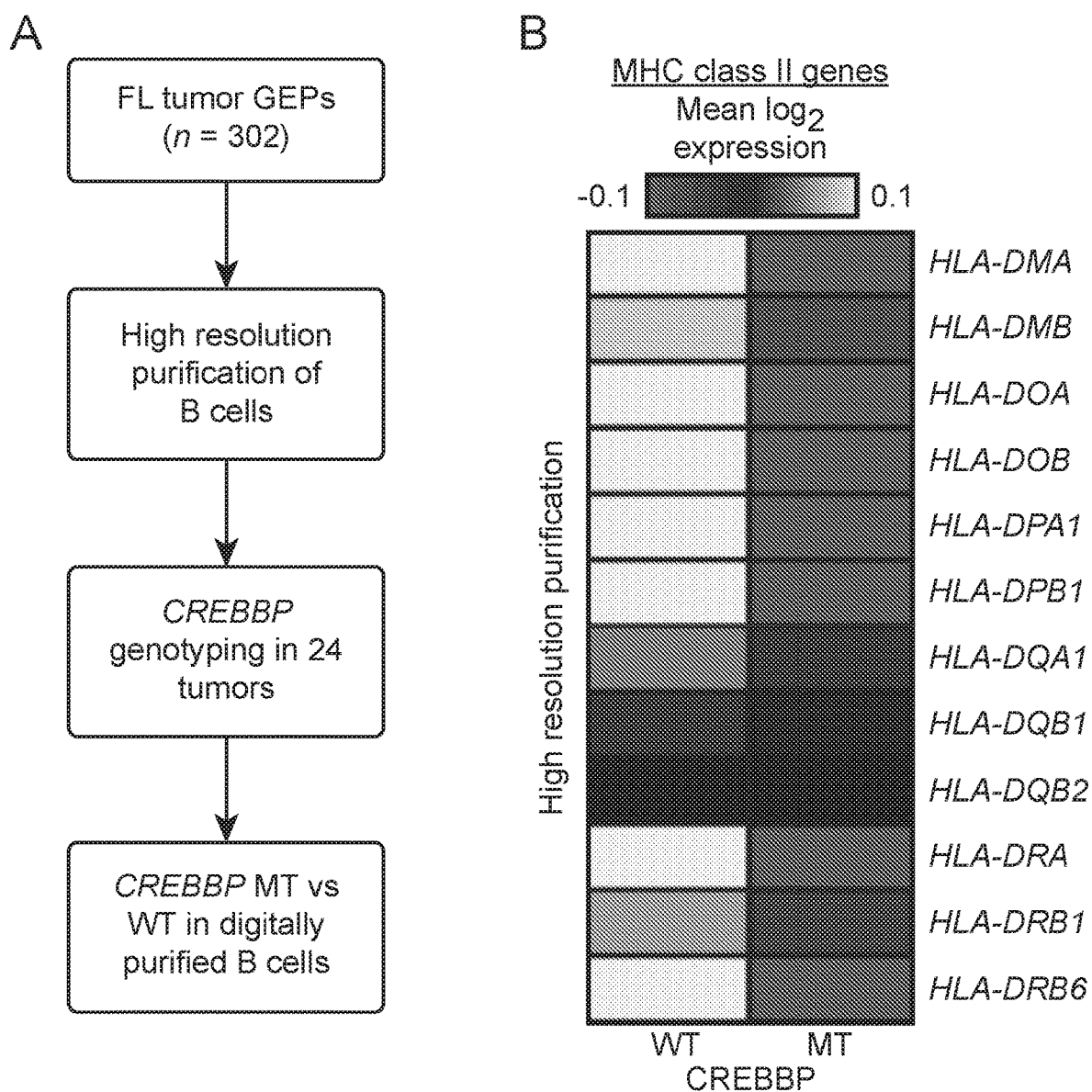
FIGS. 5a-f illustrate high resolution expression profiling of bulk tumor biopsies. (5a)-(5c) Analysis of CREBBP mutation-associated expression changes in B cells from follicular lymphoma (FL) tumors. (5a) Schema. (5b) Heat map (left) and scatter plot (right) confirming loss of MHC class II expression in CREBBP-mutant FL B cell GEPs inferred by CIBERSORTx. Expression values were median-centered prior to plotting. (5c) Analysis of published gene sets associated with lower (left) or higher (right) B cell expression in CREBBP-mutant FL tumors. Scatter plots show the corresponding $\log_2$ expression of each gene in digitally sorted B cell GEPs, after median centering and averaging by CREBBP mutation status. Group comparisons in b and c were assessed by a Wilcoxon signed-rank test. WT, wildtype (n=9); MT, mutant (n=15). (5d)-(5f) High resolution expression profiling of tumor cell subpopulations from non-small cell lung cancer (NSCLC) tumors. (5d) Schema for profiling and validating expression signatures of epithelial cells (Epith., EpCAM$^+$), immune cells (Imm., CD45$^+$), fibroblasts (Fib., CD10$^+$), and endothelial cells (Endo., CD31$^+$) in 1,020 NSCLC tumor GEPs from TCGA. (5e) Left: tSNE plots showing population-specific transcriptional diversity imputed from 1,020 NSCLC tumors, color-coded to denote tumor histology and adjacent normal tissues. Plots were created with perplexity set to 10. Right: PCA plots of GEPs from corresponding FACS-purified populations, color-coded by tumor histology. Histological differences are also highlighted by shaded ovals. (5f) Heat maps showing DEGs in epithelial, immune, and fibroblast populations identified in TCGA (left) and RNA-Seq profiles of corresponding FACS-purified populations from 20 NSCLC patients (right). Median centering was applied to each cell population separately. LUAD, lung adenocarcinoma; LUSC, lung squamous cell carcinoma.
Figure 5:
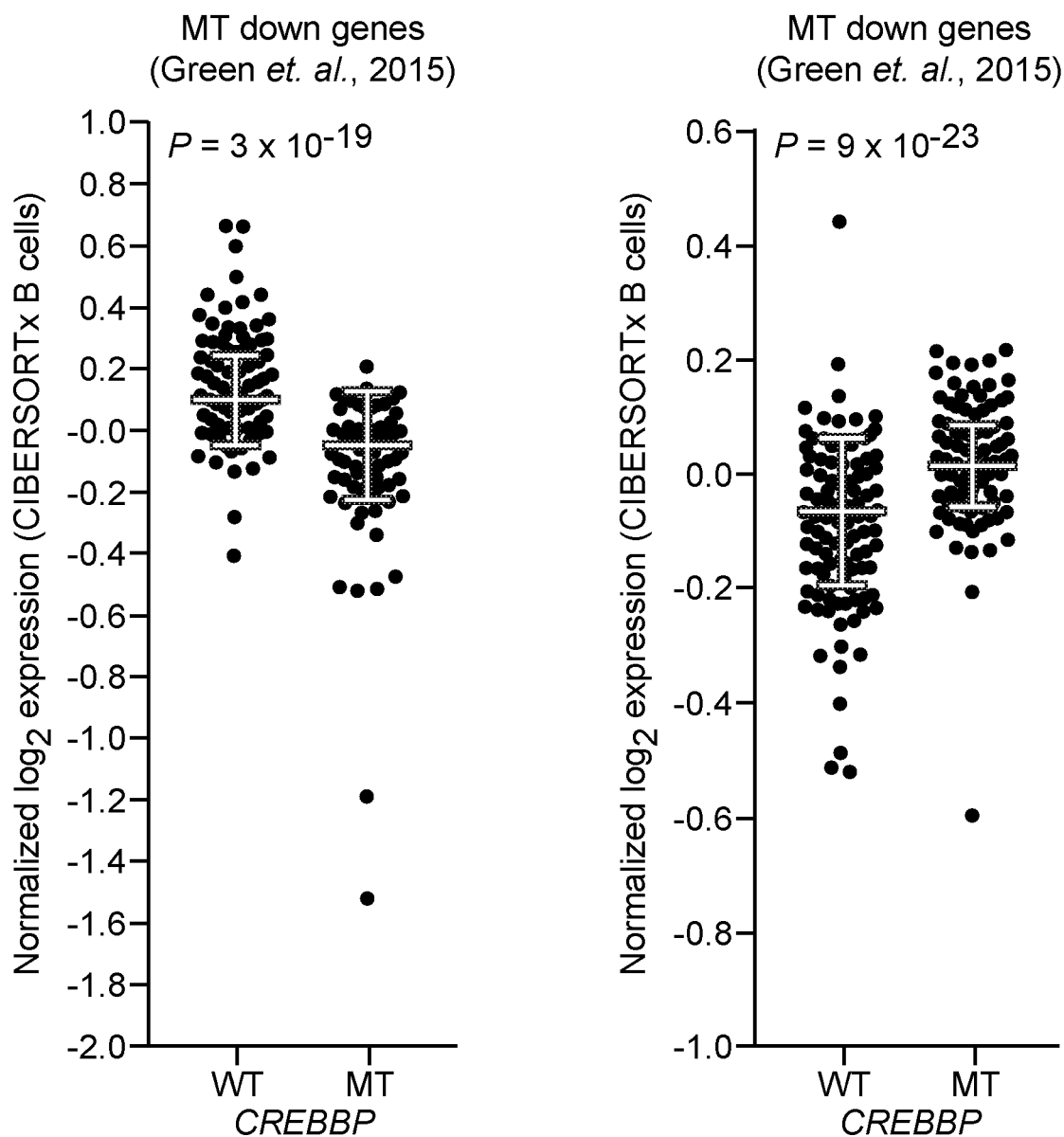
Figure 5:
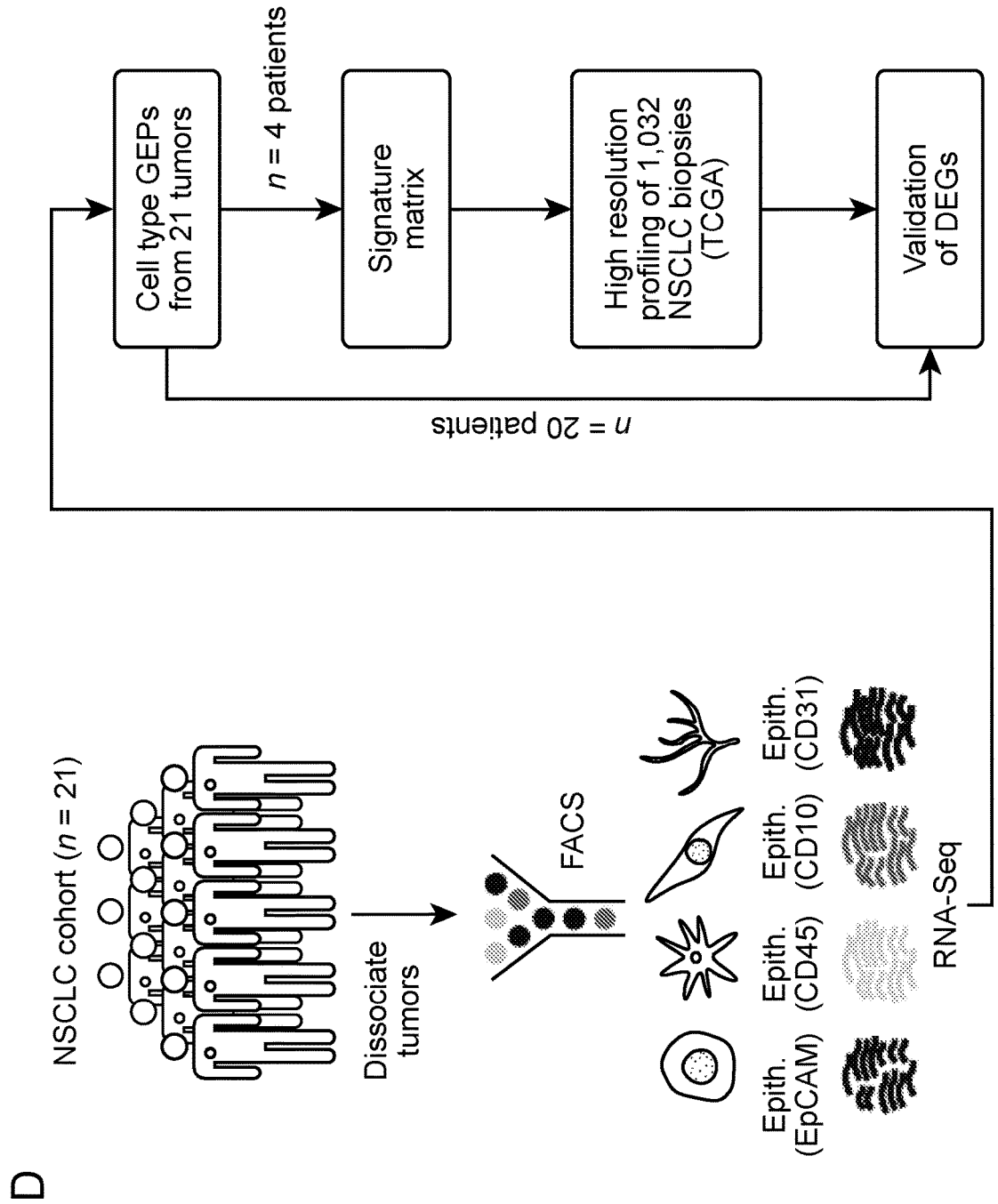
Figure 5:
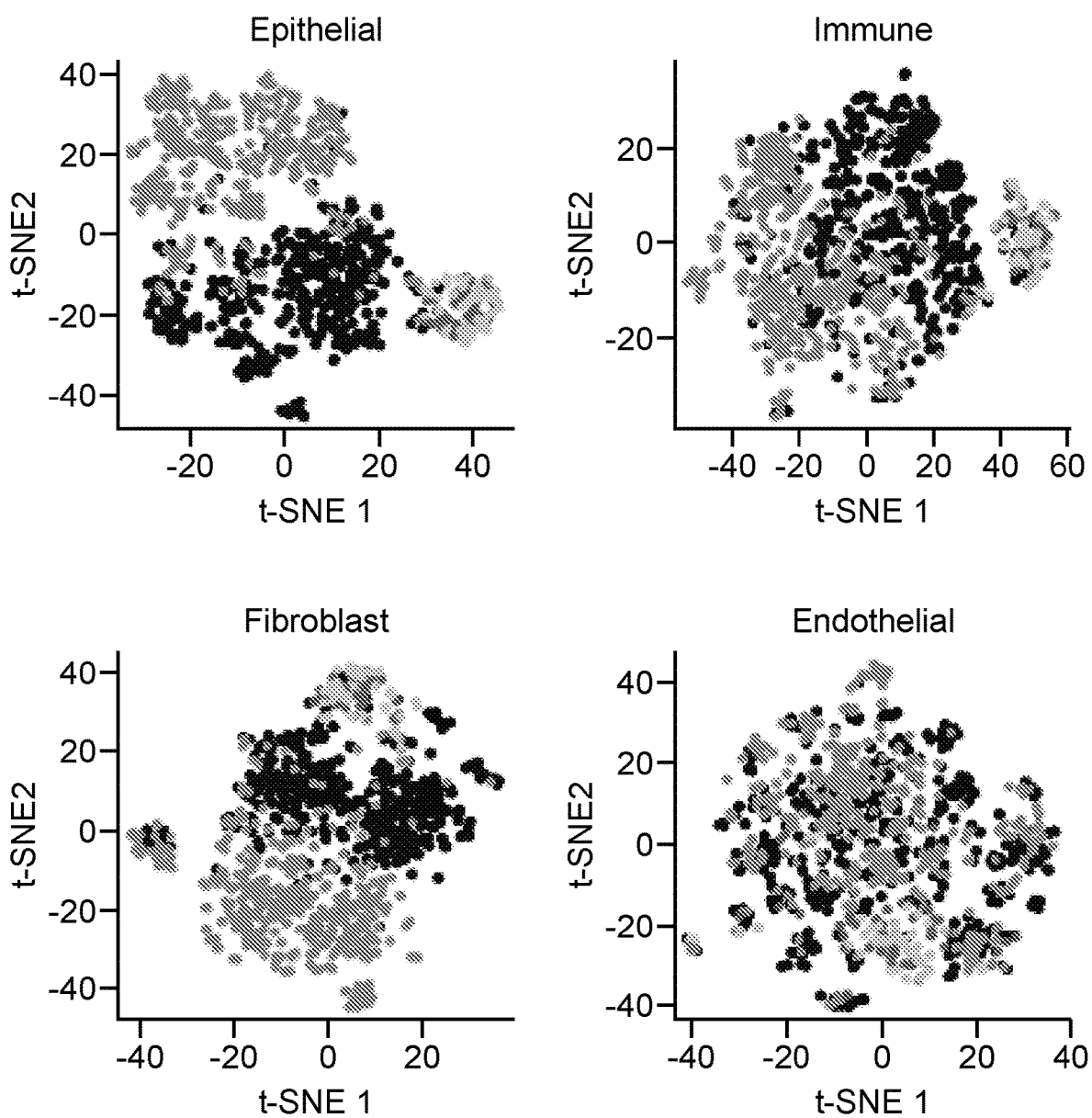
Figure 5:
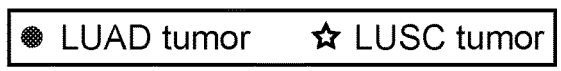
Figure 5:
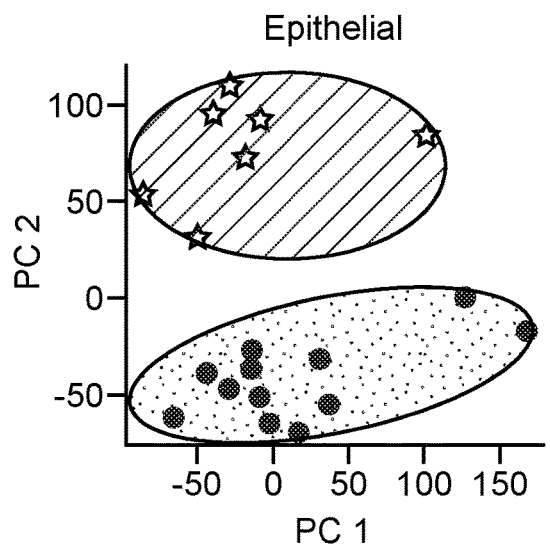
Figure 5:
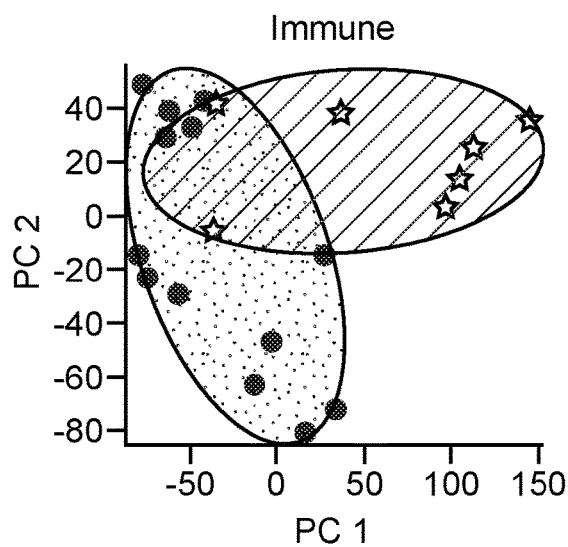
Figure 5:
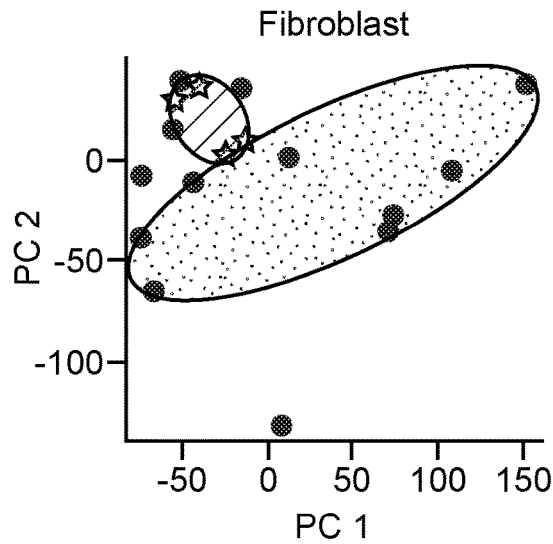
Figure 5:
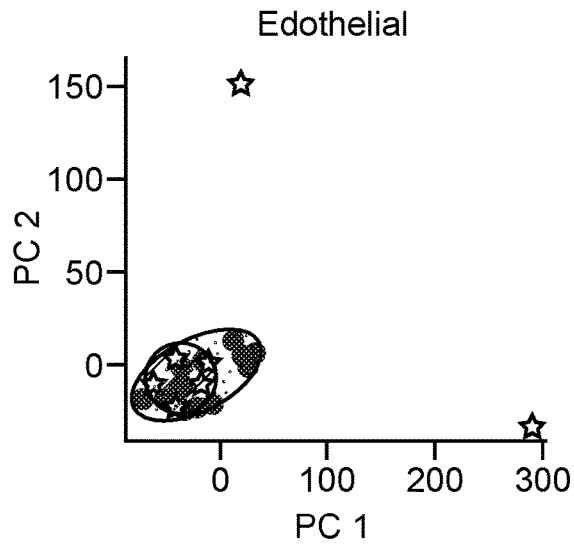
Figure 5:
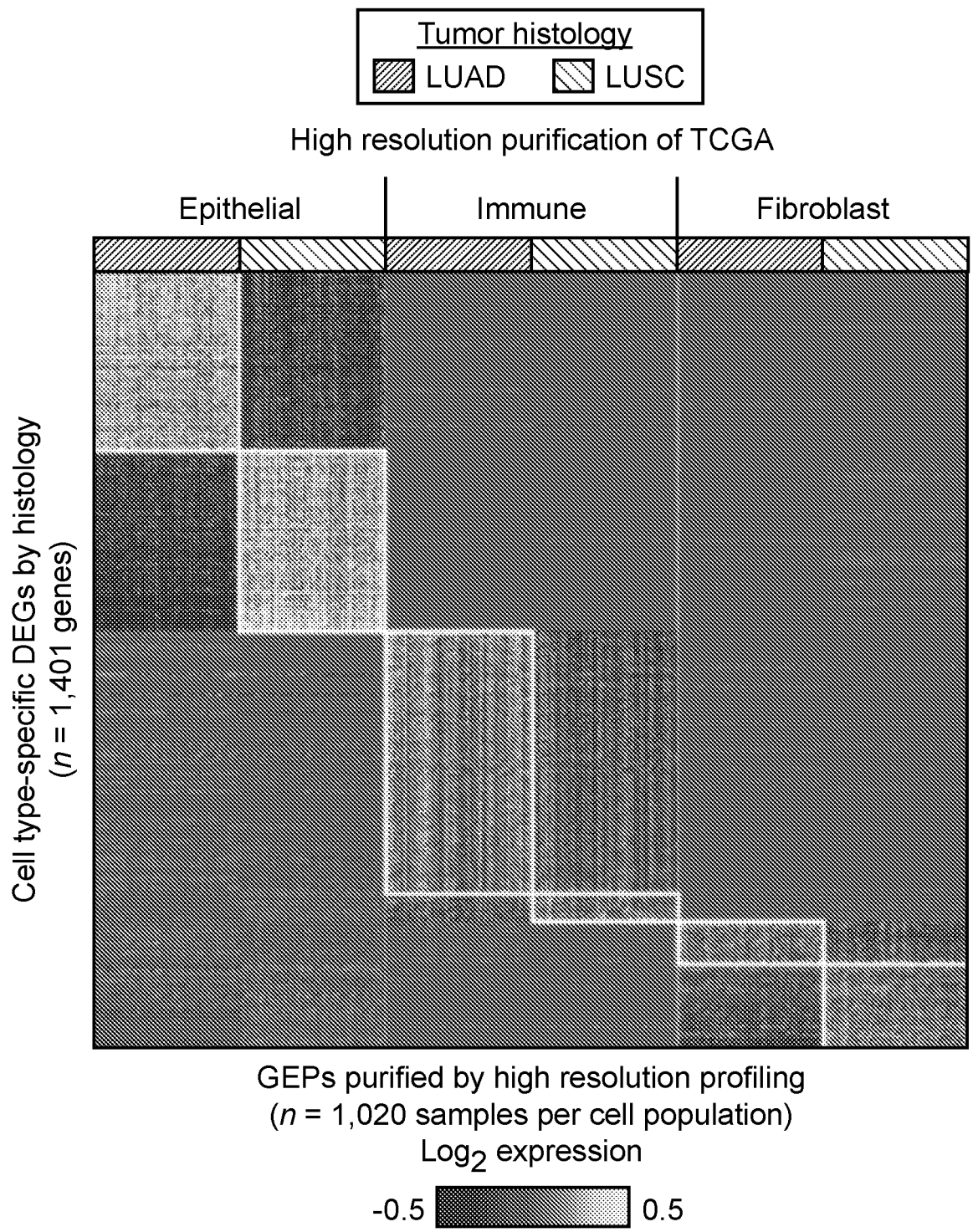
Figure 5:
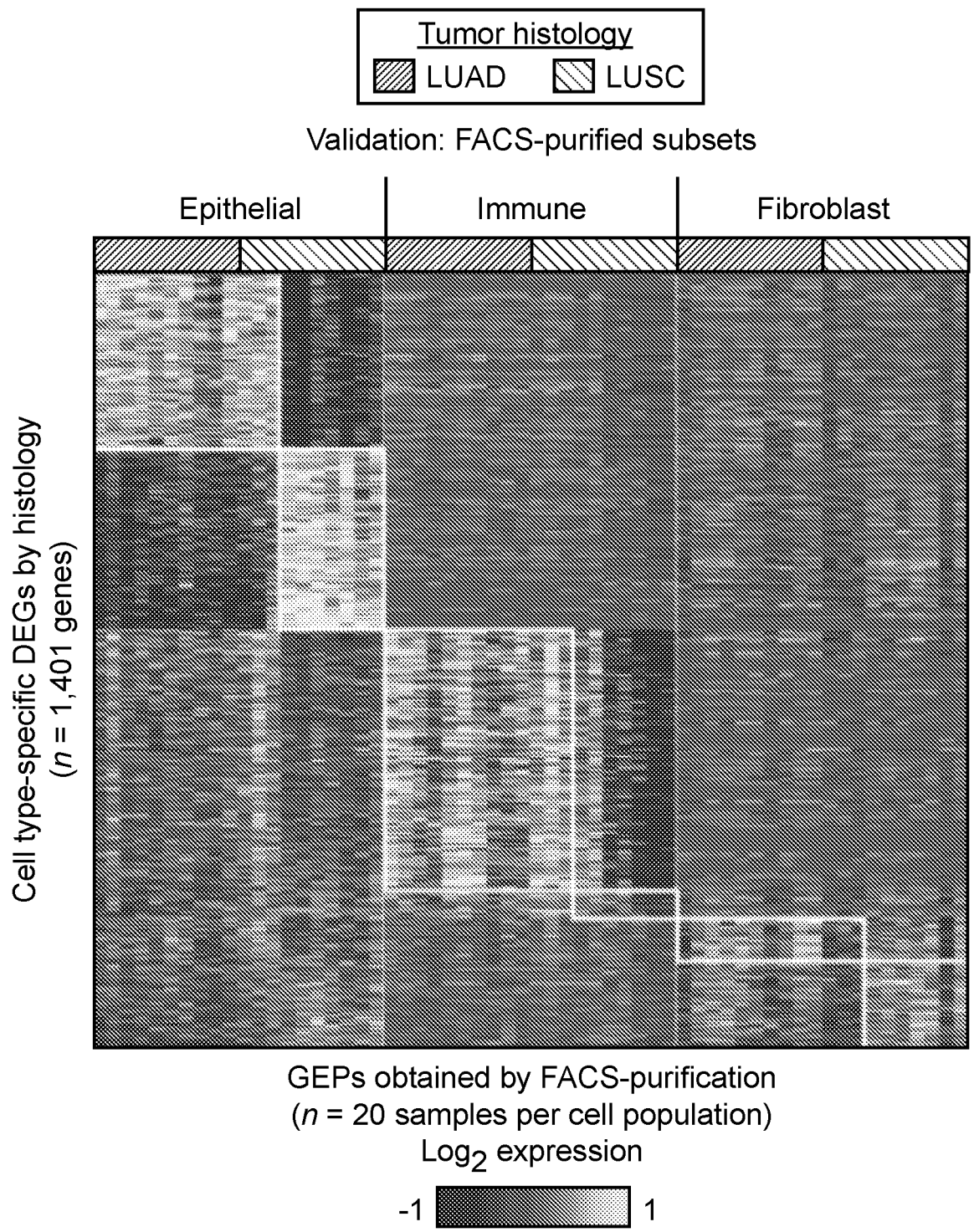

Simulated GEP mixtures in FIG. 4a may be created using reference profiles of k=4 cell types (naïve B cells, CD8 T cells, NK cells, and monocytes) obtained from the source data underlying LM22. As an initial proof of concept, the analysis may be restricted to 1,000 randomly selected genes from the transcriptome, along with all 547 genes from the LM22 signature matrix. Next, the four cell type expression vectors may be log$_2$-adjusted and each of them may be copied m=400 times. Variability may be introduced by calculating the standard deviation sd$_j$ of each gene j across the four cell types, and by replacing each gene's expression value v by drawing random values from the distribution N(v, sd$_j$/5). To simulate biological groupings, DEGs may be added to each cell type, such that the first 200 and second 200 samples are stratified into two classes. Overlapping DEG patterns may be inserted into monocyte, B cell, CD8 T cell, and NK cell GEPs, as depicted by orange cells, green cells, blue cells, and purple cells, respectively, in FIG. 4a (left panel). DEGs may be created to reflect a five-fold higher level of expression. Next, an m×k matrix may be generated of mixture coefficients randomly drawn from a normal distribution with N(1/k, 1/(2k)). Coefficients for each mixture may be normalized to sum to 1. Prior to mixing, synthetic cell type GEPs may be converted to non-log linear space. Next, they may be combined according to their corresponding mixing coefficients, yielding 400 simulated tissue GEPs. High-resolution CIBERSORTx may be performed on the resulting admixture dataset using, for example, a window size of 20 (=5×k) and LM4, a subset of the LM22 signature matrix containing barcode genes for monocytes, B cells, CD8 T cells, and NK cells.

For the synthetic dataset in FIG. 4d, the above approach may be repeated with m=11,845 (the full list of genes in the source dataset from which LM22 was derived), and the following changes. First, up-regulated DEGs may be embedded in the shape of a 'bullseye' target (three concentric circles) into monocyte GEPs. To mask the DEG image in bulk admixtures, DEGs may be added every 22 genes into monocyte GEPs; the inverse (downregulated DEGs of equal fold change) may be added into the remaining cell type GEPs (n=3) in alternating order (e.g., every 66 genes). Next, a high-resolution CIBERSORTx method may be applied as described above to recover the embedded bullseye.

Figure 14:
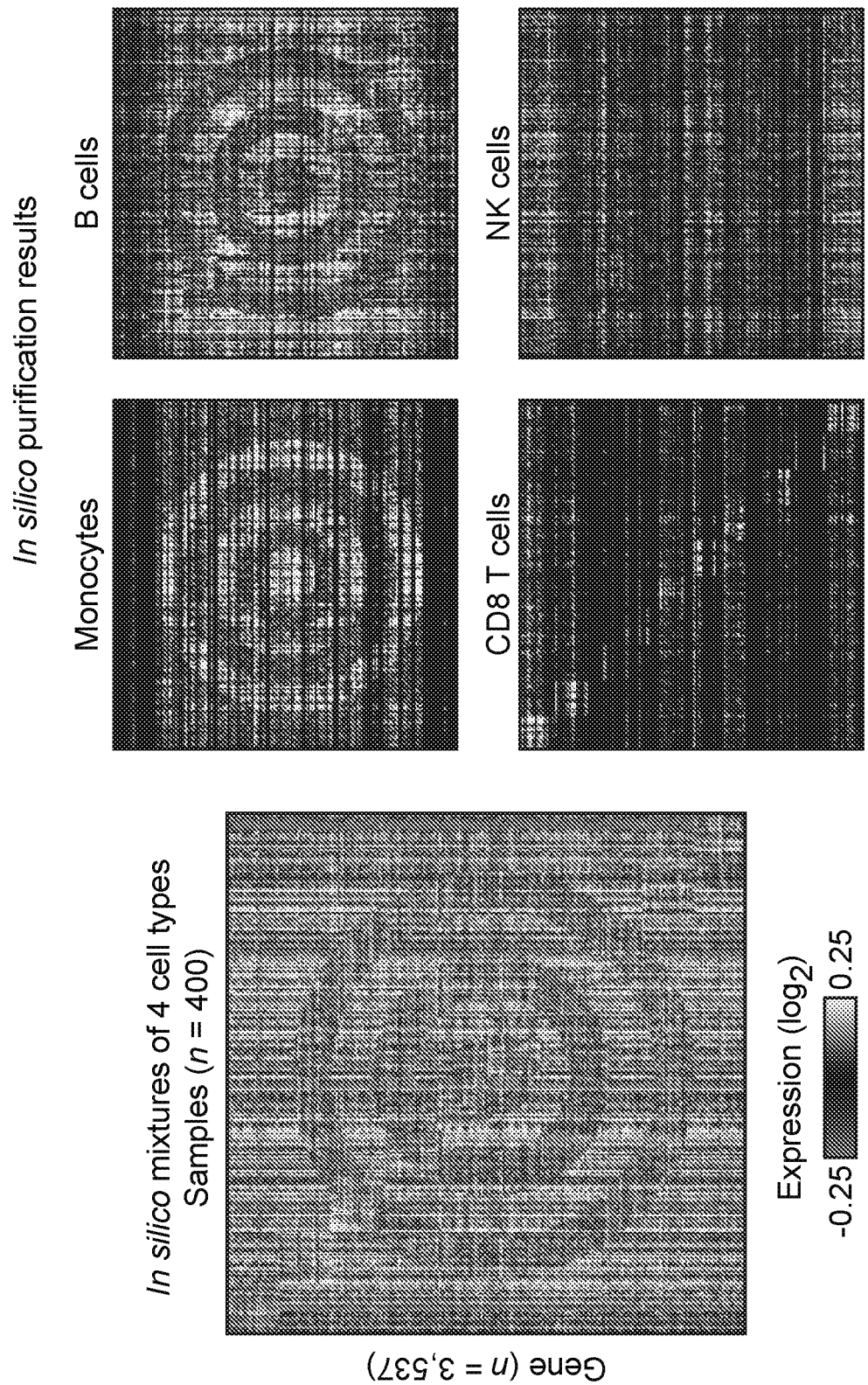
FIG. 14 illustrates high-resolution purification of DEGs with overlapping patterns. Left: Heat map showing 400 synthetic GEP admixtures of four immune subsets, each containing a unique cell type-specific DEG pattern: a target, a series of diagonally aligned squares, and the inverse of each. Right: Heat maps showing high-resolution CIBERSORTx results.

For the synthetic dataset in FIG. 14, the approach used for FIG. 4d may be repeated, with the exception that the analysis is restricted to a random selection of 3,000 genes along with all genes in LM22. Next, two upregulated DEG patterns may be embedded: a target into monocyte GEPs (as shown in FIG. 4d, but inserted every other gene), and a set of 10 diagonally aligned squares into CD8 T cell GEPs (added to every gene). To obfuscate these DEGs in admixture profiles, downregulated DEGs may inserted into B cells and NK cells in a reciprocal manner that complements the respective patterns. High-resolution CIBERSORTx may be applied as described above.

Analysis of Cell Type-Specific DEG Detection with High-Resolution CIBERSORTx

Synthetic tumors with five cell types may be analyzed as follows. Simulated mixtures may be created as described elsewhere herein, except in this case, k may be set to 50 mixtures, m may be set to 3,000 genes (containing LM22), and DEGs may be exclusively inserted into CD8 T cell profiles (samples 26-50; all DEGs were over-expressed relative to baseline levels). To assess performance across a range of realistic settings, a distinct set of 50 mixtures may be evaluated for different combinations of (1) DEG fold changes (1.5 to 5-fold) and (2) average fractional abundances of CD8 T cells (1% to 25%) (FIG. 4e). A high-resolution CIBERSORTx method may be performed on all mixture samples using the LM4 signature matrix (described above) using, for example, a window of length 16 (=4k). To evaluate the presence of unknown mixture content (e.g., malignant cells in a tumor), the analysis may be repeated by adding an average of 50% HCT116, a colon cancer cell line, to each mixture dataset and by applying high-resolution CIBERSORTx with batch correction. The same strategy may be applied for simulating mixing coefficients, as described elsewhere herein, except the mean proportions of CD8 T cells and HCT116 may be set to their target abundances. The same HCT116 GEP dataset and expression normalization steps as described previously may be used. The area under the curve may be assessed by calculating gene-level fold changes in $\log_2$ space between known DEG classes (25 samples each), and by comparing the resulting quantities between known DE genes (positives) and remaining genes (negatives). To evaluate specificity, this process may be repeated for each imputed cell type GEP.

Simulated melanoma tumors with eight cell types may be analyzed as follows. Single-cell RNA-Seq profiles from melanoma patients may be obtained, as described elsewhere herein, and labeled according to seven previously annotated cell phenotypes: B cells, T cells, NK cells, macrophages, endothelial cells, cancer-associated fibroblasts, and malignant cells. T lymphocytes may be divided into CD8 and CD4 T cells by the expression of CD8A or CD8B (non-log TPM>0), for a total of k=8 evaluable cell types. Next, in order to simulate melanoma tumors, an approach that mirrors the distribution of cell type frequencies across dissociated tumors may be used. Specifically, to build each synthetic tumor, each cell type may be iterated through, one at a time, and all single cells corresponding to that cell type may be selected from a randomly chosen tumor in the original cohort.

Figure 15A:
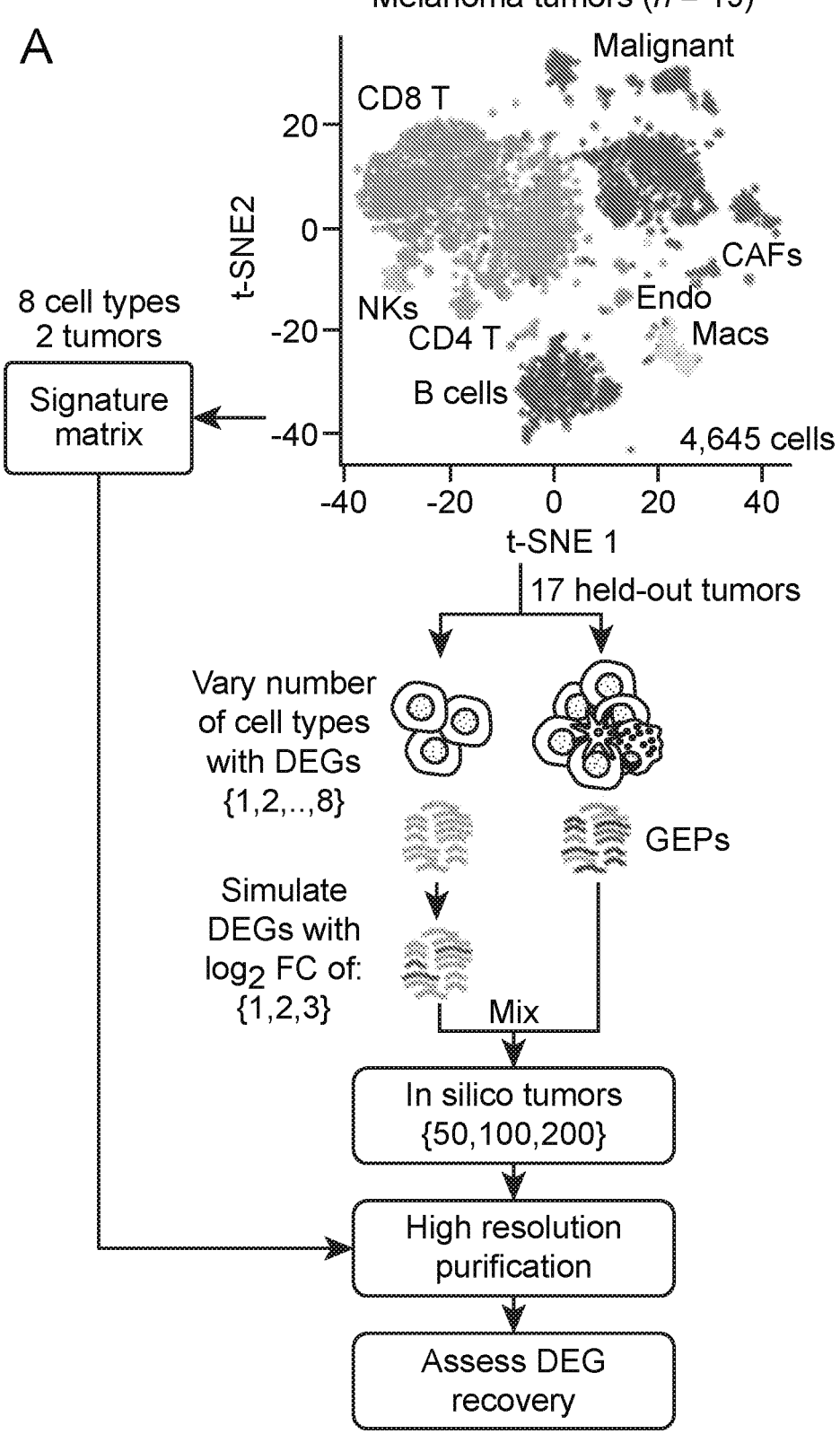
FIGS. 15a-c illustrate parameter sweep of high resolution expression purification. (15a) Schema depicting a parameter sweep to evaluate DEG recovery in reconstituted melanoma tumors containing 8 major cell types. Performance was assessed by systematically varying: (i) the total number of cell types with DEGs (1, 2, 3, . . . , 8), (ii) the total number of tumor samples (50, 100, 200), and (iii) the $\log_2$ fold change of DEGs (1, 2, and 3). DEG recovery was evaluated as in FIG. 4e. Cell fractions were sampled uniformly according to their frequencies in the original dataset. (15b) Heat map showing the mean area under the curve (AUC) for the recovery of known cell type-specific DEGs in different numbers of in silico tumors as a function of (Top) the number of cell types with artificial DEGs and (Bottom) the $\log_2$ fold change of DEGs. (15c) Same as (15b), except the AUC is calculated with respect to imputed genes with non-zero variance. Thus, genes with insufficient evidence of expression are excluded from consideration. Vertical lines in the color bar show AUC intervals of 0.1. As shown in panel (15b), DEG recovery is highly specific; when known DEGs from one cell type are assessed in another, the false detection rate is no greater than random chance (AUCs of about 0.5). DEG detection rates increase as more tumor samples are profiled and as higher fold changes were evaluated. A modest reduction in performance can be seen as a function of the number of cell types with DEGs. However, these results reflect all genes, including those with insignificant evidence of cell type-specific expression. As shown in panel 15(c), when considering performance among genes with variable expression (e.g., imputed with nonzero variance), the AUC for DEG recovery is consistently high (mean=0.93, s.d.=0.04).
Figure 15:
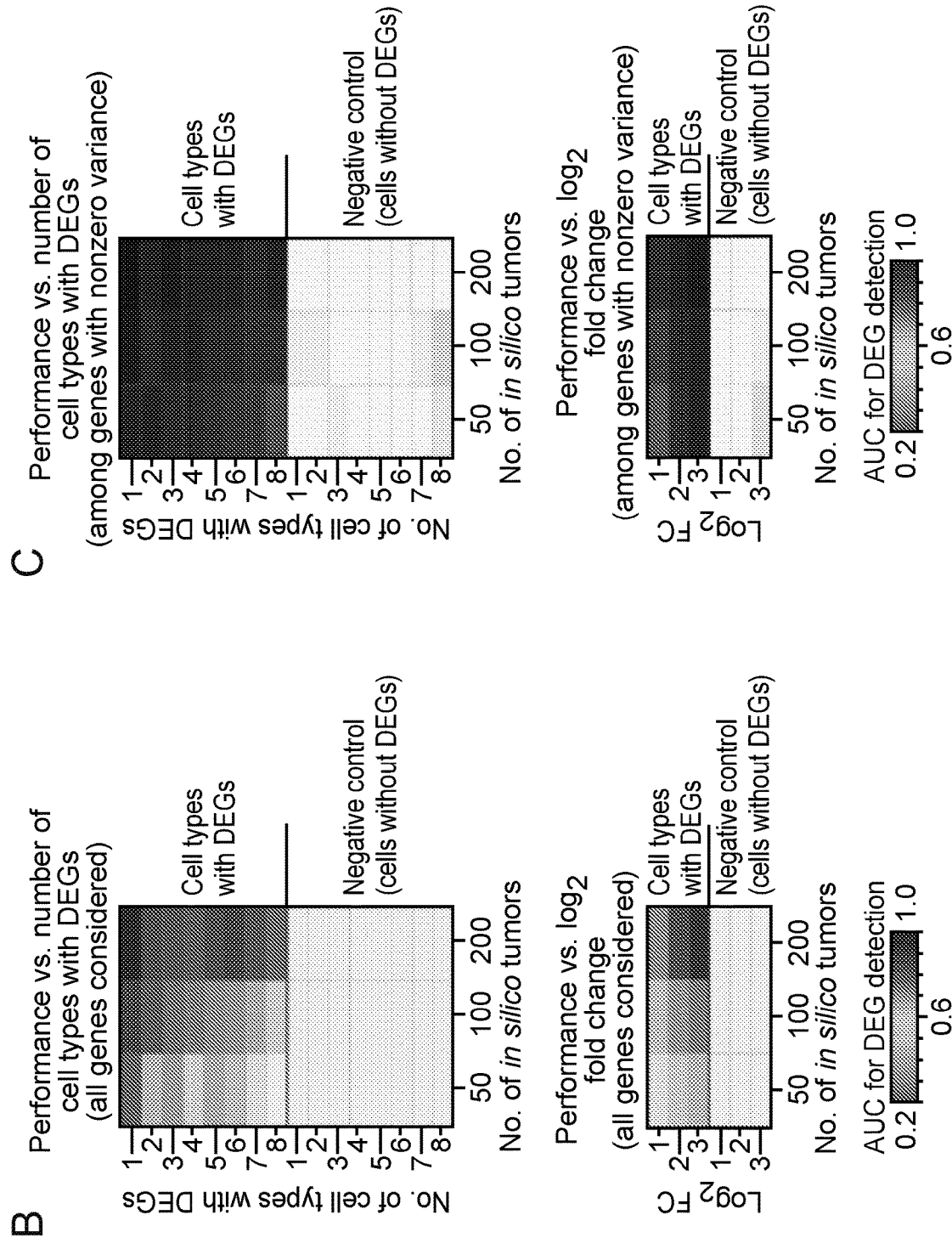
Figure 16:
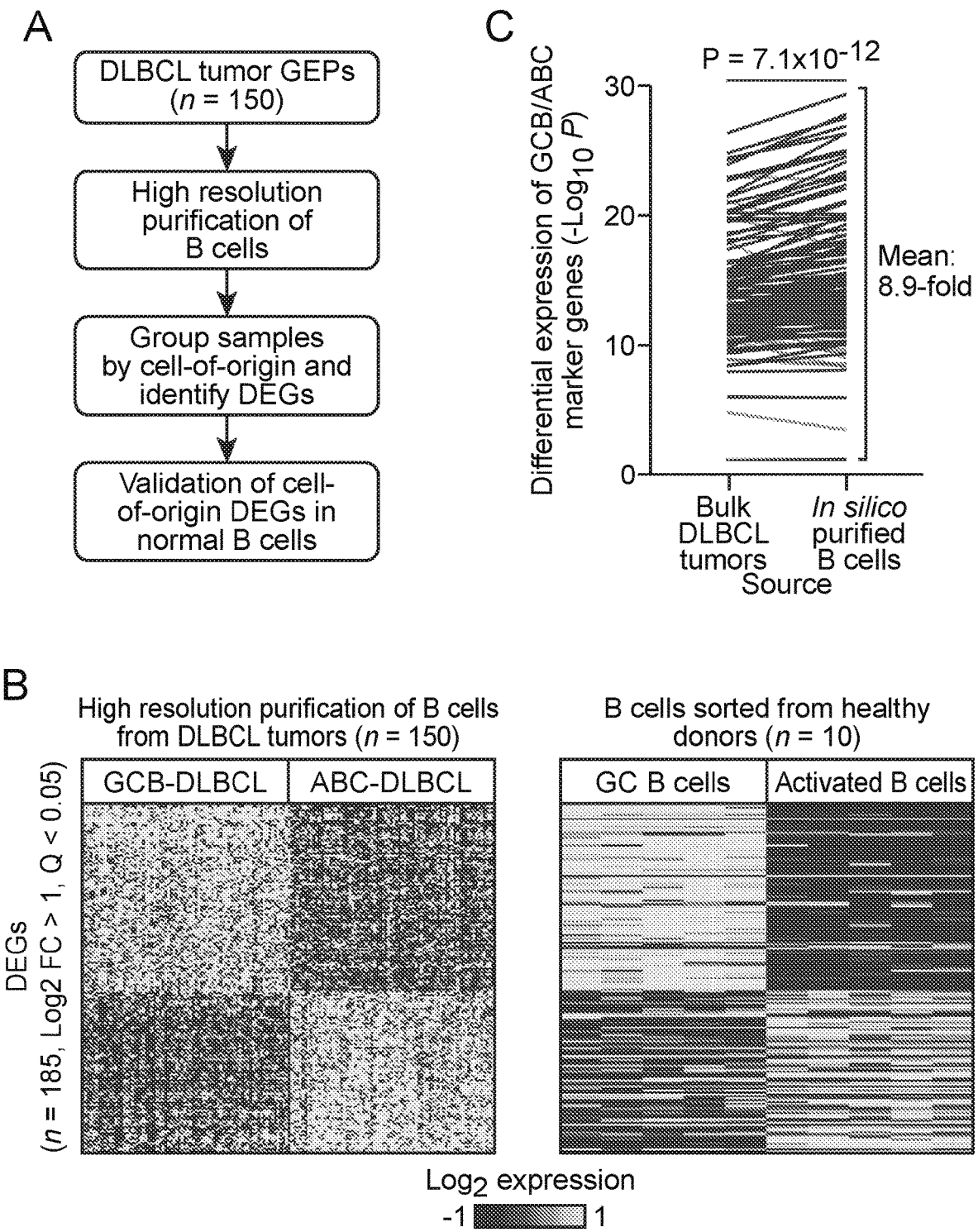
FIGS. 16a-c illustrate high-resolution purification of DLBCL molecular subtypes. (16a) Schema for dissecting diffuse large B-cell lymphoma (DLBCL) tumors (GCB/ABC DLBCL, CHOP cohort, as described, for example, by Lenz et al. (Stromal Gene Signatures in Large-B-Cell Lymphomas, *New England Journal of Medicine* 359, 2313-2323 (2008), which is hereby incorporated by reference in its entirety)) by high resolution purification. (16b) Left: Heat map showing DEGs identified between ABC and GCB DLBCL within B cell transcriptomes digitally purified from DLBCL tumors. Samples are grouped by previously annotated subtypes. Right: Heat map depicting the same genes in the same ordering as the left panel, but shown for germinal center and activated B cells derived from healthy donors. Expression data in both heat maps were $\log_2$ adjusted and median-centered for each gene prior to rendering the heat maps. (16c) Significance of differential expression between GCB and ABC DLBCL for previously published marker genes ($-\log_{10}$ p value from a two-sided unpaired t test with unequal variance), comparing bulk DLBCL tumors and digitally purified B cells. The statistical significance between groups was determined using a two-sided paired t test. Only marker genes with non-zero expression in digitally purified B cells were evaluated (n=141 of 144 genes; SPINK2, TOX2, and FAM46C were assigned to other cell types).

This process may be iterated to create cohorts of multiple tumors (e.g., 50, 100, or 200). For each synthetic tumor, single-cell GEPs in non-log linear space may be aggregated by summation and normalized by TPM. For each cohort, the following may be varied: (1) the total number of cell types with artificial DEGs (d=1, 2, 3, . . . , 8), and (2) the $\log_2$ fold change of DEGs (fc=1, 2, and 3) (FIG. 15a). For each value of d and fc, artificial DEGs may be created by adding expression values drawn from a normal distribution to a set of multiple (e.g., about 2,000) randomly selected genes, e.g., with a mean of fc and s.d. of 0.5. Differential expression may be simulated differently depending on d, the number of cell types with DEGs. For d=1, half of the cell type GEPs may be assigned to a class with artificial DEGs and half may retain their baseline values. For d>1, a goal may be to simulate DEGs in a manner that would impede their recovery in bulk tumor transcriptomes. To do this, the class size may be set to equal to 25% greater than the number of tumors divided by d, and the resulting DEG classes may be tiled evenly across cell types. To enumerate cell proportions, a melanoma signature matrix derived from two tumors capturing the same eight cell types may be used (FIG. 8b). All synthetic tumors may be derived from the remaining 17 held-out tumors. A window of length 32 (=4k) may be used for high-resolution transcriptome purification. Accuracy may be evaluated as described above for synthetic tumors with five cell types. A $\log_2$ fold change that maximizes DEG recovery may be obtained (e.g., a mean of 0.11 with a 95% confidence interval of +/−0.009).

Analysis of Primary Tumor Specimens with High-Resolution CIBERSORTx

Lymphoma. For FIGS. 5a-c and 16, a window of length 40 (=4k) was used, and LM22 was collapsed into k=10 major leukocyte subsets following cell type enumeration and preceding transcriptome purification.

NSCLC. For FIGS. 5d-f and 18c-e, a window of length 20 was used to enumerate k=4 cell types using the signature matrix described elsewhere herein. For high resolution purification of TCGA (The Cancer Genome Atlas) samples, RNA-Seq profiles of LUAD and LUSC tumors (and their adjacent normal tissues) may be uniformly processed and normalized, merged into a single expression matrix, and visualized by t-SNE for evidence of possible outliers and batch effects. Putative outlier samples may be identified and omitted from further analysis. Following high resolution purification, cell type-specific DEGs may be identified between LUAD and LUSC tumor samples. To filter DEGs for significance, an empirically derived threshold may be applied (e.g., a $\log_2$ fold change of, e.g., greater than 0.1) that maximizes the sensitivity and specificity of DEG recovery in simulated melanoma tumors (FIGS. 15a-c) coupled with a Q value threshold of, e.g., less than 0.5 for additional stringency.

Melanoma. For FIG. 6b, a window of length 32 (=4k) may be used, and a single cell-derived melanoma signature matrix targeting k=8 major cell types may be employed (FIG. 8b). DEGs may be filtered as described above for NSCLC.

Analysis of PDCD1$^+$/CTLA4$^+$ CD8 T Cells in Bulk Melanoma Biopsies

Figure 21:
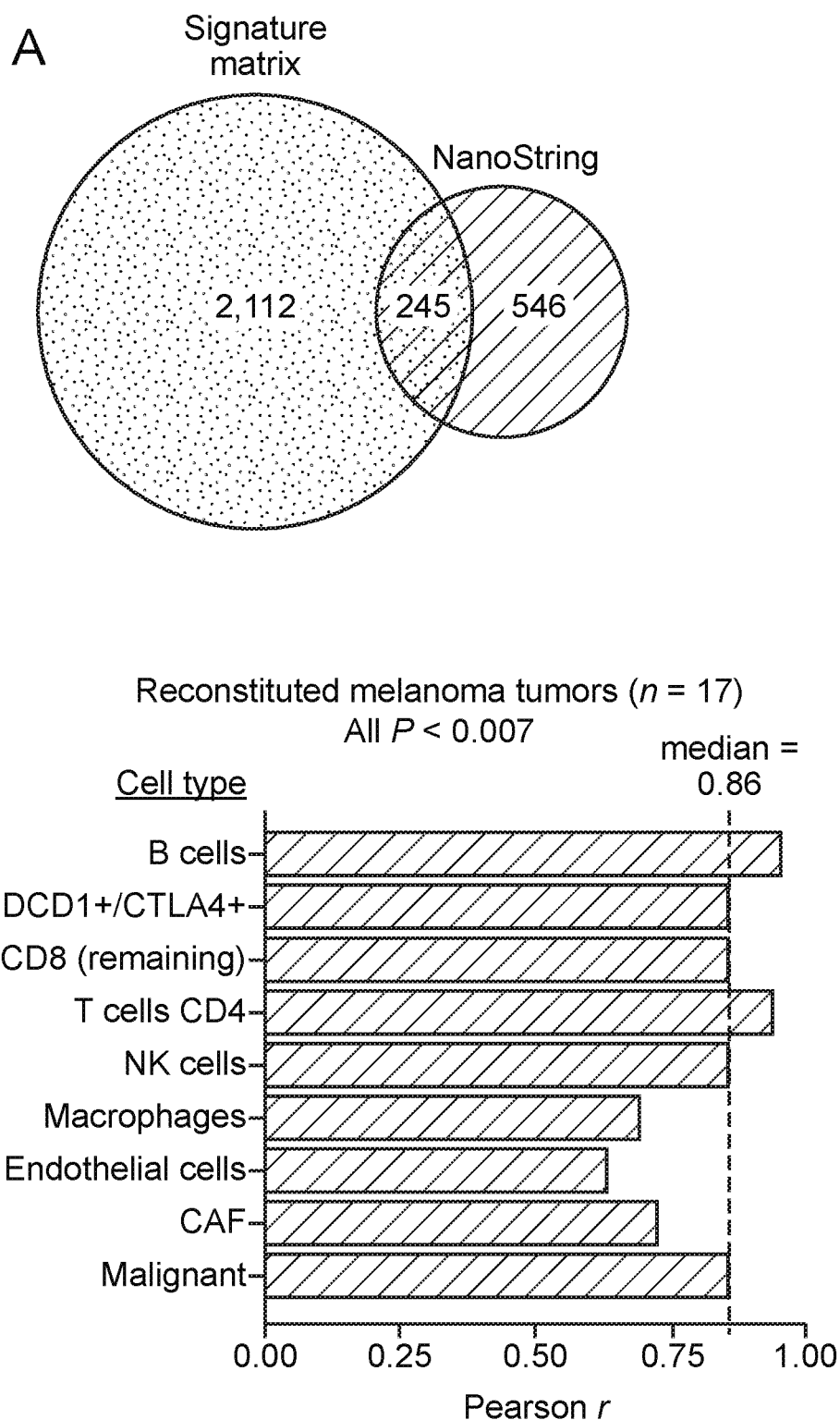
FIGS. 21a-f illustrate survival analysis of PDCD1+/CTLA4+ CD8 T cells in melanoma patients. (21a) Venn diagram depicting the overlap between a single cell-derived melanoma signature matrix distinguishing 9 tumor cell subsets (FIG. 9b, top left) and an nCounter NanoString platform (as described, for example, by Chen et al., Analysis of immune signatures in longitudinal tumor samples yields insight into biomarkers of response and mechanisms of resistance to immune checkpoint blockade, *Cancer Discovery* (2016), which is hereby incorporated by reference in its entirety). (21b) Same analysis as FIG. 9b (top left panel), but using the 245 signature matrix genes that overlap the NanoString nCounter assay, related to panel (21a). All tumors were reconstructed from single-cell GEPs held-out from signature matrix construction. (21c)-(21f) Gene expression signatures versus deconvolution for predicting response to immune checkpoint blockade. (21c) Kaplan-Meier survival plots showing the relationship between estimated levels of PCDC1+/CLTA4+ CD8 T cells and overall survival in datasets (as described, for example, by Van Allen et al. and by Nathanson et al. (Somatic Mutations and Neoepitope Homology in Melanomas Treated with CTLA-4 Blockade, *Cancer Immunology Research* (2016)), which is hereby incorporated by reference in its entirety). PCDC1+/CLTA4+ CD8 T cell levels were stratified by their median value in each dataset. (21d) Kaplan Meier plots comparing deconvolution of PDCD1+CTLA4+ CD8 T cells to surrogate gene expression signatures for predicting overall survival in melanoma patients treated with anti-CTLA4 therapy. Both gene expression and imputed fractions were stratified by median split and significance was assessed by a logrank test. Gene expression signatures were calculated as the geometric mean of PDCD1, CTLA4, and CD8A (Center) or PDCD1 and CTLA4 (Right). Statistical significance in (21c) and (21d) was determined using the log rank test. HR indicates hazard ratio. 95% HR confidence intervals are shown in brackets. (21e) Binary association between response to immunotherapy and PDCD1+CTLA4+ CD8 T cells levels or expression signatures (same as panel (21d)). Significance was evaluated with a Wilcoxon rank-sum test and is expressed as −log 10 p-values. (21f) Spearman correlation between the duration of response to anti-CTLA4 therapy and CIBERSORTx estimates of cell type abundance (Left) or average expression of selected genes in $\log_2$ FPKM (fragments per kilobase of transcript per million) space (Right) in the dataset (as described, for example, by Nathanson et al.).
Figure 21:
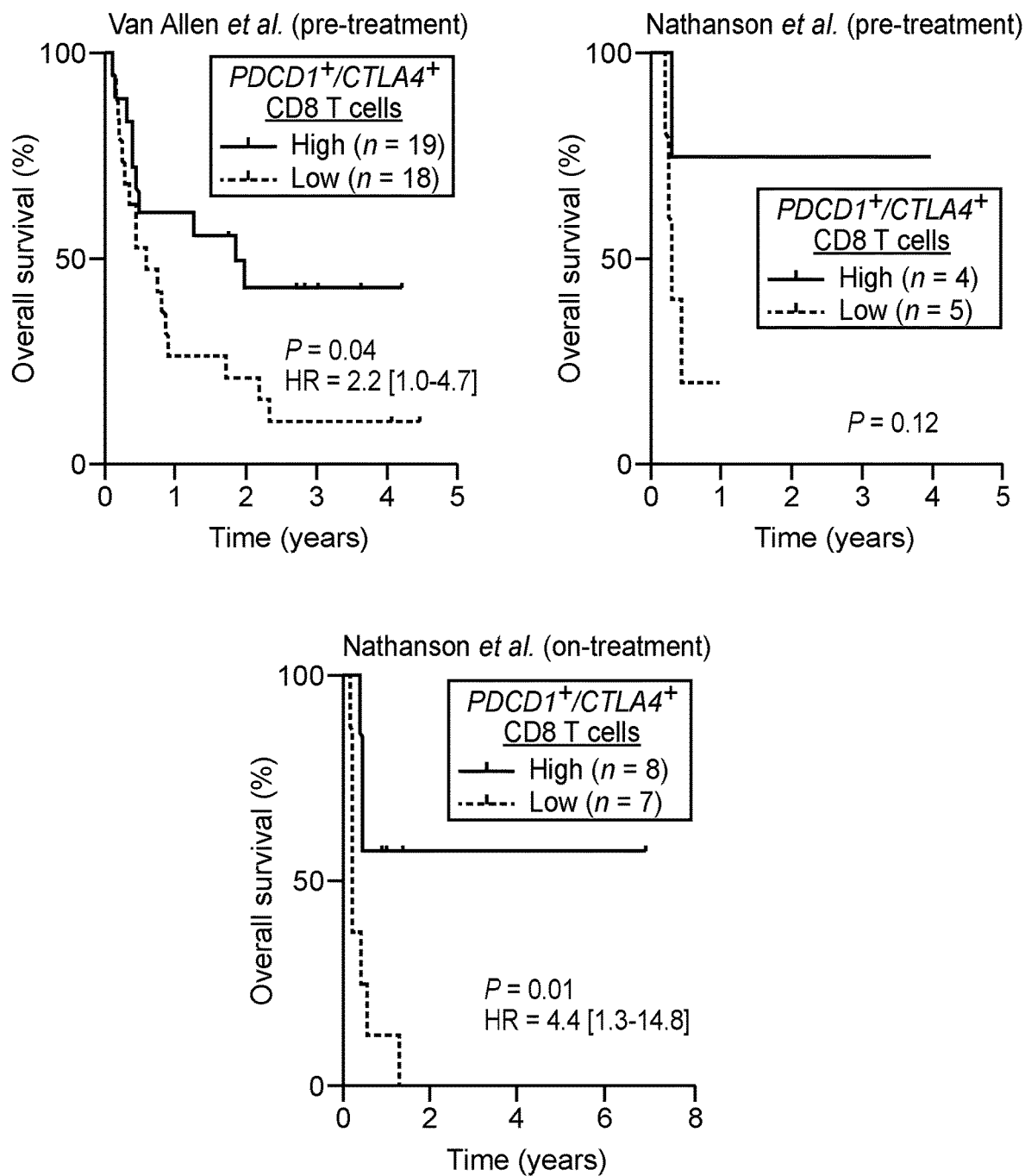
Figure 21:
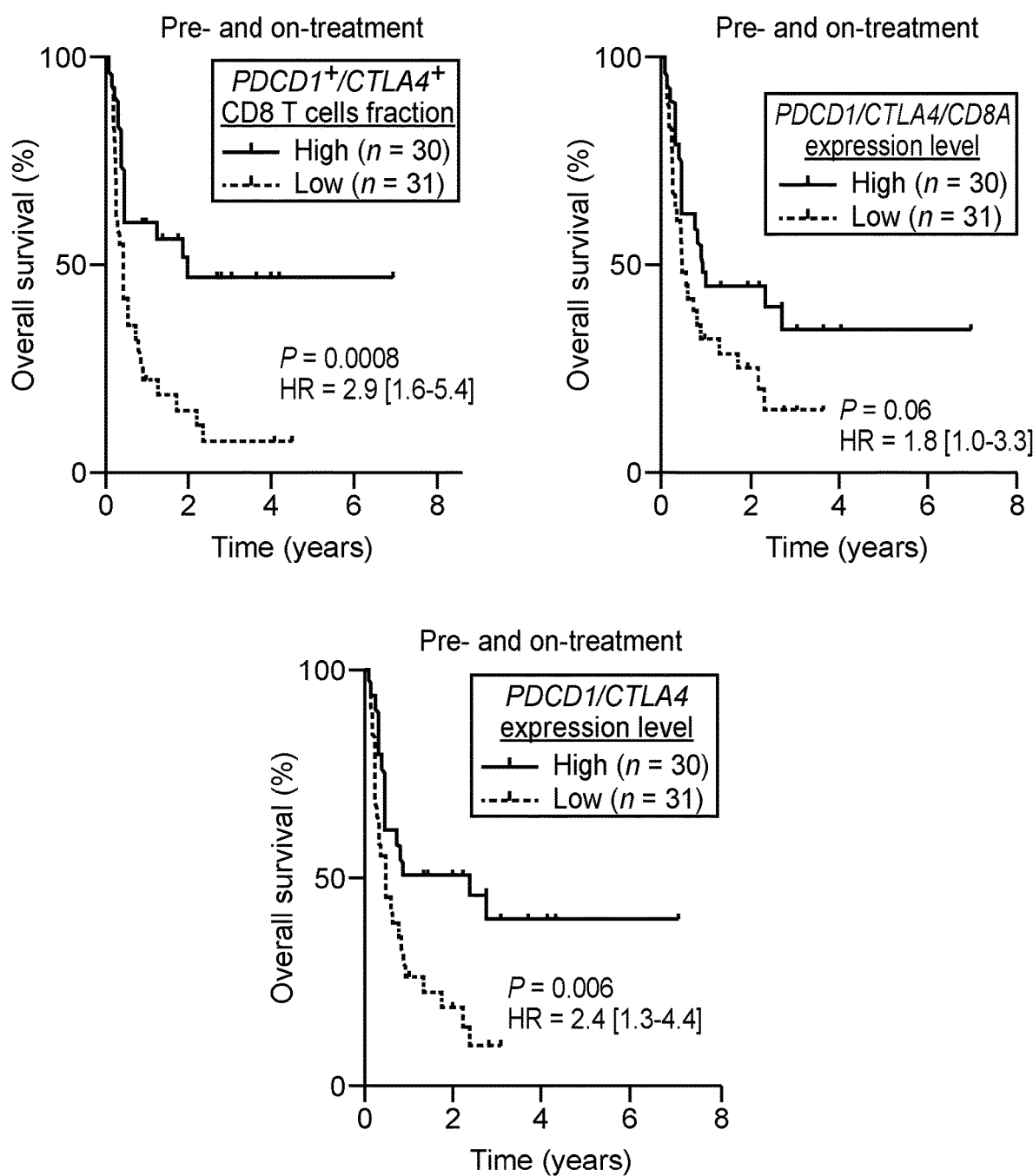
Figure 21:
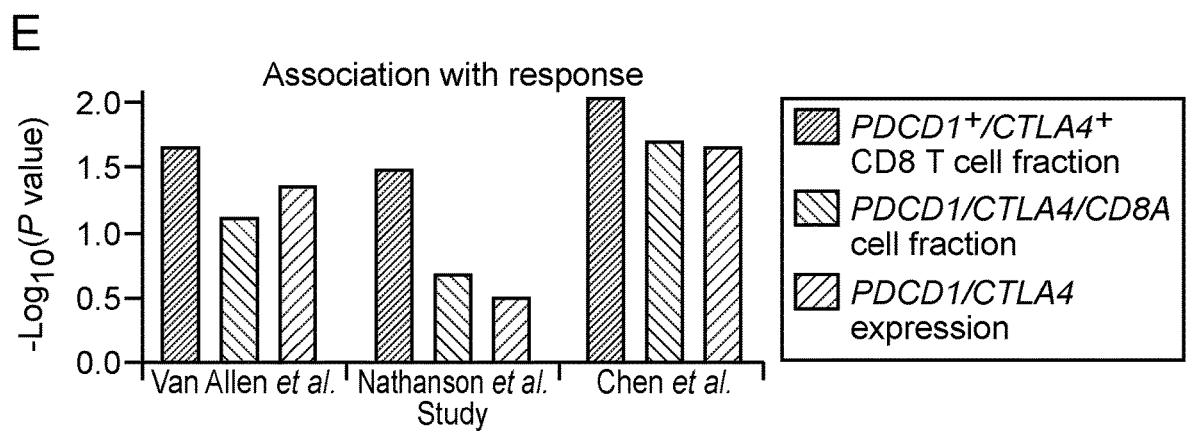
Figure 21:
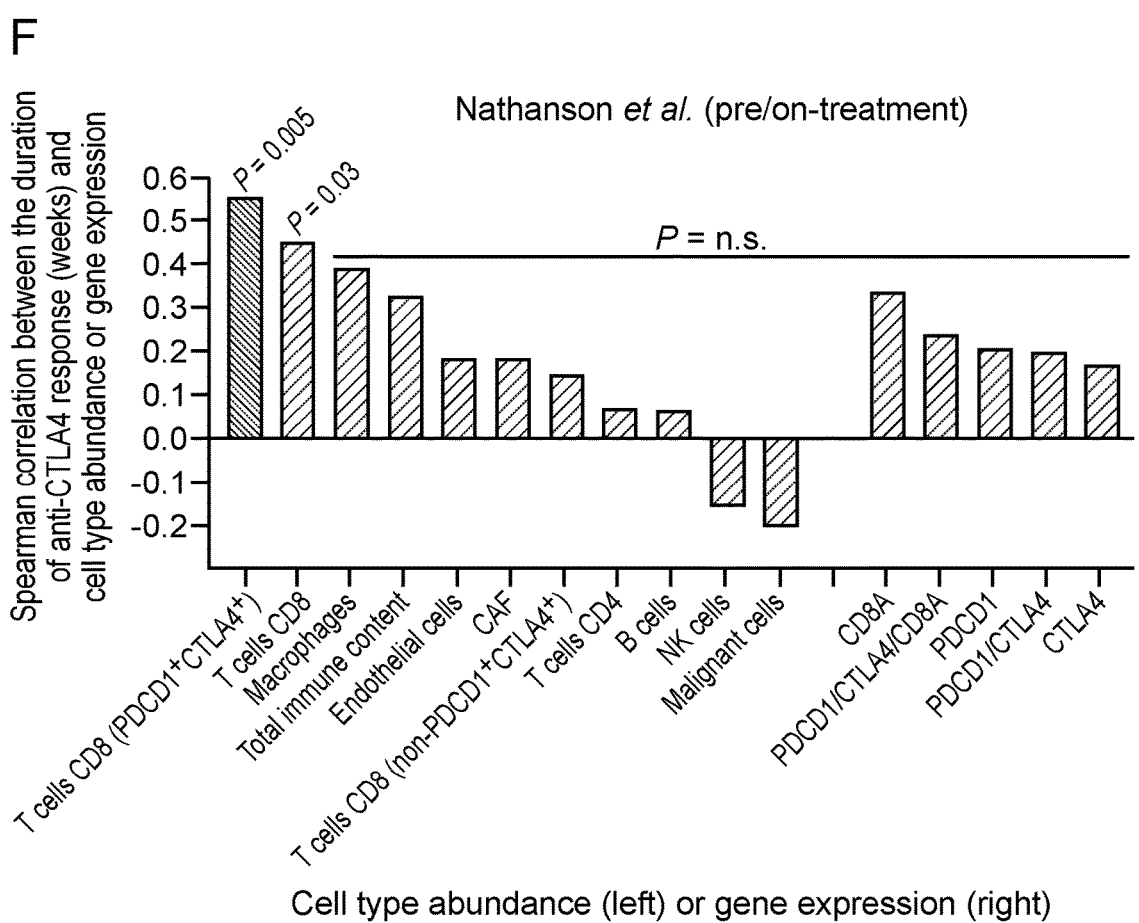

The CIBERSORTx method may be applied with batch correction to enumerate cell composition in bulk melanoma tumors from three datasets, two profiled by RNA-Seq and one by NanoString, using a melanoma signature matrix designed to enumerate PDCD1$^+$/CTLA4+ CD8 T cells along with eight other major cell types (FIG. 9). Given the small number of genes interrogated by NanoString nCounter, overlapping genes within the signature matrix may be benchmarked on melanoma tumors reconstituted from single cells and found to exhibit favorable performance (FIGS. 21a-b).

Statistical Analysis

Linear concordance between known and predicted cell-type features (e.g., proportions or GEPs) may be determined by Pearson correlation (r) or Spearman correlation (rho), as indicated. A concordance correlation coefficient (CCC) may be determined by comparing predicted and expected $\log_2$-adjusted expression profiles using, e.g., the CCC function from the R package, DescTools. When data are normally distributed, group comparisons may be determined using a two-sided t test with unequal variance or a paired t test, as appropriate; otherwise, a two-sided Wilcoxon test may be applied. Multiple hypothesis testing may performed using, e.g., the Benjamin and Hochberg method. Results with P<0.05 may be considered significant. Statistical analyses may be performed with R and Prism v7 (GraphPad Software, Inc.). Sample-size estimates may not be performed to ensure adequate power to detect a pre-specified effect size.

Computer Systems

Figure 22:
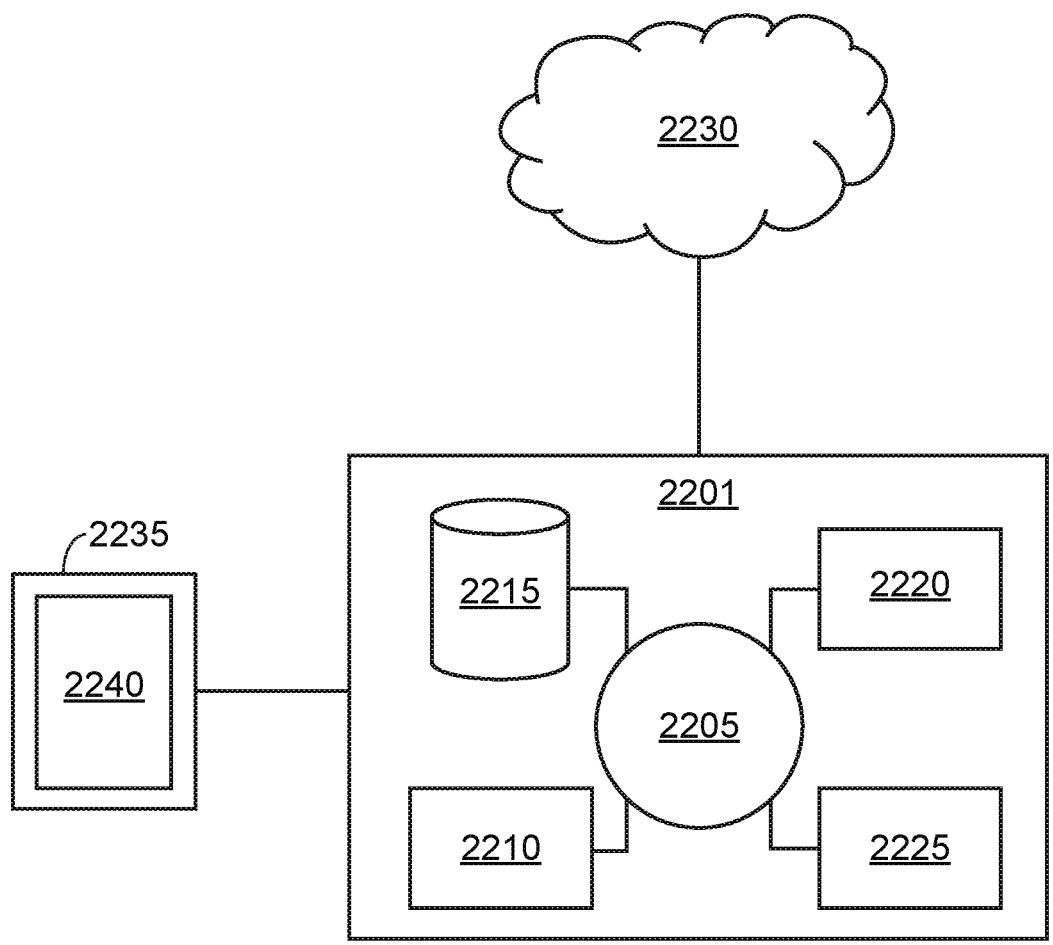
FIG. 22 illustrates a computer system that is programmed or otherwise configured to implement methods of the present disclosure.

The present disclosure provides computer systems that are programmed to implement methods of the present disclosure. FIG. 22 shows a computer system 2201 that is programmed or otherwise configured to, for example, generate feature profiles from biological samples, optimize regressions between feature profiles and reference matrices of feature signatures for distinct cell types, and quantify in biological samples the abundance of distinct cell types.

The computer system 2201 can regulate various aspects of analysis, calculation, and generation of the present disclosure, such as, for example, generating feature profiles from biological samples, optimizing regressions between feature profiles and reference matrices of feature signatures for distinct cell types, and quantifying in biological samples the abundance of distinct cell types. The computer system 2201 can be an electronic device of a user or a computer system that is remotely located with respect to the electronic device. The electronic device can be a mobile electronic device.

The computer system 2201 includes a central processing unit (CPU, also "processor" and "computer processor" herein) 2205, which can be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 can be a data storage unit (or data repository) for storing data. The computer system 2201 can be operatively coupled to a computer network ("network") 2250 with the aid of the communication interface 2220. The network 2230 can be the Internet, an internet and/or extranet, or an intranet and/or extranet that is in communication with the Internet.

The network 2230 in some cases is a telecommunication and/or data network. The network 2230 can include one or more computer servers, which can enable distributed computing, such as cloud computing. For example, one or more computer servers may enable cloud computing over the network 2230 ("the cloud") to perform various aspects of analysis, calculation, and generation of the present disclosure, such as, for example, generating feature profiles from biological samples, optimizing regressions between feature profiles and reference matrices of feature signatures for distinct cell types, and quantifying in biological samples the abundance of distinct cell types. Such cloud computing may be provided by cloud computing platforms such as, for example, Amazon Web Services (AWS), Microsoft Azure, Google Cloud Platform, and IBM cloud. The network 2230, in some cases with the aid of the computer system 2201, can implement a peer-to-peer network, which may enable devices coupled to the computer system 2201 to behave as a client or a server.

The CPU 2205 may comprise one or more computer processors and/or one or more graphics processing units (GPUs). The CPU 2205 can execute a sequence of machine-readable instructions, which can be embodied in a program or software. The instructions may be stored in a memory location, such as the memory 2210. The instructions can be directed to the CPU 2205, which can subsequently program or otherwise configure the CPU 2205 to implement methods of the present disclosure. Examples of operations performed by the CPU 2205 can include fetch, decode, execute, and writeback.

The CPU 2205 can be part of a circuit, such as an integrated circuit. One or more other components of the system 2201 can be included in the circuit. In some cases, the circuit is an application specific integrated circuit (ASIC).

The storage unit 2215 can store files, such as drivers, libraries and saved programs. The storage unit 2215 can store user data, e.g., user preferences and user programs. The computer system 2201 in some cases can include one or more additional data storage units that are external to the computer system 2201, such as located on a remote server that is in communication with the computer system 2201 through an intranet or the Internet.

The computer system 2201 can communicate with one or more remote computer systems through the network 2230. For instance, the computer system 2201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2201 via the network 2230.

Methods as described herein can be implemented by way of machine (e.g., computer processor) executable code stored on an electronic storage location of the computer system 2201, such as, for example, on the memory 2210 or electronic storage unit 2215. The machine executable or machine readable code can be provided in the form of software. During use, the code can be executed by the processor 2205. In some cases, the code can be retrieved from the storage unit 2215 and stored on the memory 2210 for ready access by the processor 2205. In some situations, the electronic storage unit 2215 can be precluded, and machine-executable instructions are stored on memory 2210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2201, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 can include or be in communication with an electronic display 2235 that comprises a user interface (UI) 2240 for providing, for example, a visual display indicative of feature profiles from biological samples, solutions of regressions between feature profiles and reference matrices of feature signatures for distinct cell types, and abundances of distinct cell types in biological samples. Examples of UI's include, without limitation, a graphical user interface (GUI) and web-based user interface.

Methods and systems of the present disclosure can be implemented by way of one or more algorithms An algorithm can be implemented by way of software upon execution by the central processing unit 2205. The algorithm can, for example, generate feature profiles from biological samples, optimize regressions between feature profiles and reference matrices of feature signatures for distinct cell types, and quantify in biological samples the abundance of distinct cell types.

A deconvolution module may comprise one or more deconvolution applications, e.g., a support vector regression (SVR) application or a non-negative matrix factorization (NMF) application, which may include one or more programs stored in the memory, and comprise instructions to perform methods according to one or more embodiments of the present disclosure. The deconvolution application (e.g., SVR application or NMF application) may include any of the following exemplary modules or a subset or a superset thereof.

In some cases, the deconvolution module may be configured to apply support vector regression, or any other regression algorithm that minimizes a linear loss function, and an L2-norm penalty function, to a feature profile of the physical sample (e.g., biological sample), using a reference matrix of distinct component, e.g., cell subsets (e.g., cell types), feature signatures, to quantify the relative proportions or abundances of distinct components, e.g., cell subsets (e.g., cell types), in the physical sample, according to one or more embodiments of the present disclosure.

The deconvolution module may comprise a Selection Module, which may be configured to select (or filter) features to include in the signature matrix and/or select feature profile(s), according to one or more embodiments of the present disclosure.

The deconvolution module may comprise an RMSE Module, which may be configured to determine the result with the lowest error over different values of nu, according to one or more embodiments of the present disclosure.

The deconvolution module may comprise a Significance Value Module, which may be configured to determine a significance value for the estimation of the relative proportions or abundance of cell subsets by selecting a subset of the feature profile by a) generating a random feature profile m* containing features randomly selected from a parent feature profile, wherein the parent feature profile comprises the feature profile and wherein m and m* have the same Euclidean norm; b) optimizing a regression between m* and the reference matrix B, wherein m* is modeled as a linear combination of B, wherein the optimizing comprises solving for f* comprising a set of regression coefficients of the regression, wherein the solution minimizes: a linear loss function; and an L2-norm penalty function; c) calculating the product of f* and the reference matrix B to generate a reconstituted feature profile; d) determining a difference measurement between the random feature profile m* and the reconstituted feature profile; and e) determining a significance value based on a distribution of the difference measurements determined from i iterations of steps a)-d), wherein i is a number greater than 1. The Significance Value Module may employ the deconvolution module, e.g., SVR module, in step b). The Significance Value Module may further be configured to perform any of the other embodiments of the present disclosure.

The deconvolution module may further include additional modules to perform any of the other embodiments of the present disclosure. In certain aspects, the deconvolution module may be stored in a portable computer readable storage medium separate from the computer.

The deconvolution module may be configurable by a user. For example, the deconvolution module may include a user interface module configured to enable a user to determine one or more settings, such as the feature profile and/or signature matrix to apply the deconvolution algorithm (e.g., SVR) to the values for nu, criteria by which features are selected by the selection module, the number of iterations to be run by the significance value module, or any other settings that would allow for one or more embodiments of the present disclosure.

EXAMPLES

The CIBERSORTx method can use, as a framework, a machine learning technique for robust assessment of cell composition from genomic profiles of bulk tissues. The CIBERSORTx method may extend the concept of in silico dissection to fluorescence activated cell sorting (FACS) and to leverage emerging single-cell sequencing efforts, thereby providing a framework for cell type enumeration and cell type-specific gene expression purification (as shown in FIG. 1). In the following Examples, this approach is described and validated, starting with the use of single-cell reference profiles to estimate cell type proportions in bulk tissues, followed by analytical techniques to purify cell type-specific gene expression signatures from RNA profiles of fresh/frozen and fixed tissue specimens.

Example 1: Tissue Dissection with scRNA-Seq

The CIBERSORTx platform can enable large-scale tissue characterization using cell signatures derived from diverse sources, including single cell reference profiles (FIG. 1, steps 1 and 2). Analytical techniques were developed for deriving a signature matrix from single-cell or bulk sorted transcriptional data while minimizing batch effects as a source of confounding technical variation (FIGS. 7*a-h* and 8*a-i*). The utility of scRNA-Seq platforms for enumerating cell proportions in RNA admixtures derived from bulk tissues was then investigated, including 10 Genomics Chromium (droplet-based) and SMART-Seq2 (plate-based, Clontech Laboratories, Inc.).

Single-cell RNA-Seq libraries were generated from two serial peripheral blood mononuclear cell (PBMC) samples obtained from a patient with non-small cell lung cancer (NSCLC) using Chromium v2 (3' assay). Unsupervised clustering and canonical marker gene assessment revealed six major leukocyte subsets in both blood draws (B cells, CD4 T cells, CD8 T cells, NKT cells, NK cells, and monocytes; as shown in FIG. 2a). To assess deconvolution performance, a signature matrix was built to distinguish these 6 cell subsets, and the signature matrix was tested on a validation cohort of bulk RNA-Seq profiles of blood obtained from 12 healthy adults.

Figure 6:
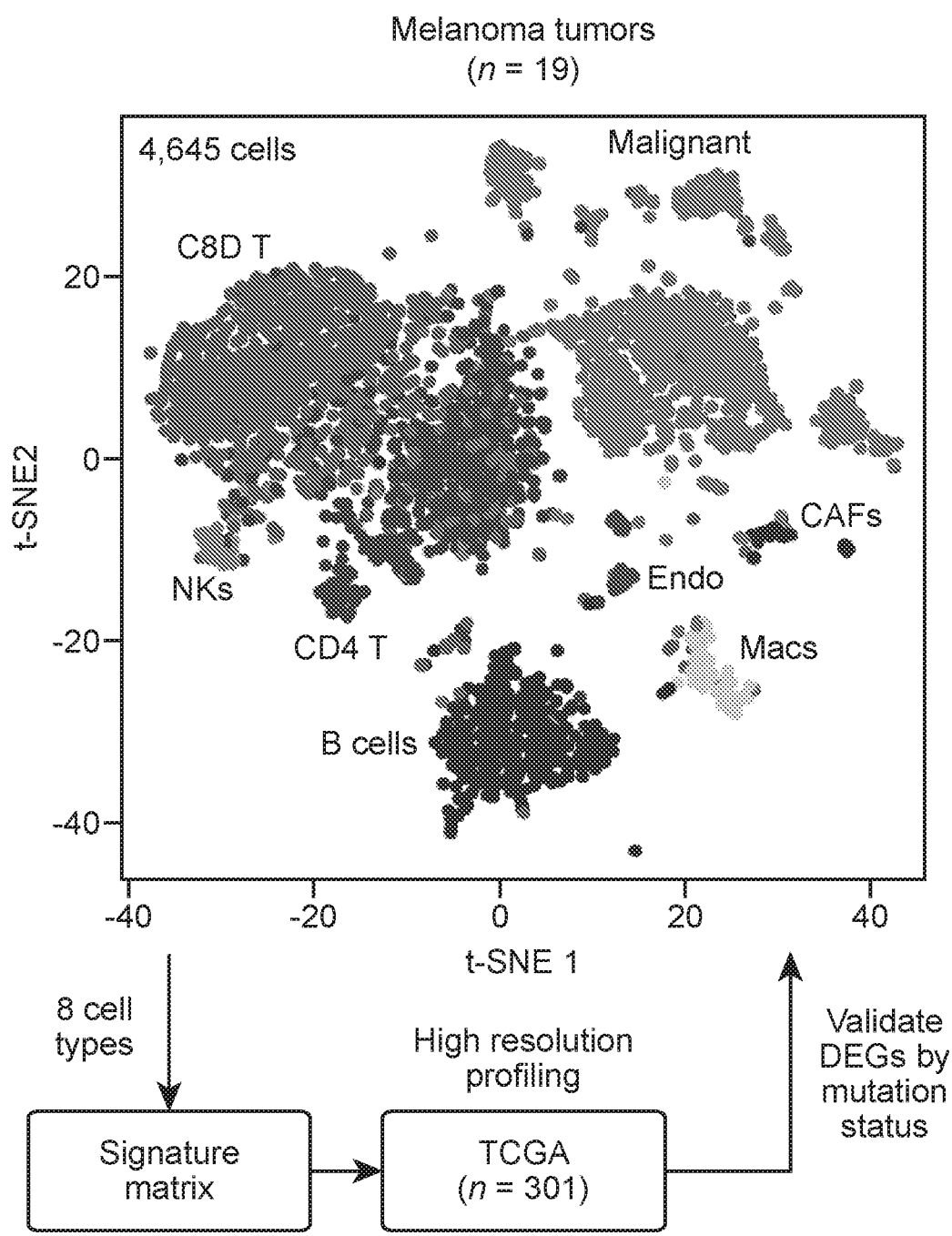
FIGS. 6a-f illustrate cellular signatures of driver mutation status and immunotherapy response in melanoma. (6a)-(6b) High resolution expression profiling of mutation-associated phenotypic states in melanoma tumor cell types. (6a) Top: tSNE plot showing 8 major cell melanoma tumor cell types profiled by scRNA-Seq. Bottom: schema for characterizing and validating context-dependent expression variation in 301 bulk melanoma tumors from TCGA. (6b) Heat maps showing cell type-specific DEGs identified by CIBERSORTx that are associated with key driver mutations in melanoma. Expression values were averaged across TCGA tumor samples (CIBERSORTx, left) and single cell GEPs (scRNA-Seq, right) for clarity. Underlying data are provided in FIG. 19. Only cell types with DEGs detected by CIBERSORTx and with available single cell validation data are shown. CAFs, cancer associated fibroblasts; MT, mutant; WT, wildtype. (6c) Left: Heat map showing the absolute difference in gene expression, expressed as ranks, between a normal CD8 T cell reference profile and the following three melanoma CD8 TIL GEPs: 'Imputed (FF)', a group-level CD8 TIL GEP imputed from 473 bulk RNA-Seq profiles of fresh/frozen (FF) tumors generated by TCGA; 'Imputed (FFPE)', a group-level CD8 TIL profile predicted from 42 formalin-fixed paraffin-embedded (FFPE) tumors; 'scRNA-Seq', a group-level CD8 TIL profile derived from aggregated single cell data of 19 melanoma patients. The heat map is ordered by the difference in ranks between the "Imputed (FF)" vector and the normal CD8 T cell GEP. All imputed profiles were processed by adaptive noise filtration. Genes predicted in the FF but not FFPE cohorts (owing to noise filtration) are colored gray in the latter. Selected T cell exhaustion genes are indicated. Right: Gene set enrichment analysis (GSEA) of a previously published melanoma CD8 TIL-associated gene set, assessed relative to the ordering of genes in the heat map. (6d) Framework for characterizing the clinical relevance of PDCD1$^+$CTLA4$^+$ CD8 T cells in bulk melanoma tumors using single reference profiles. PDCD1$^+$CTLA4$^+$ CD8 T cells and remaining CD8 T cells are indicated by orange and navy blue. (6e) Estimated levels of PDCD1+ CTLA4+ CD8 T cells in bulk tumor expression profiles from melanoma patients who received immunotherapy, stratified by responders and non-responders. Data are expressed as box plots with whiskers encompassing the entire data range. Statistical comparisons were performed using a Mann-Whitney test. (6f) Kaplan-Meier plot showing differences in overall survival between melanoma patients with high and low estimated levels of PDCD1+ CTLA4+ CD8 T cells in pretreatment tumors. Patients were split by the median estimated fractional abundance of PDCD1+ CTLA4+ CD8 T cells into high and low groups, and subsequently pooled across two studies with available overall survival data. Statistical significance was calculated by a log-rank test. HR indicates hazard ratio. 95% HR confidence intervals are shown in brackets.
Figure 6:
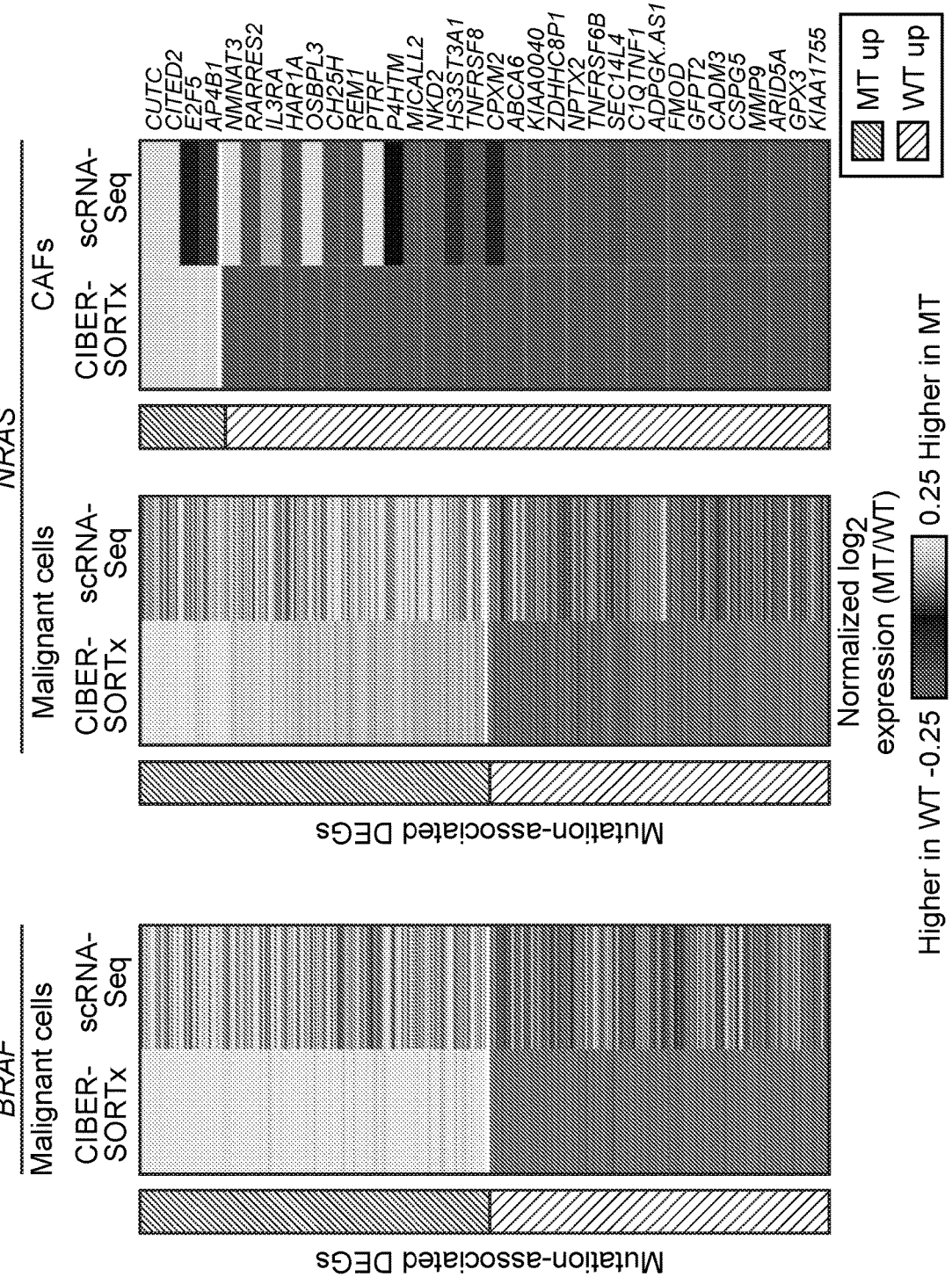
Figure 6:
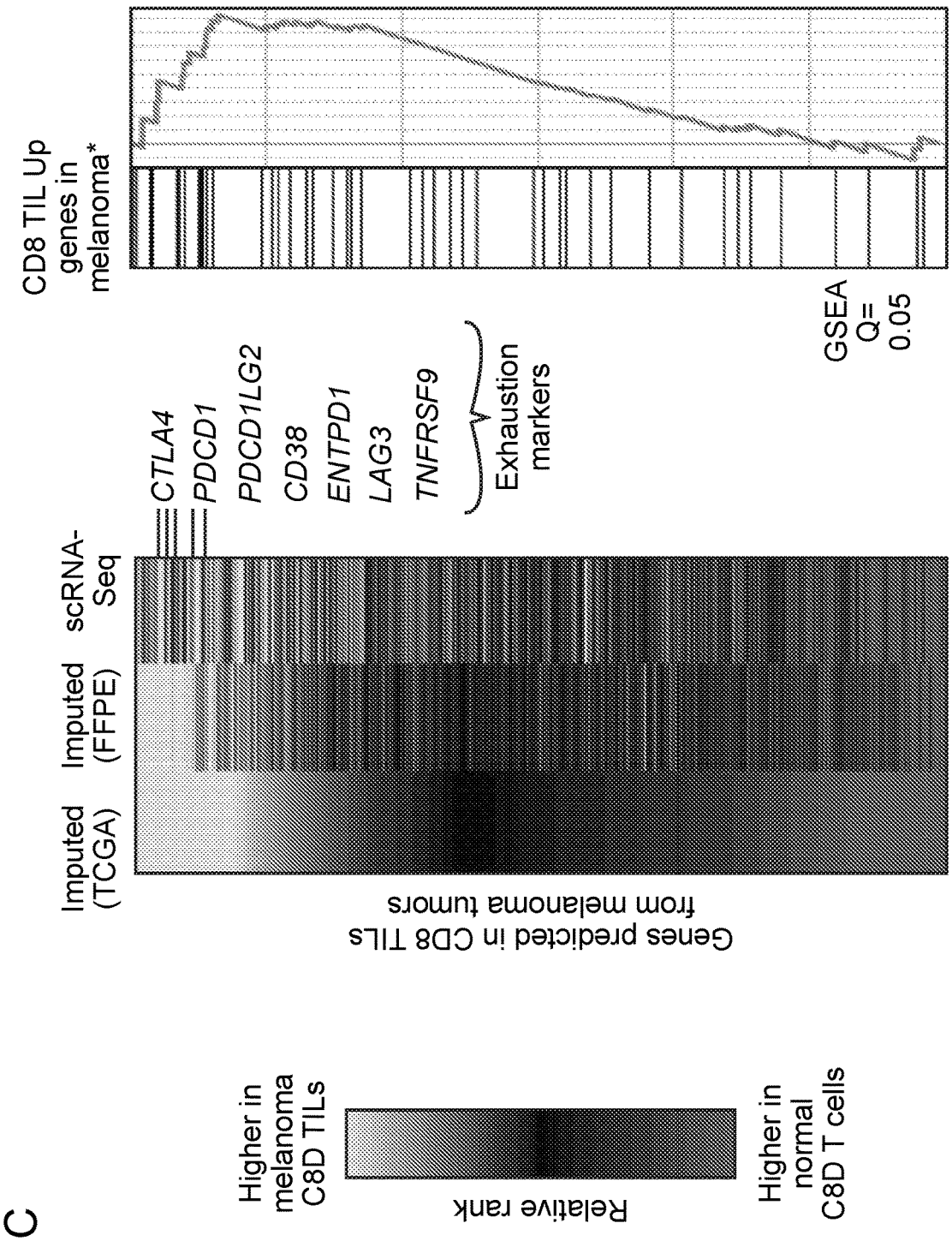
Figure 6:
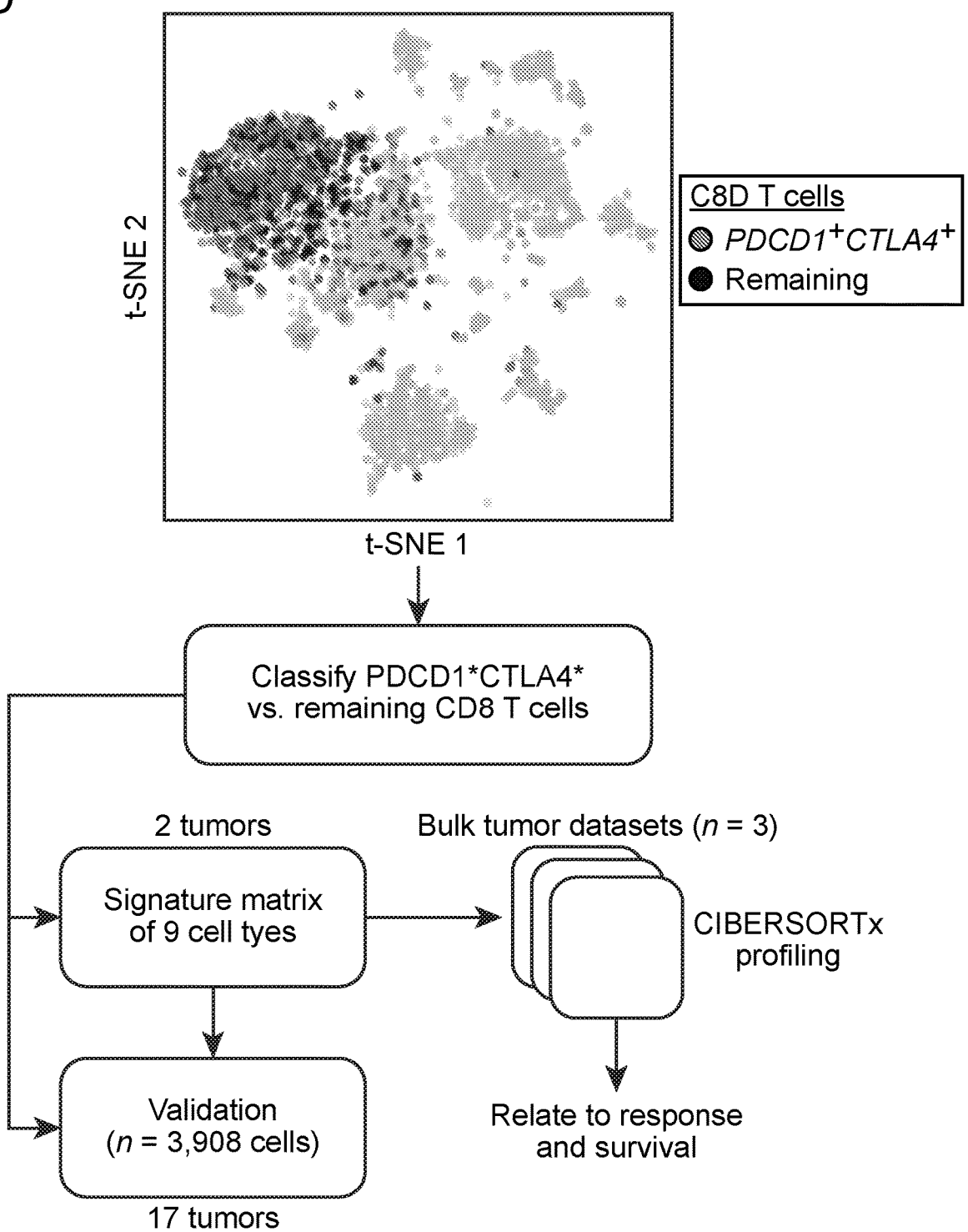
Figure 6:
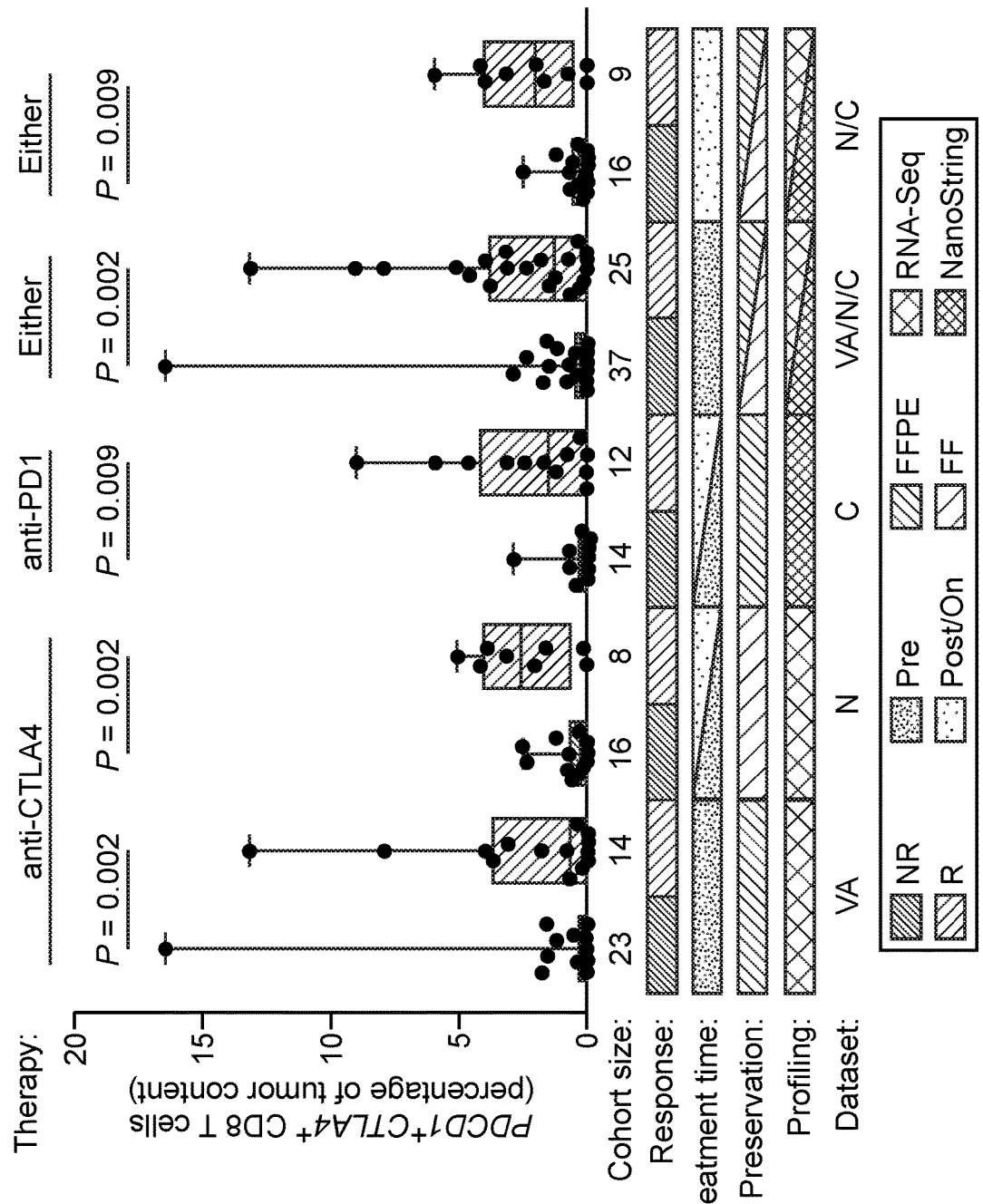
Figure 6:
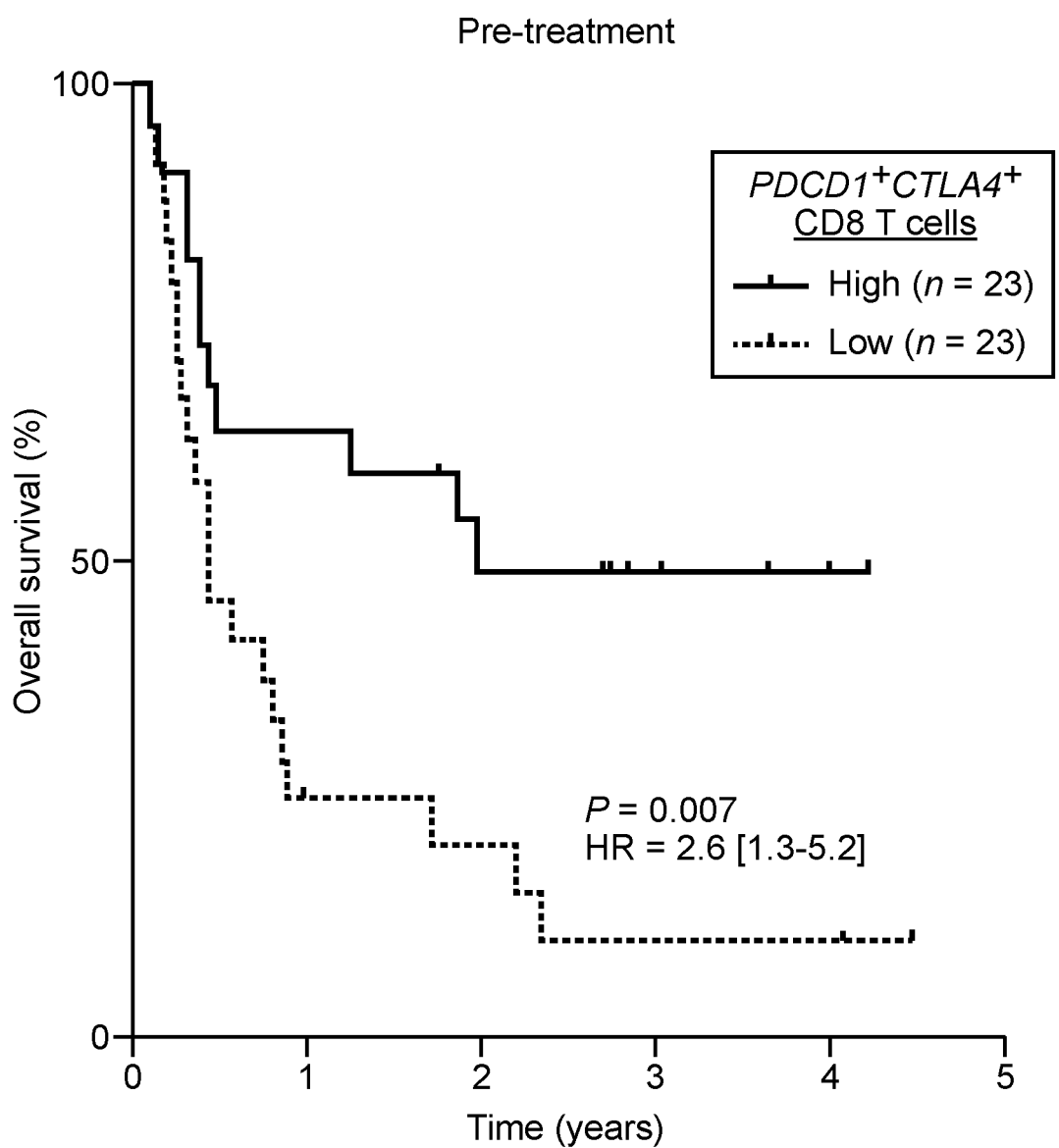

Compared to ground truth cell proportions as determined by direct cytometry and fluorescence immunophenotyping, uncorrected deconvolution results showed clear estimation biases for some cell types in bulk admixtures (FIGS. 2b and 6). Such biases may be driven by platform-specific variation between the signature matrix and bulk RNA-Seq data, as may be introduced, for example, by the variable use of unique molecular identifiers during library preparation, or differential 3' bias along transcripts. Indeed, following application of a batch correction scheme (FIG. 6a), deconvolution results compared favorably to ground truth cell proportions (FIGS. 2b and 6e). Similar gains in performance were obtained through batch correction when analyzing other datasets and signature matrices, including publicly available Chromium v2 PBMC data (3' and 5' kits) and purified leukocyte subsets profiled using microarrays (FIGS. 6d-g). Given these systematic improvements, batch correction was applied in all subsequent cross-platform analyses, unless stated otherwise. These data highlight the value of minimizing cross-platform variation in deconvolution experiments and the promise of scRNA-Seq profiles for dissecting bulk tissue composition.

Next, the analysis was extended to solid tumor biopsies where single cells were profiled by SMART-Seq2. Focusing on head and neck squamous cell carcinomas (HNSCC) and melanomas (n=18 and 19 patients, respectively), deconvolution performance was initially tested in a setting that controlled for dissociation-related artifacts and heterogeneity in phenotypic definitions. In a dataset of 18 primary tumors and 5 lymph node metastases from patients with HNSCC, a signature matrix was created from a training cohort comprising 2 primary tumor specimens and 1 lymph node biopsy. This matrix distinguished all 10 major cell types in these tumors: malignant cells, CD4 and CD8 T cells, B cells, macrophages, dendritic cells, mast cells, endothelial cells, myocytes, and cancer-associated fibroblasts (FIG. 2c). When evaluated using held-out tumors reconstructed from single cells with annotated phenotypes, deconvolution results were highly concordant with ground truth proportions (FIG. 2d and FIG. 7a). Moreover, these results were not dependent on the specific combination of tumors and lymph nodes used to build the signature matrix. Strong performance was also maintained across tumor types (HNSCC or melanoma) and cell types, including within rare or difficult to isolate cell subpopulations, such as distinct CD8 T cell subsets infiltrating melanomas with potential relevance to immunotherapy response (FIGS. 7b-d and 8).

Given these favorable results, the impact of key signature matrix-related parameters on CIBERSORTx deconvolution was explored, including the number of cells per phenotype and the number of analyzed donor samples. Across a range of parameter values, a modest effect on cell proportion estimates was observed (FIGS. 9a-b). Moreover, regardless of their source, CIBERSORTx signature matrices showed strong generalizability, whether applied across platforms, datasets, or tissues (FIG. 2e).

Next, having validated technical aspects of single cell-guided deconvolution, its utility was investigated for characterization of real biological admixtures, using diverse primary tissues. Leveraging a single cell-derived signature matrix from melanoma biopsies described above, CIBERSORTx was applied to dissect melanoma RNA-Seq profiles from The Cancer Genome Atlas (TCGA). Unexpectedly, striking differences were observed in the fractional representation of B/T lymphocytes and macrophages when comparing predicted cell type proportions in bulk tumors and the original scRNA-Seq results (FIG. 7e). Since these cell subsets were unselected relative to one another in the scRNA-Seq dataset, such compositional distortions may have arisen either from technical artifacts owing to single cell isolation and sequencing, or from the deconvolution approach itself. In support of the former, CIBERSORTx estimates were highly consistent with direct TIL enumeration in situ by immunohistochemistry (IHC) in an independent melanoma cohort (FIG. 7e). Moreover, the same distortion phenomenon was observed in a dataset of human pancreatic islets profiled by scRNA-Seq (SMART-Seq2), bulk RNA-Seq, and IHC (FIGS. 2f and 7f-i). In a direct comparison of matching islet specimens, cell fractions determined by IHC in bulk tissues were strongly correlated with bulk islet deconvolution results, but not scRNA-Seq (FIGS. 2f and 7i). These data further validate CIBERSORTx and highlight its value for characterizing solid tissue composition while mitigating dissociation-related distortions.

Example 2: Cell Type-Specific Gene Expression without Physical Cell Isolation

Cell-type specific transcriptome profiles derived from single cells or bulk sorted populations can provide valuable insights into cell identity and function. However, such profiles may be difficult to obtain, for example for large cohorts and fixed clinical samples. Even when purified cell types are available, tissue dissociation and preservation conditions can cause non-biological alterations in gene expression that obscure downstream analyses. Mathematical separation of bulk tissue RNA profiles into cell type-specific transcriptomes can potentially overcome these problems, however such techniques may require rigorous validation using real tissue samples. Therefore, it was evaluated whether a signature matrix, comprising highly optimized marker genes, can be used to learn biologically meaningful transcriptome profiles from non-disaggregated tissue samples, including fresh/frozen and fixed tumors (FIG. 3a).

To test whether representative cell type-specific transcriptomes can be accurately inferred from fresh/frozen primary tumor biopsies, 302 tumors were profiled from patients with untreated follicular lymphoma (FL) and a common approach was tested in which the proportions of each cell type are used to infer a single representative GEP for each cell type from a group of mixture samples. Since B cells, CD8 T cells, and CD4 T cells may comprise the vast majority of FL tumor cellularity and can be readily purified by FACS, these 3 subsets were used to assess the accuracy of the approach. Although CIBERSORTx also supports single cell-derived signature matrices, a previous method (termed CIBERSORT) was applied with LM22 (a microarray-derived signature matrix for distinguishing 22 human hematopoietic cell subsets) and non-negative least squares regression (NNLS) to enumerate immune proportion while directly controlling for technical factors. Importantly, LM22 was previously validated against flow cytometry for its ability to accurately resolve the same 3 FL cell subsets using paired samples. In addition, all expression data in this experiment were profiled by Affymetrix microarrays, allowing the assessment of the feasibility of in silico expression purification independently of platform-specific factors. Initially, B cells and CD8 T cells were examined as examples of highly abundant and less abundant cell types in FL lymph nodes (>50% versus ~5-10%, respectively).

Although imputed and FACS-purified cell type transcriptomes were reasonably well correlated, considerable noise distorted expression estimates of many genes across a broad range of expression levels (FIG. 3b). Therefore, an adaptive noise filter to eliminate unreliably estimated genes for each cell type (FIG. 3c) was defined. This strategy significantly improved correlations between in silico purified transcriptomes and those from FACS-purified cells (FIGS. 3d and 11a).

Figure 10:
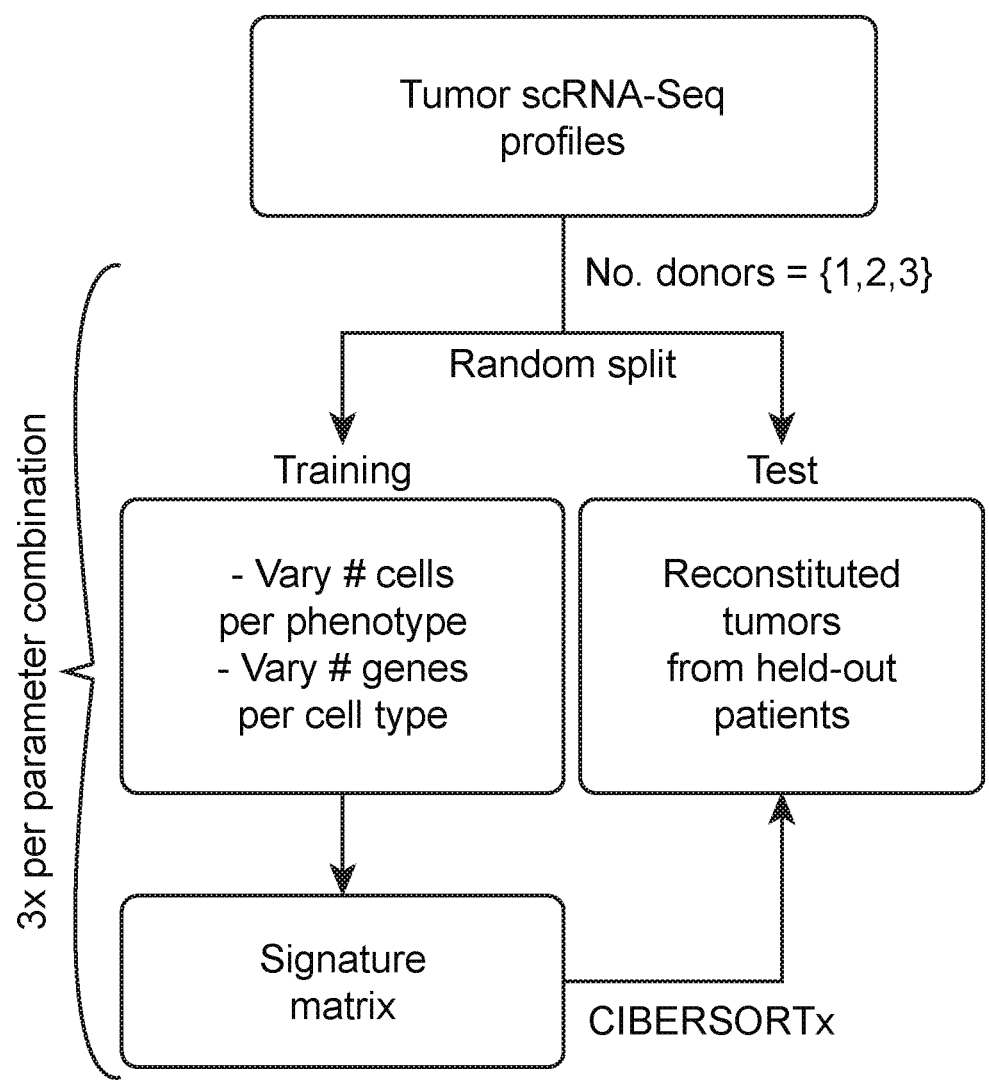
FIGS. 10a-c illustrate impact of key parameters on single cell-guided deconvolution. (10a) Schema of the parameter sweep. Deconvolution performance for estimating cell proportions was assessed in relation to the number of single cells per phenotype, the number of donors per signature matrix, and the range of marker genes per phenotype. (10b) Results of the parameter sweep in panel (10a) for two tumor types profiled by single cell RNA-Seq: head and neck squamous cell carcinoma (HNSCC) tumors and melanoma tumors. The concordance between inferred and known cell proportions was assessed for each cell type by Pearson correlation, and the median correlation coefficient for each parameter combination is shown in tabular format. Gold and gray colors indicate higher and lower correlation coefficients, respectively. (10c) Consistency of signature matrices defined from opposite ends of the parameter range (denoted by green and red rectangles in panel (10b) for resolving group-level GEPs from bulk melanoma tumors profiled by TCGA). Pearson correlations were performed on $\log_2$-adjusted expression values. Only genes with detectable expression after adaptive filtering were analyzed.
Figure 10:
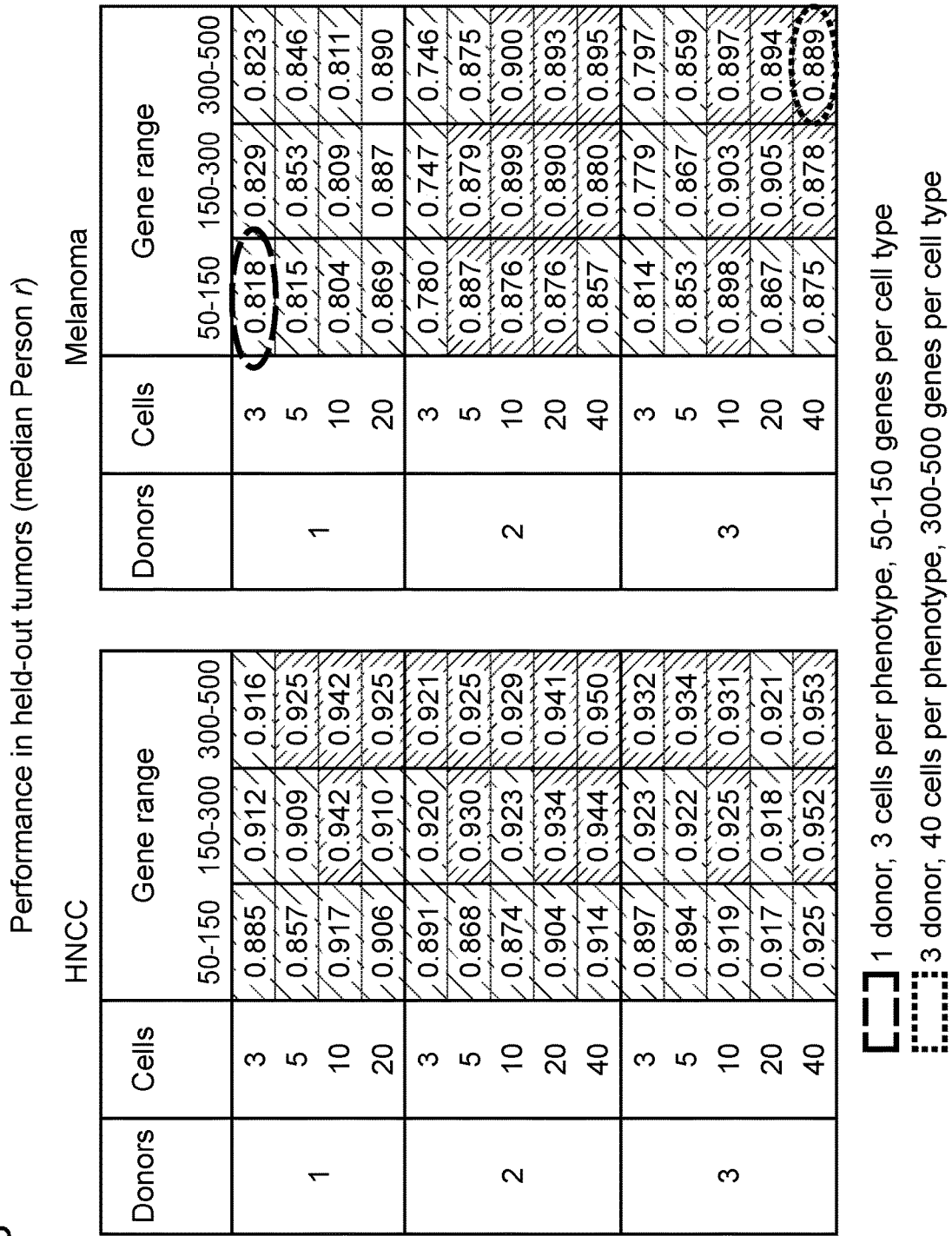
Figure 10:
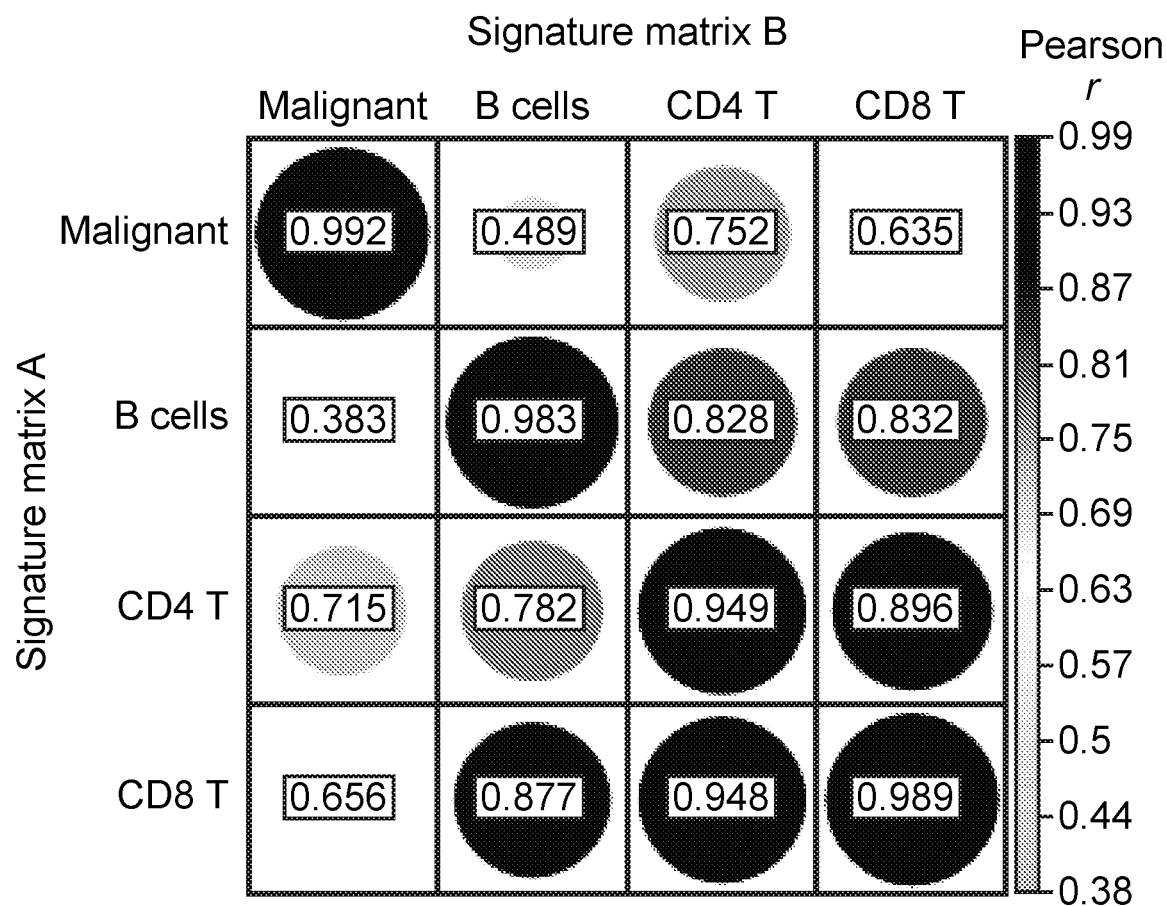

Key factors that influence the accuracy of transcriptome reconstruction were then investigated (FIGS. 3e and 11a-h). Using a set of 302 FL GEPs, a predictable relationship was observed between the number of tumors profiled and the accuracy of transcriptome imputation across B cells, CD4 T cells, and CD8 T cells, each of which can vary more than 10-fold in frequency between FL tumors (FIGS. 3e and 11b). Although the largest gains were achieved when analyzing at least 4-5 fold more mixture samples than cell types (FIG. 3e), a filtration scheme uniformly improved performance as compared to previous approaches irrespective of cohort size (c), the number of cell types (k), and overall cell type abundance (provided that c>k; FIGS. 3e, 11b-e, and 11g). Favorable performance was observed for resolving previously identified markers of cell identity (FIG. 3f). Similar results were obtained for other cell types, including follicular helper T cells in FL lymph nodes (FIG. 11d), leukocyte subsets in PBMCs (FIGS. 11e-h), and epithelial, immune, and stromal subsets from RNA-Seq profiles of NSCLC tumors (FIG. 3g). Moreover, the use of different single cell-derived signature matrices did not significantly impact results, provided that identical cell types were interrogated (FIGS. 10b-c).

Example 3: Cell Type-Specific Expression Purification at High Resolution

Cell type-specific differential expression can be inferred from bulk specimens. In some cases, the above-mentioned strategy may be limited to learning a single representative expression profile for each cell type given a group of mixture samples (e.g., "group-level" GEPs, FIG. 1, step 3). Such profiles may not be sample-specific, and may require generation for each condition of interest in order to perform downstream analyses, such as identification of differentially expressed genes (DEGs) between them. Although published approaches for sample-level deconvolution have been described, they may only consider mixtures with two cellular components. The CIBERSORTx method can model gene expression deconvolution as a non-negative matrix factorization problem with partial observations, using bulk gene expression and imputed cell proportions as inputs (FIG. 12a-c). This approach performs separation of a single matrix of mixture GEPs into a set of underlying cell type-specific expression matrices (FIGS. 4a-b). After these expression profiles are obtained, they can be analyzed post hoc to gain insights into sample-level variation and patterns of gene expression for individual cell types of interest. To solve the matrix factorization problem, which may comprise numerical approximation, an algorithm (e.g., a divide-and-conquer algorithm) can be used to produce biologically realistic solutions (FIGS. 12a-c and 13a-b).

A series of synthetic mixtures, each containing DEGs in one or more cell types, was created to test the method's capability for "high-resolution" cell purification (FIG. 1, step 4). These simulated DEGs included block-like patterns, reminiscent of those seen in real tissues, and non-linear geometries, all of which may be difficult to ascertain by previous computational techniques. Remarkably, this method recovered expected DEG patterns in all tested cases, including a hidden target ("bulls-eye") (FIGS. 4b-d and 14). Moreover, unlike group mode (FIG. 1, step 3), the resulting high-resolution profiles were inherently amenable to standard methods for unsupervised analysis and class discovery (e.g., FIG. 4c). Thus, high resolution purification may be a versatile approach for unmasking diverse sample-level expression patterns without prior knowledge (e.g., of biologically or functionally defined groupings).

Next, the analytical performance (e.g., sensitivity and specificity) of the method for the detection of DEGs in modeled tumor admixtures was evaluated. Simulated DEGs were "spiked into" CD8 T cell transcriptomes to create two known CD8 phenotypic classes. These CD8 GEPs were then randomly mixed in silico with three other immune subsets in modeled tumors, and a colon cancer cell line was included to simulate 50% unknown content (FIG. 4e, Left). Following high resolution purification, cell type-specific transcriptomes were grouped into defined DEG classes to assess performance Across a broad range of cell spike-in levels and expression fold changes, previously defined DEGs were recovered in CD8 T cells with high sensitivity and specificity (FIG. 4e, Right). Moreover, at 12.5% and 5% fractional abundance, expected DEGs were detectable in CD8 T cells with as little as a two-fold (AUC=0.84) or four-fold (AUC=0.85) change in expression, respectively (FIG. 4e, right). Similar analytical sensitivity and specificity were observed in another experiment, in which melanoma tumors were simulated using pooled scRNA-Seq data and performance was assessed in relation to cohort size, the number of cell types with DEGs, and the magnitude of differential expression (FIGS. 15a-c).

Example 4: High Resolution Profiling of Diverse Tumor Subpopulations

The strong technical performance of high resolution GEP purification suggest its utility for dissecting real bulk tissue samples, including tumors. Therefore, its ability to resolve cellular states in several human tumor types was examined, starting with two cancers in which patterns of molecular heterogeneity in malignant cells have been previously described.

Diffuse large B cell lymphoma (DLBCL) can be classified into two major molecular subtypes based on differences in B cell differentiation states: germinal center-like (GCB) and activated B cell-like (ABC) DLBCL. Importantly, the GEPs underlying these B-cell subsets may be evident in purified primary DLBCL tumor B cells and in tumor cell lines, but not in other TILs, which have distinct signatures. Using GEPs of 150 DLBCL lymph node biopsies with previously annotated cell-of-origin subtypes, high resolution profiling of 10 major leukocyte subsets was evaluated for its performance in correctly attributing known GCB/ABC differences to B cells. Although this approach was blinded to class labels, subtype-specific expression differences in B cells were identified that were highly consistent with those of normal GC and activated B cells, and about 9-fold more significant on average than in bulk DLBCL tumors (FIGS. 16a-c). These results were compared with two alternative methods: (1) a common approach for assigning bulk tissue expression patterns to individual cell types based on correlations with cell abundance, and (2) a previously described technique for imputing cell type-specific DEGs when phenotypic classes and cell type frequencies are known. In both cases, CIBERSORTx exhibited superior performance, both in relation to cell type specificity and the number of detectable DEGs at a given significance threshold (FIGS. 17a-e and 18a-b).

FL may be a very common indolent Non-Hodgkin lymphoma, and CREBBP mutations in FL tumors may be associated with loss of antigen presentation in B cells. Since this association was observed using FACS-purified FL B cells, but not normal B-cells or other cell types in these tumors, high resolution purification was evaluated for its ability to recapitulate this result starting from bulk tumor GEPs and paired tumor genotypes (FIG. 5a). Indeed, after stratifying tumors by CREBBP mutation status, previously described signatures were readily detectable in digitally sorted B cell expression profiles, including loss of MHC II expression in CREBBP mutant tumors (FIG. 5b-c). As observed for DLBCL (FIGS. 17a-e), the majority of these genes did not correlate with B cell abundance, hindering their discovery in bulk tissues without deconvolution. Therefore, in two distinct malignancies, CIBERSORTx readily confirmed known context-dependent cellular states without physical cell isolation or prior knowledge of phenotypic groupings, underscoring its promise for uncovering novel biology.

Figure 18:
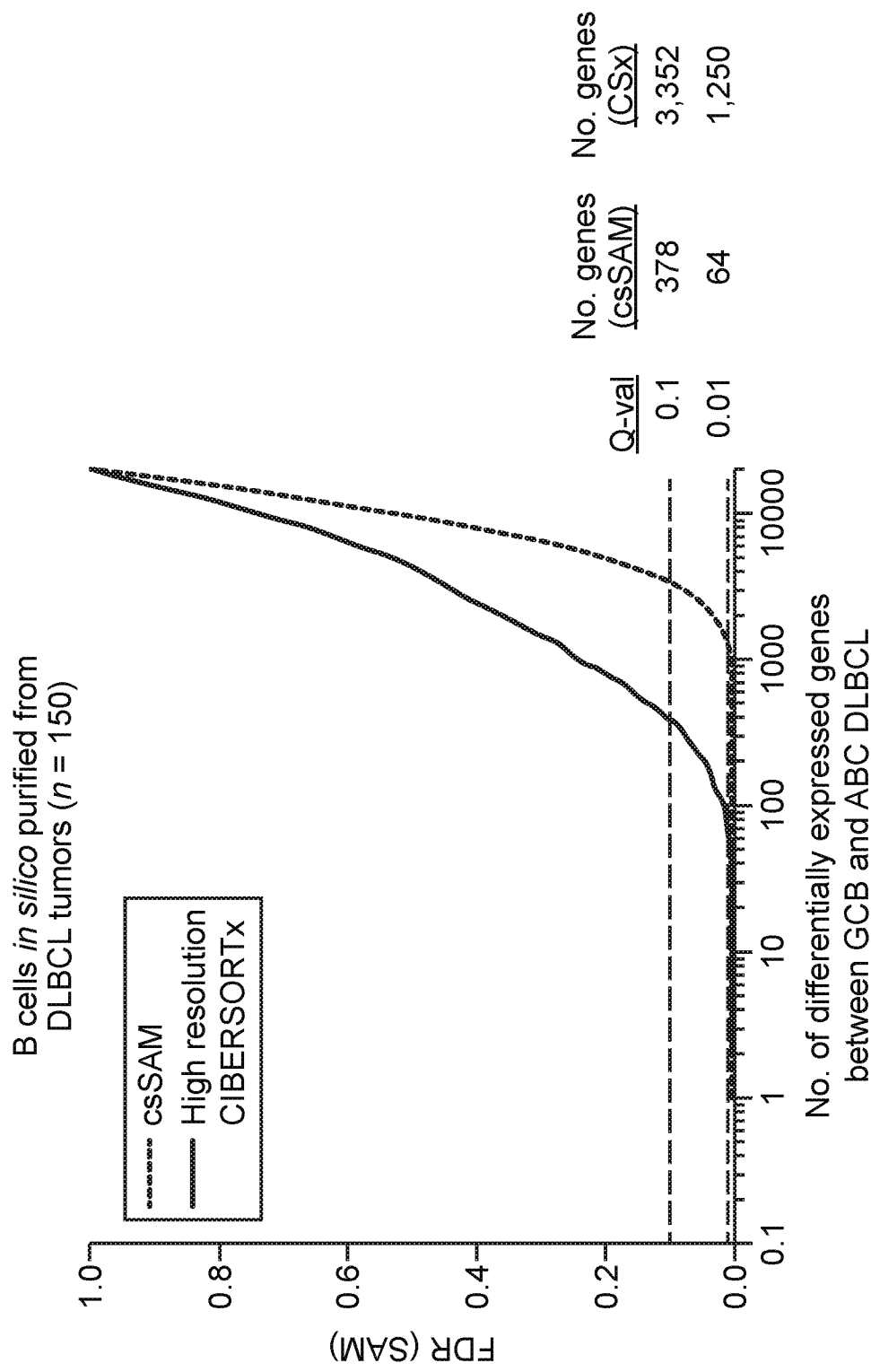
FIGS. 18a-e illustrate benchmarking of high resolution gene expression purification against previous methods. (18a) Analysis of DEGs identified in B cells between germinal center B cell (GCB) and activated B cell (ABC) DLBCL (n=150 tumors; GCB/ABC DLBCL, CHOP cohort, as described by Lenz et al.). Performance is shown for high resolution purification and csSAM in relation to the false discovery rate (FDR) (y-axis) and number (x-axis) of DEGs. Cell proportion estimates were obtained using LM22 and the same estimates were used as input for both methods. While GCB and ABC labels were provided as input to csSAM, CIBERSORTx was run without prior knowledge of class labels. Significance analysis of microarrays (SAM) was applied to CIBERSORTx results in order to identify DEGs between GCB and ABC DLBCL. SAM was run with 100 permutations for both methods. (18b) Gene set enrichment analysis of CIBERSORTx-imputed DEGs (from panel (18a)) for their enrichment in activated or germinal center B cell GEPs derived from healthy donors. NES, normalized enrichment score. (18c) Schema for benchmarking CIBERSORTx against ISOpure for sample-level GEP estimation of epithelial cells from 18 bulk RNA-Seq profiles of NSCLC tumors. (18d) Each imputed epithelial transcriptome from panel (18c) was compared against its corresponding FACS-purified GEP from the same patient by Pearson correlation, and the results are shown as boxplots (18 samples). The difference between methods was assessed by a Wilcoxon signed-rank test. (18e) Accuracy of high resolution CIBERSORTx for inferring the transcriptomes of four major cell subsets purified from bulk RNA-Seq profiles of 18 bulk NSCLC tumors. To assess performance, each sample-level transcriptome was compared to RNA-Seq profiles of (i) corresponding unsorted bulk tumors and (ii) corresponding FACS-purified cell subsets from the same patients. The cell sorting scheme is provided in FIG. 5d. Group comparisons were evaluated by a Wilcoxon signed-rank test.
Figure 18:
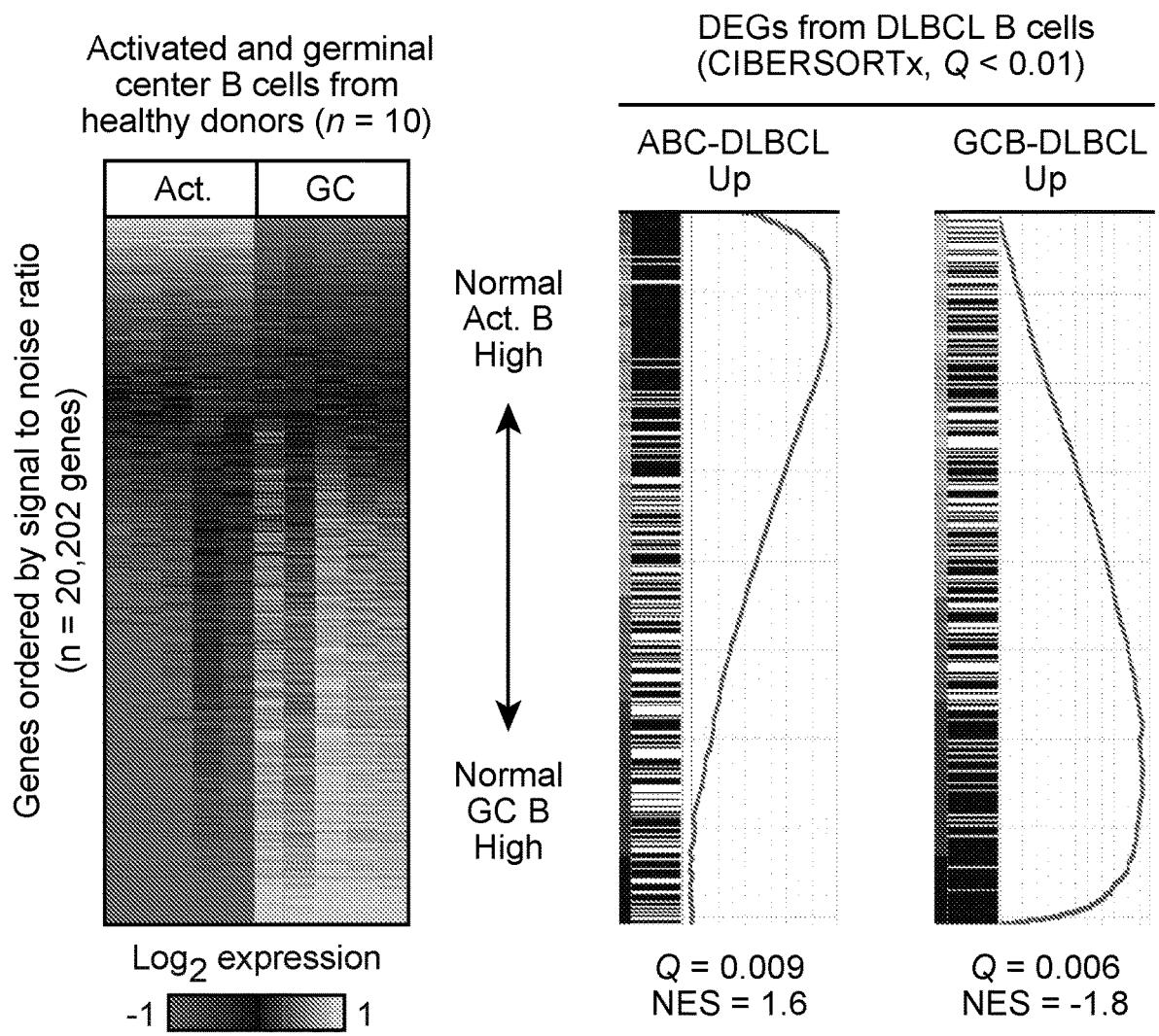
Figure 18:
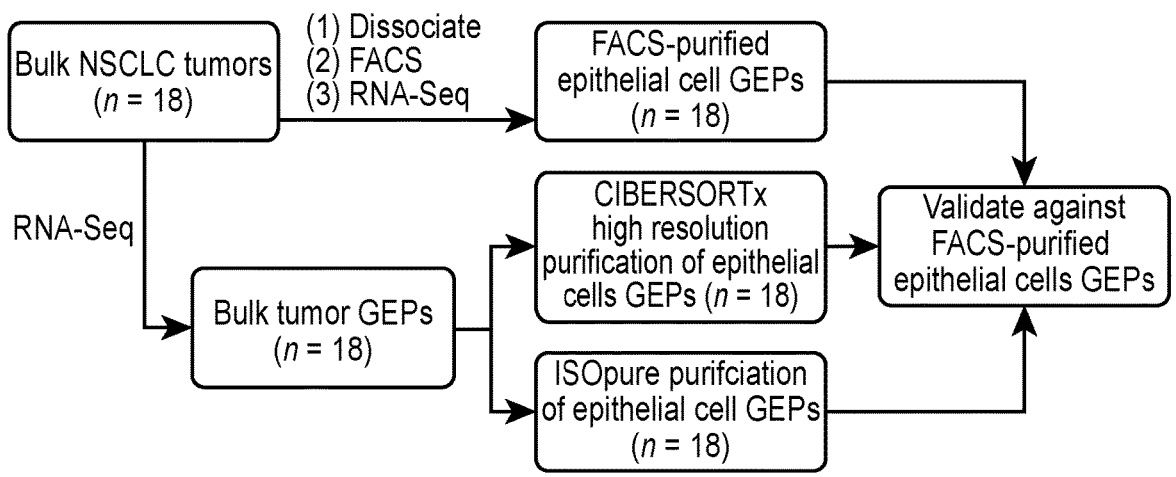
Figure 18:
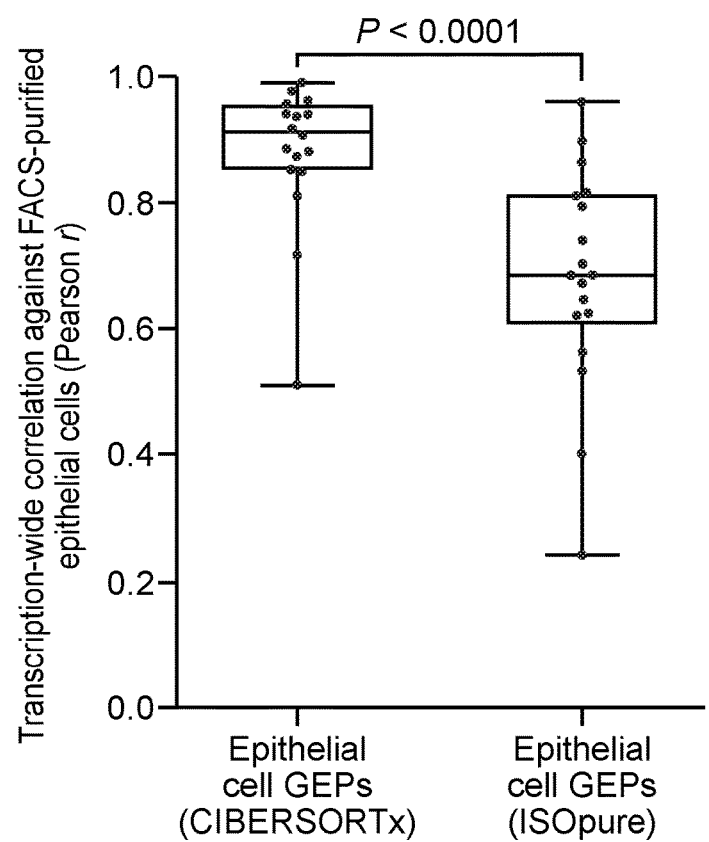
Figure 18:
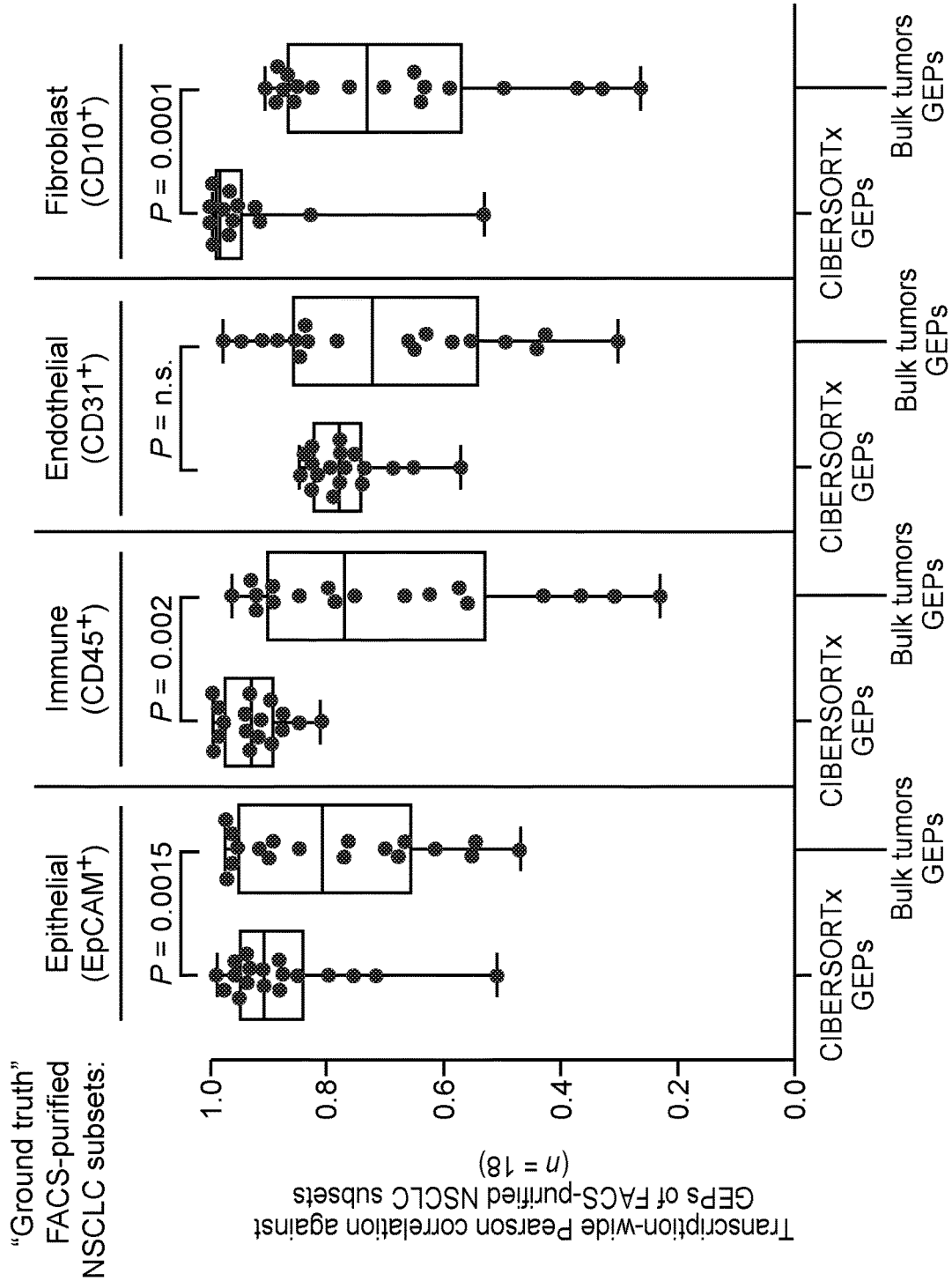
Figure 19:
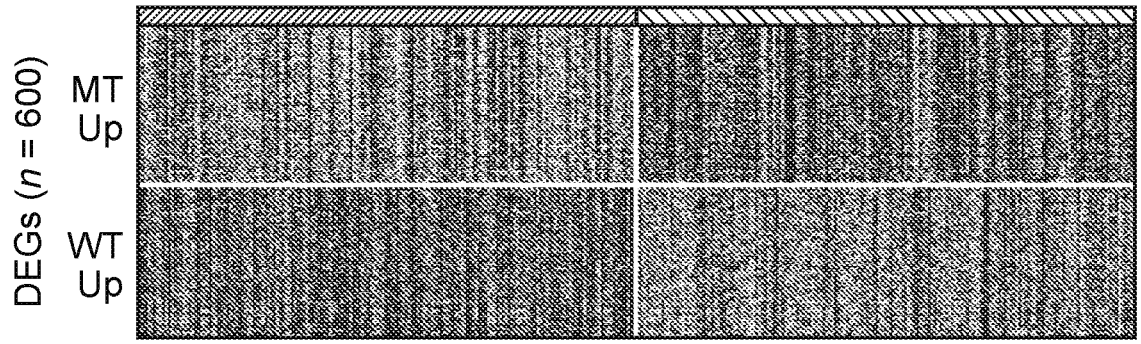
FIGS. 19a-b illustrate prediction and validation of driver mutation-associated DEGs in melanoma tumor cell subsets. Heat maps depicting cell type-specific DEGs associated with (19a) BRAF or (19b) NRAS mutation status, as identified by high resolution purification of bulk melanoma tumors (TCGA), related to FIG. 6b. Results are shown for in silico purified transcriptomes from TCGA (Left) and scRNA-Seq profiles in a validation cohort (Right). Genes are organized top to bottom by their $log_2$ fold change between mutant and wild-type groups in digitally purified transcriptomes. Only the top 300 over- or under-expressed genes are shown. Owing to sparsity of expression, scRNA-Seq profiles are also averaged by mutation status on the far right. Gene-level expression data were Z-score normalized in $log_2$ space prior to plotting.
Figure 19:
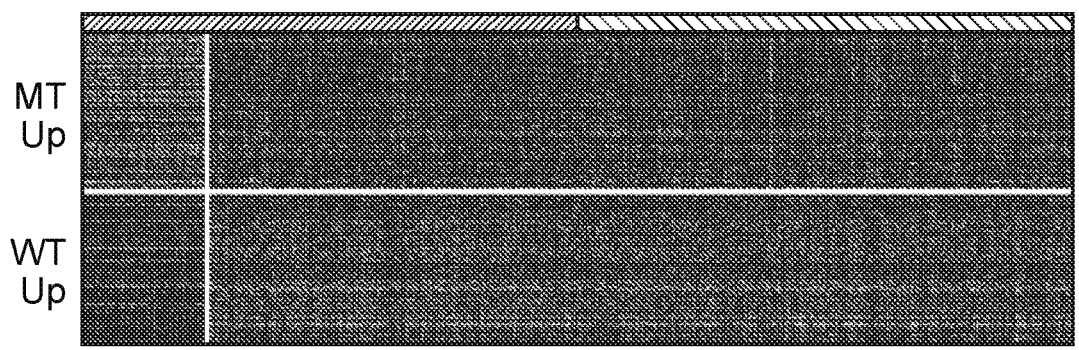
Figure 19:
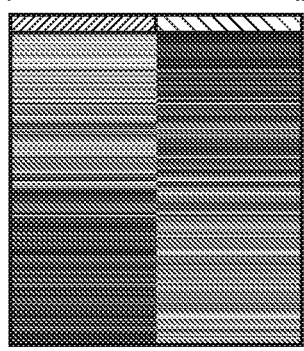
Figure 19:
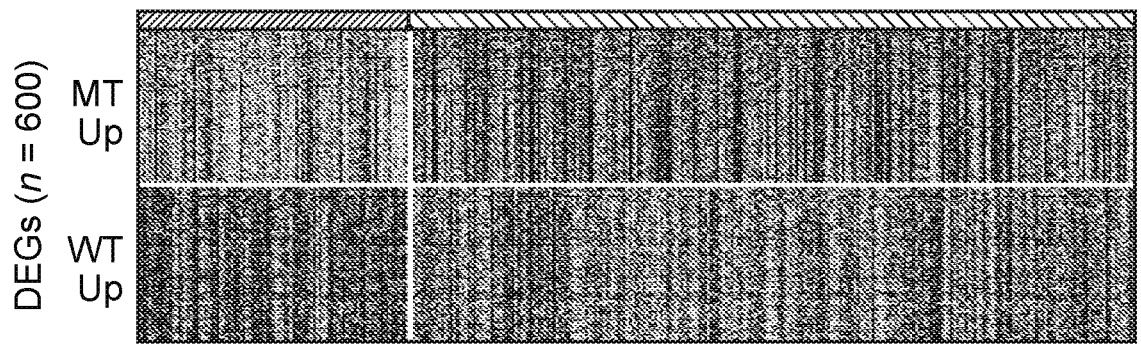
Figure 19:
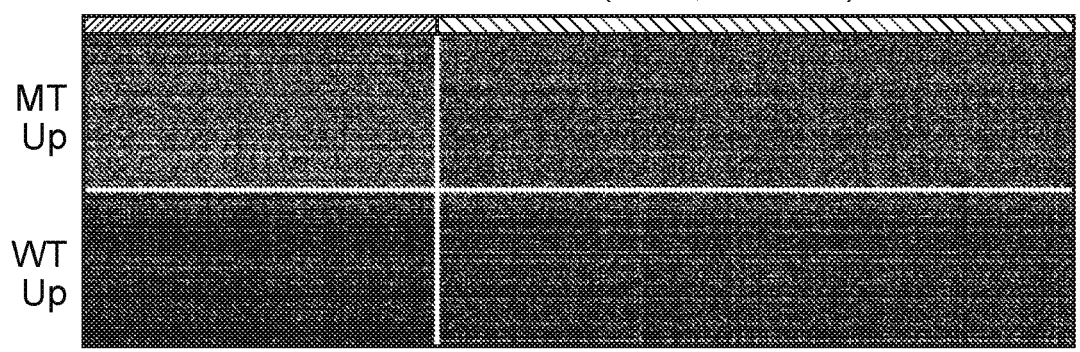
Figure 19:
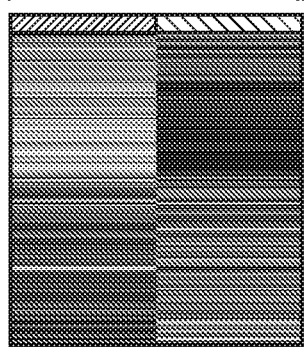
Figure 19:
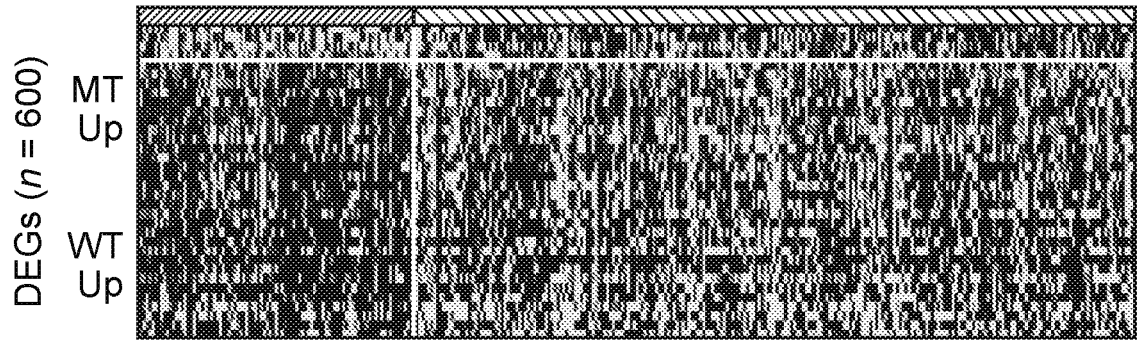
Figure 19:
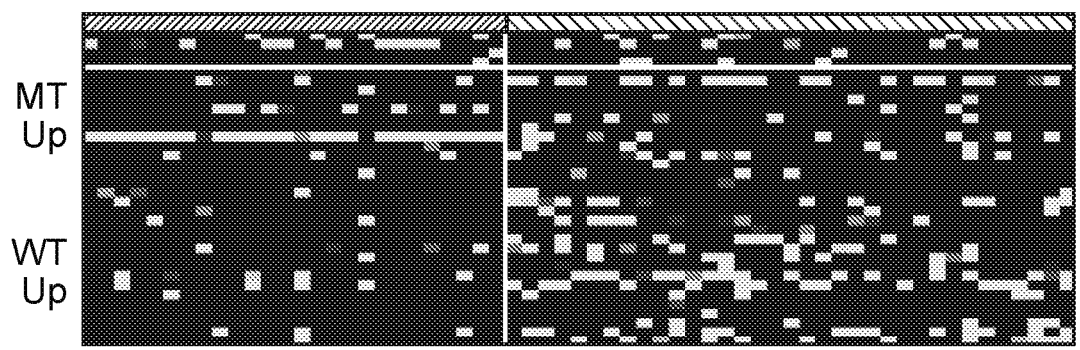
Figure 19:
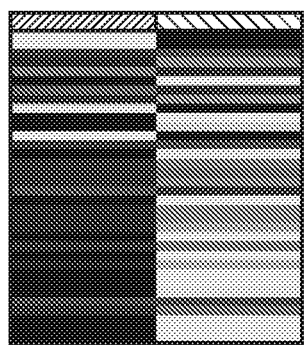
Figure 19:

To illustrate this application while also extending our analysis to multiple cell types, RNA-Seq libraries were generated from 22 surgically-resected NSCLC bulk tumor biopsies, including epithelial, hematopoietic, endothelial, and fibroblast subsets FACS-purified from the same specimens (FIG. 5d). After deriving a signature matrix from a subset of 4 patients, high resolution profiling was applied to digitally dissect these four populations from a validation set of 18 tumor GEPs. In a direct comparison against FACS-purified cell populations on matching patient samples, in silico profiles showed strong evidence of successful purification (FIGS. 18c-e). In addition, CIBERSORTx showed a significant advantage when compared to a previous method for purifying GEPs of epithelial cells from bulk tumors (FIGS. 18c-d).

Accordingly, the same signature matrix was applied to resolve epithelial, hematopoietic, endothelial, and fibroblast GEPs from bulk RNA-Seq profiles of 518 lung adenocarcinoma (LUAD) tumors, 502 lung squamous cell carcinoma (LUSC) tumors, and 110 adjacent normal tissues from TCGA (FIG. 5d). T-SNE was used to visualize and explore the distribution of in silico purified cell populations (FIG. 5e). The following putative outlier samples were identified and omitted from further analysis: TCGA.44.6775.01C.02R.A277.07, TCGA.44.3918.01A.01R.A278.07, TCGA.44.2656.01A.02R.A278.07, TCGA.44.4112.01A.01R.A278.07, TCGA.44.2665.01B.06R.A277.07, TCGA.44.2668.01A.01R.A278.07, TCGA.44.2666.01A.01R.A278.07, TCGA.44.6775.01A.11R.A278.07, TCGA.44.6147.01A.11R.A278.07, TCGA.44.2665.01A.01R.A278.07, TCGA.44.2662.01A.01R.A278.07, TCGA.44.6146.01A.11R.A278.07, TCGA.44.5645.01A.01R.A278.07, TCGA.44.3917.01A.01R.A278.07, TCGA.44.6147.01B.06R.A277.07, TCGA.44.2666.01B.02R.A277.07, TCGA.44.4112.01B.06R.A277.07, TCGA.44.3918.01B.02R.A277.07, TCGA.44.3917.01B.02R.A277.07, TCGA.44.2668.01B.02R.A277.07, TCGA.44.6146.01B.04R.A277.07, TCGA.44.2662.01B.02R.A277.07, TCGA.44.5645.01B.04R.A277.07, and TCGA.44.2656.01B.06R.A277.07. This allowed unsupervised discovery of differential expression patterns for each NSCLC histological subtype (e.g., LUAD versus LUSC), including distinct phenotypic shifts in cancer-associated fibroblasts (CAFs). By contrast, tumor-associated endothelial cells and adjacent normal tissues clustered together regardless of histological subtype. To verify these results, they were compared with FACS-purified NSCLC cell types from 20 patients. Strong concordance was observed both at the whole transcriptome level and in relation to patterns of differential expression in isolated cell subsets, validating the in silico findings (FIGS. 5e-f). Moreover, the results were consistent with other reported scRNA-Seq profiles of cellular heterogeneity in NSCLC.

Identifiers of bulk tumors and FACS-purified cell subsets from NSCLC patients are shown in Table 1.

TABLE 1

| | | Samples with bulk RNA-Seq profiles (1 = yes; 0 = no) | | | | |
|---|---|---|---|---|---|---|
| Tumor ID | Histology | Bulk tumor | EpCAM+ (epith.) | CD45+ (immune) | CD10+ (fibro.) | CD31+ (endo.) | Signature matrix |
| T2 | NOS | 0 | 1 | 1 | 1 | 1 | 1 |
| T3 | LUSC | 1 | 1 | 1 | 1 | 1 | 1 |
| T8 | LUAD | 1 | 1 | 1 | 1 | 1 | 1 |
| T9 | ADSQ | 1 | 1 | 1 | 1 | 1 | 1 |
| T5 | LUAD | 1 | 1 | 1 | 1 | 1 | 0 |
| T6 | LUAD | 1 | 1 | 1 | 1 | 1 | 0 |
| T7 | LUAD | 1 | 1 | 1 | 1 | 1 | 0 |
| T10 | LUAD | 1 | 1 | 1 | 1 | 1 | 0 |
| T12 | LUAD | 1 | 1 | 1 | 1 | 1 | 0 |
| T15 | LUSC | 1 | 1 | 1 | 1 | 1 | 0 |
| T17 | LUSC | 1 | 1 | 1 | 1 | 1 | 0 |
| T18 | LUSC | 1 | 1 | 1 | 1 | 1 | 0 |
| T20 | LUSC | 1 | 1 | 1 | 1 | 1 | 0 |
| T26 | LUAD | 1 | 1 | 1 | 1 | 1 | 0 |
| T27 | LUAD | 1 | 1 | 1 | 1 | 1 | 0 |
| T28 | LUAD | 1 | 1 | 1 | 1 | 1 | 0 |
| T35 | LUAD | 1 | 1 | 1 | 1 | 1 | 0 |
| T36 | LUAD | 1 | 1 | 1 | 1 | 1 | 0 |
| T38 | LUAD | 1 | 1 | 1 | 1 | 1 | 0 |
| T39 | LUSC | 1 | 1 | 1 | 1 | 1 | 0 |
| T40 | LUSC | 1 | 1 | 1 | 1 | 1 | 0 |
| T4 | LUSC | 1 | 1 | 1 | 1 | 1 | 0 |
| T11 | LUAD | 1 | 1 | 1 | 1 | 1 | 0 |
| T30 | LUAD | 1 | 1 | 1 | 1 | 1 | 0 |
| T34 | LUSC | 1 | 1 | 1 | 1 | 1 | 0 |
| T37 | Other | 1 | 1 | 1 | 1 | 1 | 0 |

Collectively, these data demonstrate the utility of digital cell sorting for learning expression variation and highlight its value for dissecting molecular pathways in bulk specimens.

Example 5: Applications of In Silico Cytometry to Melanoma

Having established an analytical workflow for digital cytometry (FIG. 1), the corresponding techniques were integrated into a comprehensive toolkit (http://cibersortx.stanford.edu). Three potential applications of CIBERSORTx were then analyzed for characterizing cellular heterogeneity in resected tumor biopsies from patients with melanoma (FIGS. 6a-h). To illustrate the method's diverse capabilities, each of the following techniques were applied in turn: high-resolution expression purification (FIG. 1, step 4; FIGS. 6a-b), group-level expression purification (FIG. 1, step 3; FIG. 6c), and enumeration of cell composition across diverse platforms using single-cell reference profiles (FIG. 1, steps 1 and 2; FIGS. 6d-f).

Oncogenic BRAF mutations may occur in over half of melanomas and can be inhibited by approved targeted therapies, whereas NRAS mutations may occur in about half of non-BRAF mutant melanoma tumors but may lack such therapies. Understanding how key mutations influence cellular states may potentially lead to novel treatment strategies. Using single cell reference profiles from melanoma tumors to build a signature matrix, high resolution expression purification was used to dissect 8 major cell types from the transcriptomes of 301 bulk melanoma tumors profiled by TCGA (FIG. 6a). Within in silico purified cell subsets, many significant DEGs were discovered within malignant cells and CAFs that distinguish melanomas according to BRAF or NRAS mutation status (FIG. 6b). These findings were verified using scRNA-Seq data from primary melanomas where mutation data were available, allowing confirmation of GEPs associated with BRAF and NRAS genotypes within individual malignant cells and/or CAFs (FIGS. 6b and 19a-b). These data validate the approach at a single cell level, and further illustrate its potential for unraveling poorly understood associations between somatic variation and cellular phenotypes in human tumor specimens.

Figure 20:
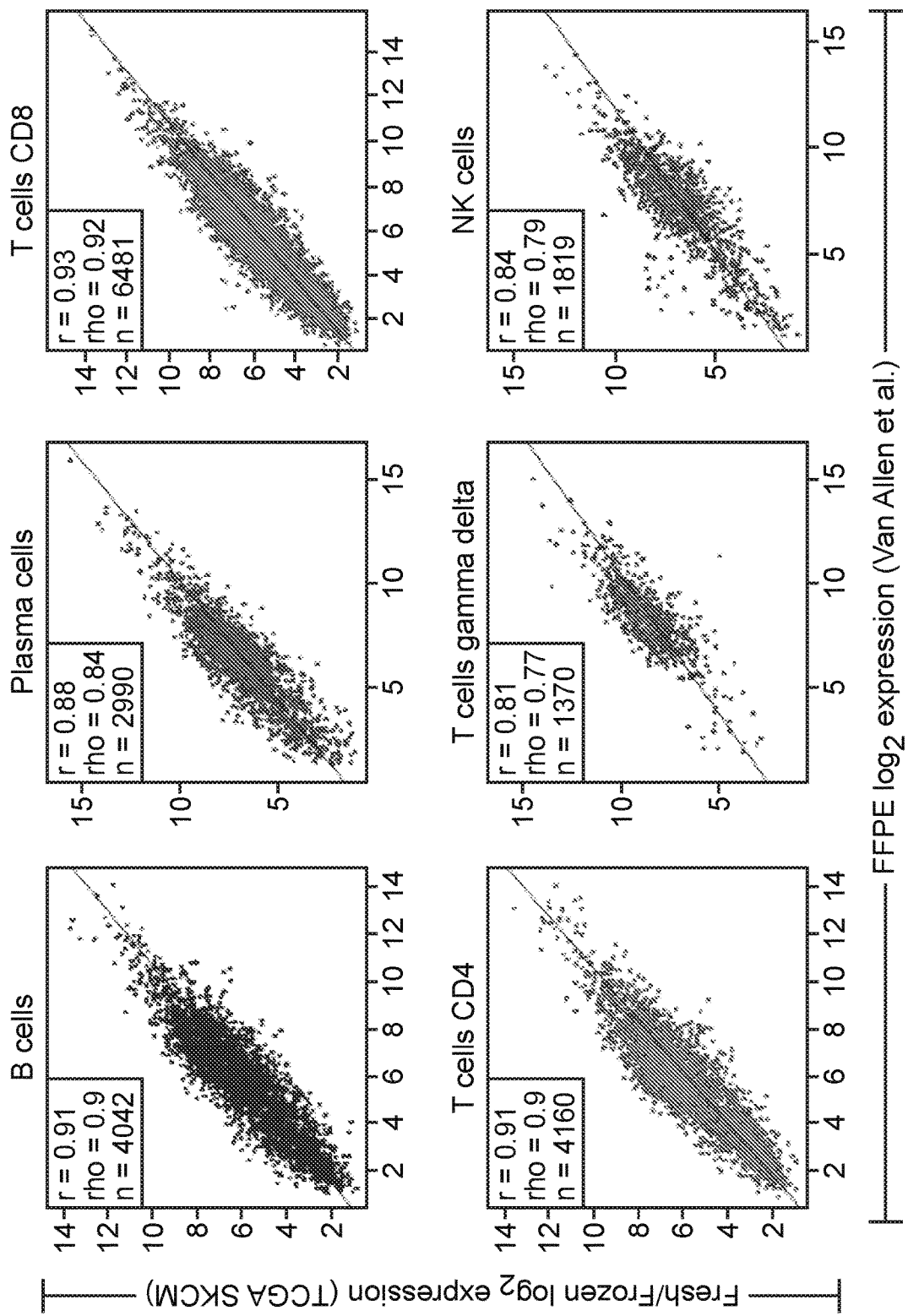
FIG. 20 illustrates comparison of TIL GEPs imputed from fresh/frozen and fixed melanoma tumors. Leukocyte transcriptomes were imputed with CIBERSORTx from independent cohorts of fresh/frozen (TCGA; n=473 tumors) and fixed (n=42 tumors) (as described, for example, by Van Allen et al., Genomic correlates of response to CTLA-4 blockade in metastatic melanoma, *Science* 350, 207-211 (2015), which is hereby incorporated by reference in its entirety) bulk melanoma tumors profiled by RNA-Seq. Only genes with nonzero expression are shown. The LM22 signature matrix was collapsed into 11 major leukocyte subsets after cell type enumeration and prior to transcriptome purification. Adaptive noise filtration was applied in both datasets. SKCM indicates skin cutaneous melanoma.
Figure 20:
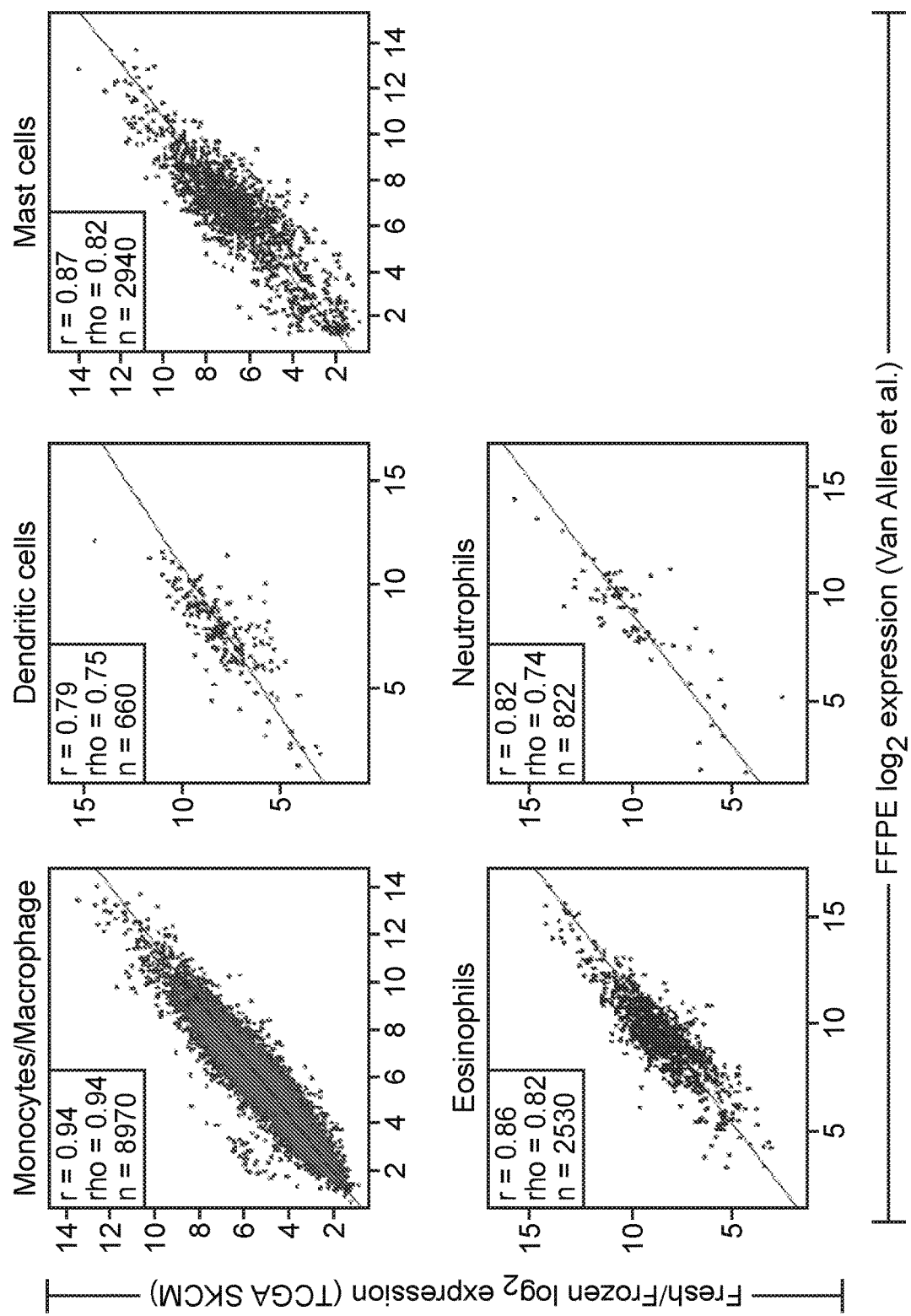

Tumor-infiltrating CD8 T cells may be driven to a state of "exhaustion" by chronic antigen stimulation or by overexposure to inflammatory signals. Given the importance of these cells for current and emerging cancer immunotherapies, CIBERSORTx was next used to examine changes in gene expression that characterize the exhaustion phenotype. Using LM22, which is derived from healthy peripheral blood leukocytes, immune composition in fresh/frozen melanoma tumors profiled by TCGA27 was enumerated. Group-level expression purification was performed to impute a representative CD8 TIL expression profile. By rank-ordering the estimated CD8 TIL GEP against a baseline reference profile of normal peripheral blood CD8 T cells, it was observed that key exhaustion markers, including PDCD1 and CTLA4, were strongly over-expressed in the inferred CD8 TIL GEP (FIG. 6c). In addition, CD8 TIL-specific genes were consistent with those observed for CD8 T cells isolated from melanoma tumors by single-cell RNA-Seq and by FACS (FIG. 6c). Similar results were also obtained when repeating the analysis on FFPE tumors from an independent cohort (FIGS. 6c and 20). Thus, CIBERSORTx can accurately learn phenotypic state changes of cell subpopulations that infiltrate complex tissues, such as fixed tumors, without the need for single-cell profiling.

Separately, regimens for metastatic melanoma can employ checkpoint blockade with single or combination agent immunotherapy targeting PD-1 and/or CTLA4 expression on exhausted T cells. Although a subset of patients may achieve durable anti-tumor T cell responses, clinical outcomes remain heterogeneous and effective predictive biomarkers can be lacking. CD8 TILs expressing high levels of PDCD1 (encoding PD-1) or CTLA4 are key targets of these therapies, suggesting that CD8 TILs expressing both markers may correlate with response, as was recently shown by flow cytometry in melanoma patients receiving PD1 blockade.

To test this hypothesis, single-cell reference profiles of melanoma tumors were used to build a signature matrix containing PDCD1+/CTLA4+ CD8 T cells along with eight other major tumor cell types (FIGS. 6d, 9b, and 21a-b). The signature matrix was applied with batch correction to interrogate three publicly available melanoma expression datasets (FIG. 6d). These included bulk expression data of FFPE and fresh/frozen melanoma tumors that were profiled by RNA-Seq or NanoString and obtained before, during, or after PD-1 or CTLA4 blockade. In support of our hypothesis, imputed levels of PDCD1+/CTLA4+ CD8 T cells were significantly associated with response in all three studies (FIG. 6e). Moreover, the detection of these cells significantly stratified overall survival in this meta-analysis, separated survival curves in individual datasets, and more significantly associated with survival and response than key marker genes (FIGS. 6f and 21c-f). These data illustrate the utility of CIBERSORTx for rapid assessment of candidate biomarkers derived from single-cell reference profiles, and suggest that further analysis of tumor-infiltrating PDCD1+/CTLA4+ CD8 T cells in melanoma patients is warranted.

Example 6: Imputation of Representative Cell Type-Specific Expression Profiles

Equations (5) to (8), shown below, may be used to perform CIBERSORTx algorithms (e.g., to impute representative cell type-specific expression profiles).

$$B \times F_{\cdot,j} = M_{\cdot,j}, \quad 1 \leq j \leq c \tag{5}$$

$$H_{i,\cdot} \times F = M_{i,\cdot}, \quad 1 \leq i \leq n \tag{6}$$

$$F \times G_{i,\cdot,\cdot} = P_{i,\cdot,\cdot}, \quad 1 \leq i \leq n \tag{7}$$

$$\mathrm{diag}(P_{i,\cdot,\cdot}) = M_{i,\cdot}, \quad 1 \leq i \leq n \tag{8}$$

Given B (which may be an m×k signature matrix (e.g., LM22) consisting of m genes by k distinct cell types) and M (which may be an n×c mixture of GEPs consisting of n genes by c samples), a goal of Equation 5 is to impute F (which may be a k×c matrix consisting of the fractional abundances of k cell subsets for each sample in M). A goal of Equation 6 is to impute H (which may be an n×k matrix of representative cell type-specific expression signatures) given F and M. A goal of Equations 7 and 8 is to impute G (which may be an n×c×k matrix consisting of n genes, c samples, and k cell types) given F and M.

Non-negative least squares regression (NNLS) using the nnls package in R was employed to solve Equation 6 for H given F and M (e.g., optimize a regression by solving for a set of regression coefficients). NNLS was selected since it can produce biologically plausible solutions by enforcing non-negativity constraints. Subsampling without replacement was incorporated to improve the reliability of the results and to compute standard errors and confidence intervals. To estimate the significance of the regression coefficients for each gene, the same approach traditionally used for ordinary linear least squares was adapted to NNLS. Here, the significance of a regression coefficient is determined by first dividing it by its analytically derived standard error, and then converting the resulting quotient to a p-value using the Student t distribution. For each cell type, p-values were corrected for multiple hypothesis testing using the Benjamini-Hochberg method. In cases where adjusted p-values (e.g., q-values) were highly significant (q-value<$10^{-5}$, by default) for a given gene i and cell type j, all other cell types with a q-value>0.25 in gene i were considered as insignificantly detected (expression set to 0). To further reduce confounding noise, genes were filtered based on their geometric coefficient of variation (geometric c.v.), which was calculated using the natural logarithm of subsampled regression coefficients. Geometric c.v. thresholds were defined using an adaptive approach. Specifically, for each cell type, each geometric c.v. was ranked in ascending order, and then each c.v. was mapped onto a two-dimensional coordinate system such that the lowest c.v. ('$cv_1$') became coordinate (1, $cv_1$), the second lowest became (2, $cv_2$), and so on, until the maximum c.v. ('$cv_{max}$') was reached, defined as the maximum of either 1 or the 75th percentile of all c.v. values. An inflection point was then identified in the c.v. curve, defined as the point farthest from (0, $cv_{max}$) in Euclidean space. The geometric c.v. corresponding to this threshold was used as an adaptive cell type-specific noise threshold (FIGS. 3b-e and 11a-h).

Example 7: Imputation of High-Resolution Cell Type-Specific Expression Profiles An algorithm for imputation of high-resolution cell type-specific expression profiles may be performed using the following major steps, which parallel the corresponding schema presented in FIG. 12c.

For each gene i in mixture matrix M, this approach starts by sorting its expression vector $M_{i,\cdot}$ (hereafter, denoted $M_i$ for simplicity) in ascending order, resulting in vector $M^*_i$ (FIG. 12c, step i). Any cell type-specific DEGs with detectable signal in the bulk mixture may influence this ordering, and the most prominent signals may skew to one side of the distribution (e.g., FIG. 13b).

Next, the mixture samples in F (denoted F*) were reordered to match the ordering of samples in $M^*_i$, and iterator t was defined, which was set equal to w, a parameter specifying the number of mixture samples to use when solving Equation 6. For each integer value of t in [w, (1+c−w)], Equation 6 was solved twice: once for mixture samples in $M^*_i$ spanning indices 1 to t, and once for mixture samples in $M^*_i$ with indices (t+1) to c. Thus, for each value of t, this process yields two vectors of representative cell type-specific gene expression coefficients, $g_1$ and $g_2$, respectively (note that the index i is omitted here for simplicity; FIG. 12c, step ii).

Let $G^t_i$ be a c×k matrix consisting of t rows of $g_1$ followed by c−t rows of $g_2$. Since $G^t_i$ captures cell type-specific expression estimates with two degrees of freedom (two possible values per gene), it is a rough approximation of $G_{i,\cdot,\cdot}$ (hereafter, denoted $G_i$). To assess the goodness of fit between the reconstituted mixture derived from $G^t_i$ and F* and the original sorted mixture $M^*_i$, the residual sum of squares was calculated, and the value of t that minimizes the following equation was determined:

$$\min_{\forall t} \sum (\mathrm{diag}(F^* \times G^t_i) - M^*_i)^2 \quad (9)$$

The value of t that minimizes Equation 9, denoted t', defines the matrix $G^{t'}_i$ and the pair of underlying expression coefficient vectors, $g'_1$ and $g'_2$, that best reconstitute $M^*_i$ given F (FIG. 12c, step iii).

Next, each gene/cell type pair is subjected to a series of statistical tests to ascertain whether the gene is (1) significantly expressed and (2) significantly different between $g'_1$ and $g'_2$ (FIG. 12c, step iv). For the former, NNLS was applied to all mixture samples using bootstrapping with 100 iterations. For each gene i, the median expression values for each cell type are saved as vector $g^{global}$. The empirical p-value for each gene/cell type pair is calculated as the number of times a coefficient is equal to zero, divided by 100. Despite the well-established advantages of this approach, it can be susceptible to inaccuracies caused by inadequate sample size or insufficient bootstrap draws. For example, the latter imposes a lower bound on empirical p-values, which may be considerably underestimated for genes with otherwise exceptional statistical support (e.g., cell type marker genes). Thus, analytically derived p-values adjusted for multiple hypothesis testing were considered, using the same approach described in Example 5. In cases where the latter is highly significant (q-value<$10^{-5}$, by default) for a given gene i and cell type j, all other cell types with q-value>0.01 in gene i are considered insignificant (q-value set to 1), whereas all other q-values are left unchanged. To combine the output of both tests, Fisher's method was used to boost or penalize p-values based on their concordance. Since these tests are not independent, the output of Fisher's method is a meta-score, denoted $p^{global}$. Gene/cell type pairs with $p^{global}$<α (=0.05, by default) are considered significantly detectable.

For gene/cell type pairs with significantly detectable expression, the null hypothesis of no differential expression between $g'_1$ and $g'_2$ was then tested. This is accomplished using the following two distinct statistical tests. First, a simplifying assumption is made that the distributions underlying the standard deviations of $g'_1$ and $g'_2$ (denoted $sd_1$ and $sd_2$, respectively), which are obtained via bootstrapping, are Gaussian. It is then trivial to calculate Z-scores for differential expression as the difference between $g'_1$ and $g'_2$ divided by the square root of the sum of the squares of $sd_1$ and $sd_2$. Resulting Z-scores are converted to two-sided p-values, one for each cell type, and stored as a vector $p_1$.

Separately, differential expression was tested using a permutation analysis. Here, the rows (e.g., samples) of F* (denoted $F^{rand}$) are shuffled, and Equation 6 is solved using $F^{rand}$ and mixture samples with indices from (t'+1) to c, yielding a randomized version of $g'_2$, denoted $g^r_2$. The difference vector, $|g^r_2 - g'_1|$, is saved, and the process is repeated 50 times. The null distribution of difference vectors is then compared to the test statistic, $|g'_2 - g'_1|$, and empirical p-values are calculated as the fraction of randomized deltas exceeding this test statistic. The resulting p-values are stored as vector $p_2$. Since each test evaluates differential expression in a highly distinct manner, $p_1$ and $p_2$ are combined into a meta-score $p^{deg}$ using Fisher's method. Despite the utility of this meta-analytical approach, the output of Fisher's method is referred to as a meta-score, and not a p-value, since the input p-values are not formally independent.

Next, global coefficients $g^{global}$ and differential cell type expression vectors $g'_1$ and $g'_2$ are updated to reflect the statistical filtering steps above (FIG. 12c, step v-ii). First, $F^*_i \leftarrow F^*$ is defined for each gene i and fractional abundance vectors in $F^*_i$ are set to zero for cell types with insignificant expression between $g'_1$ and $g'_2$ in gene i. Then, $g^{global}$ is recalculated for each gene using $F^*_i$ and the same procedure described above for computing $g^{global}$. To update $g'_1$ and $g'_2$, $F^*_i$ is used rather than F* to identify a new optimal cut point t' and corresponding matrix $G^{t'}_I$ using Equation 9.

A series of steps is then performed to further refine $g'_1$, $g'_2$ based on the meta-score vector $p^{deg}$. Specifically, for a given gene i and cell type j, the difference between paired expression coefficients in $g'_1$, $g'_2$ is reduced in a manner that reflects the estimated statistical confidence in the differential expression of each cell type (FIG. 12c, step v-ii). To accomplish this, first the correlations (and corresponding $-\log_{10}$ p-values, denoted $p^{cor}$ between the fractions of each cell subset j and the expression vector $M_i$ are calculated after regressing out the remaining cell subsets in the signature matrix. Then 1 is set equal to the $-\log_{10}$ p-value of $p^{deg}$ (described above); alternatively, if no cell subsets are significant at a p-value threshold of 0.05, I is set equal to $p^{cor}$. Since I is in $-\log_{10}$ space, it is then divided by its maximum value $I^{max}$ (if significant at a threshold of $-\log_{10}(0.05)$), and the maximum value is calculated separately for cell subsets with higher expression in $g'_1$ than in $g'_2$, and vice versa. This yields a new vector 1*, which is used to adjust $g'_1$ and $g'_2$ such that the fold change between expression coefficients for a given cell subset is reduced in proportion to I*, which captures the estimated statistical confidence in differential expression. After adjustment, paired expression coefficients in $g'_1$ and $g'_2$ with a fold change <1.1 (by default) are considered insignificantly different and are set to their corresponding global coefficients in $g^{global}$. Although heuristic, this approach can greatly reduce erroneous differences in imputed expression while simultaneously preserving the delta for the gene/cell type pairs that are most significant. Once $g'_1$ and $g'2$ are adjusted, $G''_i$ is re-estimated using Equation 9.

Despite the improvements thus far, $G''_i$ can still be restricted to at most 2 distinct values per gene/cell type pair. To impute smooth expression coefficients with multiple degrees of freedom, Equation 6 is sequentially solved within a sliding window of length w for all possible window positions in $M^*_i$, yielding matrix $Q_i$ (FIG. 12c, step v-i). Because $Q_i$ has w−1 fewer rows than $G_i$, two versions of $Q_i$ are created: one with w−1 copies of row 1 added to the top of $Q_i$, denoted $Q'_i$, and one with w−1 copies of row c added to the bottom of $Q_i$, denoted $Q''_i$. These two matrices are then averaged, setting $Q_i \leftarrow (Q'_i + Q''_i)/2$. Although this procedure results in smooth expression vectors harboring c degrees of freedom, it may rely on an assumption that the mixture samples within each window are sufficiently similar with minimal cell type-specific expression variation. In other words, sample-specific expression differences for a given cell type may be averaged out within a given window, despite being captured across windows. This issue can be partially addressed by decreasing the size of w, albeit at the risk of numerical instability within the regression framework.

Additionally, since bulk expression in $M^*_i$ is sorted, windows that cover regions with low expression may lead to imprecise estimates owing to inadequate information content. The same issue can arise from windows of insufficient size. To help address these potential problems, expression coefficients in $Q_i$ are adjusted based on the final values of $g'_1$ and $g'_2$ within $G''_i$ (FIG. 12c, step v-iii). Specifically, for each cell type j, the expression coefficients in $Q_{i,j,\cdot}$ are individually fit to $G''_{i,j,\cdot}$ using ordinary least squares regression. This allows $g'_1$ and $g'_2$ to serve as anchor points and to ensure that the directionality of cell type-specific expression differences (e.g., high to low, or low to high) across the ordered mixture is maintained. RLR is employed since it allows for some flexibility in fitting rigid vectors with at most 2 distinct values (as compared to linear least squares), though other approaches may be used. The resulting matrix is denoted $Q'_i$.

Finally, for each gene, the original ordering of mixture samples in $Q'_i$ is restored, which we save as $G_i$ (FIG. 12c, step v-iv). Following aggregation of $G_i$ across all genes into 3D matrix G, each cell type-specific expression matrix is written to disk.

Example 8: Batch Correction for Deconvolution

Figure 23:
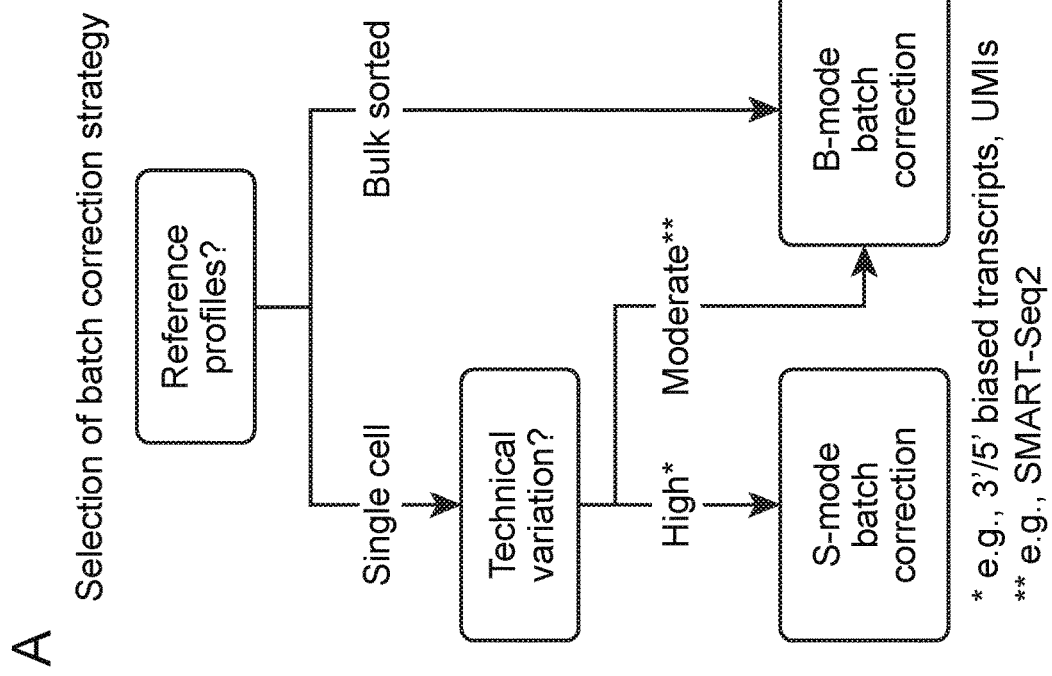
FIGS. 23a-l illustrate cross-platform deconvolution using CIBERSORTx. (23a) Decision tree for selecting the most appropriate CIBERSORTx batch correction strategy for a given input signature matrix: (1) single cell reference mode ('S-mode', panels (23g)-(23i) or (2) bulk reference mode ('B-mode', panels (23d)-(23f). (23b-c) Schematics for S-mode (23b) and B-mode (23c) batch correction. (23d) Analysis of deconvolution performance using the signature matrix and mixture dataset from FIG. 2b, but comparing the relative utility of B-mode and S-mode batch correction for overcoming technical variation. (23e) t-SNE projections of two publicly available single cell transcriptome datasets of PBMCs profiled by 10× Genomics using 3' and 5' kits. Cell labels were determined manually using Seurat (e.g., v1.4.0.16) and canonical marker gene assessment, and used to generate two signature matrices, 3' PBMC and 5' PBMC. (23f) t-SNE plot showing platform-specific batch effects between the datasets from panel (23e). (23g)-(23j) Evaluation of S-mode for adjusting cell type reference profiles derived from single cell transcriptome data. (23g) Schematic of the experimental approach, using datasets in panel (23e) to illustrate the application of S-mode to minimize technical variation between reference profiles derived from distinct 10× Chromium kits (panel (23f)). Here, a signature matrix from the 3' kit was applied to reconstituted blood samples derived from the 5' kit. Following S-mode batch correction, the adjusted 3' cell type reference profiles are more closely aligned with their corresponding reference profiles from the 5' kit, as demonstrated by heat maps (23h) and Pearson correlation (23i). (23j) Same as (23g), but replacing the 5' PBMC single cell dataset with sorted leukocyte subsets profiled by microarray. Cell subsets are colored as in panel (23i). For panels (23g)-(23j), only genes in the 3' PBMC signature matrix were considered as reference profiles for each cell type. (k) Evaluation of S-mode, showing leukocyte deconvolution of whole blood from healthy donors (n=12 RNA-Seq profiles) using single cell reference profiles of PBMC subsets generated by 10× Chromium. Pearson correlation (Left) and RMSE (Right) before and after S-mode batch correction. Ground truth cell proportions were determined by flow cytometry and complete blood counts. Group differences were evaluated by a Wilcoxon signed-rank test. (23l) Impact of B-mode batch correction on cell subset enumeration with LM22 (Affymetrix microarrays) across 5 platforms, 3 tissue types, and fresh/frozen vs. fixed tissue preservation states: Illumina Beadchip microarrays of cryopreserved PBMCs vs. flow cytometry (GSE65133), bulk RNA-Seq of fresh whole blood vs. flow cytometry/CBCs (as disclosed elsewhere herein), bulk RNA-Seq of FFPE melanoma (Mel.) tumors vs. surrogate cell markers, and reconstituted bulk melanoma (Mel) and HNSCC tumors from scRNA-Seq profiles (Smart-Seq2; TIL subset frequencies in reconstituted single cell expression data from melanoma and HNSCC tumors, respectively). Points represent Pearson correlation coefficients between expected and inferred levels for each cell type, and bar plots show medians with 95% confidence intervals expressed as error bars. Details of evaluable cell types and ground truth estimates are provided elsewhere herein. To evaluate performance without ground truth proportions for FFPE melanomas, deconvolution results for selected leukocyte subpopulations were compared to the expression of canonical marker genes in unadjusted RNA-Seq data (PTPRC vs. inferred immune content, CD19 vs. B cells, CD3D vs. T cells, CD8A vs. CD8 T cells, CD68 vs. monocytes/macrophages), and CIBERSORTx results were scaled by total immune to calculate a 'normalized immune index' for each tumor sample. Data in panels (23d), (23i), and (23j) are expressed as means+/−s.d.
Figure 23:
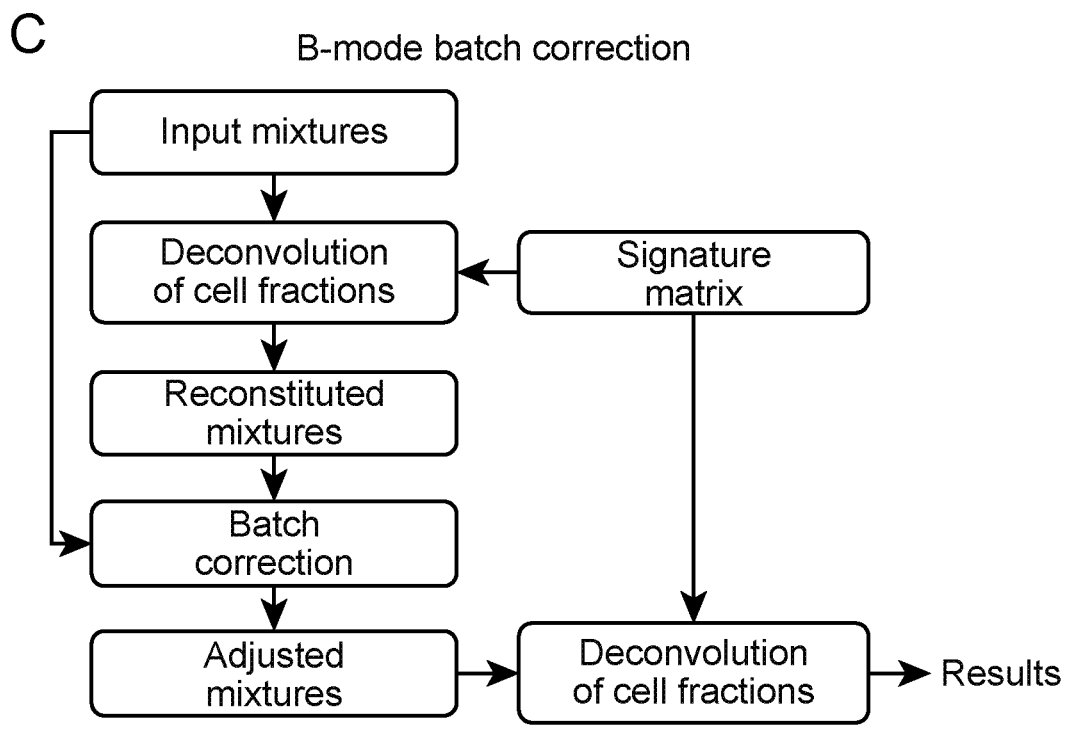
Figure 23:
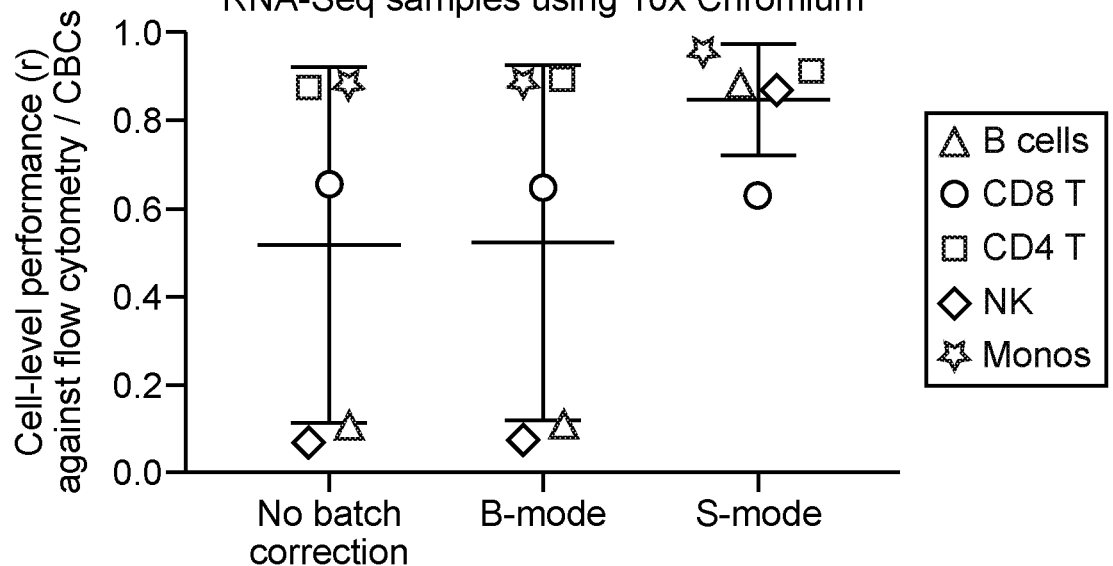
Figure 23:
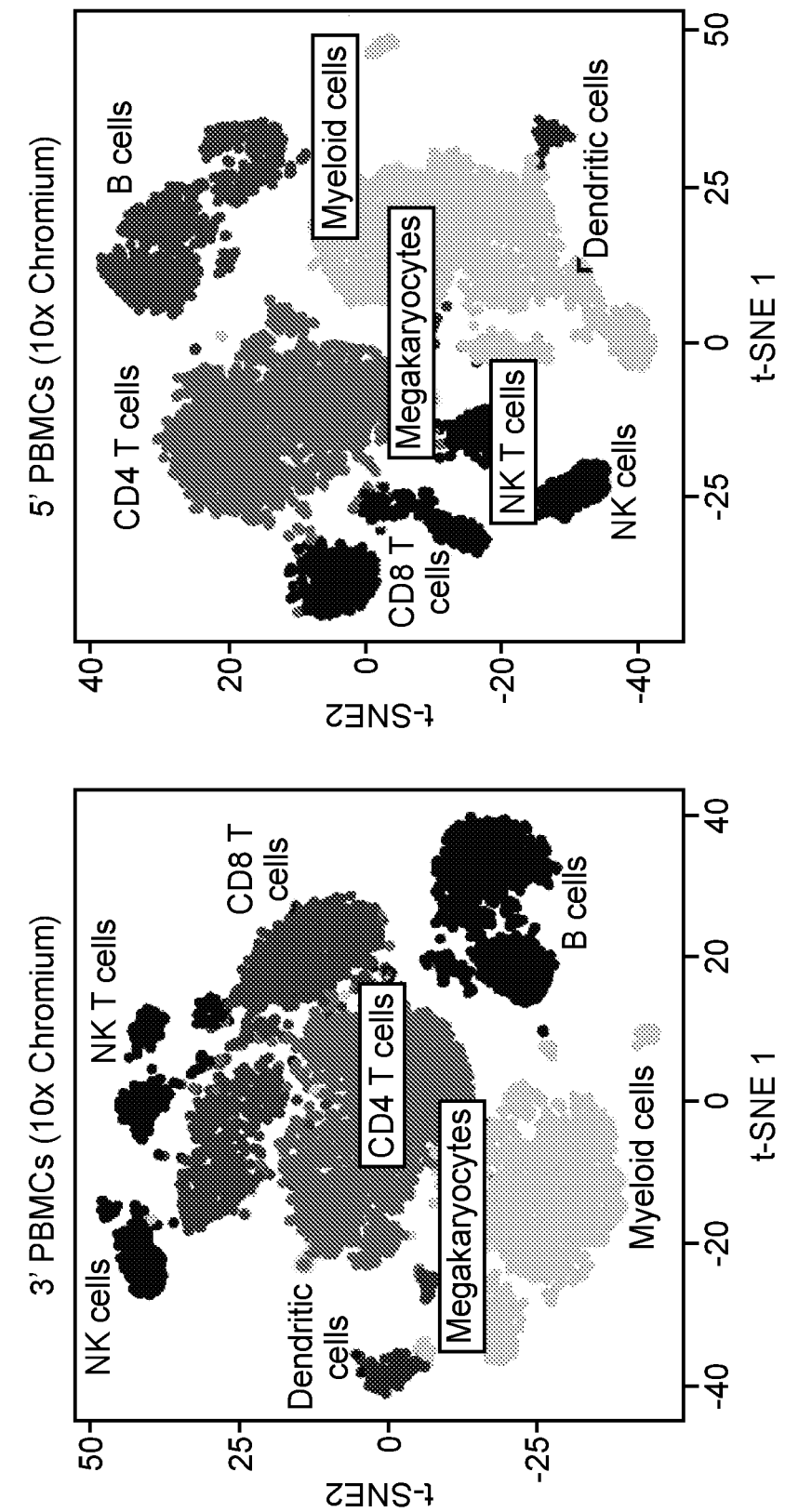
Figure 23:
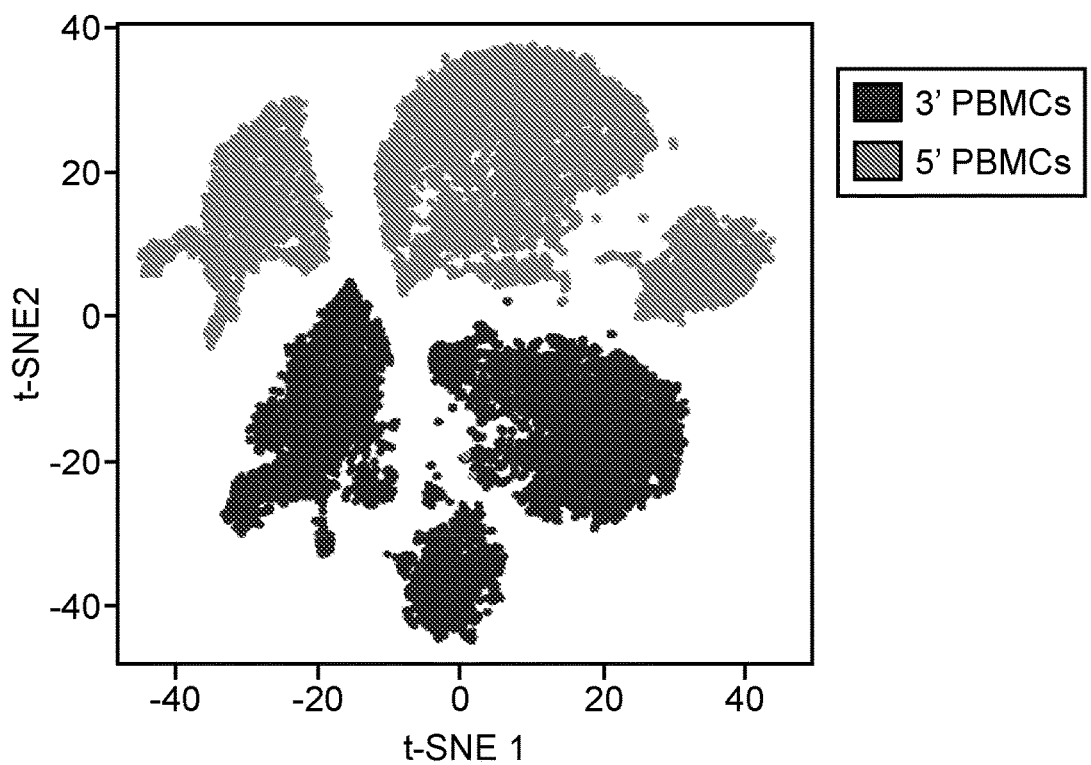
Figure 23:
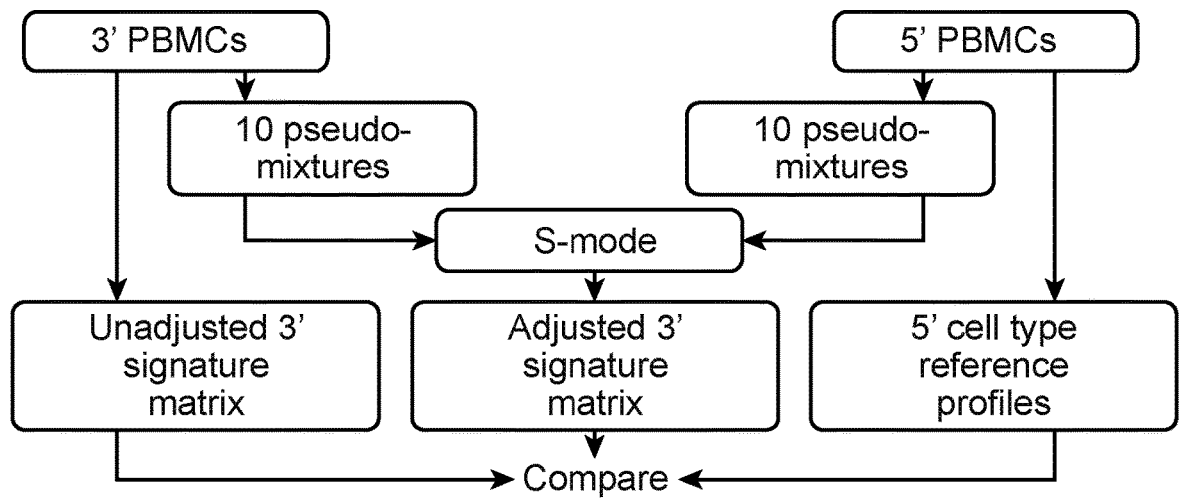
Figure 23:
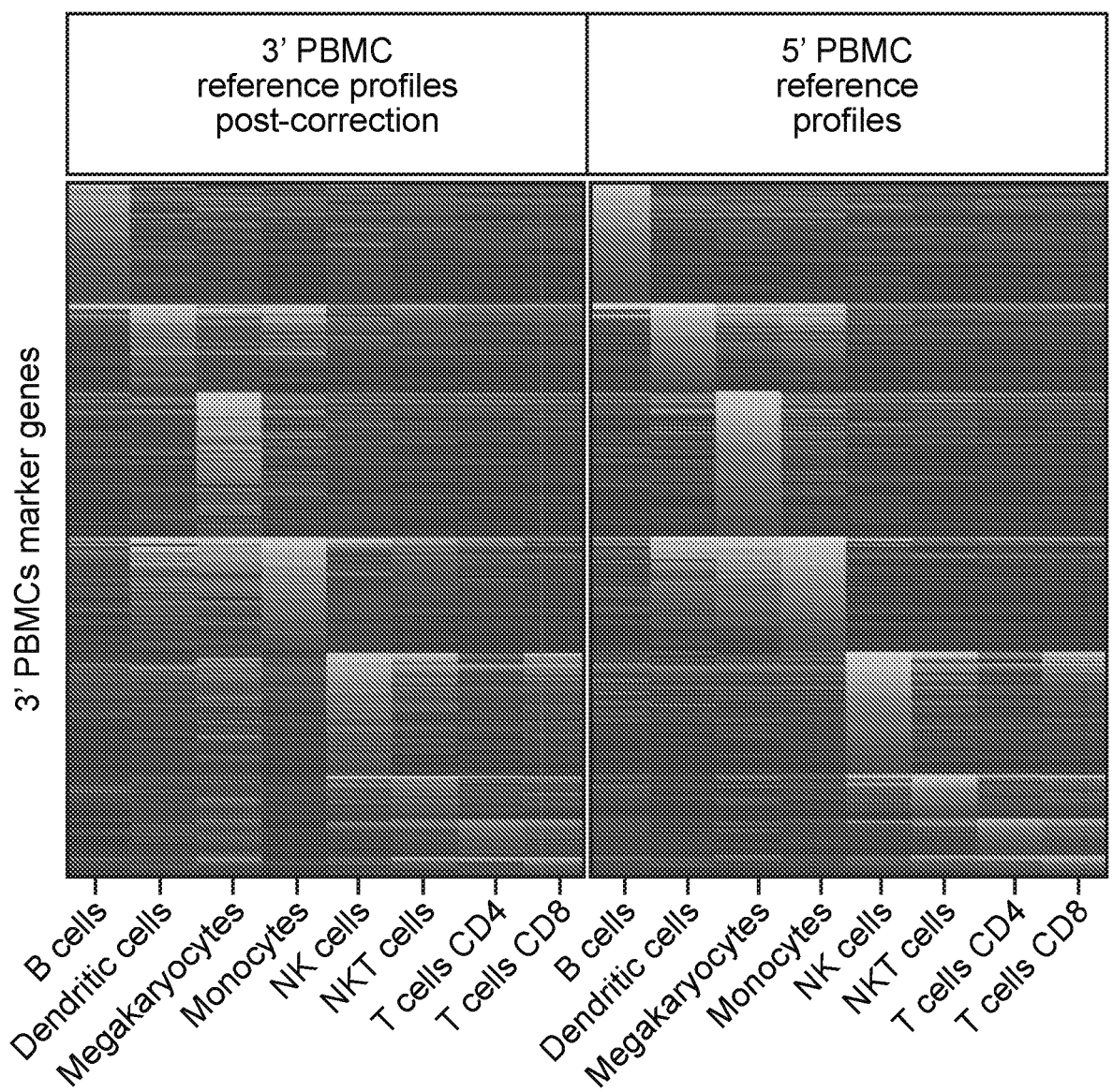
Figure 23:
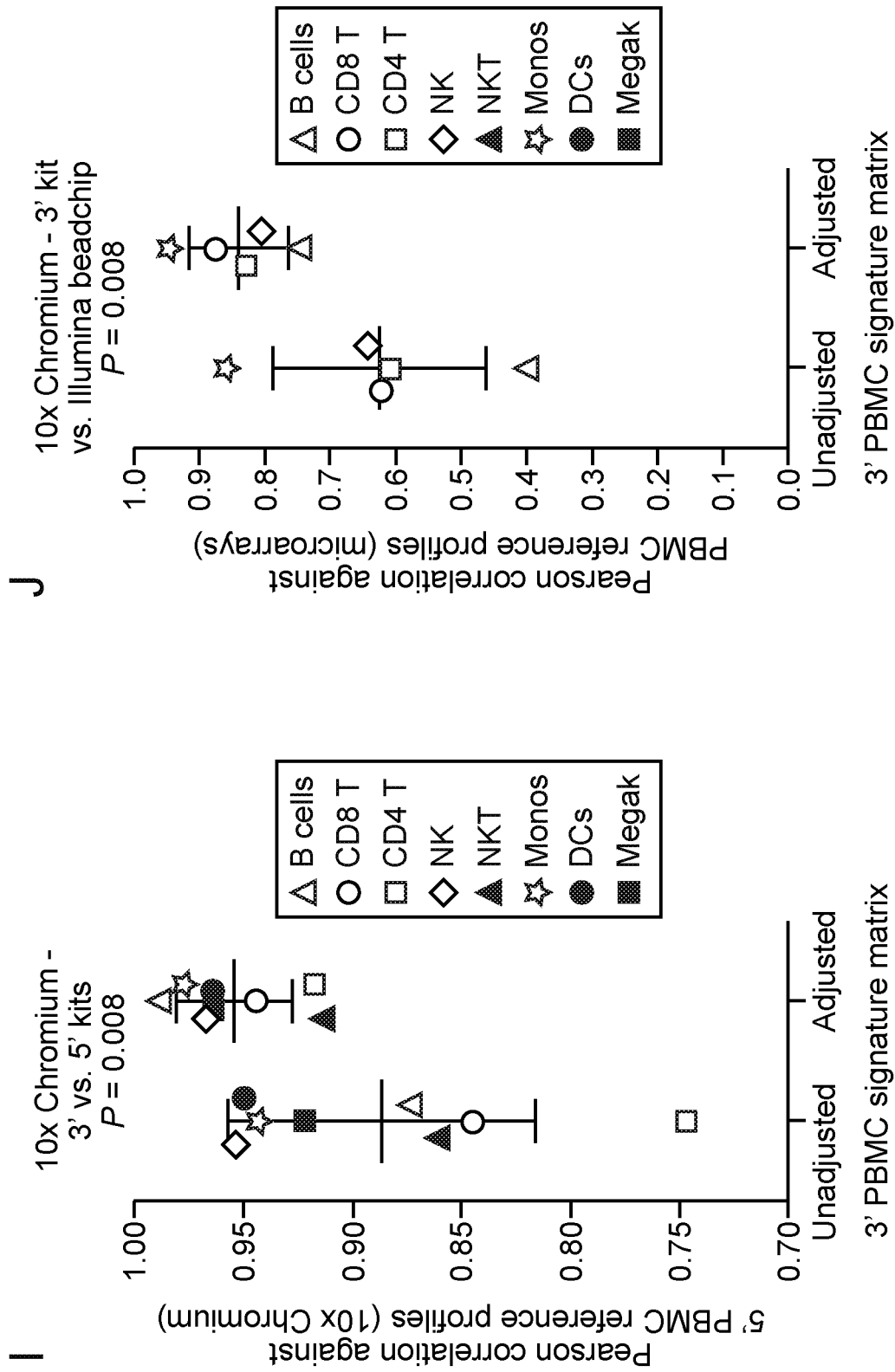
Figure 23:
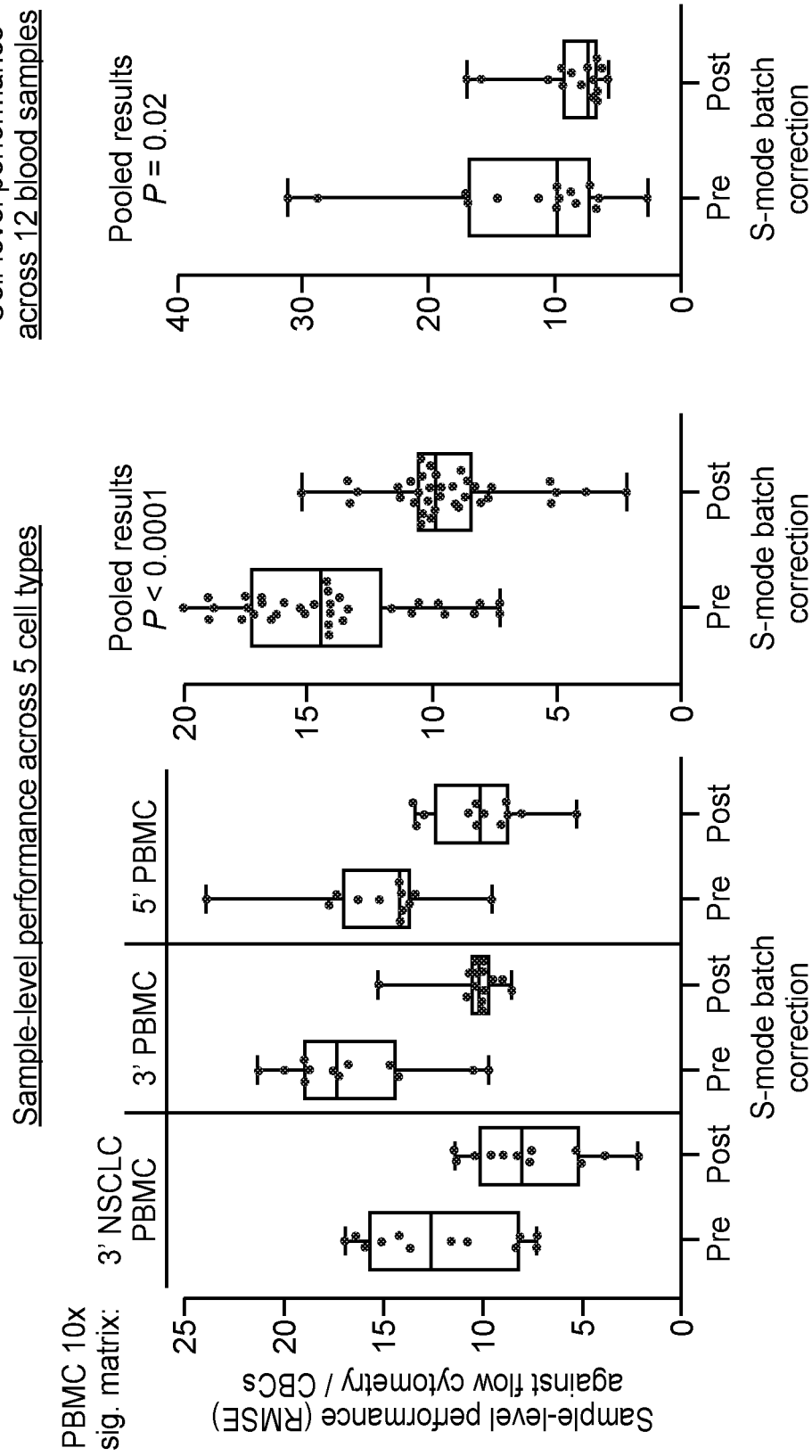
Figure 23:
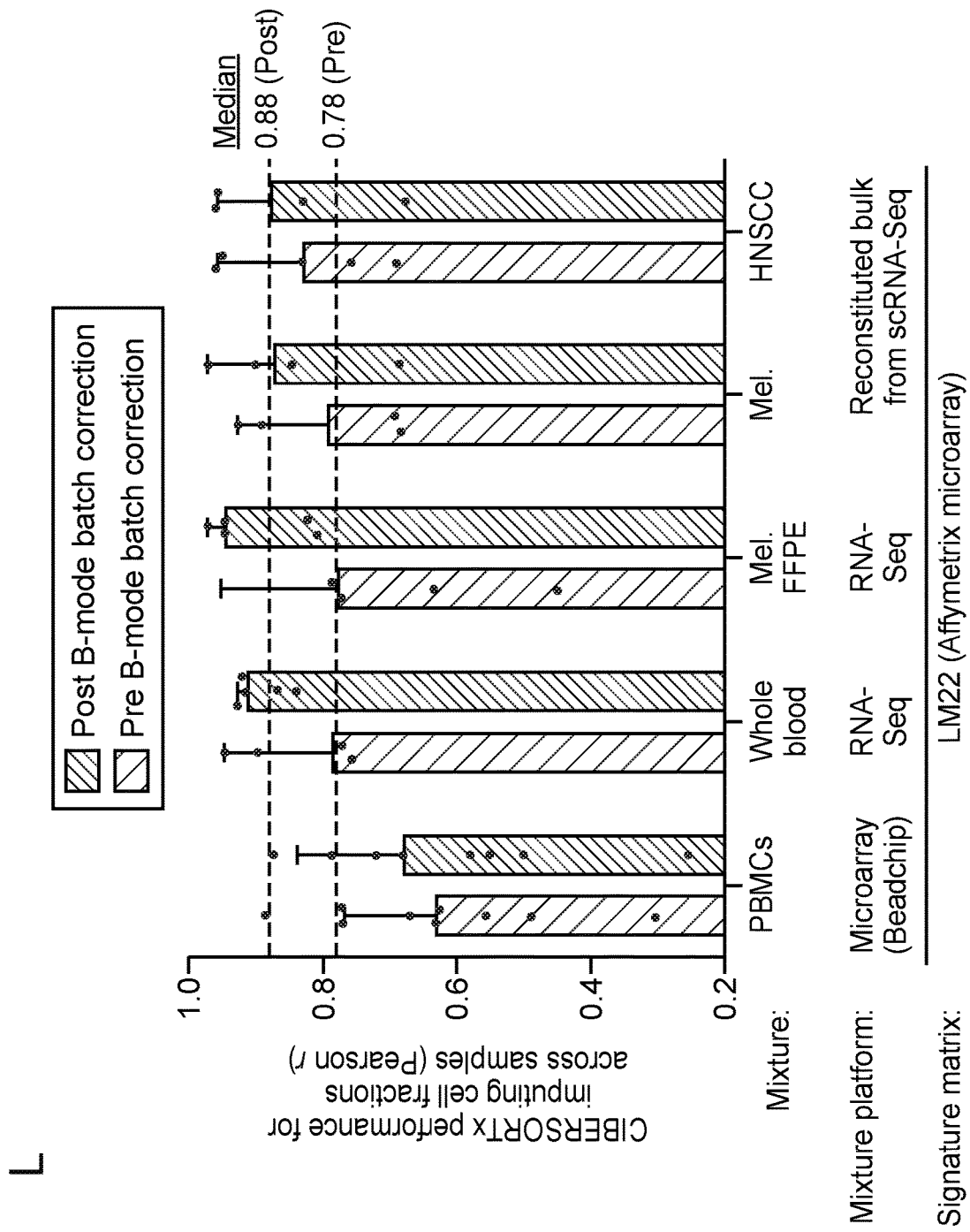

Cell type enumeration of 12 whole blood RNA-Seq samples using 10× Chromium was performed. As shown in FIG. 23d, results indicate significant improvement in cell-level performance using S-mode correction. In addition, as shown in FIG. 23f, platform-specific technical variation arising from batch effects were observed between datasets generated by profiling two publicly available single cell transcriptome datasets of PBMCs by 10× Genomics using 3' and 5' kits (FIG. 23e). As shown in the schematic in FIG. 23g, an S-mode batch correction was applied to these datasets to minimize technical variation between reference profiles derived from distinct 10× Chromium kits). A signature matrix from the 3' kit was applied to reconstituted blood samples derived from the 5' kit. Following S-mode batch correction, the adjusted 3' cell type reference profiles are more closely aligned with their corresponding reference profiles from the 5' kit, as demonstrated by heat maps (FIG. 23h) and Pearson correlation (FIG. 23i). As shown in FIG. 23j, a similar result as in FIG. 23g was observed, when the 5' PBMC single cell dataset was replaced with sorted leukocyte subsets profiled by microarray.

Example 9: Tumor Genotyping

Bulk RNA-Seq was performed using microarrays as follows. Total RNA was extracted from bulk FL specimens and sorted B cells, and assessed for yield and quality. cRNA was prepared from 100 ng of total RNA following linear amplification (3' IVT Express, Affymetrix) and then hybridized to HGU133 Plus 2.0 microarrays (Affymetrix) according to the manufacturer's protocol. All CEL files were pooled with a publicly available Affymetrix dataset containing CD4 and CD8 TILs FACS-sorted from FL lymph nodes (GSE27928). The resulting dataset was then RMA normalized using the "affy" package in Bioconductor, mapped to NCBI Entrez gene identifiers using a custom chip definition file (Brainarray version 21.0; http://brainarray.mbni.med.umich.edu/Brainarray/), and converted to HUGO gene symbols. Replicates of sorted cell subsets were combined to create ground truth reference profiles (e.g., as in FIG. 3b) using the geometric mean of expression values.

Cancer Personalized Profiling by Deep Sequencing (CAPP-Seq) was applied to 12 cryopreserved FL tumor biopsies from this cohort using a dedicated lymphoma targeted sequencing panel and sample processing protocol (as described, for example, Newman et al., An ultrasensitive method for quantitating circulating tumor DNA with broad patient coverage, *Nature Medicine* 20, 548 (2014), which is hereby incorporated by reference in its entirety). Variant calling was performed with matching peripheral blood leukocytes employed as germline controls. High-throughput sequencing was performed using 2×100 bp reads on an Illumina HiSeq 2500 instrument. Since CREBBP hotspot mutations may occur within the lysine acetyltransferase (KAT) domain, only non-silent variants (single nucleotide variants and insertions/deletions) within the KAT domain were considered "mutant". To increase the sample size, the CREBBP mutation status of 12 previously genotyped patients from the FL cohort was also analyzed.

Example 10: Parameter Sweep of Single Cell-Derived Reference Profiles

To systematically evaluate the impact of key signature matrix parameters on deconvolution performance, a parameter sweep was performed to assess: (1) the number of cells per phenotype (3, 5, 10, 20 and 40), (2) the number of signature genes per cell type (ranges of 50-150, 150-300, and 300-500), and (3) the number of donor samples (1, 2, or 3) (FIG. 10a). We created separate single cell-derived signature matrices for melanoma and HNSCC tumors within a training/validation framework (FIG. 10a). Each parameter combination was tested in triplicate by random sampling in order to ensure the robustness of the results (FIG. 10a). In addition, the analysis was restricted to the following cell phenotypes, each of which was selected to ensure sufficient representation in both the training and validation datasets across all evaluated parameter settings: malignant cells (HNSCC, melanoma), CD8 and CD4 T cells (HNSCC, melanoma), B cells (melanoma), and fibroblasts (HNSCC). Donors were sampled from a set of samples that had at least 20 cells per cell phenotype (donor IDs HN16_T, HN17_T, HN25_LN, HN25_T, HN18_T for HNSCC tumors; donor IDs 79, 80, 88, 89 for melanoma tumors). Four HNSCC samples (HN10_T, HN13_T, HN24_LN, and HN7_T) were excluded since they each contained <50 cells total across the evaluated phenotypes. When sampling only one donor, melanoma donor 88 was also excluded owing to insufficient cells (<50). In all, 126 signature matrices were tested per dataset. Performance was quantified as the median cell-level correlation against ground truth cell proportions from reconstituted tumor samples held out from signature matrix construction (FIG. 10b).

In addition, single cell-guided deconvolution was evaluated across three scRNA-Seq methods (SmartSeq2, 3'- and 5'-biased 10× Chromium expression profiling kits) and three tissue types (reconstituted melanoma tumors, reconstituted HNSCC tumors, and peripheral blood). In all cases, imputed proportions were compared against ground truth frequencies quantified by flow cytometry/Coulter counter (blood samples) or scRNA-Seq (melanoma, HNSCC). LM22, a microarray-derived signature matrix for distinguishing 22 hematopoietic subsets derived from healthy donors, was also tested. Only cell types present in both the signature matrix and tissue samples were considered, and all cell fractions were normalized to one prior to comparison (FIG. 2e). Only previously annotated cell phenotypes were assessed, with the exception of CD8/CD4 T cells in HNSCC and melanoma tumors, which were defined as described elsewhere herein and evaluated in HNSCC tumors using a melanoma signature matrix, and vice versa. In all cases, deconvolution was applied with batch correction, using S-mode batch correction for 10×-derived signature matrices and B-mode batch correction for the remaining signature matrices.

Example 11: Signature Matrices

Following cell fraction estimation but prior to expression imputation, LM22 deconvolution results were collapsed by summation into the major phenotypic groups indicated in FIG. 25, with corresponding Figures indicated in column B. Of note, in LM22-merge10, gd T cells were merged with CD8 T cells owing to high CD8 expression levels in both subsets and the absence of gd T cell depletion in publicly available CD8 T cell ground truth profiles derived from FACS-sorted cell populations (GSE28491, GSE27928).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:
1. A method comprising:
(a) obtaining a biological sample comprising a plurality of biological macromolecules from a plurality of distinct cell types from a subject having cancer;
(b) processing said biological sample to generate a feature profile of said plurality of biological macromolecules, wherein said feature profile comprises a plurality of features associated with said plurality of distinct cell types;
(c) computer processing said feature profile, using a deconvolution module, to (1) quantify an abundance of at least one of said plurality of distinct cell types in said biological sample, wherein quantifying said abundance comprises applying a batch correction procedure to remove technical variation in said abundance, and (2) generate one or more differential gene expression profiles that are differential across subtypes of said at least one of said plurality of distinct cell types,
wherein said batch correction procedure removes said technical variation between a reference matrix B of a plurality of feature signatures and said feature profile,
wherein said batch correction procedure is applied in a single cell reference mode (S-mode) or a bulk reference mode (B-mode),
(i) wherein said applying said batch correction procedure in said S-mode comprises removing technical differences between said reference matrix B derived from a set of single cell reference profiles and an input set of mixture samples M by:
(1) obtaining a plurality of estimates of a plurality of cell frequencies F* within said input set of mixture samples M, given said reference matrix B and said set of single cell reference profiles R, and
(2) refining said plurality of estimates of said plurality of cell frequencies F* by performing said batch correction procedure on said reference matrix B to obtain an adjusted reference matrix, and applying said adjusted reference matrix to said input set of mixture samples M, and

(ii) wherein said applying said batch correction procedure in said B-mode comprises removing said technical differences between said reference matrix B derived from bulk reference profiles and an input set of mixture samples M by:
(1) generating a plurality of mixture samples M* comprising a linear combination of a plurality of imputed cell type proportions in said input set of mixture samples M and corresponding profiles in said reference matrix B, and
(2) performing said batch correction on said input set of mixture samples M to eliminate said batch effects between said input set of mixture samples M and said plurality of mixture samples M*;
(d) predicting a clinical outcome of a cancer therapy on said subject for said cancer, based at least in part on said abundance and said one or more differential gene expression profiles of said at least one of said plurality of distinct cell types in said biological sample, wherein said at least one of said plurality of distinct cell types in said biological sample comprises a type of cancer cell; and
(e) administering said cancer therapy to said subject based on said predicted clinical outcome of said cancer therapy, wherein said cancer therapy is selected from the group consisting of a chemotherapy, an immunotherapy, and an immunochemotherapy.

2. The method of claim 1, wherein obtaining said biological sample does not comprise physical isolation of cells from said biological sample.

3. The method of claim 1, wherein said feature profile is generated from single-cell gene expression measurements of a plurality of cells of each of said plurality of distinct cell types.

4. The method of claim 3, wherein said single-cell gene expression measurements are generated by single-cell RNA sequencing (scRNA-Seq).

5. The method of claim 1, wherein said abundance is a fractional abundance of said at least one of said plurality of distinct cell types in said biological sample.

6. The method of claim 1, wherein quantifying said abundance comprises optimizing a regression between said feature profile and said reference matrix B of feature signatures for a second plurality of distinct cell types, wherein said feature profile is modeled as a linear combination of said reference matrix B.

7. The method of claim 6, wherein optimizing said regression comprises solving for a set of regression coefficients of said regression, wherein said solution minimizes a linear loss function and an $L_2$-norm penalty function.

8. The method of claim 7, wherein said linear loss function is a linear E-insensitive loss function.

9. The method of claim 6, wherein optimizing said regression comprises using a support vector regression (SVR) or a non-negative matrix factorization (NMF).

10. The method of claim 9, wherein said SVR is $\varepsilon$-SVR or $v$ (nu)-SVR.

11. The method of claim 1, wherein said biological sample comprises bulk tissue, a formalin-fixed, paraffin-embedded (FFPE) tissue, a frozen tissue, a blood sample, a sample derived from a solid tissue sample, or a tumor sample.

12. The method of claim 1, wherein said biological macromolecules comprise nucleic acids, proteins, metabolites, carbohydrates, sugars, lipids, or a combination thereof.

13. The method of claim 1, wherein said batch correction procedure is applied in said single cell reference mode (S-mode).

14. The method of claim 1, further comprising generating a cell-type-specific state for said at least one of said plurality of distinct cell types.

15. The method of claim 14, wherein said cell-type-specific state is a sample-level cell-type-specific state.

16. The method of claim 14, wherein said cell-type-specific state is a group-level cell-type-specific state.

17. The method of claim 1, wherein said batch correction procedure is applied in said bulk reference mode (B-mode).

18. The method of claim 1, wherein said one or more differential gene expression profiles processing is generated at least in part by:
(a) stratifying one or more gene expression profiles of said plurality of biological macromolecules into two or more subtypes based on bulk expression; and
(b) determining one or more cell type-specific gene expression coefficients for each of said two or more subtypes.

19. The method of claim 18, wherein said plurality of biological samples are obtained from a plurality of conditions of interest such that said cell type-specific gene expression coefficients are differential across said plurality of conditions of interest.

* * * * *